US009023633B2

(12) United States Patent
Faurholm et al.

(10) Patent No.: US 9,023,633 B2
(45) Date of Patent: May 5, 2015

(54) CHIMERIC DNA POLYMERASES

(75) Inventors: Bjarne Faurholm, Western Cape (ZA);
Paul McEwan, Western Cape (ZA);
William Bourn, Western Cape (ZA);
Gavin Rush, Western Cape (ZA)

(73) Assignee: Kapa Biosystems, Woburn, MA (US)

( * ) Notice: Subject to any disclaimer, the term of this patent is extended or adjusted under 35 U.S.C. 154(b) by 562 days.

(21) Appl. No.: 13/127,420

(22) PCT Filed: Nov. 3, 2009

(86) PCT No.: PCT/US2009/063166
§ 371 (c)(1),
(2), (4) Date: Jul. 19, 2011

(87) PCT Pub. No.: WO2010/062776
PCT Pub. Date: Jun. 3, 2010

(65) Prior Publication Data
US 2012/0115188 A1 May 10, 2012

Related U.S. Application Data

(60) Provisional application No. 61/110,862, filed on Nov. 3, 2008.

(51) Int. Cl.
*C12N 9/00* (2006.01)
*C12N 9/12* (2006.01)
*C12P 19/34* (2006.01)
(52) U.S. Cl.
CPC ............ *C12N 9/1252* (2013.01); *C12N 9/1241* (2013.01); *C12P 19/34* (2013.01)
(58) Field of Classification Search
None
See application file for complete search history.

(56) References Cited

U.S. PATENT DOCUMENTS

| 5,948,663 | A | 9/1999 | Mathur |
| 6,225,065 | B1 | 5/2001 | Kitabayashi et al. |
| 2002/0119461 | A1 | 8/2002 | Chatterjee |

FOREIGN PATENT DOCUMENTS

| JP | 7-298879 | | 11/1995 |
| JP | 2002/506637 | A | 3/2002 |
| JP | 2004/502443 | A | 1/2004 |
| JP | 2006/513726 | A | 4/2006 |
| JP | 2007/298879 | A | 11/2007 |
| JP | 5-328696 | B2 | 10/2013 |
| JP | 2005/328969 | B2 | 10/2013 |
| WO | WO 98/33900 | A1 | 8/1998 |
| WO | WO-01/18213 | A1 | 3/2001 |
| WO | WO 01/61015 | A2 | 8/2001 |
| WO | WO-2004/058942 | A2 | 7/2004 |
| WO | WO 2005/113760 | A2 | 12/2005 |
| WO | WO 2005/118866 | A2 | 12/2005 |

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
"DNA Polymerase SEQ ID No. 5," Feb. 23, 2006.
"Heat-resistant Pfu DNA synthetase I," Nov. 19, 1998.
Pavlov A. R. et al., "Helix-hairpin-helix motifs confer salt resistance and processivity on chimeric DNA polymerases," Proceedings of the National Academy of Sciences, National Academy of Sciences, Washington, CD; US, vol. 99, No. 21, Oct. 15, 2002, pp. 13510-13515.
Supplementary European Search Report, EP 09829689, published as EP 2352818 on Aug. 10, 2011, mailed on Apr. 24, 2012.
International Search Report for PCT/US09/63166, 4 pages, Jul. 1, 2010.
NCBI database 1WNS_A (Aug. 9, 2004).
NCBI database NP_577941 (Feb. 26, 2002).
Written Opinion for PCT/US09/63166, 5 pages, Jul. 1, 2010.

* cited by examiner

*Primary Examiner* — Richard Hutson
(74) *Attorney, Agent, or Firm* — Choate Hall & Stewart LLP; Brenda Herschbach Jarrell

(57) ABSTRACT

The present invention provides, among other things, chimeric DNA polymerases containing heterologous domains having sequences derived from at least two DNA polymerases that have at least one distinct functional characteristics (e.g., elongation rate, processivity, error rate or fidelity, salt tolerance or resistance) and methods of making and using the same. In some embodiments, the present invention can combine desired functional characteristics (e.g., high processivity; high elongation rate; thermostability; resistance to salt, PCR additives (e.g., PCR enhancers) and other impurities; and high fidelity) of different DNA polymerases in a chimeric polymerase.

5 Claims, 7 Drawing Sheets

SEQUENCE LISTING

```
<160> NUMBER OF SEQ ID NOS: 45

<210> SEQ ID NO 1
<211> LENGTH: 2328
<212> TYPE: DNA
<213> ORGANISM: Pyrococcus furiosus

<400> SEQUENCE: 1
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacgggga  aaggcatgga     180 aagattgtga gaattgttga tgtagagaag gttgagaaaa agtttctcgg caagcctatt     240
accgtgtgga aactttattt ggaacatccc caagatgttc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gatatagaaa ccctctatca cgaaggagaa gagtttggaa aaggcccaat tataatgatt     480
agttatgcag atgaaaatga agcaaaggtg attacttgga aaaacataga tcttccatac     540
gttgaggttg tatcaagcga gagagagatg ataaagagat ttctcaggat tatcagggag     600
aaggatcctg acattatagt tacttataat ggagactcat tcgacttccc atatttagcg     660
aaaagggcag aaaaacttgg gattaaatta accattggaa gagatggaag cgagcccaag     720
atgcagagaa taggcgatat gacggctgta gaagtcaagg gaagaataca tttcgacttg     780
tatcatgtaa taacaaggac aataaatctc ccaacataca cactagaggc tgtatatgaa     840 gcaattttg  gaaagccaaa ggagaaggta tacgccgacg agatagcaaa agcctgggaa     900
agtggagaga accttgagag agttgccaaa tactcgatgg aagatgcaaa ggcaacttat     960
gaactcggga aagaattcct tccaatggaa attcagcttt caagattagt tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaaagggggtt gtgggaaaac    1200 atagtatacc tagattttag agccctatat ccctcgatta taattaccca caatgtttct    1260
cccgatactc taaatcttga gggatgcaag aactatgata tcgctcctca agtaggccac    1320
aagttctgca aggacatccc tggtttttata ccaagtctct tgggacattt gttagaggaa    1380
agacaaaaga ttaagacaaa aatgaaggaa actcaagatc ctatagaaaa aatactcctt    1440
```

| | |
|---|---|
| gactatagac aaaaagcgat aaaactctta gcaaattctt tctacggata ttatggctat | 1500 |
| gcaaaagcaa gatggtactg taaggagtgt gctgagagcg ttactgcctg gggaagaaag | 1560 |
| tacatcgagt tagtatggaa ggagctcgaa gaaaagtttg gatttaaagt cctctacatt | 1620 |
| gacactgatg gtctctatgc aactatccca ggaggagaaa gtgaggaaat aaagaaaaag | 1680 |
| gctctagaat ttgtaaaata cataaattca aagctccctg gactgctaga gcttgaatat | 1740 |
| gaagggtttt ataagagggg attcttcgtt acgaagaaga ggtatgcagt aatagatgaa | 1800 |
| gaaggaaaag tcattactcg tggtttagag atagttagga gagattggag tgaaattgca | 1860 |
| aaagaaactc aagctagagt tttggagaca atactaaaac acggagatgt tgaagaagct | 1920 |
| gtgagaatag taaaagaagt aatacaaaag cttgccaatt atgaaattcc accagagaag | 1980 |
| ctcgcaatat atgagcagat aacaagacca ttacatgagt ataaggcgat aggtcctcac | 2040 |
| gtagctgttg caaagaaact agctgctaaa ggagttaaaa taaagccagg aatggtaatt | 2100 |
| ggatacatag tacttagagg cgatggtcca attagcaata gggcaattct agctgaggaa | 2160 |
| tacgatccca aaaagcacaa gtatgacgca gaatattaca ttgagaacca ggttcttcca | 2220 |
| gcggtactta ggatattgga gggatttgga tacagaaagg aagacctcag ataccaaaag | 2280 |
| acaagacaag tcggcctaac ttcctggctt aacattaaaa aatcctag | 2328 |

<210> SEQ ID NO 2
<211> LENGTH: 2325
<212> TYPE: DNA
<213> ORGANISM: Thermococcus sp.

<400> SEQUENCE: 2

| | |
|---|---|
| atgatcctcg acactgacta cataaccgag gatggaaagc ctgtcataag aattttcaag | 60 |
| aaggaaaacg gcgagtttaa gattgagtac gaccggactt ttgaacccta cttctacgcc | 120 |
| ctcctgaagg acgattctgc cattgaggaa gtcaagaaga taaccgccga gaggcacggg | 180 |
| acggttgtaa cggttaagcg ggttgaaaag gttcagaaga agttcctcgg agaccagtt | 240 |
| gaggtctgga aactctactt tactcatccg caggacgtcc cagcgataag ggacaagata | 300 |
| cgagagcatc cagcagttat tgacatctac gagtacgaca tacccttcgc caagcgctac | 360 |
| ctcatagaca agggattagt gccaatggaa ggcgacgagg agctgaaaat gctcgccttc | 420 |
| gacattgaaa ctctctacca tgagggcgag gagttcgccg aggggccaat ccttatgata | 480 |
| agctacgccg acgaggaagg ggccagggtg ataacttgga agaacgtgga tctcccctac | 540 |
| gttgacgtcg tctcgacgga gagggagatg ataaagcgct cctccgtgt tgtgaaggag | 600 |
| aaagacccgg acgttctcat aacctacaac ggcgacaact tcgacttcgc ctatctgaaa | 660 |
| aagcgctgtg aaaagctcgg aataaacttc gccctcggaa gggatggaag cgagccgaag | 720 |
| attcagagga tgggcgacag gtttgccgtc gaagtgaagg gacggataca cttcgatctc | 780 |
| tatcctgtga taagacggac gataaaacctg cccacataca cgcttgaggc cgtttatgaa | 840 |
| gccgtcttcg gtcagccgaa ggagaaggtt tacgctgagg aaataaccac agcctgggaa | 900 |
| accggcgaga accttgagag agtcgcccgc tactcgatgg aagatgcgaa ggtcacatac | 960 |
| gagcttggga aggagttcct tccgatggag gcccagcttt tcgcttaat cggccagtcc | 1020 |
| ctctgggacg tctcccgctc cagcactggc aacctcgttg agtggttcct cctcaggaag | 1080 |
| gcctatgaga ggaatgagct ggccccgaac aagcccgatg aaaaggagct ggccagaaga | 1140 |
| cggcagagct atgaaggagg ctatgtaaaa gagcccgaga gagggttgtg ggagaacata | 1200 |
| gtgtacctag attttagatc cctgtacccc tcaatcatca tcacccacaa cgtctcgccg | 1260 |

```
gatacgctca acagagaagg atgcaaggaa tatgacgttg ccccacaggt cggccaccgc    1320
ttctgcaagg acttcccagg atttatcccg agcctgcttg agacctcct agaggagagg    1380 cagaagataa agaagaagat gaaggccacg attgacccga tcgagaggaa gctcctcgat    1440
tacaggcaga gggccatcaa gatcctggca acagctact acggttacta cggctatgca    1500
agggcgcgct ggtactgcaa ggagtgtgca gagagcgtaa cggcctgggg aagggagtac    1560
ataacgatga ccatcaagga gatagaggaa aagtacggc ttaaggtaat ctacagcgac     1620
accgacggat ttttgccac aatacctgga gccgatgctg aaaccgtcaa aagaaggct      1680 atggagttcc tcaagtatat caacgccaaa cttccgggcg cgcttgagct cgagtacgag    1740
ggcttctaca acgcggctt cttcgtcacg aagaagaagt atgcggtgat agacgaggaa     1800
ggcaagataa caacgcgcgg acttgagatt gtgaggcgtg actggagcga gatagcgaaa    1860
gagacgcagg cgagggttct tgaagctttg ctaaaggacg gtgacgtcga aaggccgtg     1920 aggatagtca agaagttac cgaaaagctg agcaagtacg aggttccgcc ggagaagctg     1980
gtgatccacg agcagataac gagggattta aaggactaca aggcaaccgg tccccacgtt    2040
gccgttgcca agaggttggc cgcgagagga gtcaaaatac gccctggaac ggtgataagc    2100
tacatcgtgc tcaagggctc tgggaggata ggcgacaggg cgataccgtt cgacgagttc    2160
gacccgacga agcacaagta cgacgccgag tactacattg agaaccaggt tctcccagcc    2220
gttgagagaa ttctgagagc cttcggttac cgcaaggaag acctgcgcta ccagaagacg    2280
agacaggttg gtttgagtgc ttggctgaag ccgaagggaa cttga                    2325
```

<210> SEQ ID NO 3
<211> LENGTH: 2328
<212> TYPE: DNA
<213> ORGANISM: Artificial Sequence
<220> FEATURE:
<223> OTHER INFORMATION: Pfu codon optimized nucleotide sequence

<400> SEQUENCE: 3

```
atgattctgg atgtggacta tatcaccgaa gagggcaaac cggttatacg tttatttaag      60
aaagagaatg gtaaattcaa gatcgagcat gaccgcacgt tccgtccata catttacgcg     120
ttgcttcggg atgatagcaa aattgaggaa gtcaaaaaga tcaccgggga acgtcatgga     180
aaaatagtaa gaattgtgga cgttgaaaaa gtcgaaaaga atttctgggg caaaccgatc     240
actgtatgga agctctatct ggaacatcct caggatgtgc ccacaattcg agaaaaagtt     300
cgtgagcacc cagccgtcgt ggatatattt gaatatgaca tccctttttgc aaaacgctac    360 ttaattgata aggcctgat cccgatggag ggggaagaag aacttaaaat tctggctttt     420
gacatagaaa cgctctatca tgagggagaa gaatttggca aaggtcccat cattatgatt    480
tcttacgcgg atgagaacga agccaaggta atcacttgga aaaatattga cctgccgtac    540
gttgaagtgg tcagttcaga gcgggaaatg attaaacgtt ttttacgcat cattagagag    600
aaagatccag atataatcgt tacatataac ggcgactcct tcgatttttcc ttacctggca    660 aaacgagctg aaaaattggg tattaaactt accatcgggc gtgacggatc ggaaccgaaa    720
atgcaacgca ttggcgatat gacggcggta gaggtgaaag tcggataca cttttgatctg    780 tatcatgtca tcacccgtac tattaatctc cccacataca cgttagaagc cgtttatgag    840
gcaatattcg gcaagccgaa agaaaaagtg tacgctgacg aaatcgcgaa ggcatgggag    900
agcggcgaaa acctggagcg cgtagcaaaa tattctatgg aagatgctaa agcgacctac    960
```

```
gaattgggga aagaatttct tccaatggaa attcagctga gtcgtttagt cggacaacct   1020
ctgtgggacg tttcacgctc ctcgactggc aatctcgtgg agtggttcct gttgagaaaa   1080
gcctatgaac gaaacgaagt agcaccgaat aaaccaagcg aggaagaata tcagcgtcgc   1140
cttcgcgagt cttacacagg tgggtttgtt aaggaaccgg agaaaggtct ttgggaaaac   1200
atcgtgtatt tagatttccg tgcgctgtac cccagtatta taatcaccca caatgtctca   1260
cctgacacgc tcaacttgga aggttgcaaa aattatgata ttgctccgca agttggacat   1320
aagttttgta agatattccc gggcttcatc ccgtccctgc ttggtcactt actggaagag   1380
cgccaaaaaa ttaagaccaa aatgaaagag actcaggatc ccattgaaaa gatcctgctc   1440
gattaccggc aaaaagccat taaattgctt gcaaactcgt tttatgggta ctatggctat   1500
gcgaaggctc gttggtactg caaagaatgt gccgagagcg tgacagcatg gggtcgcaaa   1560
tatatagaat tagtatggaa ggagctggaa gaaaaattcg gattcaaagt cctgtacatc   1620 gatacgatg gcctctatgc gaccattcct ggtggggagt ctgaagaaat caagaaaaaa   1680
gccttggaat tcgttaagta cattaatagt aaattaccgg gactgcttga actggagtat   1740
gaaggcttct acaaaagagg ttttttcgtt actaagaaac gatatgccgt aatagatgaa   1800
gaggggaaag tcatcacacg tggcctcgag attgttcgcc gggactggtc agagatagca   1860
aaggaaacgc aggcgcgcgt gctcgaaacc atcttgaaac atggtgatgt gaggaagcc   1920 gtccgcattg ttaaagaggt gatccagaag ttagcaaact atgaaattcc accggaaaaa   1980
ctggcgatat acgagcaaat cactcgtccc cttcacgaat ataaagctat tggacctcat   2040
gtagccgtcg cgaagaaact ggctgcaaaa ggcgttaaga taaaaccagg tatggtgatc   2100
gggtacattg tactccgcgg cgacggtccg atttccaata gagccatctt ggcggaggaa   2160
tatgatccta aaaagcataa atacgacgct gaatattaca ttgagaacca ggtcttgccg   2220
gcagttctgc ggatacttga aggatttggc tatcgtaaag aagatctgcg ctatcaaaag   2280
acgcgacagg tgggtctgac tagctggttg aatatcaaaa aatcgtaa                2328

<210> SEQ ID NO 4
<211> LENGTH: 2337
<212> TYPE: DNA
<213> ORGANISM: Artificial Sequence
<220> FEATURE:
<223> OTHER INFORMATION: Pfu codon optimized nucleotide sequence, extra
      9 nt in 5' area

<400> SEQUENCE: 4
atggctagcg ccattctgga tgtggactat atcaccgaag agggcaaacc ggttatacgt     60
ttatttaaga aagagaatgg taaattcaag atcgagcatg accgcacgtt ccgtccatac    120
atttacgcgt tgcttcggga tgatagcaaa attgaggaag tcaaaaagat caccggggaa    180
cgtcatggaa aaatagtaag aattgtggac gttgaaaaag tcgaaaagaa atttctgggc    240
aaaccgatca ctgtatggaa gctctatctg aacatcctca ggatgtgcc cacaattcga    300 gaaaaagttc gtgagcaccc agccgtcgtg gatatatttg aatatgacat ccctttttgca   360 aaacgctact aaattgataa aggcctgatc ccgatggagg gggaagaaga acttaaaatt    420
ctggcttttg acatagaaac gctctatcat gagggagaag aatttggcaa aggtcccatc    480
attatgattt cttacgcgga tgagaacgaa gccaaggtaa tcacttggaa aaatattgac    540
ctgccgtacg ttgaagtggt cagttcagag cgggaaatga ttaaacgttt ttacgcatc    600 attagagaga aagatccaga tataatcgtt acatataacg gcgactcctt cgattttcct    660
```

```
tacctggcaa aacgagctga aaaattgggt attaaactta ccatcgggcg tgacggatcg       720
gaaccgaaaa tgcaacgcat tggcgatatg acggcggtag aggtgaaagg tcggatacac       780
tttgatctgt atcatgtcat cacccgtact attaatctcc ccacatacac gttagaagcc       840
gtttatgagg caatattcgg caagccgaaa gaaaaagtgt acgctgacga aatcgcgaag       900
gcatgggaga gcggcgaaaa cctggagcgc gtagcaaaat attctatgga agatgctaaa       960
gcgacctacg aattggggaa agaatttctt ccaatggaaa ttcagctgag tcgtttagtc      1020
ggacaacctc tgtgggacgt ttcacgctcc tcgactggca atctcgtgga gtggttcctg      1080
ttgagaaaag cctatgaacg aaacgaagta gcaccgaata aaccaagcga ggaagaatat      1140
cagcgtcgcc ttcgcgagtc ttacacaggt gggtttgtta aggaaccgga aaaggtctt       1200 tgggaaaaca tcgtgtattt agatttccgt gcgctgtacc ccagtattat aatcacccac      1260
aatgtctcac ctgacacgct caacttggaa ggttgcaaaa attatgatat tgctccgcaa      1320
gttggacata gtttttgtaa agatattccg ggcttcatcc cgtccctgct ggtcactta       1380 ctggaagagc gccaaaaaat taagaccaaa atgaaagaga ctcaggatcc cattgaaaag      1440
atcctgctcg attaccggca aaaagccatt aaattgcttg caaactcgtt ttatgggtac      1500
tatggctatg cgaaggctcg ttggtactgc aaagaatgtg ccgagagcgt gacagcatgg      1560
ggtcgcaaat atatagaatt agtatggaag gagctggaag aaaaaattcgg attcaaagtc      1620 ctgtacatcg atacggatgg cctctatgcg accattcctg gtggggagtc tgaagaaatc      1680
aagaaaaaag ccttggaatt cgttaagtac attaatagta aattaccggg actgcttgaa      1740
ctggagtatg aaggcttcta caaaagaggt ttttcgtta ctaagaaacg atatgccgta      1800
atagatgaag aggggaaagt catcacacgt ggcctcgaga ttgttcgccg ggactggtca      1860
gagatagcaa aggaaacgca ggcgcgcgtg ctcgaaacca tcttgaaaca tggtgatgta      1920
gaggaagccg tccgcattgt taaagaggtg atccagaagt tagcaaacta tgaaattcca      1980
ccggaaaaac tggcgatata cgagcaaatc actcgtcccc ttcacgaata taaagctatt      2040
ggacctcatg tagccgtcgc gaagaaactg gctgcaaaag gcgttaagat aaaaccaggt      2100
atggtgatcg ggtacattgt actccgcggc gacggtccga tttccaatag agccatcttg      2160
gcggaggaat atgatcctaa aaagcataaa tacgacgctg aatattacat tgagaaccag      2220
gtcttgccgg cagttctgcg gatacttgaa ggatttggct atcgtaaaga agatctgcgc      2280
tatcaaaaga cgcgacaggt gggtctgact agctggttga atatcaaaaa atcgtaa        2337
```

<210> SEQ ID NO 5
<211> LENGTH: 2325
<212> TYPE: DNA
<213> ORGANISM: Artificial Sequence
<220> FEATURE:
<223> OTHER INFORMATION: KOD codon optimized nucleotide sequence

<400> SEQUENCE: 5

```
atgattctgg ataccgacta tatcacggaa gatggcaaac cggtgatacg tattttttaag       60 aaagagaatg gtgagttcaa aatcgagtac gaccgcactt ttgagccata tttctacgcg      120
ttactgaagg acgatagcgc cattgaagaa gttaaaaaaa tcaccgcaga gcggcatggg      180
acagtggtaa ccgtgaagag agttgaaaaa gtccagaaaa aatttttggg acgacctgta      240
gaagtgtgga actttattt cactcacccc caagatgttc cggctatacg tgataaaatt      300
cgcgaacatc cagcggtcat tgatatttac gaatatgata taccttttgc caagcgttac      360
ctcatcgaca aaggcctggt gccgatggaa ggtgatgaag aattaaaaat gttggcattc      420
```

```
gacattgaaa cactttatca cgagggggaa gagtttgctg agggtcccat cctgatgatt      480
tcttatgcgg atgaagaggg tgcccgcgta ataacctgga agaacgttga tctcccgtac      540
gtggacgtcg ttagtacgga acgggaaatg atcaaacgtt tcctgcgcgt agtgaaagag      600
aaagatccag acgtcttaat tacctataat ggtgataact ttgattttgc atacctgaaa      660
aaaagatgcg aaaagttggg cataaatttc gctcttggtc gagacgggtc agagcctaaa      720
atccagcgta tgggagatcg ctttgcggtt gaagtgaaag gccggattca tttcgacctg      780
tatccggtaa ttcgtcgcac tatcaacctc cccacataca cgttagaagc cgtctatgag      840 gcagttttg gtcaaccgaa ggaaaaagtt tacgctgagg aaattaccac tgcgtgggaa       900
acaggcgaga atctggaacg tgtagcccgc tattctatgg aggatgcaaa agttacctat      960
gaattgggta aggaatttct tccaatggag gcgcagctgt cgagattaat agggcagagc     1020
ctgtgggacg tgtctcgaag ttcaacggga aacctcgtcg aatggtttct gttgcggaaa     1080
gcatacgagc gtaatgaact tgccctaac aaaccggatg aaaaggagct ggcacgccgt      1140
cgccaatcct atgaaggcgg ttacgttaaa gaaccagagc gggggttatg ggaaaatatc     1200
gtgtatctgg atttccgttc gctctacccg agcattatca ttaccacaa cgtatctccc      1260 gacactttga atcgcgaggg ctgtaaagaa tatgatgtcg cgccgcaggt tggtcataga    1320
ttttgcaagg acttcccggg atttatacca agtctgcttg gcgatttact ggaagagcga    1380
caaaaaatca aaagaaaat gaaagctaca atcgatccga tagaacgtaa gctgctcgac     1440
taccgccagc gggccatcaa aattttggca aactcatatt atggttacta tgggtacgcg    1500
cgtgctcgct ggtattgtaa agagtgcgcc gaatccgtga cggcatgggg ccgtgaatac    1560
atcaccatga ctattaagga gatagaagag aaatatggtt tcaaagtaat ctactcggat    1620
acagacggat tctttgcgac gattcccggt gccgatgcag aaaccgtcaa gaaaaaagcg    1680
atggaattcc ttaagtatat aaatgctaaa ttacctggtg ccctggagct ggaatacgaa    1740
gggttttaca acgcggatt cttttgttact aagaaaaat atgcggtgat cgacgaggaa      1800
ggcaagatta cgaccagagg cctcgagatt gtacggcgtg attggagcga aatcgctaaa    1860
gaaacacagg cacgtgtctt ggaggcatta ctgaaagatg gggacgttga aaaggcggtg    1920
cgaattgtaa agaagtcac cgaaaaactt tctaagtacg aagttccgcc agagaaactg     1980
gtgatacacg aacaaatcac tcgtgatctg aaagactata aggctacagg cccgcatgta    2040
gcagtcgcca aacgcctcgc ggctcggggt gttaaaattc gtcccggaac ggtgatcagt    2100
tacattgtat tgaagggctc aggtcgcata ggggatagca caatcccttt cgacgagttt    2160
gatccaacca aacacaaata tgatgccgaa tactatattg aaaaccaggt cttgccggcg    2220
gttgagcgta tactgcgcgc tttcggctat cgaaggaag atcttcgtta ccaaaaaact     2280
agacaggtgg gtctgtccgc atggctcaaa cctaagggaa cgtaa                    2325
```

<210> SEQ ID NO 6
<211> LENGTH: 2334
<212> TYPE: DNA
<213> ORGANISM: Artificial Sequence
<220> FEATURE:
<223> OTHER INFORMATION: KOD codon optimized nucleotide sequence, extra
      9 nt in 5' area.

<400> SEQUENCE: 6

```
atggctagcg ccattctgga taccgactat atcacggaag atggcaaacc ggtgatacgt       60 attttttaaga aagagaatgg tgagttcaaa atcgagtacg accgcacttt tgagccatat      120
```

| | |
|---|---|
| ttctacgcgt tactgaagga cgatagcgcc attgaagaag ttaaaaaaat caccgcagag | 180 |
| cggcatggga cagtggtaac cgtgaagaga gttgaaaaag tccagaaaaa attttggga | 240 |
| cgacctgtag aagtgtggaa actttatttc actcaccccc aagatgttcc ggctatacgt | 300 |
| gataaaattc gcgaacatcc agcggtcatt gatatttacg aatatgatat acctttgcc | 360 |
| aagcgttacc tcatcgacaa aggcctggtg ccgatggaag gtgatgaaga attaaaaatg | 420 |
| ttggcattcg acattgaaac actttatcac gaggggggaag agtttgctga gggtcccatc | 480 |
| ctgatgattt cttatgcgga tgaagagggt gcccgcgtaa taacctggaa gaacgttgat | 540 |
| ctcccgtacg tggacgtcgt tagtacgaaa cgggaaatga tcaaacgttt cctgcgcgta | 600 |
| gtgaaagaga aagatccaga cgtcttaatt acctataatg gtgataactt tgattttgca | 660 |
| tacctgaaaa aaagatgcga aaagttgggc ataaatttcg ctcttggtcg agacgggtca | 720 |
| gagcctaaaa tccagcgtat gggagatcgc tttgcggttg aagtgaaagg ccggattcat | 780 |
| ttcgacctgt atccggtaat tcgtcgcact atcaacctcc ccacatacac gttagaagcc | 840 |
| gtctatgagg cagttttttgg tcaaccgaag gaaaagtttt acgctgagga aattaccact | 900 |
| gcgtgggaaa caggcgagaa tctggaacgt gtagcccgct attctatgga ggatgcaaaa | 960 |
| gttacctatg aattgggtaa ggaatttctt ccaatggagg cgcagctgtc gagattaata | 1020 |
| gggcagagcc tgtgggacgt gtctcgaagt tcaacgggaa acctcgtcga atggtttctg | 1080 |
| ttgcggaaag catacgagcg taatgaactt gcccctaaca aaccggatga aaaggagctg | 1140 |
| gcacgccgtc gccaatccta tgaaggcggt tacgttaaag aaccagagcg ggggttatgg | 1200 |
| gaaaatatcg tgtatctgga tttccgttcg ctctacccga gcattatcat tacccacaac | 1260 |
| gtatctcccg acactttgaa tcgcgagggc tgtaaagaat atgatgtcgc gccgcaggtt | 1320 |
| ggtcatagat tttgcaagga cttcccggga tttataccaa gtctgcttgg cgatttactg | 1380 |
| gaagagcgac aaaaaatcaa aagaaaatg aaagctacaa tcgatccgat agaacgtaag | 1440 |
| ctgctcgact accgccagcg ggccatcaaa attttggcaa actcatatta tggttactat | 1500 |
| gggtacgcgc gtgctcgctg gtattgtaaa gagtgcgccg aatccgtgac ggcatggggc | 1560 |
| cgtgaataca tcaccatgac tattaaggag atagaagaga aatatggttt caaagtaatc | 1620 |
| tactcggata cagacggatt ctttgcgacg attcccggtg ccgatgcaga aaccgtcaag | 1680 |
| aaaaaagcga tggaattcct taagtatata atgctaaat tacctggtgc cctggagctg | 1740 |
| gaatacgaag ggttttacaa acgcggattc tttgttacta agaaaaaata tgcggtgatc | 1800 |
| gacgaggaag gcaagattac gaccagaggc ctcgagattg tacggcgtga ttggagcgaa | 1860 |
| atcgctaaag aaacacaggc acgtgtcttg gaggcattac tgaaagatgg ggacgttgaa | 1920 |
| aaggcggtgc gaattgtaaa agaagtcacc gaaaaacttt ctaagtacga agttccgcca | 1980 |
| gagaaactgg tgatacacga acaaatcact cgtgatctga agactataa ggctacaggc | 2040 |
| ccgcatgtag cagtcgccaa acgctcgcg gctcggggtg ttaaaattcg tcccggaacg | 2100 |
| gtgatcagtt acattgtatt gaagggctca ggtcgcatag gggatagagc aatcccttc | 2160 |
| gacgagtttg atccaaccaa acacaaatat gatgccgaat actatattga aaaccaggtc | 2220 |
| ttgccggcgg ttgagcgtat actgcgcgct tcggctatc gaaaggaaga tcttcgttac | 2280 |
| caaaaaacta gacaggtggg tctgtccgca tggctcaaac ctaagggaac gtaa | 2334 |

<210> SEQ ID NO 7
<211> LENGTH: 5017
<212> TYPE: DNA

<213> ORGANISM: Artificial Sequence
<220> FEATURE:
<223> OTHER INFORMATION: pKB13 - Pfu codon optimized nucleotide sequence in pUC19 vector

<400> SEQUENCE: 7

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | cggtctcagc | gccattctgg | 420 |
| ataccgacta | tatcacggaa | gatggcaaac | cggtgatacg | tatttttaag | aaagagaatg | 480 |
| gtgagttcaa | aatcgagtac | gaccgcactt | ttgagccata | tttctacgcg | ttactgaagg | 540 |
| acgatagcgc | cattgaagaa | gttaaaaaaa | tcaccgcaga | gcggcatggg | acagtggtaa | 600 |
| ccgtgaagag | agttgaaaaa | gtccagaaaa | aatttttggg | acgacctgta | gaagtgtgga | 660 |
| aactttattt | cactcacccc | caagatgttc | cggctatacg | tgataaaatt | cgcgaacatc | 720 |
| cagcggtcat | tgatatttac | gaatatgata | ccttttgc | caagcgttac | ctcatcgaca | 780 |
| aaggcctggt | gccgatggaa | ggtgatgaag | aattaaaaat | gttggcattc | gacattgaaa | 840 |
| cactttatca | cgaggggggaa | gagtttgctg | agggtcccat | cctgatgatt | tcttatgcgg | 900 |
| atgaagaggg | tgcccgcgta | ataacctgga | agaacgttga | tctcccgtac | gtggacgtcg | 960 |
| ttagtacgga | acgggaaatg | atcaaacgtt | tcctgcgcgt | agtgaaagag | aaagatccag | 1020 |
| acgtcttaat | tacctataat | ggtgataact | ttgattttgc | atacctgaaa | aaaagatgcg | 1080 |
| aaaagttggg | cataaatttc | gctcttggtc | gagacgggtc | agagcctaaa | atccagcgta | 1140 |
| tgggagatcg | ctttgcggtt | gaagtgaaag | gccggattca | tttcgacctg | tatccggtaa | 1200 |
| ttcgtcgcac | tatcaacctc | cccacataca | cgttagaagc | cgtctatgag | gcagttttg | 1260 |
| gtcaaccgaa | ggaaaaagtt | tacgctgagg | aaattaccac | tgcgtgggaa | acaggcgaga | 1320 |
| atctggaacg | tgtagcccgc | tattctatgg | aggatgcaaa | agttacctat | gaattgggta | 1380 |
| aggaatttct | tccaatggag | gcgcagctgt | cgagattaat | agggcagagc | ctgtgggacg | 1440 |
| tgtctcgaag | ttcaacggga | aacctcgtcg | aatggtttct | gttgcggaaa | gcatacgagc | 1500 |
| gtaatgaact | tgcccctaac | aaaccggatg | aaaaggagct | ggcacgccgt | cgccaatcct | 1560 |
| atgaaggcgg | ttacgttaaa | gaaccagagc | gggggttatg | ggaaaatatc | gtgtatctgg | 1620 |
| atttccgttc | gctctacccg | agcattatca | ttacccacaa | cgtatctccc | gacactttga | 1680 |
| atcgcgaggg | ctgtaaagaa | tatgatgtcg | cgccgcaggt | tggtcataga | ttttgcaagg | 1740 |
| acttcccggg | atttatacca | agtctgcttg | gcgatttact | ggaagagcga | caaaaaatca | 1800 |
| aaagaaaat | gaaagctaca | atcgatccga | tagaacgtaa | gctgctcgac | taccgccagc | 1860 |
| gggccatcaa | aattttggca | aactcatatt | atggttacta | tgggtacgcg | cgtgctcgct | 1920 |
| ggtattgtaa | agagtcgcc | gaatccgtga | cggcatgggg | ccgtgaatac | atcaccatga | 1980 |
| ctattaagga | gatagaagag | aaatatggtt | tcaaagtaat | ctactcggat | acagacggat | 2040 |
| tctttgcgac | gattcccggt | gccgatgcag | aaaccgtcaa | gaaaaagcg | atggaattcc | 2100 |
| ttaagtatat | aaatgctaaa | ttacctggtg | ccctggagct | ggaatacgaa | gggttttaca | 2160 |

```
aacgcggatt ctttgttact aagaaaaaat atgcggtgat cgacgaggaa ggcaagatta    2220
cgaccagagg cctcgagatt gtacggcgtg attggagcga aatcgctaaa gaaacacagg    2280
cacgtgtctt ggaggcatta ctgaaagatg gggacgttga aaaggcggtg cgaattgtaa    2340
aagaagtcac cgaaaaactt tctaagtacg aagttccgcc agagaaactg gtgatacacg    2400
aacaaatcac tcgtgatctg aaagactata aggctacagg cccgcatgta gcagtcgcca    2460
aacgcctcgc ggctcggggt gttaaaattc gtcccggaac ggtgatcagt tacattgtat    2520
tgaagggctc aggtcgcata ggggatagag caatccctt cgacgagttt gatccaacca    2580
aacacaaata tgatgccgaa tactatattg aaaaccaggt cttgccggcg gttgagcgta    2640
tactgcgcgc tttcggctat cgaaaggaag atcttcgtta ccaaaaaact agacaggtgg    2700
gtctgtccgc atggctcaaa cctaaggaa cgtaatgata tgagaccgga tcctctagag    2760
tcgacctgca ggcatgcaag cttggcgtaa tcatggtcat agctgtttcc tgtgtgaaat    2820
tgttatccgc tcacaattcc acacaacata cgagccggaa gcataaagtg taaagcctgg    2880
ggtgcctaat gagtgagcta actcacatta attgcgttgc gctcactgcc cgctttccag    2940
tcgggaaacc tgtcgtgcca gctgcattaa tgaatcggcc aacgcgcggg gagaggcggt    3000
ttgcgtattg ggcgctcttc cgcttcctcg ctcactgact cgctgcgctc ggtcgttcgg    3060
ctgcggcgag cggtatcagc tcactcaaag gcggtaatac ggttatccac agaatcaggg    3120
gataacgcag gaaagaacat gtgagcaaaa ggccagcaaa aggccaggaa ccgtaaaaag    3180
gccgcgttgc tggcgttttt ccataggctc cgcccccctg acgagcatca caaaaatcga    3240
cgctcaagtc agaggtggcg aaacccgaca ggactataaa gataccaggc gtttccccct    3300
ggaagctccc tcgtgcgctc tcctgttccg accctgccgc ttaccggata cctgtccgcc    3360
tttctccctt cgggaagcgt ggcgctttct catagctcac gctgtaggta tctcagttcg    3420
gtgtaggtcg ttcgctccaa gctgggctgt gtgcacgaac cccccgttca gcccgaccgc    3480
tgcgccttat ccggtaacta tcgtcttgag tccaacccgg taagacacga cttatcgcca    3540
ctggcagcag ccactggtaa caggattagc agagcgaggt atgtaggcgg tgctacagag    3600
ttcttgaagt ggtggcctaa ctacggctac actagaagaa cagtatttgg tatctgcgct    3660
ctgctgaagc cagttacctt cggaaaaaga gttggtagct cttgatccgg caaacaaacc    3720
accgctggta gcggtggttt ttttgtttgc aagcagcaga ttacgcgcag aaaaaaagga    3780
tctcaagaag atcctttgat cttttctacg gggtctgacg ctcagtggaa cgaaaactca    3840
cgttaaggga ttttggtcat gagattatca aaaaggatct tcacctagat ccttttaaat    3900
taaaaatgaa gttttaaatc aatctaaagt atatatgagt aaacttggtc tgacagttac    3960
caatgcttaa tcagtgaggc acctatctca gcgatctgtc tatttcgttc atccatagtt    4020
gcctgactcc ccgtcgtgta gataactacg atacgggagg gcttaccatc tggccccagt    4080
gctgcaatga taccgcgaga cccacgctca ccggctccag atttatcagc aataaaccag    4140
ccagccggaa gggccgagcg cagaagtggt cctgcaactt tatccgcctc catccagtct    4200
attaattgtt gccgggaagc tagagtaagt agttcgccag ttaatagttt gcgcaacgtt    4260
gttgccattg ctacaggcat cgtggtgtca cgctcgtcgt ttggtatggc ttcattcagc    4320
tccggttccc aacgatcaag gcgagttaca tgatccccca tgttgtgcaa aaaagcggtt    4380
agctccttcg gtcctccgat cgttgtcaga agtaagttgg ccgcagtgtt atcactcatg    4440
gttatggcag cactgcataa ttctcttact gtcatgccat ccgtaagatg cttttctgtg    4500
actggtgagt actcaaccaa gtcattctga gaatagtgta tgcggcgacc gagttgctct    4560
```

```
tgcccggcgt caatacggga taataccgcg ccacatagca gaactttaaa agtgctcatc    4620
attggaaaac gttcttcggg gcgaaaactc tcaaggatct taccgctgtt gagatccagt    4680
tcgatgtaac ccactcgtgc acccaactga tcttcagcat cttttacttt caccagcgtt    4740
tctgggtgag caaaaacagg aaggcaaaat gccgcaaaaa agggaataag ggcgacacgg    4800
aaatgttgaa tactcatact cttcctttt  caatattatt gaagcattta tcagggttat    4860
tgtctcatga gcggatacat atttgaatgt atttagaaaa ataaacaaat aggggttccg    4920
cgcacatttc cccgaaaagt gccacctgac gtctaagaaa ccattattat catgacatta    4980
acctataaaa ataggcgtat cacgaggccc tttcgtc                            5017
```

<210> SEQ ID NO 8
<211> LENGTH: 5017
<212> TYPE: DNA
<213> ORGANISM: Artificial Sequence
<220> FEATURE:
<223> OTHER INFORMATION: pKB8 - KOD codon optimized nucleotide sequence in pUC19 vector

<400> SEQUENCE: 8

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg  cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cggtctcagc gccattctgg     420
ataccgacta tatcacggaa gatggcaaac cggtgatacg tattttaag  aaagagaatg     480 gtgagttcaa aatcgagtac gaccgcactt ttgagccata tttctacgcg ttactgaagg     540
acgatagcgc cattgaagaa gttaaaaaaa tcaccgcaga gcggcatggg acagtggtaa     600
ccgtgaagag agttgaaaaa gtccagaaaa attttttggg acgacctgta gaagtgtgga     660 aactttatt  cactcacccc caagatgttc cggctatacg tgataaaatt cgcgaacatc     720
cagcggtcat tgatatttac gaatatgata taccttttgc caagcgttac ctcatcgaca     780
aaggcctggt gccgatggaa ggtgatgaag aattaaaaat gttggcattc gacattgaaa     840
cactttatca cgaggggggaa gagtttgctg agggtcccat cctgatgatt tcttatgcgg     900
atgaagaggg tgcccgcgta ataacctgga agaacgttga tctcccgtac gtggacgtcg     960
ttagtacgga acgggaaatg atcaaacgtt tcctgcgcgt agtgaaagag aaagatccag    1020
acgtcttaat tacctataat ggtgataact ttgattttgc atacctgaaa aaaagatgcg    1080
aaaagtgggg cataaatttc gctcttggtc gagacgggtc agagcctaaa atccagcgta    1140
tgggagatcg ctttgcggtt gaagtgaaag gccggattca tttcgacctg tatccggtaa    1200
ttcgtcgcac tatcaacctc cccacataca cgttagaagc cgtctatgag gcagttttg    1260 gtcaaccgaa ggaaaaagtt tacgctgagg aaattaccac tgcgtgggaa acaggcgaga    1320
atctggaacg tgtagcccgc tattctatgg aggatgcaaa agttacctat gaattgggta    1380
aggaatttct tccaatggag gcgcagctgt cgagattaat agggcagagc ctgtgggacg    1440
tgtctcgaag ttcaacggga aacctcgtcg aatggtttct gttgcggaaa gcatacgagc    1500
gtaatgaact tgcccctaac aaaccggatg aaaaggagct ggcacgccgt cgccaatcct    1560
```

```
atgaaggcgg ttacgttaaa gaaccagagc gggggttatg ggaaaatatc gtgtatctgg    1620
atttccgttc gctctacccg agcattatca ttacccacaa cgtatctccc gacactttga    1680
atcgcgaggg ctgtaaagaa tatgatgtcg cgccgcaggt tggtcataga ttttgcaagg    1740
acttcccggg atttatacca agtctgcttg gcgatttact ggaagagcga caaaaaatca    1800
aaaagaaaat gaaagctaca atcgatccga tagaacgtaa gctgctcgac taccgccagc    1860
gggccatcaa aattttggca aactcatatt atggttacta tgggtacgcg cgtgctcgct    1920
ggtattgtaa agagtgcgcc gaatccgtga cggcatgggg ccgtgaatac atcaccatga    1980
ctattaagga gatagaagag aaatatggtt tcaaagtaat ctactcggat acagacggat    2040
tctttgcgac gattcccggt gccgatgcag aaaccgtcaa gaaaaaagcg atggaattcc    2100
ttaagtatat aaatgctaaa ttacctggtg ccctggagct ggaatacgaa gggttttaca    2160
aacgcggatt ctttgttact aagaaaaaat atgcggtgat cgacgaggaa ggcaagatta    2220
cgaccagagg cctcgagatt gtacggcgtg attggagcga aatcgctaaa gaaacacagg    2280
cacgtgtctt ggaggcatta ctgaaagatg gggacgttga aaaggcggtg cgaattgtaa    2340
aagaagtcac cgaaaaactt tctaagtacg aagttccgcc agagaaactg gtgatacacg    2400
aacaaatcac tcgtgatctg aaagactata aggctacagg cccgcatgta gcagtcgcca    2460
aacgcctcgc ggctcggggt gttaaaattc gtcccggaac ggtgatcagt tacattgtat    2520
tgaagggctc aggtcgcata ggggatagag caatcccttt cgacgagttt gatccaacca    2580
aacacaaata tgatgccgaa tactatattg aaaaccaggt cttgccggcg gttgagcgta    2640
tactgcgcgc tttcggctat cgaaaggaag atcttcgtta ccaaaaaact agacaggtgg    2700
gtctgtccgc atggctcaaa cctaagggaa cgtaatgata tgagaccgga tcctctagag    2760
tcgacctgca ggcatgcaag cttggcgtaa tcatggtcat agctgtttcc tgtgtgaaat    2820
tgttatccgc tcacaattcc acacaacata cgagccggaa gcataaagtg taaagcctgg    2880
ggtgcctaat gagtgagcta actcacatta attgcgttgc gctcactgcc cgctttccag    2940
tcgggaaacc tgtcgtgcca gctgcattaa tgaatcggcc aacgcgcggg gagaggcggt    3000
ttgcgtattg ggcgctcttc cgcttcctcg ctcactgact cgctgcgctc ggtcgttcgg    3060
ctgcggcgag cggtatcagc tcactcaaag gcggtaatac ggttatccac agaatcaggg    3120
gataacgcag gaaagaacat gtgagcaaaa ggccagcaaa aggccaggaa ccgtaaaaag    3180
gccgcgttgc tggcgttttt ccataggctc cgcccccctg acgagcatca caaaaatcga    3240
cgctcaagtc agaggtggcg aaacccgaca ggactataaa gataccaggc gtttccccct    3300
ggaagctccc tcgtgcgctc tcctgttccg accctgccgc ttaccggata cctgtccgcc    3360
tttctccctt cgggaagcgt ggcgctttct catagctcac gctgtaggta tctcagttcg    3420
gtgtaggtcg ttcgctccaa gctgggctgt gtgcacgaac cccccgttca gcccgaccgc    3480
tgcgccttat ccggtaacta tcgtcttgag tccaacccgg taagacacga cttatcgcca    3540
ctggcagcag ccactggtaa caggattagc agagcgaggt atgtaggcgg tgctacagag    3600
ttcttgaagt ggtggcctaa ctacggctac actagaagaa cagtatttgg tatctgcgct    3660
ctgctgaagc cagttacctt cggaaaaaga gttggtagct cttgatccgg caaacaaacc    3720
accgctggta gcggtggttt ttttgtttgc aagcagcaga ttacgcgcag aaaaaaagga    3780
tctcaagaag atcctttgat cttttctacg gggtctgacg ctcagtggaa cgaaaactca    3840
cgttaaggga ttttggtcat gagattatca aaaaggatct tcacctagat ccttttaaat    3900
```

| | |
|---|---|
| taaaaatgaa gttttaaatc aatctaaagt atatatgagt aaacttggtc tgacagttac | 3960 |
| caatgcttaa tcagtgaggc acctatctca gcgatctgtc tatttcgttc atccatagtt | 4020 |
| gcctgactcc ccgtcgtgta gataactacg atacgggagg gcttaccatc tggcccagt | 4080 |
| gctgcaatga taccgcgaga cccacgctca ccggctccag atttatcagc aataaaccag | 4140 |
| ccagccggaa gggccgagcg cagaagtggt cctgcaactt tatccgcctc catccagtct | 4200 |
| attaattgtt gccgggaagc tagagtaagt agttcgccag ttaatagttt gcgcaacgtt | 4260 |
| gttgccattg ctacaggcat cgtggtgtca cgctcgtcgt ttggtatggc ttcattcagc | 4320 |
| tccggttccc aacgatcaag gcgagttaca tgatccccca tgttgtgcaa aaaagcggtt | 4380 |
| agctccttcg gtcctccgat cgttgtcaga agtaagttgg ccgcagtgtt atcactcatg | 4440 |
| gttatggcag cactgcataa ttctcttact gtcatgccat ccgtaagatg cttttctgtg | 4500 |
| actggtgagt actcaaccaa gtcattctga gaatagtgta tgcggcgacc gagttgctct | 4560 |
| tgcccggcgt caatacggga taataccgcg ccacatagca gaactttaaa agtgctcatc | 4620 |
| attggaaaac gttcttcggg gcgaaaactc tcaaggatct taccgctgtt gagatccagt | 4680 |
| tcgatgtaac ccactcgtgc acccaactga tcttcagcat cttttacttt caccagcgtt | 4740 |
| tctgggtgag caaaaacagg aaggcaaaat gccgcaaaaa agggaataag gcgacacgg | 4800 |
| aaatgttgaa tactcatact cttcctttt caatattatt gaagcattta tcagggttat | 4860 |
| tgtctcatga gcggatacat atttgaatgt atttagaaaa ataaacaaat aggggttccg | 4920 |
| cgcacatttc cccgaaaagt gccacctgac gtctaagaaa ccattattat catgacatta | 4980 |
| acctataaaa ataggcgtat cacgaggccc tttcgtc | 5017 |

<210> SEQ ID NO 9
<211> LENGTH: 775
<212> TYPE: PRT
<213> ORGANISM: Pyrococcus furiosus

<400> SEQUENCE: 9

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

```
Asp Leu Pro Tyr Val Glu Val Val Ser Ser Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
```

```
                    595                 600                 605
Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                    645                 650                 655

Pro Pro Glu Lys Leu Ala Ile Tyr Glu Gln Ile Thr Arg Pro Leu His
                    660                 665                 670

Glu Tyr Lys Ala Ile Gly Pro His Val Ala Val Ala Lys Lys Leu Ala
                    675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                    725                 730                 735

Gln Val Leu Pro Ala Val Leu Arg Ile Leu Glu Gly Phe Gly Tyr Arg
                    740                 745                 750

Lys Glu Asp Leu Arg Tyr Gln Lys Thr Arg Gln Val Gly Leu Thr Ser
                    755                 760                 765

Trp Leu Asn Ile Lys Lys Ser
770                 775

<210> SEQ ID NO 10
<211> LENGTH: 778
<212> TYPE: PRT
<213> ORGANISM: Artificial Sequence
<220> FEATURE:
<223> OTHER INFORMATION: Pfu amino acid sequence, extra 3 aa in 5' area.

<400> SEQUENCE: 10

Met Ala Ser Ala Ile Leu Asp Val Asp Tyr Ile Thr Glu Glu Gly Lys
1               5                   10                  15

Pro Val Ile Arg Leu Phe Lys Lys Glu Asn Gly Lys Phe Lys Ile Glu
                20                  25                  30

His Asp Arg Thr Phe Arg Pro Tyr Ile Tyr Ala Leu Leu Arg Asp Asp
            35                  40                  45

Ser Lys Ile Glu Glu Val Lys Lys Ile Thr Gly Glu Arg His Gly Lys
        50                  55                  60

Ile Val Arg Ile Val Asp Val Glu Lys Val Glu Lys Lys Phe Leu Gly
65                  70                  75                  80

Lys Pro Ile Thr Val Trp Lys Leu Tyr Leu Glu His Pro Gln Asp Val
                85                  90                  95

Pro Thr Ile Arg Glu Lys Val Arg Glu His Pro Ala Val Val Asp Ile
            100                 105                 110

Phe Glu Tyr Asp Ile Pro Phe Ala Lys Arg Tyr Leu Ile Asp Lys Gly
        115                 120                 125

Leu Ile Pro Met Glu Gly Glu Glu Leu Lys Ile Leu Ala Phe Asp
130                 135                 140

Ile Glu Thr Leu Tyr His Glu Gly Glu Glu Phe Gly Lys Gly Pro Ile
145                 150                 155                 160

Ile Met Ile Ser Tyr Ala Asp Glu Asn Glu Ala Lys Val Ile Thr Trp
                165                 170                 175

Lys Asn Ile Asp Leu Pro Tyr Val Glu Val Val Ser Ser Glu Arg Glu
```

```
            180                 185                 190
Met Ile Lys Arg Phe Leu Arg Ile Arg Glu Lys Asp Pro Asp Ile
            195                 200                 205
Ile Val Thr Tyr Asn Gly Asp Ser Phe Asp Phe Pro Tyr Leu Ala Lys
        210                 215                 220
Arg Ala Glu Lys Leu Gly Ile Lys Leu Thr Ile Gly Arg Asp Gly Ser
225                 230                 235                 240
Glu Pro Lys Met Gln Arg Ile Gly Asp Met Thr Ala Val Glu Val Lys
                245                 250                 255
Gly Arg Ile His Phe Asp Leu Tyr His Val Ile Thr Arg Thr Ile Asn
            260                 265                 270
Leu Pro Thr Tyr Thr Leu Glu Ala Val Tyr Glu Ala Ile Phe Gly Lys
        275                 280                 285
Pro Lys Glu Lys Val Tyr Ala Asp Glu Ile Ala Lys Ala Trp Glu Ser
        290                 295                 300
Gly Glu Asn Leu Glu Arg Val Ala Lys Tyr Ser Met Glu Asp Ala Lys
305                 310                 315                 320
Ala Thr Tyr Glu Leu Gly Lys Glu Phe Leu Pro Met Glu Ile Gln Leu
                325                 330                 335
Ser Arg Leu Val Gly Gln Pro Leu Trp Asp Val Ser Arg Ser Ser Thr
                340                 345                 350
Gly Asn Leu Val Glu Trp Phe Leu Leu Arg Lys Ala Tyr Glu Arg Asn
            355                 360                 365
Glu Val Ala Pro Asn Lys Pro Ser Glu Glu Tyr Gln Arg Arg Leu
        370                 375                 380
Arg Glu Ser Tyr Thr Gly Gly Phe Val Lys Glu Pro Glu Lys Gly Leu
385                 390                 395                 400
Trp Glu Asn Ile Val Tyr Leu Asp Phe Arg Ala Leu Tyr Pro Ser Ile
                405                 410                 415
Ile Ile Thr His Asn Val Ser Pro Asp Thr Leu Asn Leu Glu Gly Cys
            420                 425                 430
Lys Asn Tyr Asp Ile Ala Pro Gln Val Gly His Lys Phe Cys Lys Asp
        435                 440                 445
Ile Pro Gly Phe Ile Pro Ser Leu Leu Gly His Leu Leu Glu Glu Arg
        450                 455                 460
Gln Lys Ile Lys Thr Lys Met Lys Glu Thr Gln Asp Pro Ile Glu Lys
465                 470                 475                 480
Ile Leu Leu Asp Tyr Arg Gln Lys Ala Ile Lys Leu Leu Ala Asn Ser
                485                 490                 495
Phe Tyr Gly Tyr Tyr Gly Tyr Ala Lys Ala Arg Trp Tyr Cys Lys Glu
                500                 505                 510
Cys Ala Glu Ser Val Thr Ala Trp Gly Arg Lys Tyr Ile Glu Leu Val
            515                 520                 525
Trp Lys Glu Leu Glu Glu Lys Phe Gly Phe Lys Val Leu Tyr Ile Asp
        530                 535                 540
Thr Asp Gly Leu Tyr Ala Thr Ile Pro Gly Gly Glu Ser Glu Glu Ile
545                 550                 555                 560
Lys Lys Lys Ala Leu Glu Phe Val Lys Tyr Ile Asn Ser Lys Leu Pro
                565                 570                 575
Gly Leu Leu Glu Leu Glu Tyr Glu Gly Phe Tyr Lys Arg Gly Phe Phe
            580                 585                 590
Val Thr Lys Lys Arg Tyr Ala Val Ile Asp Glu Glu Gly Lys Val Ile
        595                 600                 605
```

```
Thr Arg Gly Leu Glu Ile Val Arg Asp Trp Ser Glu Ile Ala Lys
        610                 615                 620

Glu Thr Gln Ala Arg Val Leu Glu Thr Ile Leu Lys His Gly Asp Val
625                 630                 635                 640

Glu Glu Ala Val Arg Ile Val Lys Glu Val Ile Gln Lys Leu Ala Asn
                645                 650                 655

Tyr Glu Ile Pro Pro Glu Lys Leu Ala Ile Tyr Glu Gln Ile Thr Arg
                660                 665                 670

Pro Leu His Glu Tyr Lys Ala Ile Gly Pro His Val Ala Val Ala Lys
                675                 680                 685

Lys Leu Ala Ala Lys Gly Val Lys Ile Lys Pro Gly Met Val Ile Gly
        690                 695                 700

Tyr Ile Val Leu Arg Gly Asp Gly Pro Ile Ser Asn Arg Ala Ile Leu
705                 710                 715                 720

Ala Glu Glu Tyr Asp Pro Lys Lys His Lys Tyr Asp Ala Glu Tyr Tyr
                725                 730                 735

Ile Glu Asn Gln Val Leu Pro Ala Val Leu Arg Ile Leu Glu Gly Phe
                740                 745                 750

Gly Tyr Arg Lys Glu Asp Leu Arg Tyr Gln Lys Thr Arg Gln Val Gly
        755                 760                 765

Leu Thr Ser Trp Leu Asn Ile Lys Lys Ser
        770                 775

<210> SEQ ID NO 11
<211> LENGTH: 774
<212> TYPE: PRT
<213> ORGANISM: Thermococcus sp.

<400> SEQUENCE: 11

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
```

-continued

```
            195                 200                 205
Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Thr Gly Asn Leu
            340                 345                 350

Val Glu Trp Phe Leu Arg Lys Ala Tyr Glu Arg Asn Glu Leu Ala
        355                 360                 365

Pro Asn Lys Pro Asp Glu Lys Glu Leu Ala Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620
```

```
Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
            755                 760                 765

Leu Lys Pro Lys Gly Thr
            770

<210> SEQ ID NO 12
<211> LENGTH: 777
<212> TYPE: PRT
<213> ORGANISM: Artificial Sequence
<220> FEATURE:
<223> OTHER INFORMATION: KOD amino acid sequence, extra 3 aa in 5' area.

<400> SEQUENCE: 12

Met Ala Ser Ala Ile Leu Asp Thr Asp Tyr Ile Thr Glu Asp Gly Lys
1               5                   10                  15

Pro Val Ile Arg Ile Phe Lys Lys Glu Asn Gly Glu Phe Lys Ile Glu
            20                  25                  30

Tyr Asp Arg Thr Phe Glu Pro Tyr Phe Tyr Ala Leu Leu Lys Asp Asp
        35                  40                  45

Ser Ala Ile Glu Glu Val Lys Lys Ile Thr Ala Glu Arg His Gly Thr
    50                  55                  60

Val Val Thr Val Lys Arg Val Glu Lys Val Gln Lys Lys Phe Leu Gly
65                  70                  75                  80

Arg Pro Val Glu Val Trp Lys Leu Tyr Phe Thr His Pro Gln Asp Val
                85                  90                  95

Pro Ala Ile Arg Asp Lys Ile Arg Glu His Pro Ala Val Ile Asp Ile
            100                 105                 110

Tyr Glu Tyr Asp Ile Pro Phe Ala Lys Arg Tyr Leu Ile Asp Lys Gly
        115                 120                 125

Leu Val Pro Met Glu Gly Asp Glu Glu Leu Lys Met Leu Ala Phe Asp
    130                 135                 140

Ile Glu Thr Leu Tyr His Glu Gly Glu Glu Phe Ala Glu Gly Pro Ile
145                 150                 155                 160

Leu Met Ile Ser Tyr Ala Asp Glu Glu Gly Ala Arg Val Ile Thr Trp
                165                 170                 175

Lys Asn Val Asp Leu Pro Tyr Val Asp Val Val Ser Thr Glu Arg Glu
            180                 185                 190

Met Ile Lys Arg Phe Leu Arg Val Val Lys Glu Lys Asp Pro Asp Val
        195                 200                 205
```

```
Leu Ile Thr Tyr Asn Gly Asp Asn Phe Asp Phe Ala Tyr Leu Lys Lys
            210                 215                 220

Arg Cys Glu Lys Leu Gly Ile Asn Phe Ala Leu Gly Arg Asp Gly Ser
225                 230                 235                 240

Glu Pro Lys Ile Gln Arg Met Gly Asp Arg Phe Ala Val Glu Val Lys
                245                 250                 255

Gly Arg Ile His Phe Asp Leu Tyr Pro Val Ile Arg Arg Thr Ile Asn
            260                 265                 270

Leu Pro Thr Tyr Thr Leu Glu Ala Val Tyr Glu Ala Val Phe Gly Gln
        275                 280                 285

Pro Lys Glu Lys Val Tyr Ala Glu Glu Ile Thr Thr Ala Trp Glu Thr
    290                 295                 300

Gly Glu Asn Leu Glu Arg Val Ala Arg Tyr Ser Met Glu Asp Ala Lys
305                 310                 315                 320

Val Thr Tyr Glu Leu Gly Lys Glu Phe Leu Pro Met Glu Ala Gln Leu
                325                 330                 335

Ser Arg Leu Ile Gly Gln Ser Leu Trp Asp Val Ser Arg Ser Ser Thr
            340                 345                 350

Gly Asn Leu Val Glu Trp Phe Leu Leu Arg Lys Ala Tyr Glu Arg Asn
        355                 360                 365

Glu Leu Ala Pro Asn Lys Pro Asp Glu Lys Glu Leu Ala Arg Arg Arg
    370                 375                 380

Gln Ser Tyr Glu Gly Gly Tyr Val Lys Glu Pro Glu Arg Gly Leu Trp
385                 390                 395                 400

Glu Asn Ile Val Tyr Leu Asp Phe Arg Ser Leu Tyr Pro Ser Ile Ile
                405                 410                 415

Ile Thr His Asn Val Ser Pro Asp Thr Leu Asn Arg Glu Gly Cys Lys
            420                 425                 430

Glu Tyr Asp Val Ala Pro Gln Val Gly His Arg Phe Cys Lys Asp Phe
        435                 440                 445

Pro Gly Phe Ile Pro Ser Leu Leu Gly Asp Leu Leu Glu Glu Arg Gln
    450                 455                 460

Lys Ile Lys Lys Lys Met Lys Ala Thr Ile Asp Pro Ile Glu Arg Lys
465                 470                 475                 480

Leu Leu Asp Tyr Arg Gln Arg Ala Ile Lys Ile Leu Ala Asn Ser Tyr
                485                 490                 495

Tyr Gly Tyr Tyr Gly Tyr Ala Arg Ala Arg Trp Tyr Cys Lys Glu Cys
            500                 505                 510

Ala Glu Ser Val Thr Ala Trp Gly Arg Glu Tyr Ile Thr Met Thr Ile
        515                 520                 525

Lys Glu Ile Glu Glu Lys Tyr Gly Phe Lys Val Ile Tyr Ser Asp Thr
    530                 535                 540

Asp Gly Phe Phe Ala Thr Ile Pro Gly Ala Asp Ala Glu Thr Val Lys
545                 550                 555                 560

Lys Lys Ala Met Glu Phe Leu Lys Tyr Ile Asn Ala Lys Leu Pro Gly
                565                 570                 575

Ala Leu Glu Leu Glu Tyr Glu Gly Phe Tyr Lys Arg Gly Phe Phe Val
            580                 585                 590

Thr Lys Lys Lys Tyr Ala Val Ile Asp Glu Glu Gly Lys Ile Thr Thr
        595                 600                 605

Arg Gly Leu Glu Ile Val Arg Arg Asp Trp Ser Glu Ile Ala Lys Glu
    610                 615                 620
```

```
Thr Gln Ala Arg Val Leu Glu Ala Leu Leu Lys Asp Gly Asp Val Glu
625                 630                 635                 640
Lys Ala Val Arg Ile Val Lys Glu Val Thr Glu Lys Leu Ser Lys Tyr
            645                 650                 655
Glu Val Pro Pro Glu Lys Leu Val Ile His Glu Gln Ile Thr Arg Asp
        660                 665                 670
Leu Lys Asp Tyr Lys Ala Thr Gly Pro His Val Ala Val Ala Lys Arg
    675                 680                 685
Leu Ala Ala Arg Gly Val Lys Ile Arg Pro Gly Thr Val Ile Ser Tyr
690                 695                 700
Ile Val Leu Lys Gly Ser Gly Arg Ile Gly Asp Arg Ala Ile Pro Phe
705                 710                 715                 720
Asp Glu Phe Asp Pro Thr Lys His Lys Tyr Asp Ala Glu Tyr Tyr Ile
            725                 730                 735
Glu Asn Gln Val Leu Pro Ala Val Glu Arg Ile Leu Arg Ala Phe Gly
        740                 745                 750
Tyr Arg Lys Glu Asp Leu Arg Tyr Gln Lys Thr Arg Gln Val Gly Leu
    755                 760                 765
Ser Ala Trp Leu Lys Pro Lys Gly Thr
770                 775
```

<210> SEQ ID NO 13
<211> LENGTH: 2334
<212> TYPE: DNA
<213> ORGANISM: Artificial Sequence
<220> FEATURE:
<223> OTHER INFORMATION: Pod codon optimized nucleotide sequence

<400> SEQUENCE: 13

```
atggctagcg ccattctgga tgtggactat atcaccgaag agggcaaacc ggttatacgt      60
ttatttaaga agagaatgg taaattcaag atcgagcatg accgcacgtt ccgtccatac     120
atttacgcgt tgcttcggga tgatagcaaa attgaggaag tcaaaaagat caccggggaa     180
cgtcatggaa aaatagtaag aattgtggac gttgaaaaag tcgaaaagaa atttctgggc     240
aaaccgatca ctgtatggaa gctctatctg gaacatcctc aggatgtgcc acaattcga     300
gaaaaagttc gtgagcaccc agccgtcgtg gatatatttg aatatgacat cccttttgca     360
aaacgctact taattgataa aggcctgatc ccgatggagg gggaagaaga acttaaaatt     420
ctggcttttg acatagaaac gctctatcat gagggagaag aatttggcaa aggtcccatc     480
attatgattt cttacgcgga tgagaacgaa gccaaggtaa tcacttggaa aaatattgac     540
ctgccgtacg ttgaagtggt cagttcagag cgggaaatga ttaaacgttt tttacgcatc     600
attagagaga agatccaga tataatcgtt acatataacg gcgactcctt cgattttcct     660
tacctggcaa acgagctga aaaattgggt attaaactta ccatcgggcg tgacggatcg     720
gaaccgaaaa tgcaacgcat tggcgatatg acggcggtag aggtgaaagg tcggatacac     780
tttgatctgt atcatgtcat cacccgtact attaatctcc ccacatacac gttagaagcc     840
gtttatgagg caatattcgg caagccgaaa gaaaaagtgt acgctgacga atcgcgaag     900
gcatgggaga gcggcgaaaa cctggagcgc gtagcaaaat attctatgga agatgctaaa     960
gcgacctacg aattggggaa agaatttctt ccaatggaaa ttcagctgtc gagattaata    1020
gggcagagcc tgtgggacgt gtctcgaagt tcaacgggaa acctcgtcga atggtttctg    1080
ttgcggaaag catacgagcg taatgaactt gcccctaaca aaccggatga aaggagctg    1140
gcacgccgtc gccaatccta tgaaggcggt tacgttaaag aaccagagcg ggggttatgg    1200
```

```
gaaaatatcg tgtatctgga tttccgttcg ctctacccga gcattatcat tacccacaac    1260
gtatctcccg acactttgaa tcgcgagggc tgtaaagaat atgatgtcgc gccgcaggtt    1320
ggtcatagat tttgcaagga cttcccggga tttataccaa gtctgcttgg cgatttactg    1380
gaagagcgac aaaaaatcaa aaagaaaatg aaagctacaa tcgatccgat agaacgtaag    1440
ctgctcgact accgccagcg ggccatcaaa attttggcaa actcatatta tggttactat    1500
gggtacgcgc gtgctcgctg gtattgtaaa gagtgcgccg aatccgtgac ggcatggggc    1560
cgtgaataca tcaccatgac tattaaggag atagaagaga aatatggttt caaagtaatc    1620
tactcggata cagacggatt ctttgcgacg attcccggtg ccgatgcaga aaccgtcaag    1680
aaaaaagcga tggaattcgt taagtacatt aatagtaaat taccgggact gcttgaactg    1740
gagtatgaag gcttctacaa aagaggtttt ttcgttacta agaaacgata tgccgtaata    1800
gatgaagagg ggaaagtcat cacacgtggc ctcgagattg ttcgccggga ctggtcagag    1860
atagcaaagg aaacgcaggc gcgcgtgctc gaaaccatct tgaaacatgg tgatgtagag    1920
gaagccgtcc gcattgttaa agaggtgatc cagaagttag caaactatga aattccaccg    1980
gaaaaactgg cgatatacga gcaaatcact cgtccccttc acgaatataa agctattgga    2040
cctcatgtag ccgtcgcgaa gaaactggct gcaaaaggcg ttaagataaa accaggtatg    2100
gtgatcgggt acattgtact ccgcggcgac ggtccgattt ccaatagagc catcttggcg    2160
gaggaatatg atcctaaaaa gcataaatac gacgctgaat attacattga gaaccaggtc    2220
ttgccggcag ttctgcggat acttgaagga tttggctatc gtaaagaaga tctgcgctat    2280
caaaagacgc gacaggtggg tctgactagc tggttgaata tcaaaaaatc gtaa          2334
```

<210> SEQ ID NO 14
<211> LENGTH: 2337
<212> TYPE: DNA
<213> ORGANISM: Artificial Sequence
<220> FEATURE:
<223> OTHER INFORMATION: Kofu codon optimized nucleotide sequence

<400> SEQUENCE: 14

```
atggctagcg ccattctgga taccgactat atcacggaag atggcaaacc ggtgatacgt     60 attttttaaga aagagaatgg tgagttcaaa atcgagtacg accgcacttt tgagccatat    120
ttctacgcgt tactgaagga cgatagcgcc attgaagaag ttaaaaaaat caccgcagag    180
cggcatggga cagtggtaac cgtgaagaga gttgaaaaag tccagaaaaa attttttggga    240 cgacctgtag aagtgtggaa actttatttc actcaccccc aagatgttcc ggctatacgt    300
gataaaattc gcgaacatcc agcggtcatt gatatttacg aatatgatat accttttgcc    360
aagcgttacc tcatcgacaa aggcctggtg ccgatggaag gtgatgaaga attaaaaatg    420
ttggcattcg acattgaaac actttatcac gagggggaag agtttgctga gggtcccatc    480
ctgatgattt cttatgcgga tgaagagggt gcccgcgtaa taccctggaa gaacgttgat    540
ctcccgtacg tggacgtcgt tagtacggaa cgggaaatga tcaaacgttt cctgcgcgta    600
gtgaaagaga aagatccaga cgtcttaatt acctataatg gtgataactt tgattttgca    660
tacctgaaaa aaagatgcga aaagttgggc ataaatttcg ctcttggtcg agacgggtca    720
gagcctaaaa tccagcgtat gggagatcgc tttgcggttg aagtgaaagg ccggattcat    780
ttcgacctgt atccggtaat tcgtcgcact atcaacctcc ccacatacac gttagaagcc    840
gtctatgagg cagttttgg tcaaccgaag gaaaagtttt acgctgagga aattaccact    900
```

```
gcgtgggaaa caggcgagaa tctggaacgt gtagcccgct attctatgga ggatgcaaaa    960
gttacctatg aattgggtaa ggaatttctt ccaatggagg cgcagctgag tcgtttagtc   1020
ggacaacctc tgtgggacgt ttcacgctcc tcgactggca atctcgtgga gtggttcctg   1080
ttgagaaaag cctatgaacg aaacgaagta gcaccgaata aaccaagcga ggaagaatat   1140
cagcgtcgcc ttcgcgagtc ttacacaggt gggtttgtta aggaaccgga gaaaggtctt   1200
tgggaaaaca tcgtgtattt agatttccgt gcgctgtacc ccagtattat aatcacccac   1260
aatgtctcac ctgacacgct caacttggaa ggttgcaaaa attatgatat tgctccgcaa   1320
gttggacata agttttgtaa agatattccg ggcttcatcc cgtccctgct ggtcactta    1380
ctggaagagc gccaaaaaat taagaccaaa atgaaagaga ctcaggatcc cattgaaaag   1440
atcctgctcg attaccggca aaaagccatt aaattgcttg caaactcgtt ttatgggtac   1500
tatggctatg cgaaggctcg ttggtactgc aaagaatgtg ccgagagcgt gacagcatgg   1560
ggtcgcaaat atatagaatt agtatggaag gagctggaag aaaaattcgg attcaaagtc   1620
ctgtacatcg atacggatgg cctctatgcg accattcctg gtggggagtc tgaagaaatc   1680
aagaaaaaag ccttggaatt ccttaagtat ataaatgcta aattacctgg tgccctggag   1740
ctggaatacg aagggtttta caaacgcgga ttctttgtta ctaagaaaaa atatgcggtg   1800
atcgacgagg aaggcaagat tacgaccaga ggcctcgaga ttgtacggcg tgattggagc   1860
gaaatcgcta agaaaacaca ggcacgtgtc ttggaggcat tactgaaaga tggggacgtt   1920
gaaaaggcgg tgcgaattgt aaaagaagtc accgaaaaac tttctaagta cgaagttccg   1980
ccagagaaac tggtgataca cgaacaaatc actcgtgatc tgaaagacta taaggctaca   2040
ggcccgcatg tagcagtcgc caaacgcctc gcggctcggg gtgttaaaat tcgtcccgga   2100
acggtgatca gttacattgt attgaagggc tcaggtcgca tagggatag agcaatccct   2160
ttcgacgagt ttgatccaac caaacacaaa tatgatgccg aatactatat tgaaaaccag   2220
gtcttgccgg cggttgagcg tatactgcgc gctttcggct atcgaaagga agatcttcgt   2280
taccaaaaaa ctagacaggt gggtctgtcc gcatggctca aacctaaggg aacgtaa     2337
```

<210> SEQ ID NO 15
<211> LENGTH: 777
<212> TYPE: PRT
<213> ORGANISM: Artificial Sequence
<220> FEATURE:
<223> OTHER INFORMATION: Pod amino acid sequence

<400> SEQUENCE: 15

```
Met Ala Ser Ala Ile Leu Asp Val Asp Tyr Ile Thr Glu Glu Gly Lys
1               5                   10                  15

Pro Val Ile Arg Leu Phe Lys Lys Glu Asn Gly Lys Phe Lys Ile Glu
            20                  25                  30

His Asp Arg Thr Phe Arg Pro Tyr Ile Tyr Ala Leu Leu Arg Asp Asp
        35                  40                  45

Ser Lys Ile Glu Glu Val Lys Lys Ile Thr Gly Glu Arg His Gly Lys
    50                  55                  60

Ile Val Arg Ile Val Asp Val Glu Lys Val Glu Lys Lys Phe Leu Gly
65                  70                  75                  80

Lys Pro Ile Thr Val Trp Lys Leu Tyr Leu Glu His Pro Gln Asp Val
                85                  90                  95

Pro Thr Ile Arg Glu Lys Val Arg Glu His Pro Ala Val Val Asp Ile
            100                 105                 110
```

-continued

```
Phe Glu Tyr Asp Ile Pro Phe Ala Lys Arg Tyr Leu Ile Asp Lys Gly
            115                 120                 125

Leu Ile Pro Met Glu Gly Glu Glu Leu Lys Ile Leu Ala Phe Asp
130                 135                 140

Ile Glu Thr Leu Tyr His Glu Gly Glu Phe Gly Lys Gly Pro Ile
145                 150                 155                 160

Ile Met Ile Ser Tyr Ala Asp Glu Asn Glu Ala Lys Val Ile Thr Trp
                165                 170                 175

Lys Asn Ile Asp Leu Pro Tyr Val Glu Val Ser Ser Glu Arg Glu
                180                 185                 190

Met Ile Lys Arg Phe Leu Arg Ile Arg Glu Lys Asp Pro Asp Ile
            195                 200                 205

Ile Val Thr Tyr Asn Gly Asp Ser Phe Asp Phe Pro Tyr Leu Ala Lys
            210                 215                 220

Arg Ala Glu Lys Leu Gly Ile Lys Leu Thr Ile Gly Arg Asp Gly Ser
225                 230                 235                 240

Glu Pro Lys Met Gln Arg Ile Gly Asp Met Thr Ala Val Glu Val Lys
                245                 250                 255

Gly Arg Ile His Phe Asp Leu Tyr His Val Ile Thr Arg Thr Ile Asn
                260                 265                 270

Leu Pro Thr Tyr Thr Leu Glu Ala Val Tyr Glu Ala Ile Phe Gly Lys
            275                 280                 285

Pro Lys Glu Lys Val Tyr Ala Asp Glu Ile Ala Lys Ala Trp Glu Ser
            290                 295                 300

Gly Glu Asn Leu Glu Arg Val Ala Lys Tyr Ser Met Glu Asp Ala Lys
305                 310                 315                 320

Ala Thr Tyr Glu Leu Gly Lys Glu Phe Leu Pro Met Glu Ile Gln Leu
                325                 330                 335

Ser Arg Leu Ile Gly Gln Ser Leu Trp Asp Val Ser Arg Ser Ser Thr
            340                 345                 350

Gly Asn Leu Val Glu Trp Phe Leu Leu Arg Lys Ala Tyr Glu Arg Asn
            355                 360                 365

Glu Leu Ala Pro Asn Lys Pro Asp Glu Lys Glu Leu Ala Arg Arg Arg
370                 375                 380

Gln Ser Tyr Glu Gly Gly Tyr Val Lys Glu Pro Glu Arg Gly Leu Trp
385                 390                 395                 400

Glu Asn Ile Val Tyr Leu Asp Phe Arg Ser Leu Tyr Pro Ser Ile Ile
                405                 410                 415

Ile Thr His Asn Val Ser Pro Asp Thr Leu Asn Arg Glu Gly Cys Lys
            420                 425                 430

Glu Tyr Asp Val Ala Pro Gln Val Gly His Arg Phe Cys Lys Asp Phe
            435                 440                 445

Pro Gly Phe Ile Pro Ser Leu Leu Gly Asp Leu Leu Glu Glu Arg Gln
450                 455                 460

Lys Ile Lys Lys Lys Met Lys Ala Thr Ile Asp Pro Ile Glu Arg Lys
465                 470                 475                 480

Leu Leu Asp Tyr Arg Gln Arg Ala Ile Lys Ile Leu Ala Asn Ser Tyr
                485                 490                 495

Tyr Gly Tyr Tyr Gly Tyr Ala Arg Ala Arg Trp Tyr Cys Lys Glu Cys
                500                 505                 510

Ala Glu Ser Val Thr Ala Trp Gly Arg Glu Tyr Ile Thr Met Thr Ile
            515                 520                 525

Lys Glu Ile Glu Glu Lys Tyr Gly Phe Lys Val Ile Tyr Ser Asp Thr
```

```
                530             535             540
Asp Gly Phe Phe Ala Thr Ile Pro Gly Ala Asp Ala Glu Thr Val Lys
545                 550                 555                 560

Lys Lys Ala Met Glu Phe Val Lys Tyr Ile Asn Ser Lys Leu Pro Gly
                565                 570                 575

Leu Leu Glu Leu Glu Tyr Glu Gly Phe Tyr Lys Arg Gly Phe Phe Val
                580                 585                 590

Thr Lys Lys Arg Tyr Ala Val Ile Asp Glu Glu Gly Lys Val Ile Thr
                595                 600                 605

Arg Gly Leu Glu Ile Val Arg Arg Asp Trp Ser Glu Ile Ala Lys Glu
                610                 615                 620

Thr Gln Ala Arg Val Leu Glu Thr Ile Leu Lys His Gly Asp Val Glu
625                 630                 635                 640

Glu Ala Val Arg Ile Val Lys Glu Val Ile Gln Lys Leu Ala Asn Tyr
                645                 650                 655

Glu Ile Pro Pro Glu Lys Leu Ala Ile Tyr Glu Gln Ile Thr Arg Pro
                660                 665                 670

Leu His Glu Tyr Lys Ala Ile Gly Pro His Val Ala Val Ala Lys Lys
                675                 680                 685

Leu Ala Ala Lys Gly Val Lys Ile Lys Pro Gly Met Val Ile Gly Tyr
                690                 695                 700

Ile Val Leu Arg Gly Asp Gly Pro Ile Ser Asn Arg Ala Ile Leu Ala
705                 710                 715                 720

Glu Glu Tyr Asp Pro Lys Lys His Lys Tyr Asp Ala Glu Tyr Tyr Ile
                725                 730                 735

Glu Asn Gln Val Leu Pro Ala Val Leu Arg Ile Leu Glu Gly Phe Gly
                740                 745                 750

Tyr Arg Lys Glu Asp Leu Arg Tyr Gln Lys Thr Arg Gln Val Gly Leu
                755                 760                 765

Thr Ser Trp Leu Asn Ile Lys Lys Ser
                770                 775
```

<210> SEQ ID NO 16
<211> LENGTH: 778
<212> TYPE: PRT
<213> ORGANISM: Artificial Sequence
<220> FEATURE:
<223> OTHER INFORMATION: Kofu amino acid sequence

<400> SEQUENCE: 16

```
Met Ala Ser Ala Ile Leu Asp Thr Asp Tyr Ile Thr Glu Asp Gly Lys
1               5                   10                  15

Pro Val Ile Arg Ile Phe Lys Lys Glu Asn Gly Glu Phe Lys Ile Glu
                20                  25                  30

Tyr Asp Arg Thr Phe Glu Pro Tyr Phe Tyr Ala Leu Leu Lys Asp Asp
                35                  40                  45

Ser Ala Ile Glu Glu Val Lys Lys Ile Thr Ala Glu Arg His Gly Thr
                50                  55                  60

Val Val Thr Val Lys Arg Val Glu Lys Val Gln Lys Lys Phe Leu Gly
65                  70                  75                  80

Arg Pro Val Glu Val Trp Lys Leu Tyr Phe Thr His Pro Gln Asp Val
                85                  90                  95

Pro Ala Ile Arg Asp Lys Ile Arg Glu His Pro Ala Val Ile Asp Ile
                100                 105                 110

Tyr Glu Tyr Asp Ile Pro Phe Ala Lys Arg Tyr Leu Ile Asp Lys Gly
```

```
                115                 120                 125
Leu Val Pro Met Glu Gly Asp Glu Glu Leu Lys Met Leu Ala Phe Asp
    130                 135                 140

Ile Glu Thr Leu Tyr His Glu Gly Glu Glu Phe Ala Glu Gly Pro Ile
145                 150                 155                 160

Leu Met Ile Ser Tyr Ala Asp Glu Glu Gly Ala Arg Val Ile Thr Trp
                165                 170                 175

Lys Asn Val Asp Leu Pro Tyr Val Asp Val Ser Thr Glu Arg Glu
                180                 185                 190

Met Ile Lys Arg Phe Leu Arg Val Val Lys Glu Lys Asp Pro Asp Val
                195                 200                 205

Leu Ile Thr Tyr Asn Gly Asp Asn Phe Asp Phe Ala Tyr Leu Lys Lys
    210                 215                 220

Arg Cys Glu Lys Leu Gly Ile Asn Phe Ala Leu Gly Arg Asp Gly Ser
225                 230                 235                 240

Glu Pro Lys Ile Gln Arg Met Gly Asp Arg Phe Ala Val Glu Val Lys
                245                 250                 255

Gly Arg Ile His Phe Asp Leu Tyr Pro Val Ile Arg Arg Thr Ile Asn
                260                 265                 270

Leu Pro Thr Tyr Thr Leu Glu Ala Val Tyr Glu Ala Val Phe Gly Gln
    275                 280                 285

Pro Lys Glu Lys Val Tyr Ala Glu Glu Ile Thr Thr Ala Trp Glu Thr
    290                 295                 300

Gly Glu Asn Leu Glu Arg Val Ala Arg Tyr Ser Met Glu Asp Ala Lys
305                 310                 315                 320

Val Thr Tyr Glu Leu Gly Lys Glu Phe Leu Pro Met Glu Ala Gln Leu
                325                 330                 335

Ser Arg Leu Val Gly Gln Pro Leu Trp Asp Val Ser Arg Ser Ser Thr
                340                 345                 350

Gly Asn Leu Val Glu Trp Phe Leu Leu Arg Lys Ala Tyr Glu Arg Asn
                355                 360                 365

Glu Val Ala Pro Asn Lys Pro Ser Glu Glu Glu Tyr Gln Arg Arg Leu
    370                 375                 380

Arg Glu Ser Tyr Thr Gly Gly Phe Val Lys Glu Pro Glu Lys Gly Leu
385                 390                 395                 400

Trp Glu Asn Ile Val Tyr Leu Asp Phe Arg Ala Leu Tyr Pro Ser Ile
                405                 410                 415

Ile Ile Thr His Asn Val Ser Pro Asp Thr Leu Asn Leu Glu Gly Cys
                420                 425                 430

Lys Asn Tyr Asp Ile Ala Pro Gln Val Gly His Lys Phe Cys Lys Asp
                435                 440                 445

Ile Pro Gly Phe Ile Pro Ser Leu Leu Gly His Leu Leu Glu Glu Arg
    450                 455                 460

Gln Lys Ile Lys Thr Lys Met Lys Glu Thr Gln Asp Pro Ile Glu Lys
465                 470                 475                 480

Ile Leu Leu Asp Tyr Arg Gln Lys Ala Ile Lys Leu Leu Ala Asn Ser
                485                 490                 495

Phe Tyr Gly Tyr Tyr Gly Tyr Ala Lys Ala Arg Trp Tyr Cys Lys Glu
                500                 505                 510

Cys Ala Glu Ser Val Thr Ala Trp Gly Arg Lys Tyr Ile Glu Leu Val
                515                 520                 525

Trp Lys Glu Leu Glu Glu Lys Phe Gly Phe Lys Val Leu Tyr Ile Asp
    530                 535                 540
```

```
Thr Asp Gly Leu Tyr Ala Thr Ile Pro Gly Gly Glu Ser Glu Glu Ile
545                 550                 555                 560

Lys Lys Lys Ala Leu Glu Phe Leu Lys Tyr Ile Asn Ala Lys Leu Pro
            565                 570                 575

Gly Ala Leu Glu Leu Glu Tyr Glu Gly Phe Tyr Lys Arg Gly Phe Phe
        580                 585                 590

Val Thr Lys Lys Tyr Ala Val Ile Asp Glu Glu Gly Lys Ile Thr
    595                 600                 605

Thr Arg Gly Leu Glu Ile Val Arg Arg Asp Trp Ser Glu Ile Ala Lys
610                 615                 620

Glu Thr Gln Ala Arg Val Leu Glu Ala Leu Leu Lys Asp Gly Asp Val
625                 630                 635                 640

Glu Lys Ala Val Arg Ile Val Lys Glu Val Thr Glu Lys Leu Ser Lys
                645                 650                 655

Tyr Glu Val Pro Pro Glu Lys Leu Val Ile His Glu Gln Ile Thr Arg
                660                 665                 670

Asp Leu Lys Asp Tyr Lys Ala Thr Gly Pro His Val Ala Val Ala Lys
            675                 680                 685

Arg Leu Ala Ala Arg Gly Val Lys Ile Arg Pro Gly Thr Val Ile Ser
690                 695                 700

Tyr Ile Val Leu Lys Gly Ser Gly Arg Ile Gly Asp Arg Ala Ile Pro
705                 710                 715                 720

Phe Asp Glu Phe Asp Pro Thr Lys His Lys Tyr Asp Ala Glu Tyr Tyr
                725                 730                 735

Ile Glu Asn Gln Val Leu Pro Ala Val Glu Arg Ile Leu Arg Ala Phe
            740                 745                 750

Gly Tyr Arg Lys Glu Asp Leu Arg Tyr Gln Lys Thr Arg Gln Val Gly
        755                 760                 765

Leu Ser Ala Trp Leu Lys Pro Lys Gly Thr
770                 775

<210> SEQ ID NO 17
<211> LENGTH: 3778
<212> TYPE: DNA
<213> ORGANISM: Artificial Sequence
<220> FEATURE:
<223> OTHER INFORMATION: Plasmid "pLACIQZa" sequence

<400> SEQUENCE: 17
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
cctctagagc cgtaatcatg gtcatagctg tttcctgtgt gaaattgtta tccgctcaca     480
attccacaca acatacgagc cggaagcata aagtgtaaag cctggggtgc ctaatgagtg     540
agctaactca cattaattgc gttgcgctca ctgcccgctt tccagtcggg aaacctgtcg     600
tgccagctgc attaatgaat cggccaacgc gcggggagag gcggtttgcg tattgggcgc     660
cagggtggtt tttcttttca ccagtgagac gggcaacagc tgattgccct tcaccgcctg     720
```

```
gccctgagag agttgcagca agcggtccac gctggtttgc cccagcaggc gaaaatcctg    780
tttgatggtg gttgacggcg ggatataaca tgagctgtct tcggtatcgt cgtatcccac    840
taccgagata tccgcaccaa cgcgcagccc ggactcggta atggcgcgca ttgcgcccag    900
cgccatctga tcgttggcaa ccagcatcgc agtgggaacg atgccctcat tcagcatttg    960
catggtttgt tgaaaaccgg acatggcact ccagtcgcct tcccgttccg ctatcggctg   1020
aatttgattg cgagtgagat atttatgcca gccagccaga cgcagacgcg ccgagacaga   1080
acttaatggg cccgctaaca gcgcgatttg ctggtgaccc aatgcgacca gatgctccac   1140
gcccagtcgc gtaccgtctt catgggagaa aataatactg ttgatgggtg tctggtcaga   1200
gacatcaaga ataacgccg gaacattagt gcaggcagct tccacagcaa tggcatcctg    1260
gtcatccagc ggatagttaa tgatcagccc actgacgcgt tgcgcgagaa gattgtgcac   1320
cgccgcttta caggcttcga cgccgcttcg ttctaccatc gacaccacca cgctggcacc   1380
cagttgatcg gcgcgagatt taatcgccgc gacaatttgc gacggcgcgt gcagggccag   1440
actggaggtg gcaacgccaa tcagcaacga ctgtttgccc gccagttgtt gtgccacgcg   1500
gttgggaatg taattcagct ccgccatcgc cgcttccact ttttcccgcg ttttcgcaga   1560
aacgtggctg gcctggttca ccacgcggga aacggtctga taagagacac cggcatactc   1620
tgcgacatcg tataacgtta ctggtttcac attcaccacc ctgaattgac tctcttccgg   1680
gcgctatcat gccataccgc gaaaggtttt gcgccattcg atggtgtcaa cgtaaatgca   1740
tgccgcttcg ccttccggcc accagaatag cctgcgccat gggcttcctc gctcactgac   1800
tcgctgcgct cggtcgttcg gctgcggcga gcggtatcag ctcactcaaa ggcggtaata   1860
cggttatcca cagaatcagg ggataacgca ggaaagaaca tgtgagcaaa aggccagcaa   1920
aaggccagga accgtaaaaa ggccgcgttg ctggcgtttt tccataggct ccgcccccct   1980
gacgagcatc acaaaaatcg acgctcaagt cagaggtggc gaaacccgac aggactataa   2040
agataccagg cgtttccccc tggaagctcc ctcgtgcgct ctcctgttcc gaccctgccg   2100
cttaccggat acctgtccgc ctttctccct tcgggaagcg tggcgctttc tcatagctca   2160
cgctgtaggt atctcagttc ggtgtaggtc gttcgctcca agctgggctg tgtgcacgaa   2220
ccccccgttc agcccgaccg ctgcgcctta tccggtaact atcgtcttga gtccaacccg   2280
gtaagacacg acttatcgcc actggcagca gccactggta acaggattag cagagcgagg   2340
tatgtaggcg gtgctacaga gttcttgaag tggtggccta actacggcta cactagaaga   2400
acagtatttg gtatctgcgc tctgctgaag ccagttacct tcggaaaaag agttggtagc   2460
tcttgatccg gcaaacaaac caccgctggt agcggtggtt ttttttgtttg caagcagcag   2520 attacgcgca gaaaaaaagg atctcaagaa gatcctttga tcttttctac ggggtctgac   2580
gctcagtgga acgaaaactc acgttaaggg attttggtca tgagattatc aaaaaggatc   2640
ttcacctaga tccttttaaa ttaaaaatga agttttaaat caatctaaag tatatatgag   2700
taaacttggt ctgacagtta ccaatgctta atcagtgagg cacctatctc agcgatctgt   2760
ctatttcgtt catccatagt tgcctgactc cccgtcgtgt agataactac gatacgggag   2820
ggcttaccat ctggccccag tgctgcaatg ataccgcgag acccacgctc accggctcca   2880
gatttatcag caataaacca gccagccgga agggccgagc gcagaagtgg tcctgcaact   2940
ttatccgcct ccatccagtc tattaattgt tgccgggaag ctagagtaag tagttcgcca   3000
gttaatagtt tgcgcaacgt tgttgccatt gctacaggca tcgtggtgtc acgctcgtcg   3060
```

-continued

```
tttggtatgg cttcattcag ctccggttcc caacgatcaa ggcgagttac atgatccccc    3120
atgttgtgca aaaaagcggt tagctccttc ggtcctccga tcgttgtcag aagtaagttg    3180
gccgcagtgt tatcactcat ggttatggca gcactgcata attctcttac tgtcatgcca    3240
tccgtaagat gctttctgt gactggtgag tactcaacca agtcattctg agaatagtgt     3300
atgcggcgac cgagttgctc ttgcccggcg tcaatacggg ataataccgc gccacatagc    3360
agaactttaa aagtgctcat cattggaaaa cgttcttcgg ggcgaaaact ctcaaggatc    3420
ttaccgctgt tgagatccag ttcgatgtaa cccactcgtg cacccaactg atcttcagca    3480
tcttttactt tcaccagcgt ttctgggtga gcaaaaacag gaaggcaaaa tgccgcaaaa    3540
aagggaataa gggcgacacg gaaatgttga atactcatac tcttcctttt tcaatattat    3600
tgaagcattt atcagggtta ttgtctcatg agcggataca tatttgaatg tatttagaaa    3660
aataaacaaa taggggttcc gcgcacattt ccccgaaaag tgccacctga cgtctaagaa    3720
accattatta tcatgacatt aacctataaa aataggcgta tcacgaggcc ctttcgtc     3778
```

```
<210> SEQ ID NO 18
<211> LENGTH: 775
<212> TYPE: PRT
<213> ORGANISM: Thermococcus sp.

<400> SEQUENCE: 18
```

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Asp Ile Glu Thr
        130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

```
His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
        290                 295                 300

Leu Glu Arg Val Ala Arg Tyr Ser Met Glu Asp Ala Lys Val Thr Tyr
305                 310                 315                 320

Glu Leu Gly Arg Glu Phe Pro Met Glu Ala Gln Leu Ser Arg Leu
                325                 330                 335

Ile Gly Gln Ser Leu Trp Asp Val Ser Arg Ser Thr Gly Asn Leu
                340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
            610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670
```

```
Tyr Lys Ala Thr Gly Pro His Val Ala Val Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 19
<211> LENGTH: 774
<212> TYPE: PRT
<213> ORGANISM: Thermococcus litoralis

<400> SEQUENCE: 19

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270
```

```
Pro Thr Tyr Thr Leu Glu Ala Val Tyr Glu Ala Val Leu Gly Lys Thr
            275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
                340                 345                 350

Asn Leu Val Glu Trp Tyr Leu Leu Arg Val Ala Tyr Ala Arg Asn Glu
            355                 360                 365

Leu Ala Pro Asn Lys Pro Asp Glu Glu Glu Tyr Lys Arg Arg Leu Arg
            370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Lys Glu Gly Cys Lys
                420                 425                 430

Asn Tyr Asp Val Ala Pro Ile Val Gly Tyr Arg Phe Cys Lys Asp Phe
            435                 440                 445

Pro Gly Phe Ile Pro Ser Ile Leu Gly Asp Leu Ile Ala Met Arg Gln
            450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
                500                 505                 510

Ala Glu Ser Val Thr Ala Trp Gly Arg His Tyr Ile Glu Met Thr Ile
            515                 520                 525

Arg Glu Ile Glu Glu Lys Phe Gly Phe Lys Val Leu Tyr Ala Asp Thr
            530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
            595                 600                 605

Arg Gly Leu Glu Val Val Arg Arg Asp Trp Ser Glu Ile Ala Lys Glu
610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
            675                 680                 685
```

```
Leu Ala Ala Arg Gly Ile Lys Val Lys Pro Gly Thr Ile Ile Ser Tyr
690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
                740                 745                 750

Tyr Arg Lys Glu Asp Leu Arg Tyr Gln Ser Ser Lys Gln Thr Gly Leu
                755                 760                 765

Asp Ala Trp Leu Lys Arg
    770

<210> SEQ ID NO 20
<211> LENGTH: 776
<212> TYPE: PRT
<213> ORGANISM: Artificial Sequence
<220> FEATURE:
<223> OTHER INFORMATION: Chimeric DNA polymerase 9N1i

<400> SEQUENCE: 20

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Asp Ile Glu Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270
```

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
        290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Tyr Leu Leu Arg Val Ala Tyr Ala Arg Asn Glu Leu Ala
        355                 360                 365

Pro Asn Lys Pro Asp Glu Glu Glu Tyr Lys Arg Arg Leu Arg Thr Thr
370                 375                 380

Tyr Leu Gly Gly Tyr Val Lys Glu Pro Glu Lys Gly Leu Trp Glu Asn
385                 390                 395                 400

Ile Ile Tyr Leu Asp Phe Arg Ser Leu Tyr Pro Ser Ile Ile Val Thr
                405                 410                 415

His Asn Val Ser Pro Asp Thr Leu Glu Lys Glu Gly Cys Lys Asn Tyr
            420                 425                 430

Asp Val Ala Pro Ile Val Gly Tyr Arg Phe Cys Lys Asp Phe Pro Gly
        435                 440                 445

Phe Ile Pro Ser Ile Leu Gly Asp Leu Ile Ala Met Arg Gln Asp Ile
        450                 455                 460

Lys Lys Lys Met Lys Ser Thr Ile Asp Pro Ile Glu Lys Lys Met Leu
465                 470                 475                 480

Asp Tyr Arg Gln Arg Ala Ile Lys Leu Leu Ala Asn Ser Tyr Tyr Gly
                485                 490                 495

Tyr Met Gly Tyr Pro Lys Ala Arg Trp Tyr Ser Lys Glu Cys Ala Glu
            500                 505                 510

Ser Val Thr Ala Trp Gly Arg His Tyr Ile Glu Met Thr Ile Arg Glu
        515                 520                 525

Ile Glu Glu Lys Phe Gly Phe Lys Val Leu Tyr Ala Asp Thr Asp Gly
530                 535                 540

Phe Tyr Ala Thr Ile Pro Gly Glu Lys Pro Glu Leu Ile Lys Lys Lys
545                 550                 555                 560

Ala Lys Glu Phe Leu Asn Tyr Ile Asn Ser Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Val Ile Asp Glu Glu Gly Lys Ile Thr Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Ala Ile Leu Lys His Gly Asp Val Glu Glu Ala
625                 630                 635                 640

Val Arg Ile Val Lys Glu Val Thr Glu Lys Leu Ser Lys Tyr Glu Val
                645                 650                 655

Pro Pro Glu Lys Leu Val Ile His Glu Gln Ile Thr Arg Asp Leu Arg
            660                 665                 670

Asp Tyr Lys Ala Thr Gly Pro His Val Ala Val Ala Lys Arg Leu Ala
        675                 680                 685

Ala Arg Gly Val Lys Ile Arg Pro Gly Thr Val Ile Ser Tyr Ile Val

```
              690             695             700
Leu Lys Gly Ser Gly Arg Ile Gly Asp Arg Ala Ile Pro Ala Asp Glu
705             710             715             720

Phe Asp Pro Thr Lys His Arg Tyr Asp Ala Glu Tyr Ile Glu Asn
                725             730             735

Gln Val Leu Pro Ala Val Glu Arg Ile Leu Lys Ala Phe Gly Tyr Arg
            740             745             750

Lys Glu Asp Leu Arg Tyr Gln Lys Thr Lys Gln Val Gly Leu Gly Ala
            755             760             765

Trp Leu Lys Val Lys Gly Lys Lys
    770             775

<210> SEQ ID NO 21
<211> LENGTH: 773
<212> TYPE: PRT
<213> ORGANISM: Artificial Sequence
<220> FEATURE:
<223> OTHER INFORMATION: Chimeric DNA polymerase Li9N

<400> SEQUENCE: 21

Met Ile Leu Asp Thr Asp Tyr Ile Thr Lys Asp Gly Lys Pro Ile Ile
1               5               10              15

Arg Ile Phe Lys Lys Glu Asn Gly Glu Phe Lys Ile Glu Leu Asp Pro
            20              25              30

His Phe Gln Pro Tyr Ile Tyr Ala Leu Leu Lys Asp Ser Ala Ile
        35              40              45

Glu Glu Ile Lys Ala Ile Lys Gly Glu Arg His Gly Lys Thr Val Arg
50              55              60

Val Leu Asp Ala Val Lys Val Arg Lys Lys Phe Leu Gly Arg Glu Val
65              70              75              80

Glu Val Trp Lys Leu Ile Phe Glu His Pro Gln Asp Val Pro Ala Met
            85              90              95

Arg Gly Lys Ile Arg Glu His Pro Ala Val Val Asp Ile Tyr Glu Tyr
            100             105             110

Asp Ile Pro Phe Ala Lys Arg Tyr Leu Ile Asp Lys Gly Leu Ile Pro
        115             120             125

Met Glu Gly Asp Glu Glu Leu Lys Leu Leu Ala Phe Asp Ile Glu Thr
130             135             140

Phe Tyr His Glu Gly Asp Glu Phe Gly Lys Gly Glu Ile Ile Met Ile
145             150             155             160

Ser Tyr Ala Asp Glu Glu Glu Ala Arg Val Ile Thr Trp Lys Asn Ile
            165             170             175

Asp Leu Pro Tyr Val Asp Val Val Ser Asn Glu Arg Glu Met Ile Lys
        180             185             190

Arg Phe Val Gln Val Val Lys Glu Lys Asp Pro Asp Val Ile Ile Thr
        195             200             205

Tyr Asn Gly Asp Asn Phe Asp Leu Pro Tyr Leu Ile Lys Arg Ala Glu
    210             215             220

Lys Leu Gly Val Arg Leu Val Leu Gly Arg Asp Lys Glu His Pro Glu
225             230             235             240

Pro Lys Ile Gln Arg Met Gly Asp Ser Phe Ala Val Glu Ile Lys Gly
            245             250             255

Arg Ile His Phe Asp Leu Phe Pro Val Val Arg Arg Thr Ile Asn Leu
            260             265             270

Pro Thr Tyr Thr Leu Glu Ala Val Tyr Glu Ala Val Leu Gly Lys Thr
```

-continued

```
              275                 280                 285
Lys Ser Lys Leu Gly Ala Glu Glu Ile Ala Ala Ile Trp Glu Thr Glu
290                 295                 300
Glu Ser Met Lys Lys Leu Ala Gln Tyr Ser Met Glu Asp Ala Arg Ala
305                 310                 315                 320
Thr Tyr Glu Leu Gly Lys Glu Phe Phe Pro Met Glu Ala Glu Leu Ala
                325                 330                 335
Lys Leu Ile Gly Gln Ser Val Trp Asp Val Ser Arg Ser Ser Thr Gly
                340                 345                 350
Asn Leu Val Glu Trp Phe Leu Leu Arg Lys Ala Tyr Lys Arg Asn Glu
                355                 360                 365
Leu Ala Pro Asn Lys Pro Asp Glu Arg Glu Leu Ala Arg Arg Arg Gly
370                 375                 380
Gly Tyr Ala Gly Gly Tyr Val Lys Glu Pro Glu Arg Gly Leu Trp Asp
385                 390                 395                 400
Asn Ile Val Tyr Leu Asp Phe Arg Ser Leu Tyr Pro Ser Ile Ile Ile
                405                 410                 415
Thr His Asn Val Ser Pro Asp Thr Leu Asn Arg Glu Gly Cys Lys Glu
                420                 425                 430
Tyr Asp Val Ala Pro Glu Val Gly His Lys Phe Cys Lys Asp Phe Pro
                435                 440                 445
Gly Phe Ile Pro Ser Leu Leu Gly Asp Leu Leu Glu Glu Arg Gln Lys
450                 455                 460
Ile Lys Arg Lys Met Lys Ala Thr Val Asp Pro Leu Glu Lys Lys Leu
465                 470                 475                 480
Leu Asp Tyr Arg Gln Arg Ala Ile Lys Ile Leu Ala Asn Ser Phe Tyr
                485                 490                 495
Gly Tyr Tyr Gly Tyr Ala Lys Ala Arg Trp Tyr Cys Lys Glu Cys Ala
                500                 505                 510
Glu Ser Val Thr Ala Trp Gly Arg Glu Tyr Ile Glu Met Val Ile Arg
                515                 520                 525
Glu Leu Glu Glu Lys Phe Gly Phe Lys Val Leu Tyr Ala Asp Thr Asp
530                 535                 540
Gly Leu His Ala Thr Ile Pro Gly Ala Asp Ala Glu Thr Val Lys Lys
545                 550                 555                 560
Lys Ala Lys Glu Phe Leu Lys Tyr Ile Asn Pro Lys Leu Pro Gly Leu
                565                 570                 575
Leu Glu Leu Glu Tyr Glu Gly Phe Tyr Leu Arg Gly Phe Phe Val Thr
                580                 585                 590
Lys Lys Arg Tyr Ala Val Ile Asp Glu Glu Gly Arg Ile Thr Thr Arg
                595                 600                 605
Gly Leu Glu Val Val Arg Arg Asp Trp Ser Glu Ile Ala Lys Glu Thr
                610                 615                 620
Gln Ala Lys Val Leu Glu Ala Ile Leu Lys Glu Gly Ser Val Glu Lys
625                 630                 635                 640
Ala Val Glu Val Val Arg Asp Val Val Glu Lys Ile Ala Lys Tyr Arg
                645                 650                 655
Val Pro Leu Glu Lys Leu Val Ile His Glu Gln Ile Thr Arg Asp Leu
                660                 665                 670
Lys Asp Tyr Lys Ala Ile Gly Pro His Val Ala Ile Ala Lys Arg Leu
                675                 680                 685
Ala Ala Arg Gly Ile Lys Val Lys Pro Gly Thr Ile Ile Ser Tyr Ile
690                 695                 700
```

```
Val Leu Lys Gly Ser Gly Lys Ile Ser Asp Arg Val Ile Leu Leu Thr
705                 710                 715                 720

Glu Tyr Asp Pro Arg Lys His Lys Tyr Asp Pro Asp Tyr Tyr Ile Glu
                725                 730                 735

Asn Gln Val Leu Pro Ala Val Leu Arg Ile Leu Glu Ala Phe Gly Tyr
            740                 745                 750

Arg Lys Glu Asp Leu Arg Tyr Gln Ser Ser Lys Gln Thr Gly Leu Asp
        755                 760                 765

Ala Trp Leu Lys Arg
        770

<210> SEQ ID NO 22
<211> LENGTH: 773
<212> TYPE: PRT
<213> ORGANISM: Thermococcus sp.

<400> SEQUENCE: 22

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
```

```
                290             295             300
Leu Glu Arg Val Ala Arg Tyr Ser Met Glu Asp Ala Lys Val Thr Tyr
305                 310             315                 320
Glu Leu Gly Lys Glu Phe Pro Met Glu Ala Gln Leu Ser Arg Leu
                325             330             335
Val Gly Gln Ser Leu Trp Asp Val Ser Arg Ser Ser Thr Gly Asn Leu
                340             345             350
Val Glu Trp Phe Leu Leu Arg Lys Ala Tyr Glu Arg Asn Glu Leu Ala
                355             360             365
Pro Asn Lys Pro Asp Glu Arg Glu Leu Ala Arg Arg Glu Ser Tyr
370                 375             380
Ala Gly Gly Tyr Val Lys Glu Pro Glu Arg Gly Leu Trp Glu Asn Ile
385                 390             395                 400
Val Tyr Leu Asp Phe Arg Ser Leu Tyr Pro Ser Ile Ile Ile Thr His
                405             410             415
Asn Val Ser Pro Asp Thr Leu Asn Arg Glu Gly Cys Glu Glu Tyr Asp
                420             425             430
Val Ala Pro Gln Val Gly His Lys Phe Cys Lys Asp Phe Pro Gly Phe
                435             440             445
Ile Pro Ser Leu Leu Gly Asp Leu Leu Glu Glu Arg Gln Lys Val Lys
                450             455             460
Lys Lys Met Lys Ala Thr Ile Asp Pro Ile Glu Lys Lys Leu Leu Asp
465                 470             475                 480
Tyr Arg Gln Arg Ala Ile Lys Ile Leu Ala Asn Ser Phe Tyr Gly Tyr
                485             490             495
Tyr Gly Tyr Ala Lys Ala Arg Trp Tyr Cys Lys Glu Cys Ala Glu Ser
                500             505             510
Val Thr Ala Trp Gly Arg Gln Tyr Ile Glu Thr Thr Ile Arg Glu Ile
                515             520             525
Glu Glu Lys Phe Gly Phe Lys Val Leu Tyr Ala Asp Thr Asp Gly Phe
                530             535             540
Phe Ala Thr Ile Pro Gly Ala Asp Ala Glu Thr Val Lys Lys Lys Ala
545                 550             555                 560
Lys Glu Phe Leu Asp Tyr Ile Asn Ala Lys Leu Pro Gly Leu Leu Glu
                565             570             575
Leu Glu Tyr Glu Gly Phe Tyr Lys Arg Gly Phe Phe Val Thr Lys Lys
                580             585             590
Lys Tyr Ala Val Ile Asp Glu Glu Asp Lys Ile Thr Thr Arg Gly Leu
                595             600             605
Glu Ile Val Arg Arg Asp Trp Ser Glu Ile Ala Lys Glu Thr Gln Ala
610                 615             620
Arg Val Leu Glu Ala Ile Leu Lys His Gly Asp Val Glu Glu Ala Val
625                 630             635                 640
Arg Ile Val Lys Glu Val Thr Glu Lys Leu Ser Lys Tyr Glu Val Pro
                645             650             655
Pro Glu Lys Leu Val Ile Tyr Glu Gln Ile Thr Arg Asp Leu Lys Asp
                660             665             670
Tyr Lys Ala Thr Gly Pro His Val Ala Val Ala Lys Arg Leu Ala Ala
                675             680             685
Arg Gly Ile Lys Ile Arg Pro Gly Thr Val Ile Ser Tyr Ile Val Leu
                690             695             700
Lys Gly Ser Gly Arg Ile Gly Asp Arg Ala Ile Pro Phe Asp Glu Phe
705                 710             715                 720
```

```
Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770

<210> SEQ ID NO 23
<211> LENGTH: 773
<212> TYPE: PRT
<213> ORGANISM: Thermococcus sp.

<400> SEQUENCE: 23

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asp Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
50                  55                  60

Val Thr Arg Ala Glu Arg Val Lys Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Arg Gly Leu Ile Pro
        115                 120                 125

Met Glu Gly Asp Glu Glu Leu Arg Met Leu Ala Phe Asp Ile Glu Thr
    130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Ala Ile Phe Gly Gln Pro Lys Glu
        275                 280                 285

Lys Val Tyr Ala Glu Glu Ile Ala Arg Ala Trp Glu Ser Gly Glu Gly
    290                 295                 300

Leu Glu Arg Val Ala Arg Tyr Ser Met Glu Asp Ala Lys Ala Thr Tyr
```

```
            305                 310                 315                 320
        Glu Leu Gly Lys Glu Phe Phe Pro Met Glu Ala Gln Leu Ser Arg Leu
                        325                 330                 335

Val Gly Gln Ser Leu Trp Asp Val Ser Arg Ser Thr Gly Asn Leu
                        340                 345                 350

Val Glu Trp Phe Leu Leu Arg Lys Ala Tyr Glu Arg Asn Glu Leu Ala
                        355                 360                 365

Pro Asn Lys Pro Asp Glu Arg Glu Leu Ala Arg Arg Ala Glu Ser Tyr
                        370                 375                 380

Ala Gly Gly Tyr Val Lys Glu Pro Glu Lys Gly Leu Trp Glu Asn Ile
        385                 390                 395                 400

Val Tyr Leu Asp Tyr Lys Ser Leu Tyr Pro Ser Ile Ile Ile Thr His
                        405                 410                 415

Asn Val Ser Pro Asp Thr Leu Asn Arg Glu Gly Cys Arg Glu Tyr Asp
                        420                 425                 430

Val Ala Pro Gln Val Gly His Arg Phe Cys Lys Asp Phe Pro Gly Phe
                        435                 440                 445

Ile Pro Ser Leu Leu Gly Asp Leu Leu Glu Glu Arg Gln Lys Val Lys
                        450                 455                 460

Lys Lys Met Lys Ala Thr Val Asp Pro Ile Glu Arg Lys Leu Leu Asp
        465                 470                 475                 480

Tyr Arg Gln Arg Ala Ile Lys Ile Leu Ala Asn Ser Tyr Tyr Gly Tyr
                        485                 490                 495

Tyr Gly Tyr Ala Asn Ala Arg Trp Tyr Cys Arg Glu Cys Ala Glu Ser
                        500                 505                 510

Val Thr Ala Trp Gly Arg Gln Tyr Ile Glu Thr Thr Met Arg Glu Ile
                        515                 520                 525

Glu Glu Lys Phe Gly Phe Lys Val Leu Tyr Ala Asp Thr Asp Gly Phe
                        530                 535                 540

Phe Ala Thr Ile Pro Gly Ala Asp Ala Glu Thr Val Lys Lys Lys Ala
        545                 550                 555                 560

Lys Glu Phe Leu Asn Tyr Ile Asn Pro Arg Leu Pro Gly Leu Leu Glu
                        565                 570                 575

Leu Glu Tyr Glu Gly Phe Tyr Arg Arg Gly Phe Phe Val Thr Lys Lys
                        580                 585                 590

Lys Tyr Ala Val Ile Asp Glu Glu Asp Lys Ile Thr Thr Arg Gly Leu
                        595                 600                 605

Glu Ile Val Arg Arg Asp Trp Ser Glu Ile Ala Lys Glu Thr Gln Ala
        610                 615                 620

Arg Val Leu Glu Ala Ile Leu Lys His Gly Asp Val Glu Glu Ala Val
        625                 630                 635                 640

Arg Ile Val Lys Glu Val Thr Glu Lys Leu Ser Arg Tyr Glu Val Pro
                        645                 650                 655

Pro Glu Lys Leu Val Ile Tyr Glu Gln Ile Thr Arg Asp Leu Arg Asp
                        660                 665                 670

Tyr Arg Ala Thr Gly Pro His Val Ala Val Ala Lys Arg Leu Ala Ala
                        675                 680                 685

Arg Gly Ile Lys Ile Arg Pro Gly Thr Val Ile Ser Tyr Ile Val Leu
                        690                 695                 700

Lys Gly Pro Gly Arg Val Gly Asp Arg Ala Ile Pro Phe Asp Glu Phe
        705                 710                 715                 720

Asp Pro Ala Lys His Arg Tyr Asp Ala Glu Tyr Tyr Ile Glu Asn Gln
                        725                 730                 735
```

```
Val Leu Pro Ala Val Glu Arg Ile Leu Arg Ala Phe Gly Tyr Arg Lys
            740                 745                 750

Glu Asp Leu Arg Tyr Gln Lys Thr Lys Gln Ala Gly Leu Gly Ala Trp
            755                 760                 765

Leu Lys Pro Lys Thr
    770

<210> SEQ ID NO 24
<211> LENGTH: 773
<212> TYPE: PRT
<213> ORGANISM: Artificial Sequence
<220> FEATURE:
<223> OTHER INFORMATION: Chimeric DNA polymerase GoZi

<400> SEQUENCE: 24

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
            35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
            85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
            165                 170                 175

Asp Leu Pro Tyr Val Asp Val Ser Thr Glu Lys Glu Met Ile Lys
            180                 185                 190

Arg Phe Leu Lys Val Val Lys Glu Lys Asp Pro Asp Val Leu Ile Thr
            195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
            275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320
```

```
Glu Leu Gly Lys Glu Phe Pro Met Glu Ala Gln Leu Ser Arg Leu
            325                 330                 335
Val Gly Gln Ser Leu Trp Asp Val Ser Arg Ser Ser Thr Gly Asn Leu
        340                 345                 350
Val Glu Trp Phe Leu Leu Arg Lys Ala Tyr Glu Arg Asn Glu Leu Ala
    355                 360                 365
Pro Asn Lys Pro Asp Glu Arg Glu Leu Ala Arg Arg Glu Ser Tyr
370                 375                 380
Ala Gly Gly Tyr Val Lys Glu Pro Glu Lys Gly Leu Trp Glu Asn Ile
385                 390                 395                 400
Val Tyr Leu Asp Tyr Lys Ser Leu Tyr Pro Ser Ile Ile Ile Thr His
                405                 410                 415
Asn Val Ser Pro Asp Thr Leu Asn Arg Glu Gly Cys Arg Glu Tyr Asp
                420                 425                 430
Val Ala Pro Gln Val Gly His Arg Phe Cys Lys Asp Phe Pro Gly Phe
            435                 440                 445
Ile Pro Ser Leu Leu Gly Asp Leu Leu Glu Glu Arg Gln Lys Val Lys
        450                 455                 460
Lys Lys Met Lys Ala Thr Val Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Asn Ala Arg Trp Tyr Cys Arg Glu Cys Ala Glu Ser
            500                 505                 510
Val Thr Ala Trp Gly Arg Gln Tyr Ile Glu Thr Thr Met Arg Glu Ile
        515                 520                 525
Glu Glu Lys Phe Gly Phe Lys Val Leu Tyr Ala Asp Thr Asp Gly Phe
    530                 535                 540
Phe Ala Thr Ile Pro Gly Ala Asp Ala Glu Thr Val Lys Lys Lys Ala
545                 550                 555                 560
Lys Glu Phe Leu Asp Tyr Ile Asn Ala Lys Leu Pro Gly Leu Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Asp Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile Tyr Glu Gln Ile Thr Arg Asp Leu Lys Asp
            660                 665                 670
Tyr Lys Ala Thr Gly Pro His Val Ala Val Ala Lys Arg Leu Ala Ala
        675                 680                 685
Arg Gly Ile Lys Ile Arg Pro Gly Thr Val Ile Ser Tyr Ile Val Leu
    690                 695                 700
Lys Gly Ser Gly Arg Ile Gly Asp Arg Ala Ile Pro Phe Asp Glu Phe
705                 710                 715                 720
Asp Pro Ala Lys His Lys Tyr Asp Ala Glu Tyr Tyr Ile Glu Asn Gln
                725                 730                 735
```

```
Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Gly Ala Trp
        755                 760                 765

Leu Lys Pro Lys Thr
        770

<210> SEQ ID NO 25
<211> LENGTH: 773
<212> TYPE: PRT
<213> ORGANISM: Artificial Sequence
<220> FEATURE:
<223> OTHER INFORMATION: Chimeric DNA polymerase ZiGo

<400> SEQUENCE: 25

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asp Tyr Asp Arg
            20                  25                  30

Asp Phe Glu Pro Tyr Ile Tyr Ala Leu Leu Lys Asp Ser Ala Ile
        35                  40                  45

Glu Asp Ile Lys Lys Ile Thr Ala Glu Arg His Gly Thr Thr Val Arg
50                  55                  60

Val Thr Arg Ala Glu Arg Val Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Arg Gly Leu Ile Pro
        115                 120                 125

Met Glu Gly Asp Glu Glu Leu Arg Met Leu Ala Phe Asp Ile Glu Thr
130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
        195                 200                 205

Tyr Asn Gly Asp Asn Phe Asp Phe Ala Tyr Leu Lys Lys Arg Ser Glu
210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Ala Ile Phe Gly Gln Pro Lys Glu
        275                 280                 285

Lys Val Tyr Ala Glu Glu Ile Ala Arg Ala Trp Glu Ser Gly Glu Gly
290                 295                 300

Leu Glu Arg Val Ala Arg Tyr Ser Met Glu Asp Ala Lys Ala Thr Tyr
305                 310                 315                 320
```

```
Glu Leu Gly Lys Glu Phe Phe Pro Met Glu Ala Gln Leu Ser Arg Leu
                325                 330                 335

Val Gly Gln Ser Leu Trp Asp Val Ser Arg Ser Thr Gly Asn Leu
        340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Ala Glu Ser Tyr
        370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
                420                 425                 430

Val Ala Pro Gln Val Gly His Lys Phe Cys Lys Asp Phe Pro Gly Phe
            435                 440                 445

Ile Pro Ser Leu Leu Gly Asp Leu Leu Glu Glu Arg Gln Lys Val Lys
        450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
        530                 535                 540

Phe Ala Thr Ile Pro Gly Ala Asp Ala Glu Thr Val Lys Lys Lys Ala
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Arg Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
        610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg Tyr Glu Val Pro
                645                 650                 655

Pro Glu Lys Leu Val Ile Tyr Glu Gln Ile Thr Arg Asp Leu Arg Asp
            660                 665                 670

Tyr Arg Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
        690                 695                 700

Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
```

```
                    740                 745                 750
Glu Asp Leu Arg Tyr Gln Lys Thr Lys Gln Ala Gly Leu Gly Ala Trp
            755                 760                 765

Leu Lys Pro Lys Thr
        770

<210> SEQ ID NO 26
<211> LENGTH: 778
<212> TYPE: PRT
<213> ORGANISM: Artificial Sequence
<220> FEATURE:
<223> OTHER INFORMATION: Chimeric DNA polymerase Kofu-II

<400> SEQUENCE: 26

Met Ala Ser Ala Ile Leu Asp Thr Asp Tyr Ile Thr Glu Asp Gly Lys
1               5                   10                  15

Pro Val Ile Arg Ile Phe Lys Lys Glu Asn Gly Glu Phe Lys Ile Glu
            20                  25                  30

Tyr Asp Arg Thr Phe Glu Pro Tyr Phe Tyr Ala Leu Leu Lys Asp Asp
        35                  40                  45

Ser Ala Ile Glu Glu Val Lys Lys Ile Thr Ala Glu Arg His Gly Thr
    50                  55                  60

Val Val Thr Val Lys Arg Val Glu Lys Val Gln Lys Lys Phe Leu Gly
65                  70                  75                  80

Arg Pro Val Glu Val Trp Lys Leu Tyr Phe Thr His Pro Gln Asp Val
                85                  90                  95

Pro Ala Ile Arg Asp Lys Ile Arg Glu His Pro Ala Val Ile Asp Ile
            100                 105                 110

Tyr Glu Tyr Asp Ile Pro Phe Ala Lys Arg Tyr Leu Ile Asp Lys Gly
        115                 120                 125

Leu Val Pro Met Glu Gly Asp Glu Glu Leu Lys Met Leu Ala Phe Asp
    130                 135                 140

Ile Glu Thr Leu Tyr His Glu Gly Glu Glu Phe Ala Glu Gly Pro Ile
145                 150                 155                 160

Leu Met Ile Ser Tyr Ala Asp Glu Glu Gly Ala Arg Val Ile Thr Trp
                165                 170                 175

Lys Asn Val Asp Leu Pro Tyr Val Asp Val Val Ser Thr Glu Arg Glu
            180                 185                 190

Met Ile Lys Arg Phe Leu Arg Val Val Lys Glu Lys Asp Pro Asp Val
        195                 200                 205

Leu Ile Thr Tyr Asn Gly Asp Asn Phe Asp Phe Ala Tyr Leu Lys Lys
    210                 215                 220

Arg Cys Glu Lys Leu Gly Ile Asn Phe Ala Leu Gly Arg Asp Gly Ser
225                 230                 235                 240

Glu Pro Lys Ile Gln Arg Met Gly Asp Arg Phe Ala Val Glu Val Lys
                245                 250                 255

Gly Arg Ile His Phe Asp Leu Tyr Pro Val Ile Arg Arg Thr Ile Asn
            260                 265                 270

Leu Pro Thr Tyr Thr Leu Glu Ala Val Tyr Glu Ala Val Phe Gly Gln
        275                 280                 285

Pro Lys Glu Lys Val Tyr Ala Glu Glu Ile Thr Thr Ala Trp Glu Thr
    290                 295                 300

Gly Glu Asn Leu Glu Arg Val Ala Lys Tyr Ser Met Glu Asp Ala Lys
305                 310                 315                 320

Ala Thr Tyr Glu Leu Gly Lys Glu Phe Leu Pro Met Glu Ile Gln Leu
```

```
                    325                 330                 335
Ser Arg Leu Val Gly Gln Pro Leu Trp Asp Val Ser Arg Ser Thr
                340                 345                 350
Gly Asn Leu Val Glu Trp Phe Leu Arg Lys Ala Tyr Glu Arg Asn
                355                 360                 365
Glu Val Ala Pro Asn Lys Pro Ser Glu Glu Tyr Gln Arg Arg Leu
370                 375                 380
Arg Glu Ser Tyr Thr Gly Gly Phe Val Lys Glu Pro Glu Lys Gly Leu
385                 390                 395                 400
Trp Glu Asn Ile Val Tyr Leu Asp Phe Arg Ala Leu Tyr Pro Ser Ile
                405                 410                 415
Ile Ile Thr His Asn Val Ser Pro Asp Thr Leu Asn Leu Glu Gly Cys
                420                 425                 430
Lys Asn Tyr Asp Ile Ala Pro Gln Val Gly His Lys Phe Cys Lys Asp
                435                 440                 445
Ile Pro Gly Phe Ile Pro Ser Leu Leu Gly His Leu Leu Glu Glu Arg
                450                 455                 460
Gln Lys Ile Lys Thr Lys Met Lys Glu Thr Gln Asp Pro Ile Glu Lys
465                 470                 475                 480
Ile Leu Leu Asp Tyr Arg Gln Lys Ala Ile Lys Leu Leu Ala Asn Ser
                485                 490                 495
Phe Tyr Gly Tyr Tyr Gly Tyr Ala Lys Ala Arg Trp Tyr Cys Lys Glu
                500                 505                 510
Cys Ala Glu Ser Val Thr Ala Trp Gly Arg Lys Tyr Ile Glu Leu Val
                515                 520                 525
Trp Lys Glu Leu Glu Glu Lys Phe Gly Phe Lys Val Leu Tyr Ile Asp
                530                 535                 540
Thr Asp Gly Leu Tyr Ala Thr Ile Pro Gly Gly Glu Ser Glu Glu Ile
545                 550                 555                 560
Lys Lys Lys Ala Leu Glu Phe Val Lys Tyr Ile Asn Ser Lys Leu Pro
                565                 570                 575
Gly Leu Leu Glu Leu Glu Tyr Glu Gly Phe Tyr Lys Arg Gly Phe Phe
                580                 585                 590
Val Thr Lys Lys Arg Tyr Ala Val Ile Asp Glu Glu Gly Lys Val Ile
                595                 600                 605
Thr Arg Gly Leu Glu Ile Val Arg Arg Asp Trp Ser Glu Ile Ala Lys
                610                 615                 620
Glu Thr Gln Ala Arg Val Leu Glu Ala Leu Leu Lys Asp Gly Asp Val
625                 630                 635                 640
Glu Lys Ala Val Arg Ile Val Lys Glu Val Thr Glu Lys Leu Ser Lys
                645                 650                 655
Tyr Glu Val Pro Pro Glu Lys Leu Val Ile His Glu Gln Ile Thr Arg
                660                 665                 670
Asp Leu Lys Asp Tyr Lys Ala Thr Gly Pro His Val Ala Val Ala Lys
                675                 680                 685
Arg Leu Ala Ala Arg Gly Val Lys Ile Arg Pro Gly Thr Val Ile Ser
                690                 695                 700
Tyr Ile Val Leu Lys Gly Ser Gly Arg Ile Gly Asp Arg Ala Ile Pro
705                 710                 715                 720
Phe Asp Glu Phe Asp Pro Thr Lys His Lys Tyr Asp Ala Glu Tyr Tyr
                725                 730                 735
Ile Glu Asn Gln Val Leu Pro Ala Val Glu Arg Ile Leu Arg Ala Phe
                740                 745                 750
```

-continued

Gly Tyr Arg Lys Glu Asp Leu Arg Tyr Gln Lys Thr Arg Gln Val Gly
        755                 760                 765

Leu Ser Ala Trp Leu Lys Pro Lys Gly Thr
    770                 775

<210> SEQ ID NO 27
<211> LENGTH: 777
<212> TYPE: PRT
<213> ORGANISM: Artificial Sequence
<220> FEATURE:
<223> OTHER INFORMATION: Chimeric DNA polymerase Pod-II

<400> SEQUENCE: 27

Met Ala Ser Ala Ile Leu Asp Val Asp Tyr Ile Thr Glu Glu Gly Lys
1               5                   10                  15

Pro Val Ile Arg Leu Phe Lys Lys Glu Asn Gly Lys Phe Lys Ile Glu
            20                  25                  30

His Asp Arg Thr Phe Arg Pro Tyr Ile Tyr Ala Leu Leu Arg Asp Asp
        35                  40                  45

Ser Lys Ile Glu Glu Val Lys Lys Ile Thr Gly Glu Arg His Gly Lys
    50                  55                  60

Ile Val Arg Ile Val Asp Val Glu Lys Val Glu Lys Lys Phe Leu Gly
65                  70                  75                  80

Lys Pro Ile Thr Val Trp Lys Leu Tyr Leu Glu His Pro Gln Asp Val
                85                  90                  95

Pro Thr Ile Arg Glu Lys Val Arg Glu His Pro Ala Val Val Asp Ile
            100                 105                 110

Phe Glu Tyr Asp Ile Pro Phe Ala Lys Arg Tyr Leu Ile Asp Lys Gly
        115                 120                 125

Leu Ile Pro Met Glu Gly Glu Glu Leu Lys Ile Leu Ala Phe Asp
    130                 135                 140

Ile Glu Thr Leu Tyr His Glu Gly Glu Glu Phe Gly Lys Gly Pro Ile
145                 150                 155                 160

Ile Met Ile Ser Tyr Ala Asp Glu Asn Glu Ala Lys Val Ile Thr Trp
                165                 170                 175

Lys Asn Ile Asp Leu Pro Tyr Val Glu Val Val Ser Ser Glu Arg Glu
            180                 185                 190

Met Ile Lys Arg Phe Leu Arg Ile Ile Arg Glu Lys Asp Pro Asp Ile
        195                 200                 205

Ile Val Thr Tyr Asn Gly Asp Ser Phe Asp Phe Pro Tyr Leu Ala Lys
    210                 215                 220

Arg Ala Glu Lys Leu Gly Ile Lys Leu Thr Ile Gly Arg Asp Gly Ser
225                 230                 235                 240

Glu Pro Lys Met Gln Arg Ile Gly Asp Met Thr Ala Val Glu Val Lys
                245                 250                 255

Gly Arg Ile His Phe Asp Leu Tyr His Val Ile Thr Arg Thr Ile Asn
            260                 265                 270

Leu Pro Thr Tyr Thr Leu Glu Ala Val Tyr Glu Ala Ile Phe Gly Lys
        275                 280                 285

Pro Lys Glu Lys Val Tyr Ala Asp Glu Ile Ala Lys Ala Trp Glu Ser
    290                 295                 300

Gly Glu Asn Leu Glu Arg Val Ala Arg Tyr Ser Met Glu Asp Ala Lys
305                 310                 315                 320

Val Thr Tyr Glu Leu Gly Lys Glu Phe Leu Pro Met Glu Ala Gln Leu
                325                 330                 335

```
Ser Arg Leu Ile Gly Gln Ser Leu Trp Asp Val Ser Arg Ser Thr
            340                 345                 350

Gly Asn Leu Val Glu Trp Phe Leu Arg Lys Ala Tyr Glu Arg Asn
            355                 360                 365

Glu Leu Ala Pro Asn Lys Pro Asp Glu Lys Glu Leu Ala Arg Arg
        370                 375                 380

Gln Ser Tyr Glu Gly Gly Tyr Val Lys Glu Pro Glu Arg Gly Leu Trp
385                 390                 395                 400

Glu Asn Ile Val Tyr Leu Asp Phe Arg Ser Leu Tyr Pro Ser Ile Ile
                405                 410                 415

Ile Thr His Asn Val Ser Pro Asp Thr Leu Asn Arg Glu Gly Cys Lys
            420                 425                 430

Glu Tyr Asp Val Ala Pro Gln Val Gly His Arg Phe Cys Lys Asp Phe
        435                 440                 445

Pro Gly Phe Ile Pro Ser Leu Leu Gly Asp Leu Leu Glu Glu Arg Gln
    450                 455                 460

Lys Ile Lys Lys Lys Met Lys Ala Thr Ile Asp Pro Ile Glu Arg Lys
465                 470                 475                 480

Leu Leu Asp Tyr Arg Gln Arg Ala Ile Lys Ile Leu Ala Asn Ser Tyr
                485                 490                 495

Tyr Gly Tyr Tyr Gly Tyr Ala Arg Ala Arg Trp Tyr Cys Lys Glu Cys
            500                 505                 510

Ala Glu Ser Val Thr Ala Trp Gly Arg Glu Tyr Ile Thr Met Thr Ile
        515                 520                 525

Lys Glu Ile Glu Glu Lys Tyr Gly Phe Lys Val Ile Tyr Ser Asp Thr
    530                 535                 540

Asp Gly Phe Phe Ala Thr Ile Pro Gly Ala Asp Ala Glu Thr Val Lys
545                 550                 555                 560

Lys Lys Ala Met Glu Phe Leu Lys Tyr Ile Asn Ala Lys Leu Pro Gly
                565                 570                 575

Ala Leu Glu Leu Glu Tyr Glu Gly Phe Tyr Lys Arg Gly Phe Phe Val
            580                 585                 590

Thr Lys Lys Lys Tyr Ala Val Ile Asp Glu Glu Gly Lys Ile Thr Thr
        595                 600                 605

Arg Gly Leu Glu Ile Val Arg Arg Asp Trp Ser Glu Ile Ala Lys Glu
    610                 615                 620

Thr Gln Ala Arg Val Leu Glu Thr Ile Leu Lys His Gly Asp Val Glu
625                 630                 635                 640

Glu Ala Val Arg Ile Val Lys Glu Val Ile Gln Lys Leu Ala Asn Tyr
                645                 650                 655

Glu Ile Pro Pro Glu Lys Leu Ala Ile Tyr Glu Gln Ile Thr Arg Pro
            660                 665                 670

Leu His Glu Tyr Lys Ala Ile Gly Pro His Val Ala Val Ala Lys Lys
        675                 680                 685

Leu Ala Ala Lys Gly Val Lys Ile Lys Pro Gly Met Val Ile Gly Tyr
    690                 695                 700

Ile Val Leu Arg Gly Asp Gly Pro Ile Ser Asn Arg Ala Ile Leu Ala
705                 710                 715                 720

Glu Glu Tyr Asp Pro Lys Lys His Lys Tyr Asp Ala Glu Tyr Tyr Ile
                725                 730                 735

Glu Asn Gln Val Leu Pro Ala Val Leu Arg Ile Leu Glu Gly Phe Gly
            740                 745                 750
```

Tyr Arg Lys Glu Asp Leu Arg Tyr Gln Lys Thr Arg Gln Val Gly Leu
            755                 760                 765

Thr Ser Trp Leu Asn Ile Lys Lys Ser
    770                 775

<210> SEQ ID NO 28
<211> LENGTH: 777
<212> TYPE: PRT
<213> ORGANISM: Artificial Sequence
<220> FEATURE:
<223> OTHER INFORMATION: Chimeric DNA polymerase Kofu-III

<400> SEQUENCE: 28

Met Ala Ser Ala Ile Leu Asp Thr Asp Tyr Ile Thr Glu Asp Gly Lys
1               5                   10                  15

Pro Val Ile Arg Ile Phe Lys Lys Glu Asn Gly Glu Phe Lys Ile Glu
                20                  25                  30

Tyr Asp Arg Thr Phe Glu Pro Tyr Phe Tyr Ala Leu Leu Lys Asp Asp
            35                  40                  45

Ser Ala Ile Glu Glu Val Lys Lys Ile Thr Ala Glu Arg His Gly Thr
        50                  55                  60

Val Val Thr Val Lys Arg Val Glu Lys Val Gln Lys Lys Phe Leu Gly
65                  70                  75                  80

Arg Pro Val Glu Val Trp Lys Leu Tyr Phe Thr His Pro Gln Asp Val
                85                  90                  95

Pro Ala Ile Arg Asp Lys Ile Arg Glu His Pro Ala Val Ile Asp Ile
            100                 105                 110

Tyr Glu Tyr Asp Ile Pro Phe Ala Lys Arg Tyr Leu Ile Asp Lys Gly
        115                 120                 125

Leu Val Pro Met Glu Gly Asp Glu Glu Leu Lys Met Leu Ala Phe Asp
130                 135                 140

Ile Glu Thr Leu Tyr His Glu Gly Glu Glu Phe Ala Glu Gly Pro Ile
145                 150                 155                 160

Leu Met Ile Ser Tyr Ala Asp Glu Glu Gly Ala Arg Val Ile Thr Trp
                165                 170                 175

Lys Asn Val Asp Leu Pro Tyr Val Asp Val Val Ser Thr Glu Arg Glu
            180                 185                 190

Met Ile Lys Arg Phe Leu Arg Val Val Lys Glu Lys Asp Pro Asp Val
        195                 200                 205

Leu Ile Thr Tyr Asn Gly Asp Asn Phe Asp Phe Ala Tyr Leu Lys Lys
210                 215                 220

Arg Cys Glu Lys Leu Gly Ile Asn Phe Ala Leu Gly Arg Asp Gly Ser
225                 230                 235                 240

Glu Pro Lys Ile Gln Arg Met Gly Asp Arg Phe Ala Val Glu Val Lys
                245                 250                 255

Gly Arg Ile His Phe Asp Leu Tyr Pro Val Ile Arg Arg Thr Ile Asn
            260                 265                 270

Leu Pro Thr Tyr Thr Leu Glu Ala Val Tyr Glu Ala Val Phe Gly Gln
        275                 280                 285

Pro Lys Glu Lys Val Tyr Ala Glu Glu Ile Thr Thr Ala Trp Glu Thr
290                 295                 300

Gly Glu Asn Leu Glu Arg Val Ala Arg Tyr Ser Met Glu Asp Ala Lys
305                 310                 315                 320

Val Thr Tyr Glu Leu Gly Lys Glu Phe Leu Pro Met Glu Ala Gln Leu
                325                 330                 335

-continued

```
Ser Arg Leu Ile Gly Gln Ser Leu Trp Asp Val Ser Arg Ser Thr
            340                 345                 350
Gly Asn Leu Val Glu Trp Phe Leu Leu Arg Lys Ala Tyr Glu Arg Asn
        355                 360                 365
Glu Leu Ala Pro Asn Lys Pro Asp Glu Lys Glu Leu Ala Arg Arg Arg
    370                 375                 380
Gln Ser Tyr Glu Gly Gly Tyr Val Lys Glu Pro Glu Lys Gly Leu Trp
385                 390                 395                 400
Glu Asn Ile Val Tyr Leu Asp Phe Arg Ala Leu Tyr Pro Ser Ile Ile
                405                 410                 415
Ile Thr His Asn Val Ser Pro Asp Thr Leu Asn Leu Glu Gly Cys Lys
            420                 425                 430
Asn Tyr Asp Ile Ala Pro Gln Val Gly His Lys Phe Cys Lys Asp Ile
        435                 440                 445
Pro Gly Phe Ile Pro Ser Leu Leu Gly His Leu Leu Glu Glu Arg Gln
    450                 455                 460
Lys Ile Lys Thr Lys Met Lys Glu Thr Gln Asp Pro Ile Glu Lys Ile
465                 470                 475                 480
Leu Leu Asp Tyr Arg Gln Lys Ala Ile Lys Leu Leu Ala Asn Ser Phe
                485                 490                 495
Tyr Gly Tyr Tyr Gly Tyr Ala Lys Ala Arg Trp Tyr Cys Lys Glu Cys
            500                 505                 510
Ala Glu Ser Val Thr Ala Trp Gly Arg Lys Tyr Ile Glu Leu Val Trp
        515                 520                 525
Lys Glu Leu Glu Glu Lys Phe Gly Phe Lys Val Leu Tyr Ile Asp Thr
    530                 535                 540
Asp Gly Leu Tyr Ala Thr Ile Pro Gly Gly Glu Ser Glu Glu Ile Lys
545                 550                 555                 560
Lys Lys Ala Leu Glu Phe Leu Lys Tyr Ile Asn Ala Lys Leu Pro Gly
                565                 570                 575
Ala Leu Glu Leu Glu Tyr Glu Gly Phe Tyr Lys Arg Gly Phe Phe Val
            580                 585                 590
Thr Lys Lys Lys Tyr Ala Val Ile Asp Glu Glu Gly Lys Ile Thr Thr
        595                 600                 605
Arg Gly Leu Glu Ile Val Arg Arg Asp Trp Ser Glu Ile Ala Lys Glu
    610                 615                 620
Thr Gln Ala Arg Val Leu Glu Ala Leu Leu Lys Asp Gly Asp Val Glu
625                 630                 635                 640
Lys Ala Val Arg Ile Val Lys Glu Val Thr Glu Lys Leu Ser Lys Tyr
                645                 650                 655
Glu Val Pro Pro Glu Lys Leu Val Ile His Glu Gln Ile Thr Arg Asp
            660                 665                 670
Leu Lys Asp Tyr Lys Ala Thr Gly Pro His Val Ala Val Ala Lys Arg
        675                 680                 685
Leu Ala Ala Arg Gly Val Lys Ile Arg Pro Gly Thr Val Ile Ser Tyr
    690                 695                 700
Ile Val Leu Lys Gly Ser Gly Arg Ile Gly Asp Arg Ala Ile Pro Phe
705                 710                 715                 720
Asp Glu Phe Asp Pro Thr Lys His Lys Tyr Asp Ala Glu Tyr Tyr Ile
                725                 730                 735
Glu Asn Gln Val Leu Pro Ala Val Glu Arg Ile Leu Arg Ala Phe Gly
            740                 745                 750
Tyr Arg Lys Glu Asp Leu Arg Tyr Gln Lys Thr Arg Gln Val Gly Leu
```

```
                  755                 760                 765
Ser Ala Trp Leu Lys Pro Lys Gly Thr
    770                 775

<210> SEQ ID NO 29
<211> LENGTH: 778
<212> TYPE: PRT
<213> ORGANISM: Artificial Sequence
<220> FEATURE:
<223> OTHER INFORMATION: Chimeric DNA polymerase Pod-III

<400> SEQUENCE: 29

Met Ala Ser Ala Ile Leu Asp Val Asp Tyr Ile Thr Glu Glu Gly Lys
1               5                   10                  15

Pro Val Ile Arg Leu Phe Lys Lys Glu Asn Gly Lys Phe Lys Ile Glu
            20                  25                  30

His Asp Arg Thr Phe Arg Pro Tyr Ile Tyr Ala Leu Leu Arg Asp Asp
        35                  40                  45

Ser Lys Ile Glu Glu Val Lys Lys Ile Thr Gly Glu Arg His Gly Lys
    50                  55                  60

Ile Val Arg Ile Val Asp Val Glu Lys Val Glu Lys Lys Phe Leu Gly
65                  70                  75                  80

Lys Pro Ile Thr Val Trp Lys Leu Tyr Leu Glu His Pro Gln Asp Val
                85                  90                  95

Pro Thr Ile Arg Glu Lys Val Arg Glu His Pro Ala Val Val Asp Ile
            100                 105                 110

Phe Glu Tyr Asp Ile Pro Phe Ala Lys Arg Tyr Leu Ile Asp Lys Gly
        115                 120                 125

Leu Ile Pro Met Glu Gly Glu Glu Leu Lys Ile Leu Ala Phe Asp
    130                 135                 140

Ile Glu Thr Leu Tyr His Glu Gly Glu Glu Phe Gly Lys Gly Pro Ile
145                 150                 155                 160

Ile Met Ile Ser Tyr Ala Asp Glu Asn Glu Ala Lys Val Ile Thr Trp
                165                 170                 175

Lys Asn Ile Asp Leu Pro Tyr Val Glu Val Val Ser Ser Glu Arg Glu
            180                 185                 190

Met Ile Lys Arg Phe Leu Arg Ile Ile Arg Glu Lys Asp Pro Asp Ile
        195                 200                 205

Ile Val Thr Tyr Asn Gly Asp Ser Phe Asp Phe Pro Tyr Leu Ala Lys
    210                 215                 220

Arg Ala Glu Lys Leu Gly Ile Lys Leu Thr Ile Gly Arg Asp Gly Ser
225                 230                 235                 240

Glu Pro Lys Met Gln Arg Ile Gly Asp Met Thr Ala Val Glu Val Lys
                245                 250                 255

Gly Arg Ile His Phe Asp Leu Tyr His Val Ile Thr Arg Thr Ile Asn
            260                 265                 270

Leu Pro Thr Tyr Thr Leu Glu Ala Val Tyr Glu Ala Ile Phe Gly Lys
        275                 280                 285

Pro Lys Glu Lys Val Tyr Ala Asp Glu Ile Ala Lys Ala Trp Glu Ser
    290                 295                 300

Gly Glu Asn Leu Glu Arg Val Ala Lys Tyr Ser Met Glu Asp Ala Lys
305                 310                 315                 320

Ala Thr Tyr Glu Leu Gly Lys Glu Phe Leu Pro Met Glu Ile Gln Leu
                325                 330                 335

Ser Arg Leu Val Gly Gln Pro Leu Trp Asp Val Ser Arg Ser Ser Thr
```

-continued

```
                340                 345                 350
Gly Asn Leu Val Glu Trp Phe Leu Leu Arg Lys Ala Tyr Glu Arg Asn
            355                 360                 365

Glu Val Ala Pro Asn Lys Pro Ser Glu Glu Tyr Gln Arg Arg Leu
        370                 375                 380

Arg Glu Ser Tyr Thr Gly Gly Phe Val Lys Glu Pro Glu Arg Gly Leu
385                 390                 395                 400

Trp Glu Asn Ile Val Tyr Leu Asp Phe Arg Ser Leu Tyr Pro Ser Ile
                405                 410                 415

Ile Ile Thr His Asn Val Ser Pro Asp Thr Leu Asn Arg Glu Gly Cys
            420                 425                 430

Lys Glu Tyr Asp Val Ala Pro Gln Val Gly His Arg Phe Cys Lys Asp
            435                 440                 445

Phe Pro Gly Phe Ile Pro Ser Leu Leu Gly Asp Leu Leu Glu Glu Arg
        450                 455                 460

Gln Lys Ile Lys Lys Lys Met Lys Ala Thr Ile Asp Pro Ile Glu Arg
465                 470                 475                 480

Lys Leu Leu Asp Tyr Arg Gln Arg Ala Ile Lys Ile Leu Ala Asn Ser
                485                 490                 495

Tyr Tyr Gly Tyr Tyr Gly Tyr Ala Arg Ala Arg Trp Tyr Cys Lys Glu
            500                 505                 510

Cys Ala Glu Ser Val Thr Ala Trp Gly Arg Glu Tyr Ile Thr Met Thr
            515                 520                 525

Ile Lys Glu Ile Glu Glu Lys Tyr Gly Phe Lys Val Ile Tyr Ser Asp
        530                 535                 540

Thr Asp Gly Phe Phe Ala Thr Ile Pro Gly Ala Asp Ala Glu Thr Val
545                 550                 555                 560

Lys Lys Lys Ala Met Glu Phe Val Lys Tyr Ile Asn Ser Lys Leu Pro
                565                 570                 575

Gly Leu Leu Glu Leu Glu Tyr Glu Gly Phe Tyr Lys Arg Gly Phe Phe
            580                 585                 590

Val Thr Lys Lys Arg Tyr Ala Val Ile Asp Glu Glu Gly Lys Val Ile
            595                 600                 605

Thr Arg Gly Leu Glu Ile Val Arg Arg Asp Trp Ser Glu Ile Ala Lys
        610                 615                 620

Glu Thr Gln Ala Arg Val Leu Glu Thr Ile Leu Lys His Gly Asp Val
625                 630                 635                 640

Glu Glu Ala Val Arg Ile Val Lys Glu Val Ile Gln Lys Leu Ala Asn
                645                 650                 655

Tyr Glu Ile Pro Pro Glu Lys Leu Ala Ile Tyr Glu Gln Ile Thr Arg
            660                 665                 670

Pro Leu His Glu Tyr Lys Ala Ile Gly Pro His Val Ala Val Ala Lys
            675                 680                 685

Lys Leu Ala Ala Lys Gly Val Lys Ile Lys Pro Gly Met Val Ile Gly
        690                 695                 700

Tyr Ile Val Leu Arg Gly Asp Gly Pro Ile Ser Asn Arg Ala Ile Leu
705                 710                 715                 720

Ala Glu Glu Tyr Asp Pro Lys Lys His Lys Tyr Asp Ala Glu Tyr Tyr
                725                 730                 735

Ile Glu Asn Gln Val Leu Pro Ala Val Leu Arg Ile Leu Glu Gly Phe
            740                 745                 750

Gly Tyr Arg Lys Glu Asp Leu Arg Tyr Gln Lys Thr Arg Gln Val Gly
            755                 760                 765
```

```
Leu Thr Ser Trp Leu Asn Ile Lys Lys Ser
    770                 775

<210> SEQ ID NO 30
<211> LENGTH: 150
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (1)..(2)
<223> OTHER INFORMATION: Xaa is any amino acid or absent
<220> FEATURE:
<221> NAME/KEY: Xaa
<222> LOCATION: (4)..(10)
<223> OTHER INFORMATION: Xaa is any amino acid or absent
<220> FEATURE:
<221> NAME/KEY: Xaa
<222> LOCATION: (13)..(13)
<223> OTHER INFORMATION: Xaa is any amino acid or absent
<220> FEATURE:
<221> NAME/KEY: Xaa
<222> LOCATION: (15)..(20)
<223> OTHER INFORMATION: Xaa is any amino acid or absent
<220> FEATURE:
<221> NAME/KEY: Xaa
<222> LOCATION: (22)..(26)
<223> OTHER INFORMATION: Xaa is any amino acid or absent
<220> FEATURE:
<221> NAME/KEY: Xaa
<222> LOCATION: (28)..(30)
<223> OTHER INFORMATION: Xaa is any amino acid or absent
<220> FEATURE:
<221> NAME/KEY: Xaa
<222> LOCATION: (32)..(41)
<223> OTHER INFORMATION: Xaa is any amino acid or absent
<220> FEATURE:
<221> NAME/KEY: Xaa
<222> LOCATION: (45)..(49)
<223> OTHER INFORMATION: Xaa is any amino acid or absent
<220> FEATURE:
<221> NAME/KEY: Xaa
<222> LOCATION: (53)..(57)
<223> OTHER INFORMATION: Xaa is any amino acid or absent
<220> FEATURE:
<221> NAME/KEY: Xaa
<222> LOCATION: (59)..(61)
<223> OTHER INFORMATION: Xaa is any amino acid or absent
<220> FEATURE:
<221> NAME/KEY: Xaa
<222> LOCATION: (63)..(64)
<223> OTHER INFORMATION: Xaa is any amino acid or absent
<220> FEATURE:
<221> NAME/KEY: Xaa
<222> LOCATION: (66)..(67)
<223> OTHER INFORMATION: Xaa is any amino acid or absent
<220> FEATURE:
<221> NAME/KEY: Xaa
<222> LOCATION: (69)..(73)
<223> OTHER INFORMATION: Xaa is any amino acid or absent
<220> FEATURE:
<221> NAME/KEY: Xaa
<222> LOCATION: (78)..(89)
<223> OTHER INFORMATION: Xaa is any amino acid or absent
<220> FEATURE:
<221> NAME/KEY: Xaa
<222> LOCATION: (91)..(92)
<223> OTHER INFORMATION: Xaa is any amino acid or absent
<220> FEATURE:
<221> NAME/KEY: Xaa
<222> LOCATION: (94)..(95)
<223> OTHER INFORMATION: Xaa is any amino acid or absent
<220> FEATURE:
<221> NAME/KEY: Xaa
<222> LOCATION: (98)..(110)
<223> OTHER INFORMATION: Xaa is any amino acid or absent
```

-continued

```
<220> FEATURE:
<221> NAME/KEY: Xaa
<222> LOCATION: (112)..(113)
<223> OTHER INFORMATION: Xaa is any amino acid or absent
<220> FEATURE:
<221> NAME/KEY: Xaa
<222> LOCATION: (115)..(130)
<223> OTHER INFORMATION: Xaa is any amino acid or absent
<220> FEATURE:
<221> NAME/KEY: Xaa
<222> LOCATION: (132)..(133)
<223> OTHER INFORMATION: Xaa is any amino acid or absent
<220> FEATURE:
<221> NAME/KEY: Xaa
<222> LOCATION: (135)..(141)
<223> OTHER INFORMATION: Xaa is any amino acid or absent
<220> FEATURE:
<221> NAME/KEY: Xaa
<222> LOCATION: (143)..(144)
<223> OTHER INFORMATION: Xaa is any amino acid or absent
<220> FEATURE:
<221> NAME/KEY: Xaa
<222> LOCATION: (147)..(149)
<223> OTHER INFORMATION: Xaa is any amino acid or absent

<400> SEQUENCE: 30

Xaa Xaa Leu Xaa Xaa Xaa Xaa Xaa Xaa Xaa Glu Gly Xaa Arg Xaa Xaa
 1               5                  10                  15

Xaa Xaa Xaa Xaa Val Xaa Xaa Xaa Xaa Asp Xaa Xaa Xaa Thr Xaa
             20                  25                  30

Xaa Xaa Xaa Xaa Xaa Xaa Xaa Xaa Val Val Lys Xaa Xaa Xaa Xaa
         35                  40                  45

Xaa Val Leu Ile Xaa Xaa Xaa Xaa Xaa Asn Xaa Xaa Xaa Ala Xaa Xaa
 50                  55                  60

Lys Xaa Xaa Cys Xaa Xaa Xaa Xaa Xaa Asn Phe Ala Leu Xaa Xaa Xaa
 65                  70                  75                  80

Xaa Xaa Xaa Xaa Xaa Xaa Xaa Xaa Ile Xaa Xaa Met Xaa Xaa Arg
             85                  90                  95

Phe Xaa Xaa Xaa Xaa Xaa Xaa Xaa Xaa Xaa Xaa Xaa Xaa Pro Xaa
            100                 105                 110

Xaa Arg Xaa Xaa Xaa Xaa Xaa Xaa Xaa Xaa Xaa Xaa Xaa Xaa Xaa
            115                 120                 125

Xaa Xaa Val Xaa Xaa Gln Xaa Xaa Xaa Xaa Xaa Xaa Glu Xaa Xaa
        130                 135                 140

Thr Thr Xaa Xaa Xaa Thr
145                 150

<210> SEQ ID NO 31
<211> LENGTH: 83
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (1)..(2)
<223> OTHER INFORMATION: Xaa is any amino acid or absent
<220> FEATURE:
<221> NAME/KEY: Xaa
<222> LOCATION: (4)..(7)
<223> OTHER INFORMATION: Xaa is any amino acid or absent
<220> FEATURE:
<221> NAME/KEY: Xaa
<222> LOCATION: (9)..(12)
<223> OTHER INFORMATION: Xaa is any amino acid or absent
<220> FEATURE:
<221> NAME/KEY: Xaa
<222> LOCATION: (14)..(15)
```

```
<223> OTHER INFORMATION: Xaa is any amino acid or absent
<220> FEATURE:
<221> NAME/KEY: Xaa
<222> LOCATION: (17)..(20)
<223> OTHER INFORMATION: Xaa is any amino acid or absent
<220> FEATURE:
<221> NAME/KEY: Xaa
<222> LOCATION: (22)..(24)
<223> OTHER INFORMATION: Xaa is any amino acid or absent
<220> FEATURE:
<221> NAME/KEY: Xaa
<222> LOCATION: (26)..(33)
<223> OTHER INFORMATION: Xaa is any amino acid or absent
<220> FEATURE:
<221> NAME/KEY: Xaa
<222> LOCATION: (35)..(38)
<223> OTHER INFORMATION: Xaa is any amino acid or absent
<220> FEATURE:
<221> NAME/KEY: Xaa
<222> LOCATION: (41)..(41)
<223> OTHER INFORMATION: Xaa is any amino acid or absent
<220> FEATURE:
<221> NAME/KEY: Xaa
<222> LOCATION: (46)..(49)
<223> OTHER INFORMATION: Xaa is any amino acid or absent
<220> FEATURE:
<221> NAME/KEY: Xaa
<222> LOCATION: (51)..(55)
<223> OTHER INFORMATION: Xaa is any amino acid or absent
<220> FEATURE:
<221> NAME/KEY: Xaa
<222> LOCATION: (57)..(57)
<223> OTHER INFORMATION: Xaa is any amino acid or absent
<220> FEATURE:
<221> NAME/KEY: Xaa
<222> LOCATION: (60)..(64)
<223> OTHER INFORMATION: Xaa is any amino acid or absent
<220> FEATURE:
<221> NAME/KEY: Xaa
<222> LOCATION: (67)..(72)
<223> OTHER INFORMATION: Xaa is any amino acid or absent
<220> FEATURE:
<221> NAME/KEY: Xaa
<222> LOCATION: (74)..(75)
<223> OTHER INFORMATION: Xaa is any amino acid or absent
<220> FEATURE:
<221> NAME/KEY: Xaa
<222> LOCATION: (77)..(77)
<223> OTHER INFORMATION: Xaa is any amino acid or absent
<220> FEATURE:
<221> NAME/KEY: Xaa
<222> LOCATION: (79)..(83)
<223> OTHER INFORMATION: Xaa is any amino acid or absent

<400> SEQUENCE: 31

Xaa Xaa Glu Xaa Xaa Xaa Xaa Tyr Xaa Xaa Xaa Glu Xaa Xaa Phe
1               5                   10                  15

Xaa Xaa Xaa Xaa Lys Xaa Xaa Xaa Ala Xaa Xaa Xaa Xaa Xaa Xaa
                20                  25                  30

Xaa Ala Xaa Xaa Xaa Xaa Thr Val Xaa Thr Val Lys Arg Xaa Xaa Xaa
        35                  40                  45

Xaa Gln Xaa Xaa Xaa Xaa Xaa Arg Xaa Val Glu Xaa Xaa Xaa Xaa
    50                  55                  60

Phe Thr Xaa Xaa Xaa Xaa Xaa Xaa Ala Xaa Xaa Asp Xaa Ile Xaa Xaa
65                  70                  75                  80

Xaa Xaa Xaa

<210> SEQ ID NO 32
<211> LENGTH: 137
<212> TYPE: PRT
<213> ORGANISM: Artificial Sequence
<220> FEATURE:
```

```
<223> OTHER INFORMATION: Consensus Sequence
<220> FEATURE:
<221> NAME/KEY: Xaa
<222> LOCATION: (1)..(16)
<223> OTHER INFORMATION: Xaa is any amino acid or absent
<220> FEATURE:
<221> NAME/KEY: Xaa
<222> LOCATION: (19)..(20)
<223> OTHER INFORMATION: Xaa is any amino acid or absent
<220> FEATURE:
<221> NAME/KEY: Xaa
<222> LOCATION: (22)..(25)
<223> OTHER INFORMATION: Xaa is any amino acid or absent
<220> FEATURE:
<221> NAME/KEY: Xaa
<222> LOCATION: (27)..(34)
<223> OTHER INFORMATION: Xaa is any amino acid or absent
<220> FEATURE:
<221> NAME/KEY: Xaa
<222> LOCATION: (37)..(38)
<223> OTHER INFORMATION: Xaa is any amino acid or absent
<220> FEATURE:
<221> NAME/KEY: Xaa
<222> LOCATION: (41)..(42)
<223> OTHER INFORMATION: Xaa is any amino acid or absent
<220> FEATURE:
<221> NAME/KEY: Xaa
<222> LOCATION: (44)..(48)
<223> OTHER INFORMATION: Xaa is any amino acid or absent
<220> FEATURE:
<221> NAME/KEY: Xaa
<222> LOCATION: (50)..(50)
<223> OTHER INFORMATION: Xaa is any amino acid or absent
<220> FEATURE:
<221> NAME/KEY: Xaa
<222> LOCATION: (52)..(56)
<223> OTHER INFORMATION: Xaa is any amino acid or absent
<220> FEATURE:
<221> NAME/KEY: Xaa
<222> LOCATION: (58)..(58)
<223> OTHER INFORMATION: Xaa is any amino acid or absent
<220> FEATURE:
<221> NAME/KEY: Xaa
<222> LOCATION: (61)..(63)
<223> OTHER INFORMATION: Xaa is any amino acid or absent
<220> FEATURE:
<221> NAME/KEY: Xaa
<222> LOCATION: (65)..(72)
<223> OTHER INFORMATION: Xaa is any amino acid or absent
<220> FEATURE:
<221> NAME/KEY: Xaa
<222> LOCATION: (74)..(76)
<223> OTHER INFORMATION: Xaa is any amino acid or absent
<220> FEATURE:
<221> NAME/KEY: Xaa
<222> LOCATION: (78)..(81)
<223> OTHER INFORMATION: Xaa is any amino acid or absent
<220> FEATURE:
<221> NAME/KEY: Xaa
<222> LOCATION: (83)..(84)
<223> OTHER INFORMATION: Xaa is any amino acid or absent
<220> FEATURE:
<221> NAME/KEY: Xaa
<222> LOCATION: (86)..(87)
<223> OTHER INFORMATION: Xaa is any amino acid or absent
<220> FEATURE:
<221> NAME/KEY: Xaa
<222> LOCATION: (88)..(92)
<223> OTHER INFORMATION: Xaa is any amino acid or absent
<220> FEATURE:
<221> NAME/KEY: Xaa
<222> LOCATION: (94)..(94)
<223> OTHER INFORMATION: Xaa is any amino acid or absent
<220> FEATURE:
<221> NAME/KEY: Xaa
<222> LOCATION: (96)..(96)
<223> OTHER INFORMATION: Xaa is any amino acid or absent
<220> FEATURE:
<221> NAME/KEY: Xaa
```

<222> LOCATION: (98)..(98)
<223> OTHER INFORMATION: Xaa is any amino acid or absent
<220> FEATURE:
<221> NAME/KEY: Xaa
<222> LOCATION: (101)..(103)
<223> OTHER INFORMATION: Xaa is any amino acid or absent
<220> FEATURE:
<221> NAME/KEY: Xaa
<222> LOCATION: (107)..(107)
<223> OTHER INFORMATION: Xaa is any amino acid or absent
<220> FEATURE:
<221> NAME/KEY: Xaa
<222> LOCATION: (109)..(110)
<223> OTHER INFORMATION: Xaa is any amino acid or absent
<220> FEATURE:
<221> NAME/KEY: Xaa
<222> LOCATION: (112)..(129)
<223> OTHER INFORMATION: Xaa is any amino acid or absent
<220> FEATURE:
<221> NAME/KEY: Xaa
<222> LOCATION: (131)..(133)
<223> OTHER INFORMATION: Xaa is any amino acid or absent
<220> FEATURE:
<221> NAME/KEY: Xaa
<222> LOCATION: (136)..(137)
<223> OTHER INFORMATION: Xaa is any amino acid or absent

<400> SEQUENCE: 32

Xaa Xaa Xaa Xaa Xaa Xaa Xaa Xaa Xaa Xaa Xaa Xaa Xaa Xaa Xaa Xaa
 1               5                  10                  15

Ala Leu Xaa Xaa Asp Xaa Xaa Xaa Lys Xaa Xaa Xaa Xaa Xaa
            20                  25                  30

Xaa Xaa Thr Glu Xaa Xaa Ser Lys Xaa Xaa Val Xaa Xaa Xaa Xaa Xaa
            35                  40                  45

Val Xaa His Xaa Xaa Xaa Xaa Xaa Asp Xaa Lys Asp Xaa Xaa Xaa Thr
 50                  55                  60

Xaa Xaa Xaa Xaa Xaa Xaa Xaa Arg Xaa Xaa Xaa Arg Xaa Xaa Xaa Xaa
 65                  70                  75                  80

Xaa Arg Xaa Xaa Thr Xaa Xaa Ser Xaa Xaa Xaa Xaa Lys Xaa Ser Xaa
                 85                  90                  95

Arg Xaa Gly Asp Xaa Xaa Xaa Pro Phe Asp Xaa Phe Xaa Xaa Thr Xaa
            100                 105                 110

Xaa Xaa Xaa Xaa Xaa Xaa Xaa Xaa Xaa Xaa Xaa Xaa Xaa Xaa Xaa Xaa
            115                 120                 125

Xaa Glu Xaa Xaa Xaa Arg Ala Xaa Xaa
            130                 135

<210> SEQ ID NO 33
<211> LENGTH: 83
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (3)..(3)
<223> OTHER INFORMATION: Xaa is any amino acid or absent, but not K
<220> FEATURE:
<221> NAME/KEY: Xaa
<222> LOCATION: (8)..(8)
<223> OTHER INFORMATION: Xaa is any amino acid or absent, but not H
<220> FEATURE:
<221> NAME/KEY: Xaa
<222> LOCATION: (13)..(13)
<223> OTHER INFORMATION: Xaa is any amino acid or absent, but not R
<220> FEATURE:
<221> NAME/KEY: Xaa
<222> LOCATION: (16)..(16)
<223> OTHER INFORMATION: Xaa is any amino acid or absent, but not I
<220> FEATURE:
<221> NAME/KEY: Xaa
<222> LOCATION: (21)..(21)
<223> OTHER INFORMATION: Xaa is any amino acid or absent, but not R
<220> FEATURE:
<221> NAME/KEY: Xaa
<222> LOCATION: (25)..(25)
<223> OTHER INFORMATION: Xaa is any amino acid or absent, but not K
<220> FEATURE:
<221> NAME/KEY: Xaa
<222> LOCATION: (34)..(34)
<223> OTHER INFORMATION: Xaa is any amino acid or absent, but not G
<220> FEATURE:
<221> NAME/KEY: Xaa
<222> LOCATION: (39)..(39)
<223> OTHER INFORMATION: Xaa is any amino acid or absent, but not K
<220> FEATURE:
<221> NAME/KEY: Xaa
<222> LOCATION: (40)..(40)
<223> OTHER INFORMATION: Xaa is any amino acid or absent, but not I
<220> FEATURE:
<221> NAME/KEY: Xaa
<222> LOCATION: (42)..(42)
<223> OTHER INFORMATION: Xaa is any amino acid or absent, but not R
<220> FEATURE:
<221> NAME/KEY: Xaa
<222> LOCATION: (43)..(43)
<223> OTHER INFORMATION: Xaa is any amino acid or absent, but not I
<220> FEATURE:
<221> NAME/KEY: Xaa
<222> LOCATION: (44)..(44)
<223> OTHER INFORMATION: Xaa is any amino acid or absent, but not V
<220> FEATURE:
<221> NAME/KEY: Xaa
<222> LOCATION: (45)..(45)
<223> OTHER INFORMATION: Xaa is any amino acid or absent, but not D
<220> FEATURE:
<221> NAME/KEY: Xaa
<222> LOCATION: (50)..(50)
<223> OTHER INFORMATION: Xaa is any amino acid or absent, but not E
<220> FEATURE:
<221> NAME/KEY: Xaa
<222> LOCATION: (56)..(56)
<223> OTHER INFORMATION: Xaa is any amino acid or absent, but not K
<220> FEATURE:
<221> NAME/KEY: Xaa
<222> LOCATION: (58)..(58)
<223> OTHER INFORMATION: Xaa is any amino acid or absent, but not I
<220> FEATURE:
<221> NAME/KEY: Xaa
<222> LOCATION: (59)..(59)
<223> OTHER INFORMATION: Xaa is any amino acid or absent, but not T
<220> FEATURE:
<221> NAME/KEY: Xaa
<222> LOCATION: (65)..(65)
<223> OTHER INFORMATION: Xaa is any amino acid or absent, but not L
<220> FEATURE:
<221> NAME/KEY: Xaa
<222> LOCATION: (66)..(66)
<223> OTHER INFORMATION: Xaa is any amino acid or absent, but not E
<220> FEATURE:
<221> NAME/KEY: Xaa
<222> LOCATION: (73)..(73)
<223> OTHER INFORMATION: Xaa is any amino acid or absent, but not T
<220> FEATURE:
<221> NAME/KEY: Xaa
<222> LOCATION: (76)..(76)
<223> OTHER INFORMATION: Xaa is any amino acid or absent, but not E
<220> FEATURE:
<221> NAME/KEY: Xaa
<222> LOCATION: (78)..(78)
<223> OTHER INFORMATION: Xaa is any amino acid or absent, but not V

<400> SEQUENCE: 33

```
Asn Gly Xaa Phe Lys Ile Glu Xaa Asp Arg Thr Phe Xaa Pro Tyr Xaa
1               5                   10                  15

Tyr Ala Leu Leu Xaa Asp Asp Ser Xaa Ile Glu Glu Val Lys Lys Ile
```

-continued

```
                        20                  25                  30
Thr Xaa Glu Arg His Gly Xaa Xaa Val Xaa Xaa Xaa Xaa Val Glu Lys
            35                  40                  45

Val Xaa Lys Lys Phe Leu Gly Xaa Pro Xaa Xaa Val Trp Lys Leu Tyr
        50                  55                  60

Xaa Xaa His Pro Gln Asp Val Pro Xaa Ile Arg Xaa Lys Xaa Arg Glu
 65                  70                  75                  80

His Pro Ala

<210> SEQ ID NO 34
<211> LENGTH: 146
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (3)..(3)
<223> OTHER INFORMATION: Xaa is any amino acid or absent, but not I
<220> FEATURE:
<221> NAME/KEY: Xaa
<222> LOCATION: (11)..(11)
<223> OTHER INFORMATION: Xaa is any amino acid or absent, but not N
<220> FEATURE:
<221> NAME/KEY: Xaa
<222> LOCATION: (12)..(12)
<223> OTHER INFORMATION: Xaa is any amino acid or absent, but not E
<220> FEATURE:
<221> NAME/KEY: Xaa
<222> LOCATION: (14)..(14)
<223> OTHER INFORMATION: Xaa is any amino acid or absent, but not K
<220> FEATURE:
<221> NAME/KEY: Xaa
<222> LOCATION: (21)..(21)
<223> OTHER INFORMATION: Xaa is any amino acid or absent, but not I
<220> FEATURE:
<221> NAME/KEY: Xaa
<222> LOCATION: (27)..(27)
<223> OTHER INFORMATION: Xaa is any amino acid or absent, but not E
<220> FEATURE:
<221> NAME/KEY: Xaa
<222> LOCATION: (31)..(31)
<223> OTHER INFORMATION: Xaa is any amino acid or absent, but not S
<220> FEATURE:
<221> NAME/KEY: Xaa
<222> LOCATION: (42)..(42)
<223> OTHER INFORMATION: Xaa is any amino acid or absent, but not I
<220> FEATURE:
<221> NAME/KEY: Xaa
<222> LOCATION: (43)..(43)
<223> OTHER INFORMATION: Xaa is any amino acid or absent, but not I
<220> FEATURE:
<221> NAME/KEY: Xaa
<222> LOCATION: (44)..(44)
<223> OTHER INFORMATION: Xaa is any amino acid or absent, but not R
<220> FEATURE:
<221> NAME/KEY: Xaa
<222> LOCATION: (50)..(50)
<223> OTHER INFORMATION: Xaa is any amino acid or absent, but not I
<220> FEATURE:
<221> NAME/KEY: Xaa
<222> LOCATION: (51)..(51)
<223> OTHER INFORMATION: Xaa is any amino acid or absent, but not I
<220> FEATURE:
<221> NAME/KEY: Xaa
<222> LOCATION: (52)..(52)
<223> OTHER INFORMATION: Xaa is any amino acid or absent, but not V
<220> FEATURE:
<221> NAME/KEY: Xaa
<222> LOCATION: (58)..(58)
<223> OTHER INFORMATION: Xaa is any amino acid or absent, but not S
<220> FEATURE:
<221> NAME/KEY: Xaa
<222> LOCATION: (62)..(62)
```

-continued

```
<223> OTHER INFORMATION: Xaa is any amino acid or absent, but not P
<220> FEATURE:
<221> NAME/KEY: Xaa
<222> LOCATION: (65)..(65)
<223> OTHER INFORMATION: Xaa is any amino acid or absent, but not A
<220> FEATURE:
<221> NAME/KEY: Xaa
<222> LOCATION: (68)..(68)
<223> OTHER INFORMATION: Xaa is any amino acid or absent, but not A
<220> FEATURE:
<221> NAME/KEY: Xaa
<222> LOCATION: (74)..(74)
<223> OTHER INFORMATION: Xaa is any amino acid or absent, but not K
<220> FEATURE:
<221> NAME/KEY: Xaa
<222> LOCATION: (75)..(75)
<223> OTHER INFORMATION: Xaa is any amino acid or absent, but not L
<220> FEATURE:
<221> NAME/KEY: Xaa
<222> LOCATION: (76)..(76)
<223> OTHER INFORMATION: Xaa is any amino acid or absent, but not T
<220> FEATURE:
<221> NAME/KEY: Xaa
<222> LOCATION: (77)..(77)
<223> OTHER INFORMATION: Xaa is any amino acid or absent, but not I
<220> FEATURE:
<221> NAME/KEY: Xaa
<222> LOCATION: (86)..(86)
<223> OTHER INFORMATION: Xaa is any amino acid or absent, but not M
<220> FEATURE:
<221> NAME/KEY: Xaa
<222> LOCATION: (89)..(89)
<223> OTHER INFORMATION: Xaa is any amino acid or absent, but not I
<220> FEATURE:
<221> NAME/KEY: Xaa
<222> LOCATION: (92)..(92)
<223> OTHER INFORMATION: Xaa is any amino acid or absent, but not M
<220> FEATURE:
<221> NAME/KEY: Xaa
<222> LOCATION: (93)..(93)
<223> OTHER INFORMATION: Xaa is any amino acid or absent, but not T
<220> FEATURE:
<221> NAME/KEY: Xaa
<222> LOCATION: (107)..(107)
<223> OTHER INFORMATION: Xaa is any amino acid or absent, but not H
<220> FEATURE:
<221> NAME/KEY: Xaa
<222> LOCATION: (110)..(110)
<223> OTHER INFORMATION: Xaa is any amino acid or absent, but not T
<220> FEATURE:
<221> NAME/KEY: Xaa
<222> LOCATION: (127)..(127)
<223> OTHER INFORMATION: Xaa is any amino acid or absent, but not I
<220> FEATURE:
<221> NAME/KEY: Xaa
<222> LOCATION: (130)..(130)
<223> OTHER INFORMATION: Xaa is any amino acid or absent, but not K
<220> FEATURE:
<221> NAME/KEY: Xaa
<222> LOCATION: (138)..(138)
<223> OTHER INFORMATION: Xaa is any amino acid or absent, but not D
<220> FEATURE:
<221> NAME/KEY: Xaa
<222> LOCATION: (141)..(141)
<223> OTHER INFORMATION: Xaa is any amino acid or absent, but not A
<220> FEATURE:
<221> NAME/KEY: Xaa
<222> LOCATION: (142)..(142)
<223> OTHER INFORMATION: Xaa is any amino acid or absent, but not K
<220> FEATURE:
<221> NAME/KEY: Xaa
<222> LOCATION: (146)..(146)
<223> OTHER INFORMATION: Xaa is any amino acid or absent, but not S

<400> SEQUENCE: 34

Pro Ile Xaa Met Ile Ser Tyr Ala Asp Glu Xaa Xaa Ala Xaa Val Ile
1               5                   10                  15
```

```
Thr Trp Lys Asn Xaa Asp Leu Pro Tyr Val Xaa Val Val Ser Xaa Glu
             20                  25                  30

Arg Glu Met Ile Lys Arg Phe Leu Arg Xaa Xaa Xaa Glu Lys Asp Pro
         35                  40                  45

Asp Xaa Xaa Xaa Thr Tyr Asn Gly Asp Xaa Phe Asp Phe Xaa Tyr Leu
     50                  55                  60

Xaa Lys Arg Xaa Glu Lys Leu Gly Ile Xaa Xaa Xaa Gly Arg Asp
 65              70                  75                  80

Gly Ser Glu Pro Lys Xaa Gln Arg Xaa Gly Asp Xaa Xaa Ala Val Glu
                 85                  90                  95

Val Lys Gly Arg Ile His Phe Asp Leu Tyr Xaa Val Ile Xaa Arg Thr
            100                 105                 110

Ile Asn Leu Pro Thr Tyr Thr Leu Glu Ala Val Tyr Glu Ala Xaa Phe
            115                 120                 125

Gly Xaa Pro Lys Glu Lys Val Tyr Ala Xaa Glu Ile Xaa Xaa Ala Trp
        130                 135                 140

Glu Xaa
145

<210> SEQ ID NO 35
<211> LENGTH: 137
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (17)..(17)
<223> OTHER INFORMATION: Xaa is any amino acid or absent, but not T
<220> FEATURE:
<221> NAME/KEY: Xaa
<222> LOCATION: (18)..(18)
<223> OTHER INFORMATION: Xaa is any amino acid or absent, but not I
<220> FEATURE:
<221> NAME/KEY: Xaa
<222> LOCATION: (21)..(21)
<223> OTHER INFORMATION: Xaa is any amino acid or absent, but not H
<220> FEATURE:
<221> NAME/KEY: Xaa
<222> LOCATION: (26)..(26)
<223> OTHER INFORMATION: Xaa is any amino acid or absent, but not E
<220> FEATURE:
<221> NAME/KEY: Xaa
<222> LOCATION: (35)..(35)
<223> OTHER INFORMATION: Xaa is any amino acid or absent, but not I
<220> FEATURE:
<221> NAME/KEY: Xaa
<222> LOCATION: (36)..(36)
<223> OTHER INFORMATION: Xaa is any amino acid or absent, but not Q
<220> FEATURE:
<221> NAME/KEY: Xaa
<222> LOCATION: (39)..(39)
<223> OTHER INFORMATION: Xaa is any amino acid or absent, but not A
<220> FEATURE:
<221> NAME/KEY: Xaa
<222> LOCATION: (40)..(40)
<223> OTHER INFORMATION: Xaa is any amino acid or absent, but not N
<220> FEATURE:
<221> NAME/KEY: Xaa
<222> LOCATION: (43)..(43)
<223> OTHER INFORMATION: Xaa is any amino acid or absent, but not I
<220> FEATURE:
<221> NAME/KEY: Xaa
<222> LOCATION: (49)..(49)
<223> OTHER INFORMATION: Xaa is any amino acid or absent, but not A
<220> FEATURE:
<221> NAME/KEY: Xaa
<222> LOCATION: (51)..(51)
<223> OTHER INFORMATION: Xaa is any amino acid or absent, but not Y
<220> FEATURE:
```

```
<221> NAME/KEY: Xaa
<222> LOCATION: (57)..(57)
<223> OTHER INFORMATION: Xaa is any amino acid or absent, but not P
<220> FEATURE:
<221> NAME/KEY: Xaa
<222> LOCATION: (59)..(59)
<223> OTHER INFORMATION: Xaa is any amino acid or absent, but not H
<220> FEATURE:
<221> NAME/KEY: Xaa
<222> LOCATION: (60)..(60)
<223> OTHER INFORMATION: Xaa is any amino acid or absent, but not E
<220> FEATURE:
<221> NAME/KEY: Xaa
<222> LOCATION: (64)..(64)
<223> OTHER INFORMATION: Xaa is any amino acid or absent, but not I
<220> FEATURE:
<221> NAME/KEY: Xaa
<222> LOCATION: (73)..(73)
<223> OTHER INFORMATION: Xaa is any amino acid or absent, but not K
<220> FEATURE:
<221> NAME/KEY: Xaa
<222> LOCATION: (77)..(77)
<223> OTHER INFORMATION: Xaa is any amino acid or absent, but not K
<220> FEATURE:
<221> NAME/KEY: Xaa
<222> LOCATION: (82)..(82)
<223> OTHER INFORMATION: Xaa is any amino acid or absent, but not K
<220> FEATURE:
<221> NAME/KEY: Xaa
<222> LOCATION: (85)..(85)
<223> OTHER INFORMATION: Xaa is any amino acid or absent, but not M
<220> FEATURE:
<221> NAME/KEY: Xaa
<222> LOCATION: (88)..(88)
<223> OTHER INFORMATION: Xaa is any amino acid or absent, but not G
<220> FEATURE:
<221> NAME/KEY: Xaa
<222> LOCATION: (93)..(93)
<223> OTHER INFORMATION: Xaa is any amino acid or absent, but not R
<220> FEATURE:
<221> NAME/KEY: Xaa
<222> LOCATION: (95)..(95)
<223> OTHER INFORMATION: Xaa is any amino acid or absent, but not D
<220> FEATURE:
<221> NAME/KEY: Xaa
<222> LOCATION: (97)..(97)
<223> OTHER INFORMATION: Xaa is any amino acid or absent, but not P
<220> FEATURE:
<221> NAME/KEY: Xaa
<222> LOCATION: (99)..(99)
<223> OTHER INFORMATION: Xaa is any amino acid or absent, but not S
<220> FEATURE:
<221> NAME/KEY: Xaa
<222> LOCATION: (100)..(100)
<223> OTHER INFORMATION: Xaa is any amino acid or absent, but not N
<220> FEATURE:
<221> NAME/KEY: Xaa
<222> LOCATION: (104)..(104)
<223> OTHER INFORMATION: Xaa is any amino acid or absent, but not L
<220> FEATURE:
<221> NAME/KEY: Xaa
<222> LOCATION: (105)..(105)
<223> OTHER INFORMATION: Xaa is any amino acid or absent, but not A
<220> FEATURE:
<221> NAME/KEY: Xaa
<222> LOCATION: (106)..(106)
<223> OTHER INFORMATION: Xaa is any amino acid or absent, but not E
<220> FEATURE:
<221> NAME/KEY: Xaa
<222> LOCATION: (108)..(108)
<223> OTHER INFORMATION: Xaa is any amino acid or absentd, but not Y
<220> FEATURE:
<221> NAME/KEY: Xaa
<222> LOCATION: (111)..(111)
<223> OTHER INFORMATION: Xaa is any amino acid or absent, but not K
<220> FEATURE:
<221> NAME/KEY: Xaa
<222> LOCATION: (130)..(130)
<223> OTHER INFORMATION: Xaa is any amino acid or absent, but not L
```

-continued

```
<220> FEATURE:
<221> NAME/KEY: Xaa
<222> LOCATION: (134)..(134)
<223> OTHER INFORMATION: Xaa is any amino acid or absent, but not E
<220> FEATURE:
<221> NAME/KEY: Xaa
<222> LOCATION: (135)..(135)
<223> OTHER INFORMATION: Xaa is any amino acid or absent, but not G

<400> SEQUENCE: 35

Arg Asp Trp Ser Glu Ile Ala Lys Glu Thr Gln Ala Arg Val Leu Glu
1               5                   10                  15

Xaa Xaa Leu Lys Xaa Gly Asp Val Glu Xaa Ala Val Arg Ile Val Lys
            20                  25                  30

Glu Val Xaa Xaa Lys Leu Xaa Xaa Tyr Glu Xaa Pro Pro Glu Lys Leu
        35                  40                  45

Xaa Ile Xaa Glu Gln Ile Thr Arg Xaa Leu Xaa Xaa Tyr Lys Ala Xaa
    50                  55                  60

Gly Pro His Val Ala Val Ala Lys Xaa Leu Ala Ala Xaa Gly Val Lys
65                  70                  75                  80

Ile Xaa Pro Gly Xaa Val Ile Xaa Tyr Ile Val Leu Xaa Gly Xaa Gly
                85                  90                  95

Xaa Ile Xaa Xaa Arg Ala Ile Xaa Xaa Xaa Glu Xaa Asp Pro Xaa Lys
            100                 105                 110

His Lys Tyr Asp Ala Glu Tyr Tyr Ile Glu Asn Gln Val Leu Pro Ala
        115                 120                 125

Val Xaa Arg Ile Leu Xaa Xaa Phe Gly
    130                 135

<210> SEQ ID NO 36
<211> LENGTH: 170
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (1)..(1)
<223> OTHER INFORMATION: Xaa is any amino acid or absent
<220> FEATURE:
<221> NAME/KEY: Xaa
<222> LOCATION: (3)..(14)
<223> OTHER INFORMATION: Xaa is any amino acid or absent
<220> FEATURE:
<221> NAME/KEY: Xaa
<222> LOCATION: (16)..(32)
<223> OTHER INFORMATION: Xaa is any amino acid or absent
<220> FEATURE:
<221> NAME/KEY: Xaa
<222> LOCATION: (34)..(37)
<223> OTHER INFORMATION: Xaa is any amino acid or absent
<220> FEATURE:
<221> NAME/KEY: Xaa
<222> LOCATION: (39)..(40)
<223> OTHER INFORMATION: Xaa is any amino acid or absent
<220> FEATURE:
<221> NAME/KEY: Xaa
<222> LOCATION: (42)..(47)
<223> OTHER INFORMATION: Xaa is any amino acid or absent
<220> FEATURE:
<221> NAME/KEY: Xaa
<222> LOCATION: (49)..(52)
<223> OTHER INFORMATION: Xaa is any amino acid or absent
<220> FEATURE:
<221> NAME/KEY: Xaa
<222> LOCATION: (54)..(62)
<223> OTHER INFORMATION: Xaa is any amino acid or absent
<220> FEATURE:
<221> NAME/KEY: Xaa
```

```
<222> LOCATION: (64)..(72)
<223> OTHER INFORMATION: Xaa is any amino acid or absent
<220> FEATURE:
<221> NAME/KEY: Xaa
<222> LOCATION: (74)..(76)
<223> OTHER INFORMATION: Xaa is any amino acid or absent
<220> FEATURE:
<221> NAME/KEY: Xaa
<222> LOCATION: (78)..(78)
<223> OTHER INFORMATION: Xaa is any amino acid or absent
<220> FEATURE:
<221> NAME/KEY: Xaa
<222> LOCATION: (80)..(83)
<223> OTHER INFORMATION: Xaa is any amino acid or absent
<220> FEATURE:
<221> NAME/KEY: Xaa
<222> LOCATION: (86)..(91)
<223> OTHER INFORMATION: Xaa is any amino acid or absent
<220> FEATURE:
<221> NAME/KEY: Xaa
<222> LOCATION: (93)..(95)
<223> OTHER INFORMATION: Xaa is any amino acid or absent
<220> FEATURE:
<221> NAME/KEY: Xaa
<222> LOCATION: (97)..(100)
<223> OTHER INFORMATION: Xaa is any amino acid or absent
<220> FEATURE:
<221> NAME/KEY: Xaa
<222> LOCATION: (102)..(108)
<223> OTHER INFORMATION: Xaa is any amino acid or absent
<220> FEATURE:
<221> NAME/KEY: Xaa
<222> LOCATION: (110)..(126)
<223> OTHER INFORMATION: Xaa is any amino acid or absent
<220> FEATURE:
<221> NAME/KEY: Xaa
<222> LOCATION: (128)..(129)
<223> OTHER INFORMATION: Xaa is any amino acid or absent
<220> FEATURE:
<221> NAME/KEY: Xaa
<222> LOCATION: (134)..(135)
<223> OTHER INFORMATION: Xaa is any amino acid or absent
<220> FEATURE:
<221> NAME/KEY: Xaa
<222> LOCATION: (137)..(139)
<223> OTHER INFORMATION: Xaa is any amino acid or absent
<220> FEATURE:
<221> NAME/KEY: Xaa
<222> LOCATION: (141)..(144)
<223> OTHER INFORMATION: Xaa is any amino acid or absent
<220> FEATURE:
<221> NAME/KEY: Xaa
<222> LOCATION: (146)..(146)
<223> OTHER INFORMATION: Xaa is any amino acid or absent
<220> FEATURE:
<221> NAME/KEY: Xaa
<222> LOCATION: (148)..(151)
<223> OTHER INFORMATION: Xaa is any amino acid or absent
<220> FEATURE:
<221> NAME/KEY: Xaa
<222> LOCATION: (154)..(158)
<223> OTHER INFORMATION: Xaa is any amino acid or absent
<220> FEATURE:
<221> NAME/KEY: Xaa
<222> LOCATION: (162)..(162)
<223> OTHER INFORMATION: Xaa is any amino acid or absent
<220> FEATURE:
<221> NAME/KEY: Xaa
<222> LOCATION: (165)..(168)
<223> OTHER INFORMATION: Xaa is any amino acid or absent
<220> FEATURE:
<221> NAME/KEY: Xaa
<222> LOCATION: (170)..(170)
<223> OTHER INFORMATION: Xaa is any amino acid or absent

<400> SEQUENCE: 36

Xaa Lys Xaa Xaa Xaa Xaa Xaa Xaa Xaa Xaa Xaa Xaa Xaa Xaa Ala Xaa
1               5                   10                  15
```

Xaa Xaa Xaa Xaa Xaa Xaa Xaa Xaa Xaa Xaa Xaa Xaa Xaa Xaa Xaa
                    20                  25                  30

Leu Xaa Xaa Xaa Xaa Asn Xaa Xaa Ile Xaa Xaa Xaa Xaa Xaa Lys
        35                  40                  45

Xaa Xaa Xaa Xaa Ile Xaa Xaa Xaa Xaa Xaa Xaa Xaa Xaa His Xaa
 50                  55                  60

Xaa Xaa Xaa Xaa Xaa Xaa Xaa Xaa Thr Xaa Xaa Xaa Glu Xaa Gln Xaa
 65                  70                  75                  80

Xaa Xaa Xaa Lys Ile Xaa Xaa Xaa Xaa Xaa Lys Xaa Xaa Xaa Leu
            85                  90                  95

Xaa Xaa Xaa Xaa Phe Xaa Xaa Xaa Xaa Xaa Xaa Lys Xaa Xaa Xaa
                100                 105                 110

Xaa Xaa Xaa Xaa Xaa Xaa Xaa Xaa Xaa Xaa Xaa Xaa Xaa Lys Xaa
            115                 120                 125

Xaa Glu Leu Val Trp Xaa Xaa Leu Xaa Xaa Xaa Phe Xaa Xaa Xaa Xaa
 130                 135                 140

Leu Xaa Ile Xaa Xaa Xaa Xaa Leu Tyr Xaa Xaa Xaa Xaa Gly Glu
145                 150                 155                 160

Ser Xaa Glu Ile Xaa Xaa Xaa Xaa Leu Xaa
        165                 170

<210> SEQ ID NO 37
<211> LENGTH: 170
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (2)..(2)
<223> OTHER INFORMATION: Xaa is any amino acid or absent, but not R
<220> FEATURE:
<221> NAME/KEY: Xaa
<222> LOCATION: (15)..(15)
<223> OTHER INFORMATION: Xaa is any amino acid or absent, but not S
<220> FEATURE:
<221> NAME/KEY: Xaa
<222> LOCATION: (33)..(33)
<223> OTHER INFORMATION: Xaa is any amino acid or absent, but not R
<220> FEATURE:
<221> NAME/KEY: Xaa
<222> LOCATION: (38)..(38)
<223> OTHER INFORMATION: Xaa is any amino acid or absent, but not E
<220> FEATURE:
<221> NAME/KEY: Xaa
<222> LOCATION: (41)..(41)
<223> OTHER INFORMATION: Xaa is any amino acid or absent, but not V
<220> FEATURE:
<221> NAME/KEY: Xaa
<222> LOCATION: (48)..(48)
<223> OTHER INFORMATION: Xaa is any amino acid or absent, but not R
<220> FEATURE:
<221> NAME/KEY: Xaa
<222> LOCATION: (53)..(53)
<223> OTHER INFORMATION: Xaa is any amino acid or absent, but not F
<220> FEATURE:
<221> NAME/KEY: Xaa
<222> LOCATION: (63)..(63)
<223> OTHER INFORMATION: Xaa is any amino acid or absent, but not D
<220> FEATURE:
<221> NAME/KEY: Xaa
<222> LOCATION: (73)..(73)
<223> OTHER INFORMATION: Xaa is any amino acid or absent, but not K
<220> FEATURE:
<221> NAME/KEY: Xaa
<222> LOCATION: (77)..(77)
<223> OTHER INFORMATION: Xaa is any amino acid or absent, but not A
<220> FEATURE:

```
<221> NAME/KEY: Xaa
<222> LOCATION: (79)..(79)
<223> OTHER INFORMATION: Xaa is any amino acid or absent, but not I
<220> FEATURE:
<221> NAME/KEY: Xaa
<222> LOCATION: (84)..(84)
<223> OTHER INFORMATION: Xaa is any amino acid or absent, but not R
<220> FEATURE:
<221> NAME/KEY: Xaa
<222> LOCATION: (85)..(85)
<223> OTHER INFORMATION: Xaa is any amino acid or absent, but not K
<220> FEATURE:
<221> NAME/KEY: Xaa
<222> LOCATION: (92)..(92)
<223> OTHER INFORMATION: Xaa is any amino acid or absent, but not R
<220> FEATURE:
<221> NAME/KEY: Xaa
<222> LOCATION: (96)..(96)
<223> OTHER INFORMATION: Xaa is any amino acid or absent, but not I
<220> FEATURE:
<221> NAME/KEY: Xaa
<222> LOCATION: (101)..(101)
<223> OTHER INFORMATION: Xaa is any amino acid or absent, but not Y
<220> FEATURE:
<221> NAME/KEY: Xaa
<222> LOCATION: (109)..(109)
<223> OTHER INFORMATION: Xaa is any amino acid or absent, but not R
<220> FEATURE:
<221> NAME/KEY: Xaa
<222> LOCATION: (127)..(127)
<223> OTHER INFORMATION: Xaa is any amino acid or absent, but not E
<220> FEATURE:
<221> NAME/KEY: Xaa
<222> LOCATION: (130)..(130)
<223> OTHER INFORMATION: Xaa is any amino acid or absent, but not T
<220> FEATURE:
<221> NAME/KEY: Xaa
<222> LOCATION: (131)..(131)
<223> OTHER INFORMATION: Xaa is any amino acid or absent, but not M
<220> FEATURE:
<221> NAME/KEY: Xaa
<222> LOCATION: (132)..(132)
<223> OTHER INFORMATION: Xaa is any amino acid or absent, but not T
<220> FEATURE:
<221> NAME/KEY: Xaa
<222> LOCATION: (133)..(133)
<223> OTHER INFORMATION: Xaa is any amino acid or absent, but not I
<220> FEATURE:
<221> NAME/KEY: Xaa
<222> LOCATION: (136)..(136)
<223> OTHER INFORMATION: Xaa is any amino acid or absent, but not I
<220> FEATURE:
<221> NAME/KEY: Xaa
<222> LOCATION: (140)..(140)
<223> OTHER INFORMATION: Xaa is any amino acid or absent, but not Y
<220> FEATURE:
<221> NAME/KEY: Xaa
<222> LOCATION: (145)..(145)
<223> OTHER INFORMATION: Xaa is any amino acid or absent, but not I
<220> FEATURE:
<221> NAME/KEY: Xaa
<222> LOCATION: (147)..(147)
<223> OTHER INFORMATION: Xaa is any amino acid or absent, but not S
<220> FEATURE:
<221> NAME/KEY: Xaa
<222> LOCATION: (152)..(152)
<223> OTHER INFORMATION: Xaa is any amino acid or absent, but not F
<220> FEATURE:
<221> NAME/KEY: Xaa
<222> LOCATION: (153)..(153)
<223> OTHER INFORMATION: Xaa is any amino acid or absent, but not F
<220> FEATURE:
<221> NAME/KEY: Xaa
<222> LOCATION: (159)..(159)
<223> OTHER INFORMATION: Xaa is any amino acid or absent, but not A
<220> FEATURE:
<221> NAME/KEY: Xaa
<222> LOCATION: (160)..(160)
<223> OTHER INFORMATION: Xaa is any amino acid or absent, but not D
```

```
<220> FEATURE:
<221> NAME/KEY: Xaa
<222> LOCATION: (161)..(161)
<223> OTHER INFORMATION: Xaa is any amino acid or absent, but not A
<220> FEATURE:
<221> NAME/KEY: Xaa
<222> LOCATION: (163)..(163)
<223> OTHER INFORMATION: Xaa is any amino acid or absent, but not T
<220> FEATURE:
<221> NAME/KEY: Xaa
<222> LOCATION: (164)..(164)
<223> OTHER INFORMATION: Xaa is any amino acid or absent, but not V
<220> FEATURE:
<221> NAME/KEY: Xaa
<222> LOCATION: (169)..(169)
<223> OTHER INFORMATION: Xaa is any amino acid or absent, but not M

<400> SEQUENCE: 37

Glu Xaa Gly Leu Trp Glu Asn Ile Val Tyr Leu Asp Phe Arg Xaa Leu
1               5                   10                  15

Tyr Pro Ser Ile Ile Ile Thr His Asn Val Ser Pro Asp Thr Leu Asn
            20                  25                  30

Xaa Glu Gly Cys Lys Xaa Tyr Asp Xaa Ala Pro Gln Val Gly His Xaa
        35                  40                  45

Phe Cys Lys Asp Xaa Pro Gly Phe Ile Pro Ser Leu Leu Gly Xaa Leu
    50                  55                  60

Leu Glu Glu Arg Gln Lys Ile Lys Xaa Lys Met Lys Xaa Thr Xaa Asp
65                  70                  75                  80

Pro Ile Glu Xaa Xaa Leu Leu Asp Tyr Arg Gln Xaa Ala Ile Lys Xaa
                85                  90                  95

Leu Ala Asn Ser Xaa Tyr Gly Tyr Tyr Gly Tyr Ala Xaa Ala Arg Trp
            100                 105                 110

Tyr Cys Lys Glu Cys Ala Glu Ser Val Thr Ala Trp Gly Arg Xaa Tyr
            115                 120                 125

Ile Xaa Xaa Xaa Xaa Lys Glu Xaa Glu Glu Lys Xaa Gly Phe Lys Val
    130                 135                 140

Xaa Tyr Xaa Asp Thr Asp Gly Xaa Xaa Ala Thr Ile Pro Gly Xaa Xaa
145                 150                 155                 160

Xaa Glu Xaa Xaa Lys Lys Lys Ala Xaa Glu
                165                 170

<210> SEQ ID NO 38
<211> LENGTH: 777
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (1)..(4)
<223> OTHER INFORMATION: Xaa is any amino acid or absent
<220> FEATURE:
<221> NAME/KEY: Xaa
<222> LOCATION: (6)..(10)
<223> OTHER INFORMATION: Xaa is any amino acid or absent
<220> FEATURE:
<221> NAME/KEY: Xaa
<222> LOCATION: (12)..(17)
<223> OTHER INFORMATION: Xaa is any amino acid or absent
<220> FEATURE:
<221> NAME/KEY: Xaa
<222> LOCATION: (19)..(24)
<223> OTHER INFORMATION: Xaa is any amino acid or absent
<220> FEATURE:
<221> NAME/KEY: Xaa
<222> LOCATION: (26)..(29)
<223> OTHER INFORMATION: Xaa is any amino acid or absent
```

```
<220> FEATURE:
<221> NAME/KEY: Xaa
<222> LOCATION: (31)..(34)
<223> OTHER INFORMATION: Xaa is any amino acid or absent
<220> FEATURE:
<221> NAME/KEY: Xaa
<222> LOCATION: (36)..(37)
<223> OTHER INFORMATION: Xaa is any amino acid or absent
<220> FEATURE:
<221> NAME/KEY: Xaa
<222> LOCATION: (39)..(42)
<223> OTHER INFORMATION: Xaa is any amino acid or absent
<220> FEATURE:
<221> NAME/KEY: Xaa
<222> LOCATION: (44)..(46)
<223> OTHER INFORMATION: Xaa is any amino acid or absent
<220> FEATURE:
<221> NAME/KEY: Xaa
<222> LOCATION: (48)..(55)
<223> OTHER INFORMATION: Xaa is any amino acid or absent
<220> FEATURE:
<221> NAME/KEY: Xaa
<222> LOCATION: (57)..(60)
<223> OTHER INFORMATION: Xaa is any amino acid or absent
<220> FEATURE:
<221> NAME/KEY: Xaa
<222> LOCATION: (63)..(63)
<223> OTHER INFORMATION: Xaa is any amino acid or absent
<220> FEATURE:
<221> NAME/KEY: Xaa
<222> LOCATION: (68)..(71)
<223> OTHER INFORMATION: Xaa is any amino acid or absent
<220> FEATURE:
<221> NAME/KEY: Xaa
<222> LOCATION: (73)..(77)
<223> OTHER INFORMATION: Xaa is any amino acid or absent
<220> FEATURE:
<221> NAME/KEY: Xaa
<222> LOCATION: (79)..(79)
<223> OTHER INFORMATION: Xaa is any amino acid or absent
<220> FEATURE:
<221> NAME/KEY: Xaa
<222> LOCATION: (82)..(86)
<223> OTHER INFORMATION: Xaa is any amino acid or absent
<220> FEATURE:
<221> NAME/KEY: Xaa
<222> LOCATION: (89)..(94)
<223> OTHER INFORMATION: Xaa is any amino acid or absent
<220> FEATURE:
<221> NAME/KEY: Xaa
<222> LOCATION: (96)..(97)
<223> OTHER INFORMATION: Xaa is any amino acid or absent
<220> FEATURE:
<221> NAME/KEY: Xaa
<222> LOCATION: (99)..(99)
<223> OTHER INFORMATION: Xaa is any amino acid or absent
<220> FEATURE:
<221> NAME/KEY: Xaa
<222> LOCATION: (101)..(106)
<223> OTHER INFORMATION: Xaa is any amino acid or absent
<220> FEATURE:
<221> NAME/KEY: Xaa
<222> LOCATION: (108)..(109)
<223> OTHER INFORMATION: Xaa is any amino acid or absent
<220> FEATURE:
<221> NAME/KEY: Xaa
<222> LOCATION: (111)..(126)
<223> OTHER INFORMATION: Xaa is any amino acid or absent
<220> FEATURE:
<221> NAME/KEY: Xaa
<222> LOCATION: (128)..(131)
<223> OTHER INFORMATION: Xaa is any amino acid or absent
<220> FEATURE:
<221> NAME/KEY: Xaa
<222> LOCATION: (133)..(136)
<223> OTHER INFORMATION: Xaa is any amino acid or absent
<220> FEATURE:
<221> NAME/KEY: Xaa
<222> LOCATION: (138)..(152)
```

```
<223> OTHER INFORMATION: Xaa is any amino acid or absent
<220> FEATURE:
<221> NAME/KEY: Xaa
<222> LOCATION: (155)..(157)
<223> OTHER INFORMATION: Xaa is any amino acid or absent
<220> FEATURE:
<221> NAME/KEY: Xaa
<222> LOCATION: (159)..(165)
<223> OTHER INFORMATION: Xaa is any amino acid or absent
<220> FEATURE:
<221> NAME/KEY: Xaa
<222> LOCATION: (168)..(168)
<223> OTHER INFORMATION: Xaa is any amino acid or absent
<220> FEATURE:
<221> NAME/KEY: Xaa
<222> LOCATION: (170)..(175)
<223> OTHER INFORMATION: Xaa is any amino acid or absent
<220> FEATURE:
<221> NAME/KEY: Xaa
<222> LOCATION: (177)..(181)
<223> OTHER INFORMATION: Xaa is any amino acid or absent
<220> FEATURE:
<221> NAME/KEY: Xaa
<222> LOCATION: (183)..(185)
<223> OTHER INFORMATION: Xaa is any amino acid or absent
<220> FEATURE:
<221> NAME/KEY: Xaa
<222> LOCATION: (187)..(196)
<223> OTHER INFORMATION: Xaa is any amino acid or absent
<220> FEATURE:
<221> NAME/KEY: Xaa
<222> LOCATION: (200)..(204)
<223> OTHER INFORMATION: Xaa is any amino acid or absent
<220> FEATURE:
<221> NAME/KEY: Xaa
<222> LOCATION: (208)..(212)
<223> OTHER INFORMATION: Xaa is any amino acid or absent
<220> FEATURE:
<221> NAME/KEY: Xaa
<222> LOCATION: (214)..(216)
<223> OTHER INFORMATION: Xaa is any amino acid or absent
<220> FEATURE:
<221> NAME/KEY: Xaa
<222> LOCATION: (218)..(219)
<223> OTHER INFORMATION: Xaa is any amino acid or absent
<220> FEATURE:
<221> NAME/KEY: Xaa
<222> LOCATION: (221)..(222)
<223> OTHER INFORMATION: Xaa is any amino acid or absent
<220> FEATURE:
<221> NAME/KEY: Xaa
<222> LOCATION: (224)..(228)
<223> OTHER INFORMATION: Xaa is any amino acid or absent
<220> FEATURE:
<221> NAME/KEY: Xaa
<222> LOCATION: (233)..(242)
<223> OTHER INFORMATION: Xaa is any amino acid or absent
<220> FEATURE:
<221> NAME/KEY: Xaa
<222> LOCATION: (244)..(245)
<223> OTHER INFORMATION: Xaa is any amino acid or absent
<220> FEATURE:
<221> NAME/KEY: Xaa
<222> LOCATION: (247)..(248)
<223> OTHER INFORMATION: Xaa is any amino acid or absent
<220> FEATURE:
<221> NAME/KEY: Xaa
<222> LOCATION: (251)..(263)
<223> OTHER INFORMATION: Xaa is any amino acid or absent
<220> FEATURE:
<221> NAME/KEY: Xaa
<222> LOCATION: (265)..(266)
<223> OTHER INFORMATION: Xaa is any amino acid or absent
<220> FEATURE:
<221> NAME/KEY: Xaa
<222> LOCATION: (268)..(283)
<223> OTHER INFORMATION: Xaa is any amino acid or absent
<220> FEATURE:
<221> NAME/KEY: Xaa
```

-continued

```
<222> LOCATION: (285)..(286)
<223> OTHER INFORMATION: Xaa is any amino acid or absent
<220> FEATURE:
<221> NAME/KEY: Xaa
<222> LOCATION: (288)..(294)
<223> OTHER INFORMATION: Xaa is any amino acid or absent
<220> FEATURE:
<221> NAME/KEY: Xaa
<222> LOCATION: (296)..(297)
<223> OTHER INFORMATION: Xaa is any amino acid or absent
<220> FEATURE:
<221> NAME/KEY: Xaa
<222> LOCATION: (300)..(302)
<223> OTHER INFORMATION: Xaa is any amino acid or absent
<220> FEATURE:
<221> NAME/KEY: Xaa
<222> LOCATION: (304)..(311)
<223> OTHER INFORMATION: Xaa is any amino acid or absent
<220> FEATURE:
<221> NAME/KEY: Xaa
<222> LOCATION: (313)..(319)
<223> OTHER INFORMATION: Xaa is any amino acid or absent
<220> FEATURE:
<221> NAME/KEY: Xaa
<222> LOCATION: (321)..(332)
<223> OTHER INFORMATION: Xaa is any amino acid or absent
<220> FEATURE:
<221> NAME/KEY: Xaa
<222> LOCATION: (334)..(338)
<223> OTHER INFORMATION: Xaa is any amino acid or absent
<220> FEATURE:
<221> NAME/KEY: Xaa
<222> LOCATION: (340)..(341)
<223> OTHER INFORMATION: Xaa is any amino acid or absent
<220> FEATURE:
<221> NAME/KEY: Xaa
<222> LOCATION: (343)..(368)
<223> OTHER INFORMATION: Xaa is any amino acid or absent
<220> FEATURE:
<221> NAME/KEY: Xaa
<222> LOCATION: (370)..(374)
<223> OTHER INFORMATION: Xaa is any amino acid or absent
<220> FEATURE:
<221> NAME/KEY: Xaa
<222> LOCATION: (376)..(376)
<223> OTHER INFORMATION: Xaa is any amino acid or absent
<220> FEATURE:
<221> NAME/KEY: Xaa
<222> LOCATION: (378)..(378)
<223> OTHER INFORMATION: Xaa is any amino acid or absent
<220> FEATURE:
<221> NAME/KEY: Xaa
<222> LOCATION: (381)..(384)
<223> OTHER INFORMATION: Xaa is any amino acid or absent
<220> FEATURE:
<221> NAME/KEY: Xaa
<222> LOCATION: (386)..(387)
<223> OTHER INFORMATION: Xaa is any amino acid or absent
<220> FEATURE:
<221> NAME/KEY: Xaa
<222> LOCATION: (389)..(390)
<223> OTHER INFORMATION: Xaa is any amino acid or absent
<220> FEATURE:
<221> NAME/KEY: Xaa
<222> LOCATION: (392)..(396)
<223> OTHER INFORMATION: Xaa is any amino acid or absent
<220> FEATURE:
<221> NAME/KEY: Xaa
<222> LOCATION: (398)..(409)
<223> OTHER INFORMATION: Xaa is any amino acid or absent
<220> FEATURE:
<221> NAME/KEY: Xaa
<222> LOCATION: (411)..(427)
<223> OTHER INFORMATION: Xaa is any amino acid or absent
<220> FEATURE:
<221> NAME/KEY: Xaa
<222> LOCATION: (429)..(432)
<223> OTHER INFORMATION: Xaa is any amino acid or absent
<220> FEATURE:
```

```
<221> NAME/KEY: Xaa
<222> LOCATION: (434)..(435)
<223> OTHER INFORMATION: Xaa is any amino acid or absent
<220> FEATURE:
<221> NAME/KEY: Xaa
<222> LOCATION: (437)..(442)
<223> OTHER INFORMATION: Xaa is any amino acid or absent
<220> FEATURE:
<221> NAME/KEY: Xaa
<222> LOCATION: (444)..(447)
<223> OTHER INFORMATION: Xaa is any amino acid or absent
<220> FEATURE:
<221> NAME/KEY: Xaa
<222> LOCATION: (449)..(457)
<223> OTHER INFORMATION: Xaa is any amino acid or absent
<220> FEATURE:
<221> NAME/KEY: Xaa
<222> LOCATION: (459)..(467)
<223> OTHER INFORMATION: Xaa is any amino acid or absent
<220> FEATURE:
<221> NAME/KEY: Xaa
<222> LOCATION: (469)..(471)
<223> OTHER INFORMATION: Xaa is any amino acid or absent
<220> FEATURE:
<221> NAME/KEY: Xaa
<222> LOCATION: (473)..(473)
<223> OTHER INFORMATION: Xaa is any amino acid or absent
<220> FEATURE:
<221> NAME/KEY: Xaa
<222> LOCATION: (475)..(478)
<223> OTHER INFORMATION: Xaa is any amino acid or absent
<220> FEATURE:
<221> NAME/KEY: Xaa
<222> LOCATION: (481)..(486)
<223> OTHER INFORMATION: Xaa is any amino acid or absent
<220> FEATURE:
<221> NAME/KEY: Xaa
<222> LOCATION: (488)..(490)
<223> OTHER INFORMATION: Xaa is any amino acid or absent
<220> FEATURE:
<221> NAME/KEY: Xaa
<222> LOCATION: (492)..(495)
<223> OTHER INFORMATION: Xaa is any amino acid or absent
<220> FEATURE:
<221> NAME/KEY: Xaa
<222> LOCATION: (497)..(503)
<223> OTHER INFORMATION: Xaa is any amino acid or absent
<220> FEATURE:
<221> NAME/KEY: Xaa
<222> LOCATION: (505)..(521)
<223> OTHER INFORMATION: Xaa is any amino acid or absent
<220> FEATURE:
<221> NAME/KEY: Xaa
<222> LOCATION: (523)..(524)
<223> OTHER INFORMATION: Xaa is any amino acid or absent
<220> FEATURE:
<221> NAME/KEY: Xaa
<222> LOCATION: (529)..(530)
<223> OTHER INFORMATION: Xaa is any amino acid or absent
<220> FEATURE:
<221> NAME/KEY: Xaa
<222> LOCATION: (532)..(534)
<223> OTHER INFORMATION: Xaa is any amino acid or absent
<220> FEATURE:
<221> NAME/KEY: Xaa
<222> LOCATION: (536)..(539)
<223> OTHER INFORMATION: Xaa is any amino acid or absent
<220> FEATURE:
<221> NAME/KEY: Xaa
<222> LOCATION: (541)..(541)
<223> OTHER INFORMATION: Xaa is any amino acid or absent
<220> FEATURE:
<221> NAME/KEY: Xaa
<222> LOCATION: (543)..(546)
<223> OTHER INFORMATION: Xaa is any amino acid or absent
<220> FEATURE:
<221> NAME/KEY: Xaa
<222> LOCATION: (549)..(553)
<223> OTHER INFORMATION: Xaa is any amino acid or absent
```

-continued

```
<220> FEATURE:
<221> NAME/KEY: Xaa
<222> LOCATION: (557)..(557)
<223> OTHER INFORMATION: Xaa is any amino acid or absent
<220> FEATURE:
<221> NAME/KEY: Xaa
<222> LOCATION: (560)..(563)
<223> OTHER INFORMATION: Xaa is any amino acid or absent
<220> FEATURE:
<221> NAME/KEY: Xaa
<222> LOCATION: (565)..(566)
<223> OTHER INFORMATION: Xaa is any amino acid or absent
<220> FEATURE:
<221> NAME/KEY: Xaa
<222> LOCATION: (568)..(571)
<223> OTHER INFORMATION: Xaa is any amino acid or absent
<220> FEATURE:
<221> NAME/KEY: Xaa
<222> LOCATION: (573)..(576)
<223> OTHER INFORMATION: Xaa is any amino acid or absent
<220> FEATURE:
<221> NAME/KEY: Xaa
<222> LOCATION: (578)..(595)
<223> OTHER INFORMATION: Xaa is any amino acid or absent
<220> FEATURE:
<221> NAME/KEY: Xaa
<222> LOCATION: (597)..(605)
<223> OTHER INFORMATION: Xaa is any amino acid or absent
<220> FEATURE:
<221> NAME/KEY: Xaa
<222> LOCATION: (608)..(631)
<223> OTHER INFORMATION: Xaa is any amino acid or absent
<220> FEATURE:
<221> NAME/KEY: Xaa
<222> LOCATION: (634)..(635)
<223> OTHER INFORMATION: Xaa is any amino acid or absent
<220> FEATURE:
<221> NAME/KEY: Xaa
<222> LOCATION: (637)..(640)
<223> OTHER INFORMATION: Xaa is any amino acid or absent
<220> FEATURE:
<221> NAME/KEY: Xaa
<222> LOCATION: (642)..(649)
<223> OTHER INFORMATION: Xaa is any amino acid or absent
<220> FEATURE:
<221> NAME/KEY: Xaa
<222> LOCATION: (652)..(653)
<223> OTHER INFORMATION: Xaa is any amino acid or absent
<220> FEATURE:
<221> NAME/KEY: Xaa
<222> LOCATION: (656)..(657)
<223> OTHER INFORMATION: Xaa is any amino acid or absent
<220> FEATURE:
<221> NAME/KEY: Xaa
<222> LOCATION: (659)..(663)
<223> OTHER INFORMATION: Xaa is any amino acid or absent
<220> FEATURE:
<221> NAME/KEY: Xaa
<222> LOCATION: (665)..(665)
<223> OTHER INFORMATION: Xaa is any amino acid or absent
<220> FEATURE:
<221> NAME/KEY: Xaa
<222> LOCATION: (667)..(671)
<223> OTHER INFORMATION: Xaa is any amino acid or absent
<220> FEATURE:
<221> NAME/KEY: Xaa
<222> LOCATION: (673)..(673)
<223> OTHER INFORMATION: Xaa is any amino acid or absent
<220> FEATURE:
<221> NAME/KEY: Xaa
<222> LOCATION: (676)..(678)
<223> OTHER INFORMATION: Xaa is any amino acid or absent
<220> FEATURE:
<221> NAME/KEY: Xaa
<222> LOCATION: (680)..(687)
<223> OTHER INFORMATION: Xaa is any amino acid or absent
<220> FEATURE:
<221> NAME/KEY: Xaa
<222> LOCATION: (689)..(691)
```

```
<223> OTHER INFORMATION: Xaa is any amino acid or absent
<220> FEATURE:
<221> NAME/KEY: Xaa
<222> LOCATION: (693)..(696)
<223> OTHER INFORMATION: Xaa is any amino acid or absent
<220> FEATURE:
<221> NAME/KEY: Xaa
<222> LOCATION: (698)..(699)
<223> OTHER INFORMATION: Xaa is any amino acid or absent
<220> FEATURE:
<221> NAME/KEY: Xaa
<222> LOCATION: (701)..(702)
<223> OTHER INFORMATION: Xaa is any amino acid or absent
<220> FEATURE:
<221> NAME/KEY: Xaa
<222> LOCATION: (704)..(707)
<223> OTHER INFORMATION: Xaa is any amino acid or absent
<220> FEATURE:
<221> NAME/KEY: Xaa
<222> LOCATION: (709)..(709)
<223> OTHER INFORMATION: Xaa is any amino acid or absent
<220> FEATURE:
<221> NAME/KEY: Xaa
<222> LOCATION: (711)..(711)
<223> OTHER INFORMATION: Xaa is any amino acid or absent
<220> FEATURE:
<221> NAME/KEY: Xaa
<222> LOCATION: (713)..(713)
<223> OTHER INFORMATION: Xaa is any amino acid or absent
<220> FEATURE:
<221> NAME/KEY: Xaa
<222> LOCATION: (716)..(718)
<223> OTHER INFORMATION: Xaa is any amino acid or absent
<220> FEATURE:
<221> NAME/KEY: Xaa
<222> LOCATION: (722)..(722)
<223> OTHER INFORMATION: Xaa is any amino acid or absent
<220> FEATURE:
<221> NAME/KEY: Xaa
<222> LOCATION: (724)..(725)
<223> OTHER INFORMATION: Xaa is any amino acid or absent
<220> FEATURE:
<221> NAME/KEY: Xaa
<222> LOCATION: (727)..(744)
<223> OTHER INFORMATION: Xaa is any amino acid or absent
<220> FEATURE:
<221> NAME/KEY: Xaa
<222> LOCATION: (746)..(748)
<223> OTHER INFORMATION: Xaa is any amino acid or absent
<220> FEATURE:
<221> NAME/KEY: Xaa
<222> LOCATION: (751)..(768)
<223> OTHER INFORMATION: Xaa is any amino acid or absent
<220> FEATURE:
<221> NAME/KEY: Xaa
<222> LOCATION: (771)..(772)
<223> OTHER INFORMATION: Xaa is any amino acid or absent
<220> FEATURE:
<221> NAME/KEY: Xaa
<222> LOCATION: (775)..(775)
<223> OTHER INFORMATION: Xaa is any amino acid or absent

<400> SEQUENCE: 38

Xaa Xaa Xaa Xaa Thr Xaa Xaa Xaa Xaa Asp Xaa Xaa Xaa Xaa Xaa
1               5                   10                  15

Xaa Ile Xaa Xaa Xaa Xaa Xaa Glu Xaa Xaa Xaa Xaa Tyr Xaa Xaa
            20                  25                  30

Xaa Xaa Glu Xaa Xaa Phe Xaa Xaa Xaa Xaa Lys Xaa Xaa Xaa Ala Xaa
        35                  40                  45

Xaa Xaa Xaa Xaa Xaa Xaa Xaa Ala Xaa Xaa Xaa Xaa Thr Val Xaa Thr
    50                  55                  60

Val Lys Arg Xaa Xaa Xaa Xaa Gln Xaa Xaa Xaa Xaa Xaa Arg Xaa Val
65                  70                  75                  80
```

-continued

```
Glu Xaa Xaa Xaa Xaa Xaa Phe Thr Xaa Xaa Xaa Xaa Xaa Ala Xaa
                85              90              95

Xaa Asp Xaa Ile Xaa Xaa Xaa Xaa Xaa Ile Xaa Xaa Tyr Xaa Xaa
        100             105             110

Xaa Xaa Xaa Xaa Xaa Xaa Xaa Xaa Xaa Xaa Xaa Xaa Xaa Val Xaa
        115             120             125

Xaa Xaa Xaa Asp Xaa Xaa Xaa Xaa Met Xaa Xaa Xaa Xaa Xaa Xaa
        130             135             140

Xaa Xaa Xaa Xaa Xaa Xaa Xaa Ala Glu Xaa Xaa Leu Xaa Xaa
145             150             155             160

Xaa Xaa Xaa Xaa Xaa Glu Gly Xaa Arg Xaa Xaa Xaa Xaa Xaa Val
                165             170             175

Xaa Xaa Xaa Xaa Xaa Asp Xaa Xaa Xaa Thr Xaa Xaa Xaa Xaa Xaa
        180             185             190

Xaa Xaa Xaa Xaa Val Val Lys Xaa Xaa Xaa Xaa Xaa Val Leu Ile Xaa
        195             200             205

Xaa Xaa Xaa Xaa Asn Xaa Xaa Xaa Ala Xaa Xaa Lys Xaa Xaa Cys Xaa
        210             215             220

Xaa Xaa Xaa Xaa Asn Phe Ala Leu Xaa Xaa Xaa Xaa Xaa Xaa Xaa
225             230             235             240

Xaa Xaa Ile Xaa Xaa Met Xaa Xaa Arg Phe Xaa Xaa Xaa Xaa Xaa
        245             250             255

Xaa Xaa Xaa Xaa Xaa Xaa Xaa Pro Xaa Xaa Arg Xaa Xaa Xaa Xaa
        260             265             270

Xaa Xaa Xaa Xaa Xaa Xaa Xaa Xaa Xaa Val Xaa Xaa Gln Xaa
        275             280             285

Xaa Xaa Xaa Xaa Xaa Xaa Glu Xaa Xaa Thr Thr Xaa Xaa Xaa Thr Xaa
        290             295             300

Xaa Xaa Xaa Xaa Xaa Xaa Arg Xaa Xaa Xaa Xaa Xaa Xaa Xaa Val
305             310             315             320

Xaa Xaa Xaa Xaa Xaa Xaa Xaa Xaa Xaa Xaa Ala Xaa Xaa
        325             330             335

Xaa Xaa Val Xaa Xaa Pro Xaa Xaa Xaa Xaa Xaa Xaa Xaa Xaa
        340             345             350

Xaa Xaa Xaa Xaa Xaa Xaa Xaa Xaa Xaa Xaa Xaa Xaa Xaa Xaa
        355             360             365

Val Xaa Xaa Xaa Xaa Ser Xaa Glu Xaa Tyr Gln Xaa Xaa Xaa
        370             375             380

Glu Xaa Xaa Thr Xaa Xaa Phe Xaa Xaa Xaa Xaa Lys Xaa Xaa Xaa
385             390             395             400

Xaa Xaa Xaa Xaa Xaa Xaa Xaa Xaa Xaa Ala Xaa Xaa Xaa Xaa Xaa
        405             410             415

Xaa Xaa Xaa Xaa Xaa Xaa Xaa Xaa Xaa Leu Xaa Xaa Xaa Xaa
        420             425             430

Asn Xaa Xaa Ile Xaa Xaa Xaa Xaa Xaa Lys Xaa Xaa Xaa Xaa Ile
        435             440             445

Xaa Xaa Xaa Xaa Xaa Xaa Xaa Xaa His Xaa Xaa Xaa Xaa Xaa
450             455             460

Xaa Xaa Xaa Thr Xaa Xaa Xaa Glu Xaa Gln Xaa Xaa Xaa Xaa Lys Ile
465             470             475             480

Xaa Xaa Xaa Xaa Xaa Xaa Lys Xaa Xaa Xaa Leu Xaa Xaa Xaa Xaa Phe
                485             490             495

Xaa Xaa Xaa Xaa Xaa Xaa Xaa Lys Xaa Xaa Xaa Xaa Xaa Xaa Xaa
```

```
                500              505              510
Xaa Xaa Xaa Xaa Xaa Xaa Xaa Xaa Lys Xaa Xaa Glu Leu Val Trp
        515                 520                 525

Xaa Xaa Leu Xaa Xaa Xaa Phe Xaa Xaa Xaa Xaa Leu Xaa Ile Xaa Xaa
        530                 535                 540

Xaa Xaa Leu Tyr Xaa Xaa Xaa Xaa Xaa Gly Glu Ser Xaa Glu Ile Xaa
545                 550                 555                 560

Xaa Xaa Xaa Leu Xaa Xaa Leu Xaa Xaa Xaa Xaa Ala Xaa Xaa Xaa Xaa
                565                 570                 575

Ala Xaa Xaa Xaa Xaa Xaa Xaa Xaa Xaa Xaa Xaa Xaa Xaa Xaa Xaa
        580                 585                 590

Xaa Xaa Xaa Lys Xaa Xaa Xaa Xaa Xaa Xaa Xaa Xaa Ile Thr Xaa
        595                 600                 605

Xaa Xaa Xaa Xaa Xaa Xaa Xaa Xaa Xaa Xaa Xaa Xaa Xaa Xaa Xaa
        610                 615                 620

Xaa Xaa Xaa Xaa Xaa Xaa Xaa Ala Leu Xaa Xaa Asp Xaa Xaa Xaa Xaa
625                 630                 635                 640

Lys Xaa Xaa Xaa Xaa Xaa Xaa Xaa Xaa Thr Glu Xaa Xaa Ser Lys Xaa
                645                 650                 655

Xaa Val Xaa Xaa Xaa Xaa Xaa Val Xaa His Xaa Xaa Xaa Xaa Xaa Asp
        660                 665                 670

Xaa Lys Asp Xaa Xaa Xaa Thr Xaa Xaa Xaa Xaa Xaa Xaa Xaa Arg
        675                 680                 685

Xaa Xaa Xaa Arg Xaa Xaa Xaa Xaa Arg Xaa Xaa Thr Xaa Xaa Ser Xaa
        690                 695                 700

Xaa Xaa Xaa Lys Xaa Ser Xaa Arg Xaa Gly Asp Xaa Xaa Xaa Pro Phe
705                 710                 715                 720

Asp Xaa Phe Xaa Xaa Thr Xaa Xaa Xaa Xaa Xaa Xaa Xaa Xaa Xaa
        725                 730                 735

Xaa Xaa Xaa Xaa Xaa Xaa Xaa Xaa Glu Xaa Xaa Xaa Arg Ala Xaa Xaa
                740                 745                 750

Xaa Xaa Xaa Xaa Xaa Xaa Xaa Xaa Xaa Xaa Xaa Xaa Xaa Xaa Xaa
        755                 760                 765

Ser Ala Xaa Xaa Lys Pro Xaa Gly Thr
        770                 775

<210> SEQ ID NO 39
<211> LENGTH: 777
<212> TYPE: PRT
<213> ORGANISM: Artificial Sequence
<220> FEATURE:
<223> OTHER INFORMATION: Consensus Sequence
<220> FEATURE:
<221> NAME/KEY: Xaa
<222> LOCATION: (1)..(1)
<223> OTHER INFORMATION: Xaa is any amino acid or absent
<220> FEATURE:
<221> NAME/KEY: Xaa
<222> LOCATION: (3)..(3)
<223> OTHER INFORMATION: Xaa is any amino acid or absent
<220> FEATURE:
<221> NAME/KEY: Xaa
<222> LOCATION: (8)..(8)
<223> OTHER INFORMATION: Xaa is any amino acid or absent
<220> FEATURE:
<221> NAME/KEY: Xaa
<222> LOCATION: (10)..(10)
<223> OTHER INFORMATION: Xaa is any amino acid or absent
<220> FEATURE:
<221> NAME/KEY: Xaa
<222> LOCATION: (13)..(13)
```

```
<223> OTHER INFORMATION: Xaa is any amino acid or absent
<220> FEATURE:
<221> NAME/KEY: Xaa
<222> LOCATION: (15)..(16)
<223> OTHER INFORMATION: Xaa is any amino acid or absent
<220> FEATURE:
<221> NAME/KEY: Xaa
<222> LOCATION: (20)..(20)
<223> OTHER INFORMATION: Xaa is any amino acid or absent
<220> FEATURE:
<221> NAME/KEY: Xaa
<222> LOCATION: (22)..(23)
<223> OTHER INFORMATION: Xaa is any amino acid or absent
<220> FEATURE:
<221> NAME/KEY: Xaa
<222> LOCATION: (27)..(29)
<223> OTHER INFORMATION: Xaa is any amino acid or absent
<220> FEATURE:
<221> NAME/KEY: Xaa
<222> LOCATION: (32)..(33)
<223> OTHER INFORMATION: Xaa is any amino acid or absent
<220> FEATURE:
<221> NAME/KEY: Xaa
<222> LOCATION: (49)..(55)
<223> OTHER INFORMATION: Xaa is any amino acid or absent
<220> FEATURE:
<221> NAME/KEY: Xaa
<222> LOCATION: (57)..(57)
<223> OTHER INFORMATION: Xaa is any amino acid or absent
<220> FEATURE:
<221> NAME/KEY: Xaa
<222> LOCATION: (63)..(63)
<223> OTHER INFORMATION: Xaa is any amino acid or absent
<220> FEATURE:
<221> NAME/KEY: Xaa
<222> LOCATION: (68)..(71)
<223> OTHER INFORMATION: Xaa is any amino acid or absent
<220> FEATURE:
<221> NAME/KEY: Xaa
<222> LOCATION: (73)..(73)
<223> OTHER INFORMATION: Xaa is any amino acid or absent
<220> FEATURE:
<221> NAME/KEY: Xaa
<222> LOCATION: (77)..(77)
<223> OTHER INFORMATION: Xaa is any amino acid or absent
<220> FEATURE:
<221> NAME/KEY: Xaa
<222> LOCATION: (79)..(79)
<223> OTHER INFORMATION: Xaa is any amino acid or absent
<220> FEATURE:
<221> NAME/KEY: Xaa
<222> LOCATION: (84)..(84)
<223> OTHER INFORMATION: Xaa is any amino acid or absent
<220> FEATURE:
<221> NAME/KEY: Xaa
<222> LOCATION: (86)..(86)
<223> OTHER INFORMATION: Xaa is any amino acid or absent
<220> FEATURE:
<221> NAME/KEY: Xaa
<222> LOCATION: (96)..(97)
<223> OTHER INFORMATION: Xaa is any amino acid or absent
<220> FEATURE:
<221> NAME/KEY: Xaa
<222> LOCATION: (99)..(99)
<223> OTHER INFORMATION: Xaa is any amino acid or absent
<220> FEATURE:
<221> NAME/KEY: Xaa
<222> LOCATION: (101)..(102)
<223> OTHER INFORMATION: Xaa is any amino acid or absent
<220> FEATURE:
<221> NAME/KEY: Xaa
<222> LOCATION: (104)..(105)
<223> OTHER INFORMATION: Xaa is any amino acid or absent
<220> FEATURE:
<221> NAME/KEY: Xaa
<222> LOCATION: (124)..(124)
<223> OTHER INFORMATION: Xaa is any amino acid or absent
<220> FEATURE:
<221> NAME/KEY: Xaa
```

```
<222> LOCATION: (134)..(134)
<223> OTHER INFORMATION: Xaa is any amino acid or absent
<220> FEATURE:
<221> NAME/KEY: Xaa
<222> LOCATION: (136)..(136)
<223> OTHER INFORMATION: Xaa is any amino acid or absent
<220> FEATURE:
<221> NAME/KEY: Xaa
<222> LOCATION: (138)..(140)
<223> OTHER INFORMATION: Xaa is any amino acid or absent
<220> FEATURE:
<221> NAME/KEY: Xaa
<222> LOCATION: (145)..(145)
<223> OTHER INFORMATION: Xaa is any amino acid or absent
<220> FEATURE:
<221> NAME/KEY: Xaa
<222> LOCATION: (150)..(150)
<223> OTHER INFORMATION: Xaa is any amino acid or absent
<220> FEATURE:
<221> NAME/KEY: Xaa
<222> LOCATION: (156)..(157)
<223> OTHER INFORMATION: Xaa is any amino acid or absent
<220> FEATURE:
<221> NAME/KEY: Xaa
<222> LOCATION: (165)..(165)
<223> OTHER INFORMATION: Xaa is any amino acid or absent
<220> FEATURE:
<221> NAME/KEY: Xaa
<222> LOCATION: (175)..(175)
<223> OTHER INFORMATION: Xaa is any amino acid or absent
<220> FEATURE:
<221> NAME/KEY: Xaa
<222> LOCATION: (188)..(188)
<223> OTHER INFORMATION: Xaa is any amino acid or absent
<220> FEATURE:
<221> NAME/KEY: Xaa
<222> LOCATION: (194)..(196)
<223> OTHER INFORMATION: Xaa is any amino acid or absent
<220> FEATURE:
<221> NAME/KEY: Xaa
<222> LOCATION: (208)..(208)
<223> OTHER INFORMATION: Xaa is any amino acid or absent
<220> FEATURE:
<221> NAME/KEY: Xaa
<222> LOCATION: (210)..(210)
<223> OTHER INFORMATION: Xaa is any amino acid or absent
<220> FEATURE:
<221> NAME/KEY: Xaa
<222> LOCATION: (216)..(216)
<223> OTHER INFORMATION: Xaa is any amino acid or absent
<220> FEATURE:
<221> NAME/KEY: Xaa
<222> LOCATION: (221)..(221)
<223> OTHER INFORMATION: Xaa is any amino acid or absent
<220> FEATURE:
<221> NAME/KEY: Xaa
<222> LOCATION: (225)..(225)
<223> OTHER INFORMATION: Xaa is any amino acid or absent
<220> FEATURE:
<221> NAME/KEY: Xaa
<222> LOCATION: (228)..(228)
<223> OTHER INFORMATION: Xaa is any amino acid or absent
<220> FEATURE:
<221> NAME/KEY: Xaa
<222> LOCATION: (233)..(233)
<223> OTHER INFORMATION: Xaa is any amino acid or absent
<220> FEATURE:
<221> NAME/KEY: Xaa
<222> LOCATION: (235)..(239)
<223> OTHER INFORMATION: Xaa is any amino acid or absent
<220> FEATURE:
<221> NAME/KEY: Xaa
<222> LOCATION: (244)..(245)
<223> OTHER INFORMATION: Xaa is any amino acid or absent
<220> FEATURE:
<221> NAME/KEY: Xaa
<222> LOCATION: (248)..(248)
<223> OTHER INFORMATION: Xaa is any amino acid or absent
<220> FEATURE:
```

```
<221> NAME/KEY: Xaa
<222> LOCATION: (254)..(254)
<223> OTHER INFORMATION: Xaa is any amino acid or absent
<220> FEATURE:
<221> NAME/KEY: Xaa
<222> LOCATION: (258)..(258)
<223> OTHER INFORMATION: Xaa is any amino acid or absent
<220> FEATURE:
<221> NAME/KEY: Xaa
<222> LOCATION: (263)..(263)
<223> OTHER INFORMATION: Xaa is any amino acid or absent
<220> FEATURE:
<221> NAME/KEY: Xaa
<222> LOCATION: (265)..(266)
<223> OTHER INFORMATION: Xaa is any amino acid or absent
<220> FEATURE:
<221> NAME/KEY: Xaa
<222> LOCATION: (268)..(268)
<223> OTHER INFORMATION: Xaa is any amino acid or absent
<220> FEATURE:
<221> NAME/KEY: Xaa
<222> LOCATION: (270)..(270)
<223> OTHER INFORMATION: Xaa is any amino acid or absent
<220> FEATURE:
<221> NAME/KEY: Xaa
<222> LOCATION: (276)..(276)
<223> OTHER INFORMATION: Xaa is any amino acid or absent
<220> FEATURE:
<221> NAME/KEY: Xaa
<222> LOCATION: (278)..(279)
<223> OTHER INFORMATION: Xaa is any amino acid or absent
<220> FEATURE:
<221> NAME/KEY: Xaa
<222> LOCATION: (283)..(283)
<223> OTHER INFORMATION: Xaa is any amino acid or absent
<220> FEATURE:
<221> NAME/KEY: Xaa
<222> LOCATION: (285)..(285)
<223> OTHER INFORMATION: Xaa is any amino acid or absent
<220> FEATURE:
<221> NAME/KEY: Xaa
<222> LOCATION: (288)..(288)
<223> OTHER INFORMATION: Xaa is any amino acid or absent
<220> FEATURE:
<221> NAME/KEY: Xaa
<222> LOCATION: (290)..(290)
<223> OTHER INFORMATION: Xaa is any amino acid or absent
<220> FEATURE:
<221> NAME/KEY: Xaa
<222> LOCATION: (292)..(294)
<223> OTHER INFORMATION: Xaa is any amino acid or absent
<220> FEATURE:
<221> NAME/KEY: Xaa
<222> LOCATION: (300)..(300)
<223> OTHER INFORMATION: Xaa is any amino acid or absent
<220> FEATURE:
<221> NAME/KEY: Xaa
<222> LOCATION: (304)..(310)
<223> OTHER INFORMATION: Xaa is any amino acid or absent
<220> FEATURE:
<221> NAME/KEY: Xaa
<222> LOCATION: (319)..(319)
<223> OTHER INFORMATION: Xaa is any amino acid or absent
<220> FEATURE:
<221> NAME/KEY: Xaa
<222> LOCATION: (322)..(322)
<223> OTHER INFORMATION: Xaa is any amino acid or absent
<220> FEATURE:
<221> NAME/KEY: Xaa
<222> LOCATION: (326)..(326)
<223> OTHER INFORMATION: Xaa is any amino acid or absent
<220> FEATURE:
<221> NAME/KEY: Xaa
<222> LOCATION: (329)..(329)
<223> OTHER INFORMATION: Xaa is any amino acid or absent
<220> FEATURE:
<221> NAME/KEY: Xaa
<222> LOCATION: (334)..(334)
<223> OTHER INFORMATION: Xaa is any amino acid or absent
```

-continued

```
<220> FEATURE:
<221> NAME/KEY: Xaa
<222> LOCATION: (336)..(337)
<223> OTHER INFORMATION: Xaa is any amino acid or absent
<220> FEATURE:
<221> NAME/KEY: Xaa
<222> LOCATION: (341)..(341)
<223> OTHER INFORMATION: Xaa is any amino acid or absent
<220> FEATURE:
<221> NAME/KEY: Xaa
<222> LOCATION: (343)..(343)
<223> OTHER INFORMATION: Xaa is any amino acid or absent
<220> FEATURE:
<221> NAME/KEY: Xaa
<222> LOCATION: (347)..(347)
<223> OTHER INFORMATION: Xaa is any amino acid or absent
<220> FEATURE:
<221> NAME/KEY: Xaa
<222> LOCATION: (358)..(358)
<223> OTHER INFORMATION: Xaa is any amino acid or absent
<220> FEATURE:
<221> NAME/KEY: Xaa
<222> LOCATION: (361)..(362)
<223> OTHER INFORMATION: Xaa is any amino acid or absent
<220> FEATURE:
<221> NAME/KEY: Xaa
<222> LOCATION: (365)..(365)
<223> OTHER INFORMATION: Xaa is any amino acid or absent
<220> FEATURE:
<221> NAME/KEY: Xaa
<222> LOCATION: (376)..(376)
<223> OTHER INFORMATION: Xaa is any amino acid or absent
<220> FEATURE:
<221> NAME/KEY: Xaa
<222> LOCATION: (381)..(381)
<223> OTHER INFORMATION: Xaa is any amino acid or absent
<220> FEATURE:
<221> NAME/KEY: Xaa
<222> LOCATION: (383)..(384)
<223> OTHER INFORMATION: Xaa is any amino acid or absent
<220> FEATURE:
<221> NAME/KEY: Xaa
<222> LOCATION: (386)..(386)
<223> OTHER INFORMATION: Xaa is any amino acid or absent
<220> FEATURE:
<221> NAME/KEY: Xaa
<222> LOCATION: (390)..(390)
<223> OTHER INFORMATION: Xaa is any amino acid or absent
<220> FEATURE:
<221> NAME/KEY: Xaa
<222> LOCATION: (393)..(393)
<223> OTHER INFORMATION: Xaa is any amino acid or absent
<220> FEATURE:
<221> NAME/KEY: Xaa
<222> LOCATION: (401)..(405)
<223> OTHER INFORMATION: Xaa is any amino acid or absent
<220> FEATURE:
<221> NAME/KEY: Xaa
<222> LOCATION: (408)..(409)
<223> OTHER INFORMATION: Xaa is any amino acid or absent
<220> FEATURE:
<221> NAME/KEY: Xaa
<222> LOCATION: (417)..(418)
<223> OTHER INFORMATION: Xaa is any amino acid or absent
<220> FEATURE:
<221> NAME/KEY: Xaa
<222> LOCATION: (427)..(427)
<223> OTHER INFORMATION: Xaa is any amino acid or absent
<220> FEATURE:
<221> NAME/KEY: Xaa
<222> LOCATION: (430)..(430)
<223> OTHER INFORMATION: Xaa is any amino acid or absent
<220> FEATURE:
<221> NAME/KEY: Xaa
<222> LOCATION: (432)..(432)
<223> OTHER INFORMATION: Xaa is any amino acid or absent
<220> FEATURE:
<221> NAME/KEY: Xaa
<222> LOCATION: (439)..(439)
```

```
<223> OTHER INFORMATION: Xaa is any amino acid or absent
<220> FEATURE:
<221> NAME/KEY: Xaa
<222> LOCATION: (442)..(442)
<223> OTHER INFORMATION: Xaa is any amino acid or absent
<220> FEATURE:
<221> NAME/KEY: Xaa
<222> LOCATION: (455)..(455)
<223> OTHER INFORMATION: Xaa is any amino acid or absent
<220> FEATURE:
<221> NAME/KEY: Xaa
<222> LOCATION: (457)..(457)
<223> OTHER INFORMATION: Xaa is any amino acid or absent
<220> FEATURE:
<221> NAME/KEY: Xaa
<222> LOCATION: (460)..(462)
<223> OTHER INFORMATION: Xaa is any amino acid or absent
<220> FEATURE:
<221> NAME/KEY: Xaa
<222> LOCATION: (465)..(466)
<223> OTHER INFORMATION: Xaa is any amino acid or absent
<220> FEATURE:
<221> NAME/KEY: Xaa
<222> LOCATION: (469)..(469)
<223> OTHER INFORMATION: Xaa is any amino acid or absent
<220> FEATURE:
<221> NAME/KEY: Xaa
<222> LOCATION: (471)..(471)
<223> OTHER INFORMATION: Xaa is any amino acid or absent
<220> FEATURE:
<221> NAME/KEY: Xaa
<222> LOCATION: (473)..(473)
<223> OTHER INFORMATION: Xaa is any amino acid or absent
<220> FEATURE:
<221> NAME/KEY: Xaa
<222> LOCATION: (477)..(477)
<223> OTHER INFORMATION: Xaa is any amino acid or absent
<220> FEATURE:
<221> NAME/KEY: Xaa
<222> LOCATION: (481)..(481)
<223> OTHER INFORMATION: Xaa is any amino acid or absent
<220> FEATURE:
<221> NAME/KEY: Xaa
<222> LOCATION: (489)..(489)
<223> OTHER INFORMATION: Xaa is any amino acid or absent
<220> FEATURE:
<221> NAME/KEY: Xaa
<222> LOCATION: (493)..(493)
<223> OTHER INFORMATION: Xaa is any amino acid or absent
<220> FEATURE:
<221> NAME/KEY: Xaa
<222> LOCATION: (500)..(500)
<223> OTHER INFORMATION: Xaa is any amino acid or absent
<220> FEATURE:
<221> NAME/KEY: Xaa
<222> LOCATION: (503)..(503)
<223> OTHER INFORMATION: Xaa is any amino acid or absent
<220> FEATURE:
<221> NAME/KEY: Xaa
<222> LOCATION: (509)..(510)
<223> OTHER INFORMATION: Xaa is any amino acid or absent
<220> FEATURE:
<221> NAME/KEY: Xaa
<222> LOCATION: (518)..(518)
<223> OTHER INFORMATION: Xaa is any amino acid or absent
<220> FEATURE:
<221> NAME/KEY: Xaa
<222> LOCATION: (529)..(529)
<223> OTHER INFORMATION: Xaa is any amino acid or absent
<220> FEATURE:
<221> NAME/KEY: Xaa
<222> LOCATION: (533)..(534)
<223> OTHER INFORMATION: Xaa is any amino acid or absent
<220> FEATURE:
<221> NAME/KEY: Xaa
<222> LOCATION: (539)..(539)
<223> OTHER INFORMATION: Xaa is any amino acid or absent
<220> FEATURE:
<221> NAME/KEY: Xaa
```

```
<222> LOCATION: (557)..(557)
<223> OTHER INFORMATION: Xaa is any amino acid or absent
<220> FEATURE:
<221> NAME/KEY: Xaa
<222> LOCATION: (561)..(563)
<223> OTHER INFORMATION: Xaa is any amino acid or absent
<220> FEATURE:
<221> NAME/KEY: Xaa
<222> LOCATION: (565)..(565)
<223> OTHER INFORMATION: Xaa is any amino acid or absent
<220> FEATURE:
<221> NAME/KEY: Xaa
<222> LOCATION: (568)..(568)
<223> OTHER INFORMATION: Xaa is any amino acid or absent
<220> FEATURE:
<221> NAME/KEY: Xaa
<222> LOCATION: (573)..(573)
<223> OTHER INFORMATION: Xaa is any amino acid or absent
<220> FEATURE:
<221> NAME/KEY: Xaa
<222> LOCATION: (584)..(584)
<223> OTHER INFORMATION: Xaa is any amino acid or absent
<220> FEATURE:
<221> NAME/KEY: Xaa
<222> LOCATION: (587)..(587)
<223> OTHER INFORMATION: Xaa is any amino acid or absent
<220> FEATURE:
<221> NAME/KEY: Xaa
<222> LOCATION: (593)..(593)
<223> OTHER INFORMATION: Xaa is any amino acid or absent
<220> FEATURE:
<221> NAME/KEY: Xaa
<222> LOCATION: (599)..(599)
<223> OTHER INFORMATION: Xaa is any amino acid or absent
<220> FEATURE:
<221> NAME/KEY: Xaa
<222> LOCATION: (604)..(605)
<223> OTHER INFORMATION: Xaa is any amino acid or absent
<220> FEATURE:
<221> NAME/KEY: Xaa
<222> LOCATION: (613)..(613)
<223> OTHER INFORMATION: Xaa is any amino acid or absent
<220> FEATURE:
<221> NAME/KEY: Xaa
<222> LOCATION: (620)..(621)
<223> OTHER INFORMATION: Xaa is any amino acid or absent
<220> FEATURE:
<221> NAME/KEY: Xaa
<222> LOCATION: (626)..(626)
<223> OTHER INFORMATION: Xaa is any amino acid or absent
<220> FEATURE:
<221> NAME/KEY: Xaa
<222> LOCATION: (628)..(628)
<223> OTHER INFORMATION: Xaa is any amino acid or absent
<220> FEATURE:
<221> NAME/KEY: Xaa
<222> LOCATION: (635)..(635)
<223> OTHER INFORMATION: Xaa is any amino acid or absent
<220> FEATURE:
<221> NAME/KEY: Xaa
<222> LOCATION: (637)..(638)
<223> OTHER INFORMATION: Xaa is any amino acid or absent
<220> FEATURE:
<221> NAME/KEY: Xaa
<222> LOCATION: (640)..(640)
<223> OTHER INFORMATION: Xaa is any amino acid or absent
<220> FEATURE:
<221> NAME/KEY: Xaa
<222> LOCATION: (644)..(645)
<223> OTHER INFORMATION: Xaa is any amino acid or absent
<220> FEATURE:
<221> NAME/KEY: Xaa
<222> LOCATION: (647)..(649)
<223> OTHER INFORMATION: Xaa is any amino acid or absent
<220> FEATURE:
<221> NAME/KEY: Xaa
<222> LOCATION: (652)..(653)
<223> OTHER INFORMATION: Xaa is any amino acid or absent
<220> FEATURE:
```

-continued

```
<221> NAME/KEY: Xaa
<222> LOCATION: (657)..(657)
<223> OTHER INFORMATION: Xaa is any amino acid or absent
<220> FEATURE:
<221> NAME/KEY: Xaa
<222> LOCATION: (660)..(660)
<223> OTHER INFORMATION: Xaa is any amino acid or absent
<220> FEATURE:
<221> NAME/KEY: Xaa
<222> LOCATION: (673)..(673)
<223> OTHER INFORMATION: Xaa is any amino acid or absent
<220> FEATURE:
<221> NAME/KEY: Xaa
<222> LOCATION: (677)..(677)
<223> OTHER INFORMATION: Xaa is any amino acid or absent
<220> FEATURE:
<221> NAME/KEY: Xaa
<222> LOCATION: (685)..(685)
<223> OTHER INFORMATION: Xaa is any amino acid or absent
<220> FEATURE:
<221> NAME/KEY: Xaa
<222> LOCATION: (690)..(691)
<223> OTHER INFORMATION: Xaa is any amino acid or absent
<220> FEATURE:
<221> NAME/KEY: Xaa
<222> LOCATION: (694)..(696)
<223> OTHER INFORMATION: Xaa is any amino acid or absent
<220> FEATURE:
<221> NAME/KEY: Xaa
<222> LOCATION: (701)..(701)
<223> OTHER INFORMATION: Xaa is any amino acid or absent
<220> FEATURE:
<221> NAME/KEY: Xaa
<222> LOCATION: (705)..(706)
<223> OTHER INFORMATION: Xaa is any amino acid or absent
<220> FEATURE:
<221> NAME/KEY: Xaa
<222> LOCATION: (713)..(713)
<223> OTHER INFORMATION: Xaa is any amino acid or absent
<220> FEATURE:
<221> NAME/KEY: Xaa
<222> LOCATION: (717)..(717)
<223> OTHER INFORMATION: Xaa is any amino acid or absent
<220> FEATURE:
<221> NAME/KEY: Xaa
<222> LOCATION: (724)..(725)
<223> OTHER INFORMATION: Xaa is any amino acid or absent
<220> FEATURE:
<221> NAME/KEY: Xaa
<222> LOCATION: (729)..(729)
<223> OTHER INFORMATION: Xaa is any amino acid or absent
<220> FEATURE:
<221> NAME/KEY: Xaa
<222> LOCATION: (732)..(733)
<223> OTHER INFORMATION: Xaa is any amino acid or absent
<220> FEATURE:
<221> NAME/KEY: Xaa
<222> LOCATION: (747)..(747)
<223> OTHER INFORMATION: Xaa is any amino acid or absent
<220> FEATURE:
<221> NAME/KEY: Xaa
<222> LOCATION: (754)..(757)
<223> OTHER INFORMATION: Xaa is any amino acid or absent
<220> FEATURE:
<221> NAME/KEY: Xaa
<222> LOCATION: (759)..(760)
<223> OTHER INFORMATION: Xaa is any amino acid or absent
<220> FEATURE:
<221> NAME/KEY: Xaa
<222> LOCATION: (762)..(764)
<223> OTHER INFORMATION: Xaa is any amino acid or absent
<220> FEATURE:
<221> NAME/KEY: Xaa
<222> LOCATION: (766)..(766)
<223> OTHER INFORMATION: Xaa is any amino acid or absent
<220> FEATURE:
<221> NAME/KEY: Xaa
<222> LOCATION: (772)..(772)
<223> OTHER INFORMATION: Xaa is any amino acid or absent
```

<220> FEATURE:
<221> NAME/KEY: Xaa
<222> LOCATION: (775)..(775)
<223> OTHER INFORMATION: Xaa is any amino acid or absent

<400> SEQUENCE: 39

```
Xaa Ile Xaa Asp Thr Asp Tyr Xaa Thr Xaa Asp Gly Xaa Pro Xaa Xaa
1               5                   10                  15

Arg Ile Phe Xaa Lys Xaa Xaa Gly Glu Phe Xaa Xaa Xaa Tyr Asp Xaa
            20                  25                  30

Xaa Phe Glu Pro Tyr Phe Tyr Ala Leu Leu Lys Asp Asp Ser Ala Ile
        35                  40                  45

Xaa Xaa Xaa Xaa Xaa Xaa Ala Xaa Arg His Gly Thr Val Xaa Thr
    50                  55                  60

Val Lys Arg Xaa Xaa Xaa Gln Xaa Lys Phe Leu Xaa Arg Xaa Val
65                  70                  75                  80

Glu Val Trp Xaa Leu Xaa Phe Thr His Pro Gln Asp Val Pro Ala Xaa
            85                  90                  95

Xaa Asp Xaa Ile Xaa Xaa His Xaa Xaa Val Ile Asp Ile Tyr Glu Tyr
            100                 105                 110

Asp Ile Pro Phe Ala Lys Arg Tyr Leu Ile Asp Xaa Gly Leu Val Pro
            115                 120                 125

Met Glu Gly Asp Glu Xaa Leu Xaa Met Xaa Xaa Xaa Asp Ile Glu Thr
130                 135                 140

Xaa Tyr His Glu Gly Xaa Glu Phe Ala Glu Gly Xaa Xaa Leu Met Ile
145                 150                 155                 160

Ser Tyr Ala Asp Xaa Glu Gly Ala Arg Val Ile Thr Trp Lys Xaa Val
                165                 170                 175

Asp Leu Pro Tyr Val Asp Val Val Ser Thr Glu Xaa Glu Met Ile Lys
            180                 185                 190

Arg Xaa Xaa Xaa Val Val Lys Glu Lys Asp Pro Asp Val Leu Ile Xaa
    195                 200                 205

Tyr Xaa Gly Asp Asn Phe Asp Xaa Ala Tyr Leu Lys Xaa Arg Cys Glu
    210                 215                 220

Xaa Leu Gly Xaa Asn Phe Ala Leu Xaa Arg Xaa Xaa Xaa Xaa Xaa Glu
225                 230                 235                 240

Pro Lys Ile Xaa Xaa Met Gly Xaa Arg Phe Ala Val Glu Xaa Lys Gly
            245                 250                 255

Arg Xaa His Phe Asp Leu Xaa Pro Xaa Xaa Arg Xaa Thr Xaa Asn Leu
    260                 265                 270

Pro Thr Tyr Xaa Leu Xaa Xaa Val Tyr Glu Xaa Val Xaa Gly Gln Xaa
        275                 280                 285

Lys Xaa Lys Xaa Xaa Xaa Glu Glu Ile Thr Thr Xaa Trp Glu Thr Xaa
    290                 295                 300

Xaa Xaa Xaa Xaa Xaa Xaa Ala Arg Tyr Ser Met Glu Asp Ala Xaa Val
305                 310                 315                 320

Thr Xaa Glu Leu Gly Xaa Glu Phe Xaa Pro Met Glu Ala Xaa Leu Xaa
            325                 330                 335

Xaa Leu Val Gly Xaa Pro Xaa Trp Asp Val Xaa Arg Ser Ser Thr Gly
            340                 345                 350

Asn Leu Val Glu Trp Xaa Leu Leu Xaa Xaa Ala Tyr Xaa Arg Asn Glu
                355                 360                 365

Val Ala Pro Asn Lys Pro Ser Xaa Glu Glu Tyr Gln Xaa Arg Xaa Xaa
            370                 375                 380
```

-continued

Glu Xaa Tyr Thr Gly Xaa Phe Val Xaa Glu Pro Lys Gly Leu Trp
385                 390                 395                 400

Xaa Xaa Xaa Xaa Xaa Leu Asp Xaa Xaa Ala Leu Tyr Pro Ser Ile Ile
            405                 410                 415

Xaa Xaa His Asn Val Ser Pro Asp Thr Leu Xaa Leu Glu Xaa Cys Xaa
        420                 425                 430

Asn Tyr Asp Ile Ala Pro Xaa Val Gly Xaa Lys Phe Cys Lys Asp Ile
            435                 440                 445

Pro Gly Phe Ile Pro Ser Xaa Leu Xaa His Leu Xaa Xaa Xaa Arg Gln
    450                 455                 460

Xaa Xaa Lys Thr Xaa Met Xaa Glu Xaa Gln Asp Pro Xaa Glu Lys Ile
465             470                 475                 480

Xaa Leu Asp Tyr Arg Gln Lys Ala Xaa Lys Leu Leu Xaa Asn Ser Phe
            485                 490                 495

Tyr Gly Tyr Xaa Gly Tyr Xaa Lys Ala Arg Trp Tyr Xaa Xaa Glu Cys
            500                 505                 510

Ala Glu Ser Val Thr Xaa Trp Gly Arg Lys Tyr Ile Glu Leu Val Trp
        515                 520                 525

Xaa Glu Leu Glu Xaa Xaa Phe Gly Phe Lys Xaa Leu Tyr Ile Asp Thr
530                 535                 540

Asp Gly Leu Tyr Ala Thr Ile Pro Gly Gly Glu Ser Xaa Glu Ile Lys
545                 550                 555                 560

Xaa Xaa Xaa Leu Xaa Phe Leu Xaa Tyr Ile Asn Ala Xaa Leu Pro Gly
            565                 570                 575

Ala Leu Glu Leu Glu Tyr Glu Xaa Phe Tyr Xaa Arg Gly Phe Phe Val
        580                 585                 590

Xaa Lys Lys Lys Tyr Ala Xaa Ile Asp Glu Glu Xaa Xaa Ile Thr Thr
        595                 600                 605

Arg Gly Leu Glu Xaa Val Arg Arg Asp Trp Ser Xaa Xaa Ala Lys Glu
    610                 615                 620

Thr Xaa Ala Xaa Val Leu Glu Ala Leu Leu Xaa Asp Xaa Xaa Val Xaa
625             630                 635                 640

Lys Ala Val Xaa Xaa Val Xaa Xaa Xaa Thr Glu Xaa Xaa Ser Lys Tyr
            645                 650                 655

Xaa Val Pro Xaa Glu Lys Leu Val Ile His Glu Gln Ile Thr Arg Asp
        660                 665                 670

Xaa Lys Asp Tyr Xaa Ala Thr Gly Pro His Val Ala Xaa Ala Lys Arg
            675                 680                 685

Leu Xaa Xaa Arg Gly Xaa Xaa Xaa Arg Pro Gly Thr Xaa Ile Ser Tyr
    690                 695                 700

Xaa Xaa Leu Lys Gly Ser Gly Arg Xaa Gly Asp Arg Xaa Ile Pro Phe
705             710                 715                 720

Asp Glu Phe Xaa Xaa Thr Lys His Xaa Tyr Asp Xaa Xaa Tyr Tyr Ile
            725                 730                 735

Glu Asn Gln Val Leu Pro Ala Val Glu Arg Xaa Leu Arg Ala Phe Gly
        740                 745                 750

Tyr Xaa Xaa Xaa Xaa Leu Xaa Xaa Gln Xaa Xaa Xaa Gln Xaa Gly Leu
            755                 760                 765

Ser Ala Trp Xaa Lys Pro Xaa Gly Thr
    770                 775

<210> SEQ ID NO 40
<211> LENGTH: 21
<212> TYPE: DNA

```
<213> ORGANISM: Artificial Sequence
<220> FEATURE:
<223> OTHER INFORMATION: Primer

<400> SEQUENCE: 40
tttggaaaca tctggagtcc t                                             21

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
gcccaaaggg aactgatagt c                                             21

<210> SEQ ID NO 42
<211> LENGTH: 17
<212> TYPE: DNA
<213> ORGANISM: Artificial Sequence
<220> FEATURE:
<223> OTHER INFORMATION: Primer

<400> SEQUENCE: 42
gttttcccag tcacgac                                                  17

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
ggtatcttta tagtcctgtc g                                             21

<210> SEQ ID NO 44
<211> LENGTH: 34
<212> TYPE: DNA
<213> ORGANISM: Artificial Sequence
<220> FEATURE:
<223> OTHER INFORMATION: Primer

<400> SEQUENCE: 44
gttttcccag tcacgacgtt gtaaaacgac ggcc                               34

<210> SEQ ID NO 45
<211> LENGTH: 775
<212> TYPE: PRT
<213> ORGANISM: Pyrococcus sp. GB-D

<400> SEQUENCE: 45
```

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

-continued

```
Glu Val Trp Arg Leu Tyr Phe Glu His Pro Gln Asp Val Pro Ala Ile
                 85                  90                  95
Arg Asp Lys Ile Arg Glu His Ser Ala Val Ile Asp Ile Phe Glu Tyr
            100                 105                 110
Asp Ile Pro Phe Ala Lys Arg Tyr Leu Ile Asp Lys Gly Leu Ile Pro
        115                 120                 125
Met Glu Gly Asp Glu Glu Leu Lys Leu Leu Ala Phe Asp Ile Glu Thr
    130                 135                 140
Leu Tyr His Glu Gly Glu Glu Phe Ala Lys Gly Pro Ile Ile Met Ile
145                 150                 155                 160
Ser Tyr Ala Asp Glu Glu Glu Ala Lys Val Ile Thr Trp Lys Lys Ile
                165                 170                 175
Asp Leu Pro Tyr Val Glu Val Ser Ser Glu Arg Glu Met Ile Lys
            180                 185                 190
Arg Phe Leu Lys Val Ile Arg Glu Lys Asp Pro Asp Val Ile Ile Thr
        195                 200                 205
Tyr Asn Gly Asp Ser Phe Asp Leu Pro Tyr Leu Val Lys Arg Ala Glu
    210                 215                 220
Lys Leu Gly Ile Lys Leu Pro Leu Gly Arg Asp Gly Ser Glu Pro Lys
225                 230                 235                 240
Met Gln Arg Leu Gly Asp Met Thr Ala Val Glu Ile Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala His Glu Ile Ala Glu Ala Trp Glu Thr Gly Lys Gly
    290                 295                 300
Leu Glu Arg Val Ala Lys Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Tyr Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
    370                 375                 380
Tyr Ala Gly Gly Tyr Val Lys Glu Pro Glu Lys Gly Leu Trp Glu Gly
385                 390                 395                 400
Leu Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
            420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Asp Glu Arg Gln Glu Ile
    450                 455                 460
Lys Arg Lys Met Lys Ala Ser Lys Asp Pro Ile Glu Lys Lys Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
```

```
                500                505                510
Ser Val Thr Ala Trp Gly Arg Glu Tyr Ile Glu Phe Val Arg Lys Glu
        515                520                525

Leu Glu Glu Lys Phe Gly Phe Lys Val Leu Tyr Ile Asp Thr Asp Gly
        530                535                540

Leu Tyr Ala Thr Ile Pro Gly Ala Lys Pro Glu Glu Ile Lys Lys Lys
545                 550                555                560

Ala Leu Glu Phe Val Asp Tyr Ile Asn Ala Lys Leu Pro Gly Leu Leu
                565                570                575

Glu Leu Glu Tyr Glu Gly Phe Tyr Val Arg Gly Phe Phe Val Thr Lys
        580                585                590

Lys Lys Tyr Ala Leu Ile Asp Glu Glu Gly Lys Ile Ile Thr Arg Gly
        595                600                605

Leu Glu Ile Val Arg Arg Asp Trp Ser Glu Ile Ala Lys Glu Thr Gln
        610                615                620

Ala Lys Val Leu Glu Ala Ile Leu Lys His Gly Asn Val Glu Glu Ala
625                 630                635                640

Val Lys Ile Val Lys Glu Val Thr Glu Lys Leu Ser Lys Tyr Glu Ile
                645                650                655

Pro Pro Glu Lys Leu Val Ile Tyr Glu Gln Ile Thr Arg Pro Leu His
        660                665                670

Glu Tyr Lys Ala Ile Gly Pro His Val Ala Val Ala Lys Arg Leu Ala
        675                680                685

Ala Arg Gly Val Lys Val Arg Pro Gly Met Val Ile Gly Tyr Ile Val
        690                695                700

Leu Arg Gly Asp Gly Pro Ile Ser Lys Arg Ala Ile Leu Ala Glu Glu
705                 710                715                720

Phe Asp Leu Arg Lys His Lys Tyr Asp Ala Glu Tyr Tyr Ile Glu Asn
                725                730                735

Gln Val Leu Pro Ala Val Leu Arg Ile Leu Glu Ala Phe Gly Tyr Arg
        740                745                750

Lys Glu Asp Leu Arg Trp Gln Lys Thr Lys Gln Thr Gly Leu Thr Ala
        755                760                765

Trp Leu Asn Ile Lys Lys Lys
770                 775
```

CHIMERIC DNA POLYMERASES

The present application is a national phase entry of international application Ser. No. PCT/US2009/063166, filed Nov. 3, 2009 which claims priority to U.S. Provisional patent application Ser. No. 61/110,862, filed Nov. 3, 2008, the entire disclosure of which is incorporated herein by reference.

The present specification makes reference to a Sequence Listing (submitted electronically as a .txt file named "Sequence Listing.txt" on May 3, 2011). The .txt file was generated on Nov. 9, 2009 and is 235 kb in size. The entire contents of the Sequence Listing are herein incorporated by reference.

BACKGROUND OF THE INVENTION

DNA polymerases are enzymes that use single-stranded DNA as a template to synthesize the complementary DNA strand. In particular, DNA polymerases can add free nucleotides to the 3' end of a newly-forming strand resulting in elongation of the new strand in a 5'-3' direction. Some DNA polymerases can correct mistakes in newly-synthesized DNA. This process is known as error correction. These polymerases can recognize an incorrectly incorporated nucleotide and the 3'->5' exonuclease activity of the enzyme allows the incorrect nucleotide to be excised (this activity is known as proofreading). Following base excision, the polymerase can re-insert the correct base and replication can continue. The proofreading function gives the DNA replication much higher fidelity than it would have if synthesis were the result of only a base-pairing selection step. Brutlag, D. and Kornberg, A., *J. Biol. Chem.*, 247:241-248 (1972). DNA polymerases with 3'-5' proofreading exonuclease activity have a substantially lower error rate when compared with a non-proofreading exonuclease-possessing polymerase. Chang, L. M. S., *J. Biol. Chem.*, 252:1873-1880 (1977). However, sometimes, the advantage of these polymerases is offset by its relatively low processivity that reduces the yield of DNA amplification products.

SUMMARY OF THE INVENTION

The present invention encompasses the discovery that domain swapping can combine desired functional characteristics (e.g., high processivity, high elongation rate, thermostability, resistance to salt, PCR additives (e.g., PCR enhancers) and other impurities, and high fidelity) of different DNA polymerases in a chimeric enzyme. Thus, the present invention provides, among other things, robust, fast and accurate DNA polymerases for DNA amplification, synthesis, detection, sequencing and other important recombinant DNA techniques.

In one aspect, the present invention provides chimeric polymerases containing a first domain having a sequence at least 80% (e.g., at least 85%, 90%, 91%, 92%, 93%, 94%, 95%, 96%, 97%, 98%, 99%) identical to an amino acid sequence found in a first DNA polymerase characterized with high processivity, elongation rate, salt resistance, thermostability or TMAC tolerance; and a second domain having a sequence at least 80% (e.g., at least 85%, 90%, 91%, 92%, 93%, 94%, 95%, 96%, 97%, 98%, 99%) identical to an amino acid sequence found in a second DNA polymerase characterized with high fidelity, wherein the chimeric polymerases are characterized with both high fidelity and high processivity, elongation rate, or salt resistance. As used herein, the term "high processivity" refers to a processivity higher than 20 nts (e.g., higher than 40 nts, 60 nts, 80 nts, 100 nts, 120 nts, 140 nts, 160 nts, 180 nts, 200 nts, 220 nts, 240 nts, 260 nts, 280 nts, 300 nts, 320 nts, 340 nts, 360 nts, 380 nts, 400 nts, or higher) per association/disassociation with the template. As used herein, the term "high elongation rate" refers to an elongation rate higher than 25 nt/s (e.g., higher than 30, 35, 40, 45, 50, 55, 60, 65, 70, 75, 80, 85, 90, 95, 100, 105, 110, 115, 120, 125, 130, 135, 140 nt/s). As used herein, the term "high salt resistance" refers to the ability of a DNA polymerase to substantially maintain its enzymatic activity at a salt concentration higher than 30 mM (e.g., higher than 35 mM, 40 mM, 45 mM, or 50 mM). As used herein, the term "high fidelity" refers to an error rate less than $4.45 \times 10^{-6}$ (e.g., less than $4.0 \times 10^{-6}$, $3.5 \times 10^{-6}$, $3.0 \times 10^{-6}$, $2.5 \times 10^{-6}$, $2.0 \times 10^{-6}$, $1.5 \times 10^{-6}$, $1.0 \times 10^{-6}$, $0.5 \times 10^{-6}$) mutations/nt/doubling. As used herein, the term "high TMAC tolerance" refers to the ability of a DNA polymerase to substantially maintain its enzymatic activity at a TMAC (tetra-methyl ammonium chloride) concentration higher than 10 mM (e.g., higher than 15 mM, 20 mM, 25 mM, 30 mM). As used herein, the term "high thermostability" refers to the ability of a DNA polymerase to substantially maintain its enzymatic activity after more than 30 minutes incubation at 98° C. (e.g., 45 min, 60 min, 90 min, 180 min, 210 min, 240 min). The terms of "processivity," "elongation rate," "fidelity," "salt resistance," "TMAC tolerance," and "thermostability" are further defined in the Definitions section.

In some embodiments, exemplary first DNA polymerases suitable for the present invention include, but are not limited to, KOD polymerase, TNA1 polymerase, *Thermococcus* sp. 9 degrees N-7, T4, T7, or phi29. In some embodiments, the first DNA polymerase is KOD polymerase. In some embodiments, exemplary second DNA polymerases suitable for the invention include, but are not limited to, polymerases isolated from *Pyrococcus furiosus, P. abyssi, T. gorgonarius, T. litoralis, T. zilligii, T.* sp. GT, or *P.* sp. GB-D. In some embodiments, the second DNA polymerase is Pfu polymerase. In particular embodiments, the first DNA polymerase is KOD polymerase and the second DNA polymerase is Pfu polymerase.

In some embodiments, suitable first domain is an exonuclease domain, N-terminal domain, and/or a thumb domain. In some embodiments, suitable second domain is palm and/or fingers domain.

In some embodiments, amino acid sequences found in the first DNA polymerase correspond to amino acid residues 26 to 105 of KOD polymerase (SEQ ID NO:11), amino acid residues 156 to 301 of KOD polymerase (SEQ ID NO:11), and/or amino acid residues 612 to 749 of KOD polymerase (SEQ ID NO:11).

In some embodiments, amino acid sequences found in the second DNA polymerase correspond to amino acid residues 394 to 563 of Pfu polymerase (SEQ ID NO:9).

In some embodiments, a chimeric polymerase in accordance with the present invention include a first domain having a consensus sequence selected from the group consisting of XXLXXXXXXXEGXRXXXXXX-
VXXXXXDXXXTXXXXXXXXXV-
VKXXXXXXVLIX XXXXNXXXAXXKXXCXXXXX-
NFALXXXXXXXXXXXXIXXMXXRFXXXXXXXXX
XXXXPXXRXXXXXXXXXXXXXXXVXX-
QXXXXXXXXEXXTTXXXT (SEQ ID NO:30), wherein X is any amino acid or a peptide bond;
XXEXXXXYXXXXEXXFXXXXKXXX-
AXXXXXXXAXXXXTVXTVKRXXXXQXXX
XXRXVEXXXXXFTXXXXXXAXXDXIXXXXX
(SEQ ID NO:31), wherein X is any amino acid or a peptide bond;

XXXXXXXXXXXXXXXX-ALXXDXXXXKXXXXXXXXTEXXVXXXXXVXHXXXXXDXKDXXX-TXXXXXXXXRXXXRXXXRXXTXX-SXXXXXKXSXRXGDXXXPF DXFXX-TXXXXXXXXXXXXXXXXXEXXXRAXX (SEQ ID NO:32), wherein X is any amino acid or a peptide bond;
NGX$_1$FKIEX$_2$DRTFX$_3$PYX$_4$YALLX$_5$DDSX$_6$IEEVKKIT-X$_7$ERHGX$_8$X$_9$VX$_{10}$X$_{11}$X$_{12}$X$_{13}$VEKVX$_{14}$KKFLGX$_{15}$-PX$_{16}$X$_{17}$VWKLYX$_{18}$X$_{19}$HPQDVPX$_{20}$IRX$_{21}$KX$_{22}$-REHPA (SEQ ID NO:33), wherein X$_1$ is not K; X$_2$ is not H; X$_3$ is not R; X$_4$ is not I; X$_5$ is not R; X$_6$ is not K; X$_7$ is not G; X$_8$ is not K; X$_9$ is not I; X$_{10}$ is not R; X$_{11}$ is not I; X$_{12}$ is not V; X$_{13}$ is not D; X$_{14}$ is not E; X$_{15}$ is not K; X$_{16}$ is not I; X$_{17}$ is not T; X$_{18}$ is not L; X$_{19}$ is not E; X$_{20}$ is not T; X$_{21}$ is not E; and X$_{22}$ is not V;
PIX$_1$MISYADEX$_2$X$_3$AX$_4$VITWKNX$_5$DLPYVX$_6$VVSX$_7$EREMIKRFLRX$_8$X$_9$X$_{10}$EKDPDX$_{11}$X$_{12}$X$_{13}$TYNGDX$_{14}$FDFX$_{15}$YLX$_{16}$KRX$_{17}$EKLGIX$_{18}$X$_{19}$X$_{20}$X$_{21}$GRDGSEP-XX$_{22}$QRX$_{23}$GDX$_{24}$X$_{25}$AVEVKGRIHFDLYX$_{26}$VIX$_{27}$R-TINLPTYTLEAVYEAX$_{28}$FGX$_{29}$PKEKVYAX$_{30}$EIX$_{31}$X$_{32}$AWEX$_{33}$ (SEQ ID NO:34), wherein X$_1$ is not I; X$_2$ is not N; X$_3$ is not E; X$_4$ is not K; X$_5$ is not I; X$_6$ is not E; X$_7$ is not S; X$_8$ is not I; X$_9$ is not I; X$_{10}$ is not R; X$_{11}$ is not I; X$_{12}$ is not I; X$_{13}$ is not V; X$_{14}$ is not S; X$_{15}$ is not P; X$_{16}$ is not A; X$_{17}$ is not A; X$_{18}$ is not K; X$_{19}$ is not L; X$_{20}$ is not T; X$_{21}$ is not I; X$_{22}$ is not M; X$_{23}$ is not I; X$_{24}$ is not M; X$_{25}$ is not T; X$_{26}$ is not H; X$_{27}$ is not T; X$_{28}$ is not I; X$_{29}$ is not K; X$_{30}$ is not D; X$_{31}$ is not A; X$_{32}$ is not K; and X$_{33}$ is not S;
RDWSEIAKETQARVLEX$_1$X$_2$LKX$_3$GDVEX$_4$AVRIVKEV X$_5$X$_6$KLX$_7$X$_8$YEX$_9$PPEKLX$_{10}$IX$_{11}$EQITRX$_{12}$LX$_{13}$X$_{14}$ YKAX$_{15}$GPHVAVAKX$_{16}$LAAX$_{17}$GVKIX$_{18}$PGX$_{19}$ VIX$_{20}$YIVLX$_{21}$GX$_{22}$GX$_{23}$IX$_{24}$X$_{25}$RAIX$_{26}$X$_{27}$X$_{28}$EX$_{29}$ DPX$_{30}$KHKYDAEYYIENQVLPAVX$_{31}$RILX$_{32}$X$_{33}$FG (SEQ ID NO:35), wherein X$_1$ is not T; X$_2$ is not I; X$_3$ is not H; X$_4$ is not E; X$_5$ is not I; X$_6$ is not Q; X$_7$ is not A; X$_8$ is not N; X$_9$ is not I; X$_{10}$ is not A; X$_{11}$ is not Y; X$_{12}$ is not P; X$_{13}$ is not H; X$_{14}$ is not E; X$_{15}$ is not I; X$_{16}$ is not K; X$_{17}$ is not K; X$_{18}$ is not K; X$_{19}$ is not M; X$_{20}$ is not G; X$_{21}$ is not R; X$_{22}$ is not D; X$_{23}$ is not P; X$_{24}$ is not S; X$_{25}$ is not N; X$_{26}$ is not L; X$_{27}$ is not A; X$_{28}$ is not E; X$_{29}$ is not Y; X$_{30}$ is not K; X$_{31}$ is not L; X$_{32}$ is not E; and X$_{33}$ is not G;
and combinations thereof;
and a second domain having a consensus sequence selected from the group consisting of
XKXXXXXXXXXXXX-AXXXXXXXXXXXXXXXXXXLXXXXNXX-IXXXXXXXKXXXI XXXXXXXXXHXXXXXXXXX-TXXXXEXQXXXXXKIXXXXXXKXXXLXXXXFXXXXX XXKXXXXXXXXXXXXXXXXXXKXX-ELVWXXLXXXFXXXXLXIXXXXLYXXXXXG ESX-EIXXXXLX (SEQ ID NO:36), wherein X is any amino acid or a peptide bond;
EX$_1$GLWENIVYLDFRX$_2$LYPSIIITHNVSPDTLNX$_3$EGC KX$_4$YDX$_5$APQVGHX$_6$FCKDX$_7$PGFIPSLLGX$_8$LLEER QKIKX$_9$KMKX$_{10}$TX$_{11}$DPIEX$_{12}$X$_{13}$LLDYRQX$_{14}$ AIKX$_{15}$LANSX$_{16}$YGYYGYAX$_{17}$ARWYCKECAESVT AWGRX$_{18}$YIX$_{19}$X$_{20}$X$_{21}$X$_{22}$KEX$_{23}$EEKX$_{24}$GFKVX$_{25}$ YX$_{26}$DTDGX$_{27}$X$_{28}$ATIPGX$_{29}$X$_{30}$X$_{31}$EX$_{32}$X$_{33}$KKKA X$_{34}$E (SEQ ID NO:37), wherein X$_1$ is not R; X$_2$ is not S; X$_3$ is not R; X$_4$ is not E; X$_5$ is not V; X$_6$ is not R; X$_7$ is not F; X$_8$ is not D; X$_9$ is not K; X$_{10}$ is not A; X$_{11}$ is not I; X$_{12}$ is not R; X$_{13}$ is not K; X$_{14}$ is not R; X$_{15}$ is not I; X$_{16}$ is not Y; X$_{17}$ is not R; X$_{18}$ is not E; X$_{19}$ is not T; X$_{20}$ is not M; X$_{21}$ is not T; X$_{22}$ is not I; X$_{23}$ is not I; X$_{24}$ is not Y; X$_{25}$ is not I; X$_{26}$ is not S; X$_{27}$ is not F; X$_{28}$ is not F; X$_{29}$ is not A; X$_{30}$ is not D; X$_{31}$ is not A; X$_{32}$ is not T; X$_{33}$ is not V; X$_{34}$ is not M,
and combinations thereof,
wherein the chimeric polymerase is characterized with high fidelity and high processivity, elongation rate, salt resistance, TMAC or other PCR enhancer tolerance or thermostability.

In some embodiments, chimeric polymerases in accordance with the present invention are defined by consensus sequence XXXXTXXXXXDXXXXXXIXXXXXX-EXXXXYXXXXEXXFXXXXKXXXAXXXXXX XXAXXXXTVXTVKRXXXXQXXXXXRX-VEXXXXXFTXXXXXXAXXDXIXXXXXXI XXYXXXXXXXXXXXXXXXX-VXXXXDXXXXMXXXXXXXXXXXXXAEXXXLX XXXXXXXEGXRXXXXXXVXXXXXDXXX-TXXXXXXXXXXXXVVKXXXXXVLIXXXXX NXXX-AXXKXXCXXXXXNFALXXXXXXXXXX-IXXMXXRFXXXXXXXXXXXXPX XRXXXXXXXXXXXXXXXXVXX-QXXXXXXXXEXXTTXXXTXXXXXXXXRXXXXX XXVXXXXXXXXXXXXAXXXXXVXX-PXXXXXXXXXXXXXXXXXXXXXXXXXV XXXXXSXEXYQXXXXEXX-TXXFXXXXXXKXXXXXXXXXX-AXXXXXXXXXXXX XXXXXLXXXXNXX-IXXXXXXKXXXIXXXXXXXXHXXXXXXXXTX-XXEXQX XXXKIXXXXXKXXX-LXXXXFXXXXXXXKXXXXXXXXXXXXXXXKX-XELVW XXLXXXFXXXXLXIXXXX-LYXXXXXXGESXEIXXXXLXXLXXXX-AXXXXXAXXXXX XXXXXXXXXXXXKXXXXXXXXX-ITXXXXXXXXXXXXXXXXXXXXXXXALX XKXXXXXKXXXXXXXTEXXSKXX-VXXXXXXVXHXXXXXDXKDXXXTXXXXXXX XRXXXXRXXXXRXXTXXTXXSXXXXKX-SXRXGDXXXPFDXFXXTXXXXXXXXXXXX XXXXX-EXXXRAXXXXXXXXXXXXXXXXXSAXXKPXGT (SEQ ID NO:38), wherein X is any amino acid or a peptide bond, and wherein the chimeric polymerase has a fidelity higher than that of KOD and a processivity, an elongation rate, a salt resistance, a TMAC or other PCR enhancer tolerance or a thermostability higher than that of Pfu.

In some embodiments, chimeric polymerases in accordance with the present invention are defined by consensus sequence XIXDTDYXTXDGX-PXXRIFXKXXGEFXXXYDXXEPYFY-ALLKDDSAIXXXXXXXA XRHGTVXTVKRXXXX-QXKFLXRXVEVWXLXFTHPQDVPAXXDXIXXHXXV-IDIYE YDIPFAKRYLIDXGLVPMEGDEX-LXMXXXDIETXYHEGXEFAEGXXLMISYADXEG ARVITWKXVDLPYVDVVSTEX-EMIKRXXXVVKEKDPDVLIXYXGDNEDXAYLKXR CEXLGXNFALXRXXXXXEPKIXXMGXR-FAVEXXGRXHFDLXPXXRXTXNLPTYXL XXVYEX-VSGQXKXKXXXXEEITTXWETXXXXXXX-ARYSMEDAXYTXELGXEFXPM EAXLXXLVGXPXWDVXRSSTGNLVEWX-LLXXAYXRNEVAPNKPSXEEYQXRXXE XYTGXFVX-EPEKGLWXXXXXLDXXALYPSIIIXXH-NVSPDTLXLEXCXNYDIAPXVG XKFCKDIPGFIPSXLXHLXXXRQXXK-TXMXEXQDPXEKIXLDYRQKAXKLLXNSFY GYXGYXKARWYXXECAESVTX-WGRKYIELVWXELEXXFGFKXLYIDTDGLYATIP GGESXEIKXXXLXFLXYINAXLPGALEL-EYEXFYXRGFFVXKKKYAXIDEEXXITTR GLEXVR-RDWSXXAKETXAXXVLEALLXDXX- VXKAVXXVXXXTEXXSKYXVPXEKL
VIHEQITRDXKDYXATGPHVAX-
AKRLXXGXXXRPGTXISYXXLKGSGRXGDRXIPF
DEFXXTKHXYDXXYYIENQVLPAVERXL-
RAFGYXXXXLXXQXXXQXGLSAWXKP XGT (SEQ ID NO:39), wherein X is any amino acid or a peptide bond.

In some embodiments, the present invention further provides chimeric polymerases containing a first domain having a sequence at least 80% (e.g., at least 85%, 90%, 91%, 92%, 93%, 94%, 95%, 96%, 97%, 98%, 99%) identical to an amino acid sequence found in an exonuclease domain, an N-terminal domain, and/or a thumb domain of a first DNA polymerase; and a second domain having a sequence at least 80% (e.g., at least 85%, 90%, 91%, 92%, 93%, 94%, 95%, 96%, 97%, 98%, 99%) identical to an amino acid sequence found in palm and/or fingers domain of a second DNA polymerase. In some embodiments, the chimeric polymerase has a fidelity higher than that of the second DNA polymerase and a processivity, an elongation rate, a salt resistance, a TMAC or other PCR enhancer tolerance or a thermostability higher than that of the first DNA polymerase.

In another aspect, the present invention provides methods of engineering chimeric polymerases. Inventive methods in accordance with the present invention include steps of: (a) providing an N-terminal domain, an exonuclease domain, and/or a thumb domain based on a first DNA polymerase; (b) providing a palm and/or fingers domain based on a second DNA polymerase; (c) combining the domains from step (a) and step (b) to form a chimeric polymerase; wherein the chimeric polymerase has a fidelity higher than that of the first DNA polymerase and a processivity, an elongation rate, a salt resistance, a TMAC or other PCR enhancer tolerance or a thermostability higher than that of the second DNA polymerase. In some embodiments, a chimeric polymerase engineered according to the present invention has a processivity, an elongation rate, a salt resistance, a TMAC or other PCR enhancer tolerance or a thermostability substantially similar to that of the first DNA polymerase and a fidelity substantially similar to that of the second DNA polymerase.

In some embodiments, exemplary first DNA polymerases suitable for the present invention include, but are not limited to, KOD polymerase, TNA1 polymerase, *Thermococcus* sp. 9 degrees N-7, T4, T7, or phi29. In some embodiments, the first DNA polymerase is KOD polymerase. In some embodiments, exemplary second DNA polymerases suitable for the invention include, but are not limited to, polymerases isolated from *Pyrococcus furiosus, P. abyssi, T. gorgonarius, T. litoralis, T. zilligii, T.* sp. GT, or *P.* sp. GB-D. In some embodiments, the second DNA polymerase is Pfu polymerase.

In some embodiments, the first DNA polymerase is KOD polymerase and the second DNA polymerase is Pfu polymerase. In some embodiments, the first DNA polymerase is Pfu polymerase and the second DNA polymerase is KOD polymerase.

In some embodiments, the present invention provides methods of improving the fidelity of a DNA polymerase. In particular embodiments, inventive methods in accordance with the invention include a step of replacing a sequence within the palm and/or fingers domain of the DNA polymerase of interest with a corresponding sequence from a different DNA polymerase that is characterized with higher fidelity relative to the DNA polymerase of interest.

In some embodiments, the present invention provides methods of improving the processivity, elongation rate, salt resistance, TMAC or other PCR enhancer tolerance or thermostability of a DNA polymerase. In particular embodiments, inventive methods in accordance with the present invention include a step of replacing a sequence within the N-terminal domain, the exonuclease domain and/or the thumb domain of the DNA polymerase of interest with a corresponding sequence from a different DNA polymerase that is characterized with higher processivity, elongation rate, salt resistance, TMAC or other PCR enhancer tolerance or thermostability relative to the DNA polymerase of interest.

The present invention provides various chimeric polymerases described herein including chimeric polymerases engineered and/or improved using inventive methods as described herein. In some embodiments, chimeric polymerases in accordance with the present invention contain an amino acid sequence at least 80% identical to SEQ ID NO:16 (the Kofu amino acid sequence as shown in the Sequences section). In particular embodiments, a chimeric polymerase in accordance with the present invention contains the amino acid sequence of SEQ ID NO:16. In some embodiments, chimeric polymerases in accordance with the present invention contain an amino acid sequence at least 80% identical to SEQ ID NO:15 (the Pod amino acid sequence as shown in the Sequences section). In particular embodiments, a chimeric polymerase in accordance with the present invention contains the amino acid sequence of SEQ ID NO:15.

The present invention also provides kits and compositions containing various chimeric polymerases described herein and uses thereof (e.g., methods of amplifying DNA fragments using chimeric DNA polymerases of the invention). In addition, the present invention provides nucleotide sequences encoding various chimeric polymerases described herein and vectors and/or cells containing the nucleotide sequences according to the invention.

BRIEF DESCRIPTION OF THE DRAWINGS

The drawings are for illustration purposes only, not for limitation.

DEFINITIONS

Figure 1A:
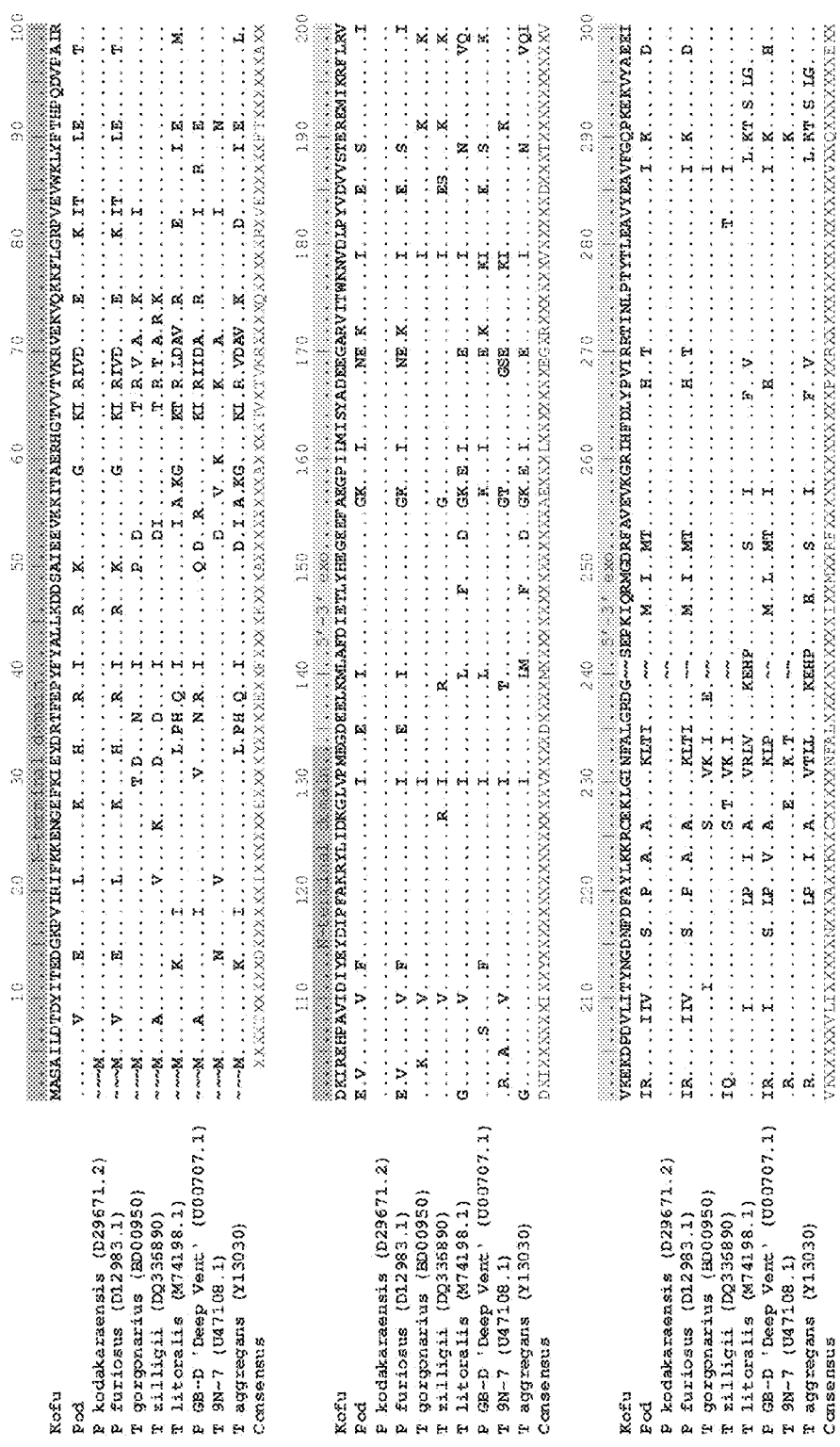
FIG. 1 depicts an alignment of domains in exemplary naturally-occurring type B DNA polymerases P. kodakarensis (SEQ ID NO:11), P. furiosus (SEQ ID NO:9), T. gorgonarius (SEQ ID NO:22), T. Zilligii (SEQ ID NO:23), T. litoralis (SEQ ID NO:19), P GN-D 'Deep Vent' (SEQ ID NO:45), T 9N-7 (SEQ ID NO:18), T. aggregans (SEQ ID NO:46); and exemplary chimeric DNA polymerases Kofu (SEQ ID NO: 16) and Pod (SEQ ID NO: 15); as compared to the generated consensus sequence (SEQ ID NO:38). The KOD and Pfu polymerase domains that were swapped in the Kofu and Pod chimeras are indicated above the alignment.

Amino acid: As used herein, term "amino acid," in its broadest sense, refers to any compound and/or substance that can be incorporated into a polypeptide chain. In some embodiments, an amino acid has the general structure $H_2N-$ C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical groups. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus.

Base Pair (bp): As used herein, base pair refers to a partnership of adenine (A) with thymine (T), or of cytosine (C) with guanine (G) in a double stranded DNA molecule.

Chimeric polymerase: As used herein, the term "chimeric polymerase" (also referred to as "chimera") refers to any polymerase containing two or more heterologous domains, amino acid sequences, peptides, and/or proteins joined either covalently or non-covalently to produce a polymerase that does not occur in nature. Typically, a chimeric polymerase contains a first domain joined to a second domain, wherein the first and second domains are not found in the same relationship in nature. Typically, the first domain is derived from a first DNA polymerase and a second domain is derived from a second DNA polymerase. Typically, the first and second DNA polymerases are characterized with at least one distinct functional characteristics (e.g., processivity, elongation rate, fidelity, salt tolerance, tolerance to PCR additives or thermostability). As used herein, a sequence derived from a DNA polymerase of interest refers to any sequence found in the DNA polymerase of interest, or any sequence having at least 70% (e.g., at least 75%, 80%, 85%, 90%, 91%, 92%, 93%, 94%, 95%, 96%, 97%, 98%, 99%) identical to an amino acid sequence found in the DNA polymerase of interest. A "chimeric polymerase" according to the invention may contain two or more amino acid sequences from related or similar polymerases (e.g., proteins sharing similar sequences and/or structures), joined to form a new functional protein. A "chimeric polymerase" according to the invention may contain two or more amino acid sequences from unrelated polymerases, joined to form a new functional protein. For example, a chimeric polymerase of the invention may be an "interspecies" or "intergenic" fusion of protein structures expressed by different kinds of organisms.

Complementary: As used herein, the term "complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

DNA binding affinity: As used herein, the term "DNA-binding affinity" typically refers to the activity of a DNA polymerase in binding DNA nucleic acid. In some embodiments, DNA binding activity can be measured in a two bandshift assay. For example, in some embodiments (based on the assay of Guagliardi et al. (1997) *J. Mol. Biol.* 267:841-848), double-stranded nucleic acid (the 452-bp HindIII-EcoRV fragment from the *S. solfataricus* lacS gene) is labeled with $^{32}$P to a specific activity of at least about $2.5 \times 10^7$ cpm/µg (or at least about 4000 cpm/fmol) using standard methods. See, e.g., Sambrook et al. (2001) Molecular Cloning: A Laboratory Manual ($3^{rd}$ ed., Cold Spring Harbor Laboratory Press, NY) at 9.63-9.75 (describing end-labeling of nucleic acids). A reaction mixture is prepared containing at least about 0.5 µg of the polypeptide in about 10 µl of binding buffer (50 mM sodium phosphate buffer (pH 8.0), 10% glycerol, 25 mM KCl, 25 mM $MgCl_2$). The reaction mixture is heated to 37° C. for 10 min. About $1 \times 10^4$ to $5 \times 10^4$ cpm (or about 0.5-2 ng) of the labeled double-stranded nucleic acid is added to the reaction mixture and incubated for an additional 10 min. The reaction mixture is loaded onto a native polyacrylamide gel in 0.5× Tris-borate buffer. The reaction mixture is subjected to electrophoresis at room temperature. The gel is dried and subjected to autoradiography using standard methods. Any detectable decrease in the mobility of the labeled double-stranded nucleic acid indicates formation of a binding complex between the polypeptide and the double-stranded nucleic acid. Such nucleic acid binding activity may be quantified using standard densitometric methods to measure the amount of radioactivity in the binding complex relative to the total amount of radioactivity in the initial reaction mixture. Other methods of measuring DNA binding affinity are known in the art (see, e.g., Kong et al. (1993) *J. Biol. Chem.* 268(3): 1965-1975).

Domain: As used herein, the term "Domain" as used herein refers to an amino acid sequence of a polypeptide (e.g., polymerase) comprising one or more defined functions or properties.

Elongation rate: As used herein, the term "elongation rate" refers to the average speed at which a DNA polymerase extends a polymer chain. As used herein, a high elongation rate refers to an elongation rate higher than 25 nt/s (e.g., higher than 30, 35, 40, 45, 50, 55, 60, 65, 70, 75, 80, 85, 90, 95, 100, 105, 110, 115, 120, 125, 130, 135, 140 nt/s).

Enzyme activity: As used herein, the term "enzyme activity" refers to the specificity and efficiency of a DNA polymerase. Enzyme activity of a DNA polymerase is also referred to as "polymerase activity," which typically refers to the activity of a DNA polymerase in catalyzing the template-directed synthesis of a polynucleotide. Enzyme activity of a polymerase can be measured using various techniques and methods known in the art. For example, serial dilutions of polymerase can be prepared in dilution buffer (e.g., 20 mM Tris.Cl, pH 8.0, 50 mM KCl, 0.5% NP 40, and 0.5% Tween-20). For each dilution, 5 µl can be removed and added to 45 µl of a reaction mixture containing 25 mM TAPS (pH 9.25), 50 mM KCl, 2 mM MgCl2, 0.2 mM dATP, 0.2 mM dGTP, 0.2 mM dTTP, 0.1 mM dCTP, 12.5 µg activated DNA, 100 µM [α-$^{32}$P]dCTP (0.05 µCi/nmol) and sterile deionized water. The reaction mixtures can be incubated at 37° C. (or 74° C. for thermostable DNA polymerases) for 10 minutes and then stopped by immediately cooling the reaction to 4° C. and adding 10 µl of ice-cold 60 mM EDTA. A 25 µl aliquot can be removed from each reaction mixture. Unincorporated radioactively labeled dCTP can be removed from each aliquot by gel filtration (Centri-Sep, Princeton Separations, Adelphia, N.J.). The column eluate can be mixed with scintillation fluid (1 ml). Radioactivity in the column eluate is quantified with a scintillation counter to determine the amount of product synthesized by the polymerase. One unit of polymerase activity can be defined as the amount of polymerase necessary to synthesize 10 nmole of product in 30 minutes (Lawyer et al. (1989) *J. Biol. Chem.* 264:6427-647). Other methods of measuring polymerase activity are known in the art (see, e.g., Sambrook et al. (2001) Molecular Cloning: A Laboratory Manual ($3^{rd}$ ed., Cold Spring Harbor Laboratory Press, NY)).

Fidelity: As used herein, the term "fidelity" refers to the accuracy of DNA polymerization by template-dependent DNA polymerase. The fidelity of a DNA polymerase is typically measured by the error rate (the frequency of incorporating an inaccurate nucleotide, i.e., a nucleotide that is not complementary to the template nucleotide). The accuracy or fidelity of DNA polymerization is maintained by both the polymerase activity and the 3'-5' exonuclease activity of a DNA polymerase. The term "high fidelity" refers to an error rate less than $4.45 \times 10^{-6}$ (e.g., less than $4.0 \times 10^{-6}$, $3.5 \times 10^{-6}$, $3.0 \times 10^{-6}$, $2.5 \times 10^{-6}$, $2.0 \times 10^{-6}$, $1.5 \times 10^{-6}$, $1.0 \times 10^{-6}$, $0.5 \times 10^{-6}$) mutations/nt/doubling. The fidelity or error rate of a DNA polymerase may be measured using assays known to the art. For example, the error rates of DNA polymerases can be tested using the lacI PCR fidelity assay described in Cline, J. et al. (1996) NAR 24: 3546-3551. Briefly, a 1.9 kb fragment encoding the lacIOlacZa target gene is amplified from pPRIAZ plasmid DNA using 2.5 U DNA polymerase (i.e., amount of enzyme necessary to incorporate 25 nmoles of total dNTPs in 30 min. at 72° C.) in the appropriate PCR buffer. The lad-containing PCR products are then cloned into lambda GT10 arms, and the percentage of lacI mutants (MF, mutation frequency) is determined in a color screening assay, as described (Lundberg, K. S., Shoemaker, D. D., Adams, M. W. W., Short, J. M., Sorge, J. A., and Mathur, E. J. (1991) Gene 180: 1-8). Error rates are expressed as mutation frequency per by per duplication (MF/bp/d), where by is the number of detectable sites in the lad gene sequence (349) and d is the number of effective target doublings. Similar to the above, any plasmid containing the lacIOlacZa target gene can be used as template for the PCR. The PCR product may be cloned into a vector different from lambda GT (e.g., plasmid) that allows for blue/white color screening.

Joined: As used herein, "joined" refers to any method known in the art for functionally connecting polypeptide domains, including without limitation recombinant fusion with or without intervening domains, inter-mediated fusion, non-covalent association, and covalent bonding, including disulfide bonding, hydrogen bonding, electrostatic bonding, and conformational bonding.

Nucleotide: As used herein, a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence," and is represented herein by a formula whose left to right orientation is in the conventional direction of 5'-terminus to 3'-terminus.

Oligonucleotide or Polynucleotide: As used herein, the term "oligonucleotide" is defined as a molecule including two or more deoxyribonucleotides and/or ribonucleotides, preferably more than three. Its exact size will depend on many factors, which in turn depend on the ultimate function or use of the oligonucleotide. The oligonucleotide may be derived synthetically or by cloning. As used herein, the term "polynucleotide" refers to a polymer molecule composed of nucleotide monomers covalently bonded in a chain. DNA (deoxyribonucleic acid) and RNA (ribonucleic acid) are examples of polynucleotides.

Polymerase: As used herein, a "polymerase" refers to an enzyme that catalyzes the polymerization of nucleotide (i.e., the polymerase activity). Generally, the enzyme will initiate synthesis at the 3'-end of the primer annealed to a polynucleotide template sequence, and will proceed towards the 5' end of the template strand. A "DNA polymerase" catalyzes the polymerization of deoxynucleotides.

Processivity: As used herein, "processivity" refers to the ability of a polymerase to remain attached to the template and perform multiple modification reactions. "Modification reactions" include but are not limited to polymerization, and exonucleolytic cleavage. In some embodiments, "processivity" refers to the ability of a DNA polymerase to perform a sequence of polymerization steps without intervening dissociation of the enzyme from the growing DNA chains. Typically, "processivity" of a DNA polymerase is measured by the length of nucleotides (for example 20 nts, 300 nts, 0.5-1 kb, or more) that are polymerized or modified without intervening dissociation of the DNA polymerase from the growing DNA chain. "Processivity" can depend on the nature of the polymerase, the sequence of a DNA template, and reaction conditions, for example, salt concentration, temperature or the presence of specific proteins. As used herein, the term "high processivity" refers to a processivity higher than 20 nts (e.g., higher than 40 nts, 60 nts, 80 nts, 100 nts, 120 nts, 140 nts, 160 nts, 180 nts, 200 nts, 220 nts, 240 nts, 260 nts, 280 nts, 300 nts, 320 nts, 340 nts, 360 nts, 380 nts, 400 nts, or higher) per association/disassociation with the template. Processivity can be measured according the methods defined herein and in WO 01/92501 A1.

Primer: As used herein, the term "primer" refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and thermostable enzyme in an appropriate buffer ("buffer" includes appropriate pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15-25 nucleotides, although it may contain more or few nucleotides. Short primer molecules generally require lower temperatures to form sufficiently stable hybrid complexes with template.

Salt resistance: As used herein, the term "salt resistance" (also referred to as salt tolerance) refers to the ability of a DNA polymerase to substantially maintain its enzymatic activity in the presence of salt or PCR additives (e.g., TMAC). In some embodiments, resistance to salt or PCR additives is measured by the maximum salt concentration at which a DNA polymerase is still active. The maximum salt concentration differs for each polymerase and is known in the art, or can be experimentally determined according to methods in the art. For example, Pfu is inhibited at 30 mM salt (in a PCR reaction).

Synthesis: As used herein, the term "synthesis" refers to any in vitro method for making new strand of polynucleotide or elongating existing polynucleotide (i.e., DNA or RNA) in a template dependent manner. Synthesis, according to the invention, includes amplification, which increases the number of copies of a polynucleotide template sequence with the use of a polymerase. Polynucleotide synthesis (e.g., amplification) results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, PCR, the labeling of polynucleotide (i.e., for probes and oligonucleotide primers), polynucleotide sequencing.

Template DNA molecule: As used herein, the term "template DNA molecule" refers to a strand of a nucleic acid from which a complementary nucleic acid strand is synthesized by a DNA polymerase, for example, in a primer extension reaction.

Template dependent manner: As used herein, the term "template dependent manner" refers to a process that involves the template dependent extension of a primer molecule (e.g., DNA synthesis by DNA polymerase). The term "template dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: Molecular Biology of the Gene, 4th Ed. , W. A. Benjamin, Inc., Menlo Park, Calif. (1987)).

Thermostable enzyme: As used herein, the term "thermostable enzyme" refers to an enzyme which is stable to heat (also referred to as heat-resistant) and catalyzes (facilitates) polymerization of nucleotides to form primer extension products that are complementary to a polynucleotide template sequence. Typically, thermostable stable polymerases are preferred in a thermocycling process wherein double stranded nucleic acids are denatured by exposure to a high temperature (e.g., about 95 C) during the PCR cycle. A thermostable enzyme described herein effective for a PCR amplification reaction satisfies at least one criteria, i.e., the enzyme do not become irreversibly denatured (inactivated) when subjected to the elevated temperatures for the time necessary to effect denaturation of double-stranded nucleic acids. Irreversible denaturation for purposes herein refers to permanent and complete loss of enzymatic activity. The heating conditions necessary for denaturation will depend, e.g., on the buffer salt concentration and the length and nucleotide composition of the nucleic acids being denatured, but typically range from about 90° C. to about 98° C. for a time depending mainly on the temperature and the nucleic acid length, typically about 0.2 to four minutes. Higher temperatures may be tolerated as the buffer salt concentration and/or GC composition of the nucleic acid is increased. In some embodiments, thermostable enzymes will not become irreversibly denatured at about 90° C. -100° C. Typically, a thermostable enzyme suitable for the invention has an optimum temperature at which it functions that is higher than about 40° C., which is the temperature below which hybridization of primer to template is promoted, although, depending on (1) magnesium and salt, concentrations and (2) composition and length of primer, hybridization can occur at higher temperature (e.g., 45° C.-70° C.). The higher the temperature optimum for the enzyme, the greater the specificity and/or selectivity of the primer-directed extension process. However, enzymes that are active below 40° C. (e.g., at 37° C.) are also with the scope of this invention provided they are heat-stable. In some embodiments, the optimum temperature ranges from about 50° C. to 90° C. (e.g., 60° C.-80° C.).

TMAC or other PCR enhancer tolerance: As used herein, the term "TMAC or other PCR enhancer tolerance" (also referred to as TMAC or other PCR enhancer resistance) refers to the ability of a DNA polymerase to substantially maintain its enzymatic activity in the presence of TMAC or other PCR enhancers (e.g., glycerol, DMSO, betaine, amides, other tetramethyl ammonium salts).

DETAILED DESCRIPTION OF THE INVENTION

The present invention provides, among other things, chimeric DNA polymerases containing heterologous domains having sequences derived from at least two DNA polymerases that have at least one distinct functional characteristics (e.g., elongation rate, processivity, error rate or fidelity, salt tolerance or resistance) and methods of making and using the same.

DNA Polymerases

Chimeric DNA polymerases in accordance with the present invention may be engineered from any DNA polymerases, in particular, thermostable polymerases. Typically, DNA polymerases are grouped into six families: A, B, C, D, X and Y. Families A, B, C are grouped based on their amino acid sequence homologies to E. coli polymerases I, II, and III, respectively. Family X has no homologous E. coli polymerases. In some embodiments, DNA polymerases suitable for the present invention are family B DNA polymerases. Family B polymerases include, but are not limited to, E. coli pol II, archaeal polymerases, PRD1, phi29, M2, T4 bacteriophage DNA polymerases, eukaryotic polymerases α, Δ, ε, and many viral polymerases. In some embodiments, DNA polymerases suitable for the invention are archaeal polymerases (e.g., euryarchaeal polymerases).

Suitable exemplary archaeal polymerases include, but are not limited to, DNA polymerases from archaea (e.g., *Thermococcus litoralis* (Vent™, GenBank: AAA72101), *Pyrococcus furiosus* (Pfu, GenBank: D12983, BAA02362), *Pyrococcus woesii, Pyrococcus* GB-D (Deep Vent™, GenBank: AAA67131), *Thermococcus kodakaraensis* KOD1 (KOD, GenBank: BD175553, BAA06142; *Thermococcus* sp. strain KOD (Pfx, GenBank: AAE68738)), *Thermococcus gorgonarius* (Tgo, Pdb: 4699806), *Sulfolobus solataricus* (GenBank: NC002754, P26811), *Aeropyrum pernix* (GenBank: BAA81109), *Archaeglobus fulgidus* (GenBank: 029753), *Pyrobaculum aerophilum* (GenBank: AAL63952), *Pyrodictium occultum* (GenBank: BAA07579, BAA07580), *Thermococcus* 9 degree Nm (GenBank: AAA88769, Q56366), *Thermococcus fumicolans* (GenBank: CAA93738, P74918), *Thermococcus hydrothermalis* (GenBank: CAC18555), *Thermococcus* sp. GE8 (GenBank: CAC12850), *Thermococcus* sp. JDF-3 (GenBank: AX135456; WO0132887), *Thermococcus* sp. TY (GenBank: CAA73475), *Pyrococcus abyssi* (GenBank: P77916), *Pyrococcus glycovorans* (GenBank: CAC12849), *Pyrococcus horikoshii* (GenBank: NP 143776), *Pyrococcus* sp. GE23 (GenBank: CAA90887), *Pyrococcus* sp. ST700 (GenBank: CAC 12847), *Thermococcus pacificus* (GenBank: AX411312.1), *Thermococcus zilligii* (GenBank: DQ3366890), *Thermococcus aggregans, Thermococcus barossii, Thermococcus celer* (GenBank: DD259850.1), *Thermococcus profundus* (GenBank: E14137), *Thermococ-* cus siculi (GenBank: DD259857.1), Thermococcus thioreducens, Thermococcus onnurineus NA1, Sulfolobus acidocaldarium, Sulfolobus tokodaii, Pyrobaculum calidifontis, Pyrobaculum islandicum (GenBank: AAF27815), Methanococcus jannaschii (GenBank: Q58295), Desulforococcus species TOK, Desulfurococcus, Pyrolobus, Pyrodictium, Staphylothermus, Vulcanisaetta, Methanococcus (GenBank: P52025) and other archaeal B polymerases, such as GenBank AAC62712, P956901, BAAA07579)). Additional representative temperature-stable family A and B polymerases include, e.g., polymerases extracted from the thermophilic bacteria Thermus species (e.g., flavus, ruber, thermophilus, lacteus, rubens, aquaticus), Bacillus stearothermophilus, Thermotoga maritima, Methanothermus fervidus.

DNA polymerases suitable for the present invention include DNA polymerases that have not yet been isolated. Suitable polymerases for the present invention include fusion polymerases. Fusion polymerases generally contain an additional protein domain at the N- or C-terminus that changes the phenotype of the fusion polymerase compared to the polymerase without the extra domain. Exemplary polymerases include, but are not limited to, polymerases with double-stranded DNA-binding domains fused at the C- or N-terminus. Further examples of fusion polymerases include those with dUTPase fused to the N-or C-terminus (U.S. patent application 20070190538).

In some embodiments, chimeric DNA polymerases according to the invention contain sequences derived from two or more DNA polymerases that have at least one distinct functional characteristic. Exemplary functional characteristics include, but are not limited to, processivity, elongation rate, fidelity, resistance to salt or PCR additive (e.g., PCR enhancers), thermostability, strand displacement activity, exonuclease activity, uracil read-ahead function, nucleotide selectivity, ability to incorporate modified analogs, and reverse transcriptase activity. For example, some DNA polymerases are characterized with high fidelity. As used herein, the term "high fidelity" refers to an error rate less than $4.45 \times 10^{-6}$ (e.g., less than $4.0 \times 10^{-6}$, $3.5 \times 10^{-6}$, $3.0 \times 10^{-6}$, $2.5 \times 10^{-6}$, $2.0 \times 10^{-6}$, $1.5 \times 10^{-6}$, $1.0 \times 10^{-6}$, $0.5 \times 10^{-6}$) mutations/nt/doubling. Some DNA polymerases are characterized with high processivity. As used herein, the term "high processivity" refers to a processivity higher than 20 nts (e.g., higher than 40 nts, 60 nts, 80 nts, 100 nts, 120 nts, 140 nts, 160 nts, 180 nts, 200 nts, 220 nts, 240 nts, 260 nts, 280 nts, 300 nts, 320 nts, 340 nts, 360 nts, 380 nts, 400 nts, or higher) per association/disassociation with the template. Some DNA polymerases are characterized with high elongation rate. As used herein, the term "high elongation rate" refers to an elongation rate higher than 25 nt/s (e.g., higher than 30, 35, 40, 45, 50, 55, 60, 65, 70, 75, 80, 85, 90, 95, 100, 105, 110, 115, 120, 125, 130, 135, 140 nt/s). Some enzymes are characterized with high resistance to salt (also referred to as salt tolerance). As used herein, the term "high resistance to salt" (also referred to as high salt tolerance) refers to the ability of a DNA polymerase to substantially maintain its activity at a salt concentration higher than 30 mM (e.g., higher than 35 mM, 40 mM, 45 mM, 50 mM). In addition, some enzymes are characterized with resistance to PCR additives. Certain PCR additives are PCR enhancers. For example, Kovarova et al. showed that TMA salts, DMSO, betaine and formamide act as PCR enhancers (Kovarova and Draber. (2000) Nucl. Acids. Res. 28(13), e70). Another example of PCR enhancers is glycerol. Some enzymes are characterized with resistance to PCR enhancers, in particular, TMAC (also referred to as TMAC tolerance). As used herein, the term "high TMAC tolerance" refers to the ability of a DNA polymerase to substantially maintain its enzymatic activity at a TMAC (tetra-methyl ammonium chloride) concentration higher than 10 mM (e.g., higher than 15 mM, 20 mM). Certain characteristics of exemplary DNA polymerases are shown in Table 1.

TABLE 1

Characteristics of exemplary DNA polymerases

| Polymerases | Fidelity/Error rate | Processivity (nts) | Elongation rate (nts/s) | Salt tolerance |
|---|---|---|---|---|
| Pfu | $2.0 \times 10^{-6}$ | >20 | 25 | 30 mM |
| KOD | $4.45 \times 10^{-6}$ | ~300 | 106-138 | |
| TNA1 | | 150 | | |
| T. zilligii | $2.0 \times 10^{-6}$ | | | |
| P. abyssi | $0.66 \times 10^{-6}$ | | | |
| T. gorgonarius | $2.2\text{-}3.4 \times 10^{-6}$ | | | |

Typically, enzymes with high salt tolerance are also characterized with high processivity and/or elongation rate. Without wishing to be bound by any theories, it is thought that salt tolerance affects the binding affinity between polymerase and DNA which, in turn, affects processivity or elongation rate. Typically, binding of polymerases to DNA involves binding interaction between positively charged amino acid residues and negatively charged DNA. At high salt concentrations, competition from the anions of the salt for the positively charged amino acid residues on the polymerases lead to diminished DNA binding affinity. See, Pavlov et al. (2002) Proc. Natl. Acad. Sci. 99(21): 13510-13515, which is incorporated by reference herein. On the other hand, increasing the contact points between DNA and polymerase may increase the salt resistance of the polymerase as well as the processivity or elongation rate because the additional contact points between DNA and polymerase may increase binding affinity of the polymerase for DNA and decrease the rate of dissociation so that the polymerase will remain associated with DNA longer, which will in turn lead to an increase in processivity. For example, Pavlov et al. added helix-hairpin-helix (HhH) motifs from topoisomerase V to Taq and Pfu. These motifs are involved in DNA binding in topoisomerase V. Pavlov et al. showed that both Pfu and Taq become more salt resistant when fused to the HhH motifs. Pavlov et al. also showed that HhH fusion to both Taq and Pfu increased the processivity of the polymerases. As another example, dsDNA binding proteins, e.g., Sso7d, can be fused to DNA polymerases to increase the number of contact points between DNA and polymerases (Wang et al. (2004) Nucl. Acids Res. 32(3): 1197-1207, which is incorporated by reference herein). Sso7d is a sequence non-specific dsDNA binding protein involved in ensuring DNA stability and/or DNA packing in Sulfolobus solfataricus. Fusion of Sso7d to both Taq and Pfu increased the salt resistance and processivity of the polymerases.

Exemplary DNA polymerases characterized with high processivity, elongation rate, thermostability, salt or PCR enhancer tolerance include, but are not limited to, KOD polymerase, TNA1 polymerase, Thermococcus sp. 9 degrees N-7, T4, T7, or phi29. Exemplary DNA polymerases characterized with high fidelity include, but are not limited to, polymerases isolated from Pyrococcus furiosus, P. abyssi, T. gorgonarius, T. litoralis, T. zilligii, T. sp. GT, or P. sp. GB-D.

As non-limiting examples, KOD, Pfu, T. gorgonarius, T. zilligii, T. litoralis and Thermococcus sp. 9N-7 polymerases are used to engineer chimeric DNA polymerases (see the Example sections).

Domains of DNA Polymerases

Typically, archaeal DNA polymerases include at least the following domains: N-terminal domain, exonuclease domain (e.g., 3'->5' exonuclease domain), palm, fingers, and thumb domain (see FIG. 1). Knowledge of domain structure, function and coordination is primary based on crystal structure studies and site-directed mutagenesis of various DNA polymerases, in particular, archaeal DNA polymerases. For example, among the first crystal structures of family B DNA polymerases obtained was that of bacteriophage RB69 DNA polymerase (Wang et al. (1997) *Cell*, 89:1087-1099, which is incorporated by reference herein). Among the first crystal structures of archaeal DNA polymerases solved was Tgo DNA polymerase (see, Hopfner et al. 1999 *Proc. Natl. Acad. Sci.* 96(7), 3600-3605, which is incorporated by reference herein). Recently, crystal structures of the following archaeal family B DNA polymerases have been reported: DNA polymerase from *Thermococcus* sp. 9° N-7 (Rodriguez et al. (2000) *J. Mol. Biol.* 299:447-462, which is incorporated by reference herein), KOD1 DNA polymerase (Hashimoto et al. 2001 *J. Mol. Biol.* 306(3), 469-477, which is incorporated by reference herein), Pfu DNA polymerase (see, U.S. Pat. Nos. 5,948, 663; 5,866, 395; 5,545, 552; 5,556, 772 and Kim et al. (2008) *Int. J. Biol. Macromol.* 42(4), 356-61, all of which are hereby incorporated by reference).

Various functions, such as substrate binding, nucleotide transfer, catalytic activity, proofreading, have been assigned to various domains based on the structural-functional analysis of DNA polymerases. It has also been suggested that the domains tightly coordinate with each other to complete the DNA replication process.

For example, the polymerase activity has been associated with palm, fingers and thumb domains. In particular, the palm subdomain is thought to be the catalytic site of the polymerase. The polymerase catalyzes a phosphoryl transfer reaction in which the alpha phosphate of the incoming dNTP undergoes nucleophilic attack from the OH primer terminus. Typically, three carboxylate side chains are important to this active site. These residues may bind two metal ions (Mg++) which may facilitate deprotonation of the OH terminus and formation of a transition state at the alpha phosphate of the dNTP. The thumb domain is believed to interact with the minor grove of the newly synthesized dsDNA and also with the incoming nucleotide. The thumb domain is less conserved but typically has a largely helical structure. The fingers domain may play a role in template fixation and nucleotide specificity. Like the thumb domain, it is likely to interact with the incoming nucleotide. The thumb domain may contain α helices, and/or β strands. It is thought that unbound DNA polymerases form open conformations of the fingers and thumb domains, and when the DNA is bound, the two domains move towards the palm domain to hold the DNA template and primer more tightly and to probe for Watson-Crick base pairing between the incoming nucleotide and the template nucleotide. The presence of a nucleotide that forms a Watson-Crick base pair with the template facilitates formation of an appropriate conformation of the active site of the polymerase and subsequent incorporation of this nucleotide. For review see Hamilton et al. (2001) BioTechniques 31:370-383. It was reported that mutagenesis in the palm/fingers domain may affects the nucleotide selectivity and affinity and mutagenesis in the thumb domain may affect the binding affinity to dsDNA. Important amino acids in the palm, fingers and thumb domain are described in U.S. Application Publication No. 20060281109, which is hereby incorporated by reference.

The uracil read-ahead function has been associated with the N-terminal domain. For example, archaeal family B DNA polymerases are able to recognize unrepaired uracil in a template strand and stall polymerization upstream of the lesion to prevent an A-T mutation. A "pocket" in the N-terminal domains of archaeal DNA polymerases was identified to be positioned to interact with the template strand and provide this uracil read-ahead function (Fogg et al. (2002) Nature Structural Biology 9(12), 922-927).

The exonuclease domain is associated with either 5'->3' exonuclease activity, 3'->5" exonuclease activity or both, which is required to remove incorrectly inserted nucleotide. When a mismatched nucleotide is incorporated, the template/primer strand binds to the polymerase more weakly and/or is misaligned with respect to the polymerase active site causing the mismatched nucleotide to be moved to the active site of the exonuclease domain and excised.

It is thought that the fidelity is affected by the ratio of the polymerase and the exonuclease activity, which may be influenced by the rate of dissociation, conformational change, and the rate of nucleotide incorporation in the presence of mismatched nucleotides. It has also been suggested that the balance between the 3'->5' exonuclease activity and the polymerase activity is mediated by a flexible loop containing the Y-GG/A motif located between the N-terminal and exonuclease domains and the C-terminal polymerase domains (i.e., the palm, fingers and thumb domains). See, Bohlke et al. (2000) *Nucl. Acids Res.* 28(20), 3910-3917. A unique loop of the exonuclease domain, and the tip of the thumb are important for the coordination of proofreading and polymerase activities in DNA polymerases. Site-directed mutagenesis in this loop, especially at H147 in KOD DNA polymerase, suggested that electrostatic and hydrophobic interactions between this loop and the thumb affect the ratio between exonuclease activity and polymerase activity and hence fidelity. See, Kuroita et al. *J. Mol. Biol.* (2005) 351, 291-298.

Domain Swapping

According to the present invention, heterologous domains from different DNA polymerases (e.g., polymerases with at least one distinct functional characteristic) may be combined to form a chimeric polymerase. Suitable domains include naturally-occurring N-terminal domains, exonuclease domains, palm, fingers, and/or thumb domains found in various DNA polymerases. Naturally-occurring N-terminal domains, exonuclease domains, palm, fingers, and/or thumb domains in various DNA polymerases are well defined. For example, an N-terminal domain may include a sequence corresponding to amino acid residues 26 to 105 of KOD polymerase (SEQ ID NO:11); an exonuclease domain may include a region corresponding to amino acid residues 156 to 301 of KOD polymerase (SEQ ID NO:11); a thumb domain may include a region corresponding to amino acid residues 612 to 749 of KOD polymerase (SEQ ID NO:11); and palm and fingers domain may include a region corresponding to amino acid residues 394 to 563 of Pfu polymerase (SEQ ID NO:9).

Figure 1B:
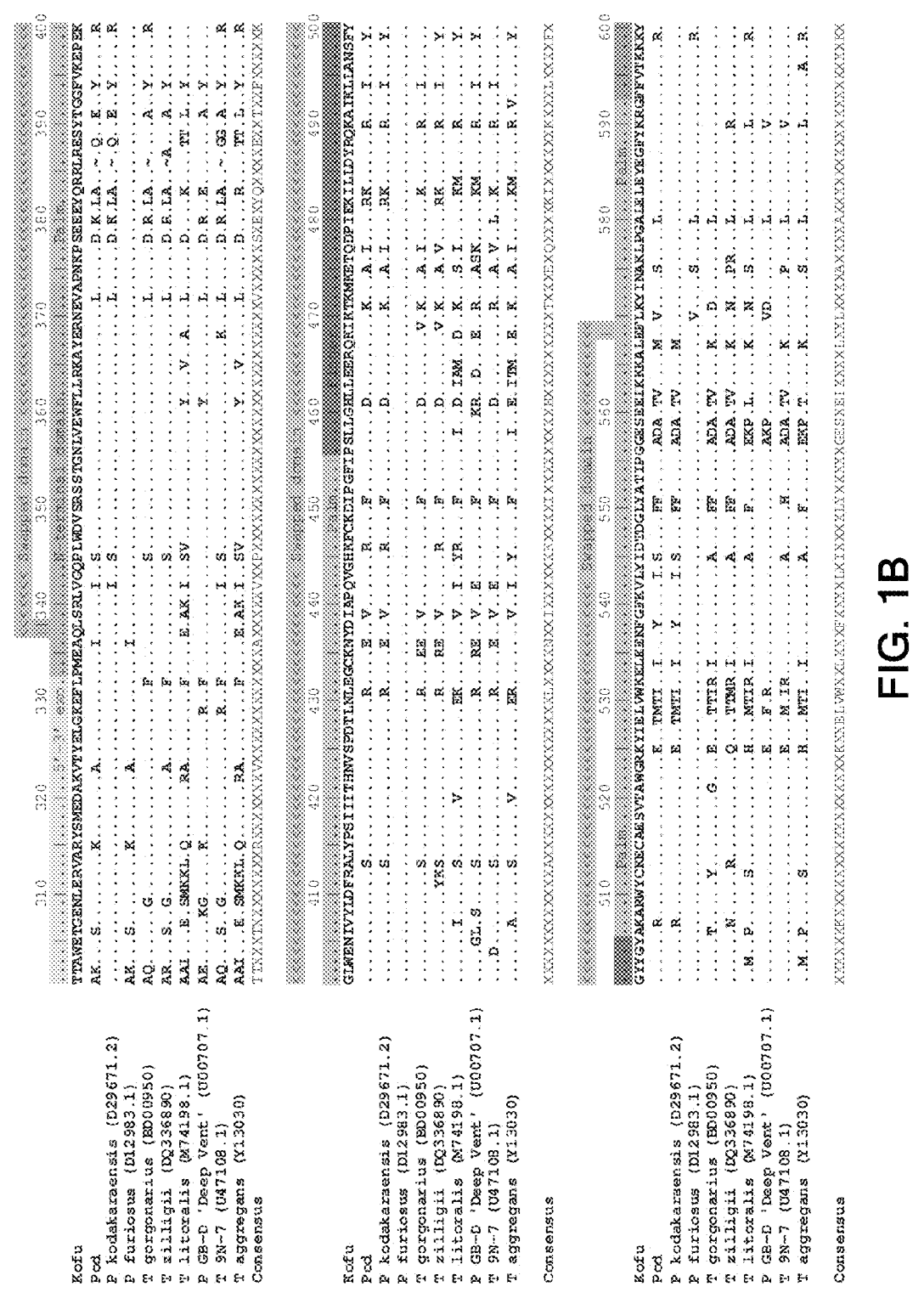
Figure 1C:
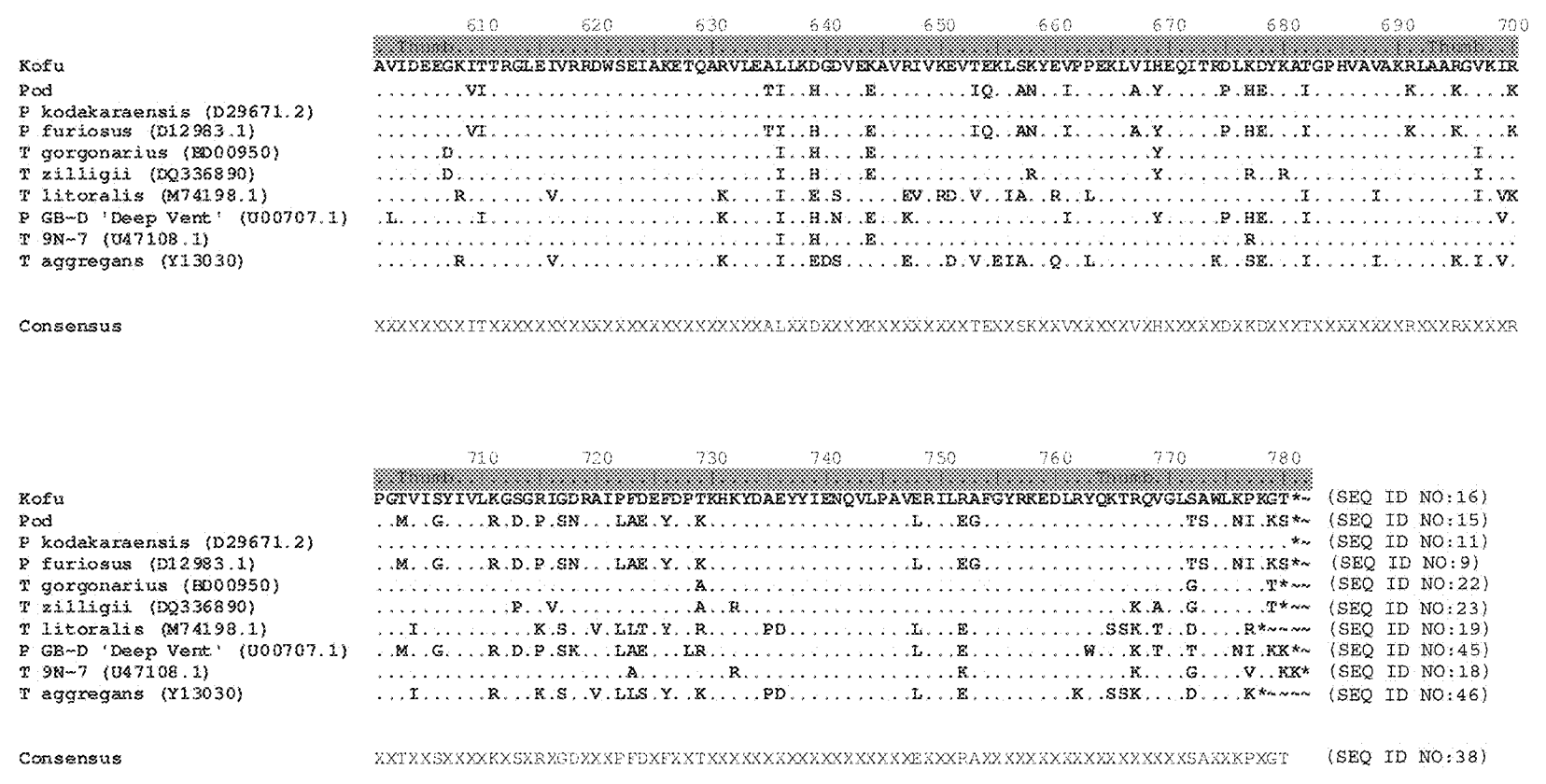

Corresponding domains or positions in various DNA polymerases can be determined by alignment of amino acid sequences. Alignment of amino acid sequences can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., *Methods in Enzymology* 266, 460-480 (1996); http://blast.wustl/edu/blast/README.html). WU-BLAST-2 uses several search parameters, most of which are set to the default values. The adjustable parameters are set with the following values: overlap span=1, overlap fraction=0.125, word threshold (T)=11. HSP score (S) and HSP S2 parameters are dynamic values and are established by the program itself, depending upon the composition of the particular sequence, however, the minimum values may be adjusted and are set as indicated above. An example of an alignment is shown in FIG. 1.

In some embodiments, a suitable domain may be a variant (e.g., mutant or fragment) of a naturally-occurring domain sequence. For example, a suitable domain may have a sequence having at least 70% (e.g., at least 75%, 80%, 85%, 90%, 91%, 92%, 93%, 94%, 95%, 96%, 97%, 98%, 99%) identical to an amino acid sequence of a naturally-occurring domain found in a DNA polymerase of interest.

It is further contemplated that sequences defining the N-terminal domain, exonuclease domain, palm, fingers, and/or thumb domains may correlate with certain enzymatic characteristics of DNA polymerases, such as, fidelity or error rate, elongation rate, processivity, and salt resistance. For example, as described in the Examples section, the present inventors have demonstrated that sequences defining the N-terminal, exonuclease, and/or thumb domain may correlate with the characteristics associated with elongation rate, processivity, thermostability, TMAC tolerance and/or salt resistance; and that sequences defining the palm and/or fingers domain may correlate with the characteristics associated with fidelity or error rate of DNA polymerases.

In addition, based on sequence alignments between various DNA polymerases (see, e.g., FIG. 1), it is further contemplated that domains correlative with high processivity, elongation rate, thermostability, TMAC tolerance and/or salt resistance may be defined by one or more of the following positive consensus sequences:

Positive Consensus Sequence 1 (Defining an N-Terminal Domain)

XXLXXXXXXXEGXRXXXXX-VXXXXXDXXXTXXXXXXXXXXV-VKXXXXXXVLIX XXXXNXXXAXXKXXCXXXXX-NFALXXXXXXXXXXXXIXXMXXRFXXXXXXXXX XXXXPXXRXXXXXXXXXXXXXXXVXX-QXXXXXXXEXXTTXXXT (SEQ ID NO:30), wherein X is any amino acid or a peptide bond;

Positive Consensus Sequence 2 (Defining an Exonuclease Domain)

XXEXXXXYXXXXEXXFXXXXKXXX-AXXXXXXXXAXXXXTVXTVKRXXXXQXXX XXRXVEXXXXXXFTXXXXXXAXXDXIXXXXX (SEQ ID NO:31), wherein X is any amino acid or a peptide bond; and Positive Consensus Sequence 3 (Defining a Thumb Domain)

XXXXXXXXXXXXXXXX-ALXXDXXXXKXXXXXXXXTEXXSKXX-VXXXXXXVXHX XXXXDXKDXXX-TXXXXXXXXXRXXXRXXXXRXXTXXSXXXXKXS-XRXGDXXXPF DXFXX-TXXXXXXXXXXXXXXXXXXXEXXXRAXX (SEQ ID NO:32), wherein X is any amino acid or a peptide bond.

Additionally or alternatively, a domain or domains correlative with high processivity, elongation rate, thermostability, TMAC tolerance and/or salt resistance may be defined by one or more of the following negative consensus sequences:

Negative Consensus Sequence 1 (Defining an N-Terminal Domain)

NGX$_1$FKIEX$_2$DRTFX$_3$PYX$_4$YALLX$_5$DDSX$_6$IEEVKKIT-X$_7$ERHGX$_8$X$_9$VX$_{10}$X$_{11}$X$_{12}$X$_{13}$VEKVX$_{14}$KKFLGX$_{15}$ PX$_{16}$X$_{17}$VWKLYX$_{18}$X$_{19}$HPQDVPX$_{20}$IRX$_{21}$KX$_{22}$ REHPA (SEQ ID NO:33), wherein X$_1$ is not K; X$_2$ is not H; X$_3$ is not R; X$_4$ is not I; X$_5$ is not R; X$_6$ is not K; X$_7$ is not G; X$_8$ is not K; X$_9$ is not I; X$_{10}$ is not R; X$_{11}$ is not I; X$_{12}$ is not V; X$_{13}$ is not D; X$_{14}$ is not E; X$_{15}$ is not K; X$_{16}$ is not I; X$_{17}$ is not T; X$_{18}$ is not L; X$_{19}$ is not E; X$_{20}$ is not T; X$_{21}$ is not E; and X$_{22}$ is not V;

Negative Consensus Sequence 2 (Defining an Exonuclease Domain)

PIX MISYADEX$_2$X$_3$AX$_4$VITWKNX$_5$DLPYVX$_6$VV SX$_7$EREMIKRFLRX$_8$X$_9$X$_{10}$EKDPDX$_{11}$X$_{12}$X$_{13}$TYNGD X$_{14}$FDFX$_{15}$YLX$_{16}$KRX$_{17}$EKLGIX$_{18}$X$_{19}$X$_{20}$X$_{21}$ GRDGSEPKX$_{22}$QRX$_{23}$GDX$_{24}$X$_{25}$AVEVKGRIHFDLY-X$_{26}$VIX$_{27}$RTINLPTYTLEAVYEAX$_{28}$FGX$_{29}$PKEKVYA X$_{30}$EIX$_{31}$X$_{32}$AWEX$_{33}$ (SEQ ID NO:34), wherein X$_1$ is not I; X$_2$ is not N; X$_3$ is not E; X$_4$ is not K; X$_5$ is not I; X$_6$ is not E; X$_7$ is not S; X$_8$ is not I; X$_9$ is not I; X$_{10}$ is not R; X$_{11}$ is not I; X$_{12}$ is not I; X$_{13}$ is not V; X$_{14}$ is not S; X$_{15}$ is not P; X$_{16}$ is not A; X$_{17}$ is not A; X$_{18}$ is not K; X$_{19}$ is not L; X$_{20}$ is not T; X$_{21}$ is not I; X$_{22}$ is not M; X$_{23}$ is not I; X$_{24}$ is not M; X$_{25}$ is not T; X$_{26}$ is not H; X$_{27}$ is not T; X$_{28}$ is not I; X$_{29}$ is not K; X$_{30}$ is not D; X$_{31}$ is not A; X$_{32}$ is not K; and X$_{33}$ is not S; and Negative Consensus Sequence 3 (Defining a Thumb Domain)

RDWSEIAKETQARVLEX$_1$X$_2$LKX$_3$GDVEX$_4$AVRIVKEV X$_5$X$_6$KLX$_7$X$_8$YEX$_9$PPEKLX$_{10}$IX$_{11}$EQITRX$_{12}$LX$_{13}$X$_{14}$ YKAX$_{15}$GPHVAVAKX$_{16}$LAAX$_{17}$GVKIX$_{18}$PGX$_{19}$ VIX$_{20}$YIVLX$_{21}$GX$_{22}$GX$_{23}$IX$_{24}$X$_{25}$RAIX$_{26}$X$_{27}$X$_{28}$EX$_{29}$ DPX$_{30}$KHKYDAEYYIENQVLPAVX$_{31}$RILX$_{32}$X$_{33}$FG (SEQ ID NO:35), wherein X$_1$ is not T; X$_2$ is not I; X$_3$ is not H; X$_4$ is not E; X$_5$ is not I; X$_6$ is not Q; X$_7$ is not A; X$_8$ is not N; X$_9$ is not I; X$_{10}$ is not A; X$_{11}$ is not Y; X$_{12}$ is not P; X$_{13}$ is not H; X$_{14}$ is not E; X$_{15}$ is not I; X$_{16}$ is not K; X$_{17}$ is not K; X$_{18}$ is not K; X$_{19}$ is not M; X$_{20}$ is not G; X$_{21}$ is not R; X$_{22}$ is not D; X$_{23}$ is not P; X$_{24}$ is not S; X$_{25}$ is not N; X$_{26}$ is not L; X$_{27}$ is not A; X$_{28}$ is not E; X$_{29}$ is not Y; X$_{30}$ is not K; X$_{31}$ is not L; X$_{32}$ is not E; and X$_{33}$ is not G.

In some embodiments, a domain correlative with high fidelity may be defined by the following positive consensus sequence (defining palm and fingers domain):

XKXXXXXXXXXXXX-AXXXXXXXXXXXXXXXXXXLXXXNXX-IXXXXXXXKXXXXI XXXXXXXHXXXXXXXXX-TXXXEXQXXXXKIXXXXXXKXXXLXXXXFXXXX X XXKXXXXXXXXXXXXXXXXXKXX-ELVWXXLXXXFXXXXLXEXXXXLYXXXXXG ESXEIXXXXLX (SEQ ID NO:36), wherein X is any amino acid or a peptide bond.

Additionally or alternatively, a domain correlative with high fidelity may be defined by the following negative consensus sequence (defining palm and fingers domain):

EX$_1$GLWENIVYLDFRX$_2$LYPSIIITHNVSPDTLNX$_3$EGC KX$_4$YDX$_5$APQVGHX$_6$FCKDX$_7$PGFIPSLLGX$_8$LLEER QKIKX$_9$KMKX$_{10}$TX$_{11}$DPIEX$_{12}$X$_{13}$LLDYRQX$_{14}$ AIKX$_{15}$LANSX$_{16}$YGYYGYAX$_{17}$ARWYCKECAESVT AWGRX$_{18}$YIX$_{19}$X$_{20}$X$_{21}$X$_{22}$KEX$_{23}$EEKX$_{24}$GFKVX$_{25}$ YX$_{26}$DTDGX$_{27}$X$_{28}$ATIPGX$_{29}$X$_{30}$X$_{31}$EX$_{32}$X$_{33}$KKKA X$_{34}$E (SEQ ID NO:37), wherein X$_1$ is not R; X$_2$ is not S; X$_3$ is not R; X$_4$ is not E; X$_5$ is not V; X$_6$ is not R; X$_7$ is not F; X$_8$ is not D; X$_9$ is not K; X$_{10}$ is not A; X$_{11}$ is not I; X$_{12}$ is not R; X$_{13}$ is not K; X$_{14}$ is not R; X$_{15}$ is not I; X$_{16}$ is not Y; X$_{17}$ is not R; X$_{18}$ is not E; X$_{19}$ is not T; X$_{20}$ is not M; X$_{21}$ is not T; X$_{22}$ is not I; X$_{23}$ is not I; X$_{24}$ is not Y; X$_{25}$ is not I; X$_{26}$ is not S; X$_{27}$ is not F; X$_{28}$ is not F; X$_{29}$ is not A; X$_{30}$ is not D; X$_{31}$ is not A; X$_{32}$ is not T; X$_{33}$ is not V; X$_{34}$ is not M.

Therefore, appropriate domains may be taken or derived from DNA polymerases with distinct functional characteristics to engineer a chimeric DNA polymerase with desirable combinations of functional features. In some embodiments, inventive methods in accordance with the present invention include steps of: (a) providing an N-terminal domain, an exonuclease domain, and/or a thumb domain based on a first DNA polymerase; (b) providing palm and/or fingers domain based on a second DNA polymerase; (c) combining the domains from step (a) and step (b) to form a chimeric polymerase. In some embodiments, the first and the second DNA polymerases are characterized with at least one distinct characteristic. For example, the first DNA polymerase may be characterized with high processivity, elongation rate, thermostability, TMAC tolerance and/or salt resistance and the second DNA polymerase may be characterized with high fidelity. In some embodiments, the first DNA polymerase may be characterized with high fidelity and the second DNA polymerase may be characterized with high processivity, elongation rate, thermostability, TMAC tolerance and/or salt resistance. In some embodiments, a chimeric polymerase engineered according to the invention has a processivity, elongation rate, thermostability, TMAC tolerance or salt resistance substantially similar to that of the first DNA polymerase and a fidelity substantially similar to that of the second DNA polymerase. In some embodiments, a chimeric polymerases engineered according to the present invention has the fidelity higher than that of the first DNA polymerase and the processivity, elongation rate or salt resistance higher than that of the second DNA polymerase.

The present invention further contemplates methods of improving the fidelity, processivity, elongation rate, thermostability, TMAC tolerance and/or salt resistance of a DNA polymerase. In some embodiments, inventive methods in accordance with the invention include a step of replacing a sequence within the palm-fingers domain of the DNA polymerase of interest with a corresponding sequence from a different DNA polymerase that is characterized with higher fidelity relative to the DNA polymerase of interest.

Additionally or alternatively, in some embodiments, inventive methods in accordance with the present invention include a step of replacing a sequence within the N-terminal domain, the exonuclease domain and/or the thumb domain of the DNA polymerase of interest with a corresponding sequence from a different DNA polymerase that is characterized with higher processivity, elongation rate, thermostability, TMAC tolerance or salt resistance relative to the DNA polymerase of interest.

As a non-limiting example, the present inventors have engineered a chimeric DNA polymerase Kofu and its reciprocal chimera POD based on KOD polymerase and Pfu polymerase (see the Examples section). As discussed in the example section, Kofu contains the N-terminal domain, the exonuclease domain and the thumb domain from KOD polymerase and the palm-fingers domain from Pfu polymerase. The sequence of Kofu polymerase is provided in SEQ ID NO:16. The reciprocal chimera POD contains the N-terminal domain, the exonuclease domain and the thumb domain from Pfu polymerase and the palm-fingers domain from KOD polymerase. The sequence of POD polymerase is provided in SEQ ID NO:15.

As discussed in the examples section, the Kofu chimeric polymerase displays the approximate replication fidelity of Pfu but the elongation speed, processivity, thermostability, TMAC tolerance and PCR performance similar to KOD. Alternatively, the Pod chimeric polymerase displays the approximate replication fidelity of KOD but the elongation speed, processivity, thermostability, TMAC tolerance and PCR performance similar to Pfu.

In some embodiments, the present invention provides variants of Kofu chimeric polymerase that contain an amino acid sequence at least 80% (e.g., at least 85%, 90%, 91%, 92%, 93%, 94%, 95%, 96%, 97%, 98%, 99%) identical to SEQ ID NO:16 (Kofu amino acid sequence). In particular embodiments, variants of Kofu chimeric polymerase in accordance with the invention have processivity, elongation rate, thermostability, TMAC tolerance and/or fidelity substantially similar to Kofu.

In some embodiments, variants of Kofu chimeric polymerases in accordance with the present invention are defined by consensus sequence XXXXTXXXXXDXXXXXX-IXXXXXXEXXXXYXXXX-EXXFXXXXKXXXAXXXXX XXAXXXXTVX-TVKRXXXXQXXXXXRXVEXXXXXFTXXXXXXAXX DXIXXXXXXI XXYXXXXXXXXXXXXXXX-VXXXXDXXXXMXXXXXXXXXXXXXAEXXXLX XXXXXXEGXRXXXXXXVXXXXXDXXX-TXXXXXXXXXXVVKXXXXXVLIXXXXX NXXX-AXXKXXCXXXXXNFALXXXXXXXXX-IXXMXXRFXXXXXXXXXXXXPX XRXXXXXXXXXXXXXXXVXX-QXXXXXXXEXXTXXXTXXXXXXXXRXXXXX XXVXXXXXXXXXXXAXXXXXVXX-PXXXXXXXXXXXXXXXXXXXXXXXV XXXX-SXEXYQXXXXEXX-TXXFXXXXXKXXXXXXXXXXAXXXXXXXXX XX XXXXXLXXXXNXIXXXXXXKXXXX-IXXXXXXXXHXXXXXXXXTXXXEXQX XXXKIXXXXXXKXXX-LXXXXFXXXXXXXKXXXXXXXXXXXXXXXKX XELVW XXLXXXFXXXXLXIXXXX-LYXXXXXXGESXEIXXXXLXXLXXXX-AXXXXAXXXXX XXXXXXXXXXXXKXXXXXXXX-ITXXXXXXXXXXXXXXXXXXXXXALX XDXXXXKXXXXXXXXTEXXSKXX-VXXXXXVXHXXXXXDXKDXXXTXXXXXXX XRXXXRXXXXRXXTXXSXXXXKX-SXRXGDXXXPFDXFXXTXXXXXXXXXXXX XXXXX-EXXXRAXXXXXXXXXXXXXXXXXSZXXKPXGT (SEQ ID NO:38), wherein X is any amino acid or a peptide bond.

In some embodiments, variants of Kofu chimeric polymerases in accordance with the present invention are defined by consensus sequence
XIXDTDYXTXDGX-
PXXRIFXKXXGEFXXXYDXXFEPYFY-
ALLKDDSAIXXXXXXXA XRHGTVXTVKRXXXX-
QXKFLXRXVEVWXLXFTHPQDVPAXXDXIXXHXX
VIDIYE YDIPFAKRYLIDXGLVPMEGDEX-
LXMXXXDIETXYHEGXEFAEGXXLMISYADXEG
ARVITWKXVDLPYVDVVSTEX-
EMIKRXXXVVKEKDPDVLIXYXGDNFDXAYLKXR
CEXLGXNFALXRXXXXXEPKIXXMGXR-
FAVEXXGRXHFDLXPXXRXTXNLPTYXL
XXVYEXVXGQXKXKXXXEEITTX-
WETXXXXXXXARYSMEDAXVTXELGXEFXPM
EAXLXXLVGPXWDVXRSSTGNLVEWX-
LLXXAYXRNEVAPNKPSXEEYQXRXXE XYT-
GXFVXEPEKGLWXXXXXLDXXALYPSI-
IXXHNVSPDTLXLEXCXNYDIAPXVG
XKFCKDIPGFIPSXLXHLXXXRQXXK-
TXMXEXQDPXEXIXLDYRQKAXKLLXNSFY
GYXGYXKARWYXXECAESVTX-
WGRKYIELVWXELEXXFGFKXLYIDTDGLYATIP GGESXEIKXXXLXFLXYINAXLPGALEL-
EYEXFYXRGFFVXKKKYAXIDEEXXITTR GLEX-
VRRDWSXXAKETXAXVLEALLXDXX-
VXKAVXXVXXXTEXXSKYXVPXEKL
VIHEQITRDXKDYXATGPHVAX-
AKRLXXRGXXXRPGTXISYXXLKGS-
GRXGDRXIPF DEFXXTKHXYDXXYYIENQVLPAV-
ERXLRAFGYXXXXLXXQXXXQXGLSAWXKP XGT
(SEQ ID NO:39), wherein X is any amino acid or a peptide bond In some embodiments, the present invention provide variants of POD chimeric polymerases that contain an amino acid sequence at least 80% (e.g., at least 85%, 90%, 91%, 92%, 93%, 94%, 95%, 96%, 97%, 98%, 99%) identical to SEQ ID NO:15 (Pod amino acid sequence). In particular embodiments, variants of POD chimeric polymerases in accordance with the present invention have processivity, elongation rate, thermostability, TMAC tolerance and/or fidelity substantially similar to POD.

Expression of Chimeric DNA Polymerases of the Invention

Standard recombinant DNA techniques (e.g., restriction enzyme digestion, ligation, PCR) can be used to engineer chimeric DNA polymerases in accordance with the present invention. Methods well known in the art may be applied to express and isolate chimeric DNA polymerases. Many bacterial expression vectors contain sequence elements or combinations of sequence elements allowing high level inducible expression of the protein encoded by a foreign sequence. Expression vectors are commercially available from, for example, Novagen (http://www.emdbiosciences.com/html/NVG/AllTables.html#).

In addition, bacteria expressing an integrated inducible form of the T7 RNA polymerase gene may be transformed with an expression vector bearing a chimeric DNA polymerase gene linked to the T7 promoter. Induction of the T7 RNA polymerase by addition of an appropriate inducer, for example, isopropyl-p-D-thiogalactopyranoside (IPTG) for a lac-inducible promoter, induces the high level expression of the chimeric gene from the T7 promoter.

Appropriate host strains of bacteria may be selected from those available in the art by one of skill in the art. As a non-limiting example, E. coli strain BL-21 is commonly used for expression of exogenous proteins since it is protease deficient relative to other strains of E. coli. For situations in which codon usage for the particular polymerase gene differs from that normally seen in E. coli genes, there are strains of BL-21 that are modified to carry tRNA genes encoding tRNAs with rarer anticodons (for example, argU, ileY, leuW, and proL tRNA genes), allowing high efficiency expression of cloned chimeric genes (several BL21-CODON PLUS™ cell strains carrying rare-codon tRNAs are available from Stratagene, for example). Additionally or alternatively, genes encoding DNA polymerases may be codon optimized to facilitate expression in E. coli. Codon optimized sequences can be chemically synthesized.

There are many methods known to those of skill in the art that are suitable for the purification of a chimeric DNA polymerase of the invention. For example, the method of Lawyer et al. (1993, PCR Meth. & App. 2: 275) is well suited for the isolation of DNA polymerases expressed in E. coli, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure DNA polymerase.

Further, DNA polymerase mutants may be isolated by an ammonium sulfate fractionation, followed by Q Sepharose and DNA cellulose columns, or by adsorption of contaminants on a HiTrap Q column, followed by gradient elution from a HiTrap heparin column.

Uses of Chimeric DNA Polymerases of the Invention

Chimeric DNA polymerases of the present invention may be used for any methods involving polynucleotide synthesis. Polynucleotide synthesis methods are well known to a person of ordinary skill in the art and can be found, for example, in Molecular Cloning second edition, Sambrook et al., Cold Spring Harbor Laboratory Press, Cold Spring Harbor, N.Y. (1989). For example, chimeric DNA polymerases of the present invention have a variety of uses in recombinant DNA technology including, but not limited to, labeling of DNA by nick translation, second-strand cDNA synthesis in cDNA cloning, DNA sequencing, and amplifying, detecting, and/or cloning nucleic acid sequences using polymerase chain reaction (PCR).

In some embodiments, the invention provides robust, fast, and accurate enzymes for PCR. PCR refers to an in vitro method for amplifying a specific polynucleotide template sequence. The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. Patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

Chimeric DNA polymerases with higher processivity, elongation rate and/or fidelity are expected to reduce error rate, improve efficiency and success rate of long-range amplification (higher yield, longer targets amplified), and/or reduce the amount of required DNA template.

Various specific PCR amplification applications are available in the art (for reviews, see for example, Erlich, 1999, Rev Immunogenet., 1: 127-34; Prediger 2001, Methods Mol. Biol. 160: 49-63; Jurecic et al., 2000, Curr. Opin. Microbiol. 3: 316-21; Triglia, 2000, Methods Mol. Biol. 130: 79-83; MaClelland et al., 1994, PCR Methods Appl. 4: S66-81; Abramson and Myers, 1993, Current Opinion in Biotechnology 4: 41-47; each of which is incorporated herein by references).

As non-limiting examples, the present invention can be used in PCR applications including, but are not limited to, i) hot-start PCR which reduces non-specific amplification; ii) touch-down PCR which starts at high annealing temperature, then decreases annealing temperature in steps to reduce non-specific PCR product; iii) nested PCR which synthesizes more reliable product using an outer set of primers and an inner set of primers; iv) inverse PCR for amplification of regions flanking a known sequence. In this method, DNA is digested, the desired fragment is circularized by ligation, then PCR using primer complementary to the known sequence extending outwards; v) AP-PCR (arbitrary primed)/RAPD (random amplified polymorphic DNA). These methods create genomic fingerprints from species with little-known target sequences by amplifying using arbitrary oligonucleotides; vi) RT-PCR which uses RNA-directed DNA polymerase (e.g., reverse transcriptase) to synthesize cDNAs which is then used for PCR. This method is extremely sensitive for detecting the expression of a specific sequence in a tissue or cells. It may also be use to quantify mRNA transcripts; vii) RACE (rapid amplification of cDNA ends). This is used where information about DNA/protein sequence is limited. The method amplifies 3' or 5' ends of cDNAs generating fragments of cDNA with only one specific primer each (plus one adaptor primer). Overlapping RACE products can then be combined to produce full length cDNA; viii) DD-PCR (differential display PCR) which is used to identify differentially expressed genes in different tissues. First step in DD-PCR involves RT-PCR, then amplification is performed using short, intentionally nonspecific primers; ix) Multiplex-PCR in which two or more unique targets of DNA sequences in the same specimen are amplified simultaneously. One DNA sequence can be use as control to verify the quality of PCR; x) Q/C-PCR (Quantitative comparative) which uses an internal control DNA sequence (but of different size) which compete with the target DNA (competitive PCR) for the same set of primers; xi) Reclusive PCR which is used to synthesize genes. Oligonucleotides used in this method are complementary to stretches of a gene (>80 bases), alternately to the sense and to the antisense strands with ends overlapping (~20 bases); xii) Asymmetric PCR; xiii) In Situ PCR; xiv) Site-directed PCR Mutagenesis; xv) DOP-PCR that uses partially degenerate primers for whole-genome amplification; xvi) quantitative PCR using SYBR green or oligonucleotide probes to detect amplification; xvii) whole-genome amplification using adaptor-ligated DNA fragment libraries as template, and xviii) error-prone PCR in which conditions are optimized to give an increased number of mutations in the PCR product.

It should be understood that this invention is not limited to any particular amplification system. As other systems are developed, those systems may benefit by practice of this invention.

Kits

The invention also contemplates kit formats which include a package unit having one or more containers containing chimeric DNA polymerases of the invention and compositions thereof. In some embodiments, the present invention provides kits further including containers of various reagents used for polynucleotide synthesis, including synthesis in PCR.

Inventive kits in accordance with the present invention may also contain one or more of the following items: polynucleotide precursors, primers, buffers, instructions, and controls. Kits may include containers of reagents mixed together in suitable proportions for performing the methods in accordance with the invention. Reagent containers preferably contain reagents in unit quantities that obviate measuring steps when performing the subject methods.

EXAMPLES

Example 1

Designs of Chimeras of KOD and Pfu DNA Polymerases

The two enzymes we chose to include in this experiment were *Pyroccocus furiosus* DNA polymerase (Pfu) and *Thermococcus Kodarensis* (KOD) DNA polymerases. The two enzymes have similar domain structure and have a 79% identity at the amino acid level using blastP alignments (see Table 2). The domain structures of Pfu and KOD are illustrated in FIG. 1.

TABLE 2

ClustalW alignment of Pfu and KOD

```
PFU   1  MILDVDYITEEGKPVIRLFKKENGKFKIEHDRTFRPYIYALLRDDSKIEEVKKITGERHG 60
KOD   1  ....T.....D......I......E....Y....E..F....K...A........A....  60

PFU  61  KIVRIVDVEKVEKKFLGKPITVWKLYLEHPQDVPTIREKVREHPAVVDIFEYDIPFAKRY 120
KOD  61  TV.TVKR....Q.....R.VE.....FT......A..D.I......I...Y..........120

PFU 121  LIDKGLIPMEGEEELKILAFDIETLYHEGEEFGKGPIIMISYADENEAKVITWKNIDLPY 180
KOD 121  ......V....D....M...............AE...L.......EG.R......V....180

PFU 181  VEVVSSEREMIKRFLRIIREKDPDIIVTYNGDSFDFPYLAKRAEKLGIKLTIGRDGSEPK 240
KOD 181  .D...T..........VVK.....VLI.....N...A..K..C.....NFAL........240

PFU 241  MQRIGDMTAVEVKGRIHFDLYHVITRTINLPTYTLEAVYEAIFGKPKEKVYADEIAKAWE 300
KOD 241  I..M..RF............P..R................V..Q.......E..TT...300

PFU 301  SGENLERVAKYSMEDAKATYELGKEFLPMEIQLSRLVGQPLWDVSRSSTGNLVEWFLLRK 360
KOD 301  T........R.......V..........A.....I..S.....................360

PFU 361  AYERNEVAPNKPSEEEYQRRLRESYTGGFVKEPEKGLWENIVYLDFRALYPSIIITHNVS 420
KOD 361  ......L.....D.K.LA..~.Q..E.. Y.....R............S...........419

PFU 421  PDTLNLEGCKNYDIAPQVGHKFCKDIPGFIPSLLGHLLEERQKIKTKMKETQDPIEKILL 480
KOD 420  .....R....E..V......R....F.........D.........K...A.I....RK..479

PFU 481  DYRQKAIKLLANSFYGYYGYAKARWYCKECAESVTAWGRKYIELVWKELEEKFGFKVLYI 540
KOD 480  ....R...I....Y.......R..................E..TMTI..I...Y....I.S539

PFU 541  DTDGLYATIPGGESEEIKKKALEFVKYINSKLPGLLELEYEGFYKRGFFVTKKRYAVIDE 600
KOD 540  ....FF.....ADA.TV....M..L.....A....A....................K......599

PFU 601  EGKVITRGLEIVRRDWSEIAKETQARVLETILKHGDVEEAVRIVKEVIQKLANYEIPPEK 660
KOD 600  ...IT....................AL..D....K........TE..SK..V....659

PFU 661  LAIYEQITRPLHEYKAIGPHVAVAKKLAAKGVKIKPGMVIGYIVLRGDGPISNRAILAEE 720
KOD 660  .V.H.....D.KD...T........R...R....R..T..S....K.S.R.GD...PFD.719
```

TABLE 2-continued

ClustalW alignment of Pfu and KOD

```
PFU 721   YDPKKHKYDAEYYIENQVLPAVLRILEGFGYRKEDLRYQKTRQVGLTSWLNIKKS*    776
KOD 720   F..T..................E...RA....................SA..KP.GT*    775
```

PFU (SEQ ID NO: 9)
KOD (SEQ ID NO: 11)

Pfu and KOD have very distinct phenotypic characteristics, in particular, with respect to elongation rate, processivity and error rate (See Table 3):

TABLE 3

|  | Pfu | KOD |
|---|---|---|
| Elongation Rate: | 25 nt/s | 106-138 nt/s (Takagi et al. 1997) |
| Processivity: | >20 nt | ~300 nt (Takagi et al. 1997) |
| Error Rate (mutations/nt/doubling): | $1.5 \times 10^{-6}$ | $4.45 \times 10^{-6}$ (internal data) |

Thus, the goal was to find chimeric combinations of these two enzymes which exhibited the error rate comparable to Pfu ($2.0 \times 10^{-6}$) with the processivity and/or elongation rate comparable to KOD (~300nt/s and 106-138nt/s respectively). An enzyme with the above mentioned characteristics has utility as a robust, fast, and accurate enzyme for PCR.

Figure 2:
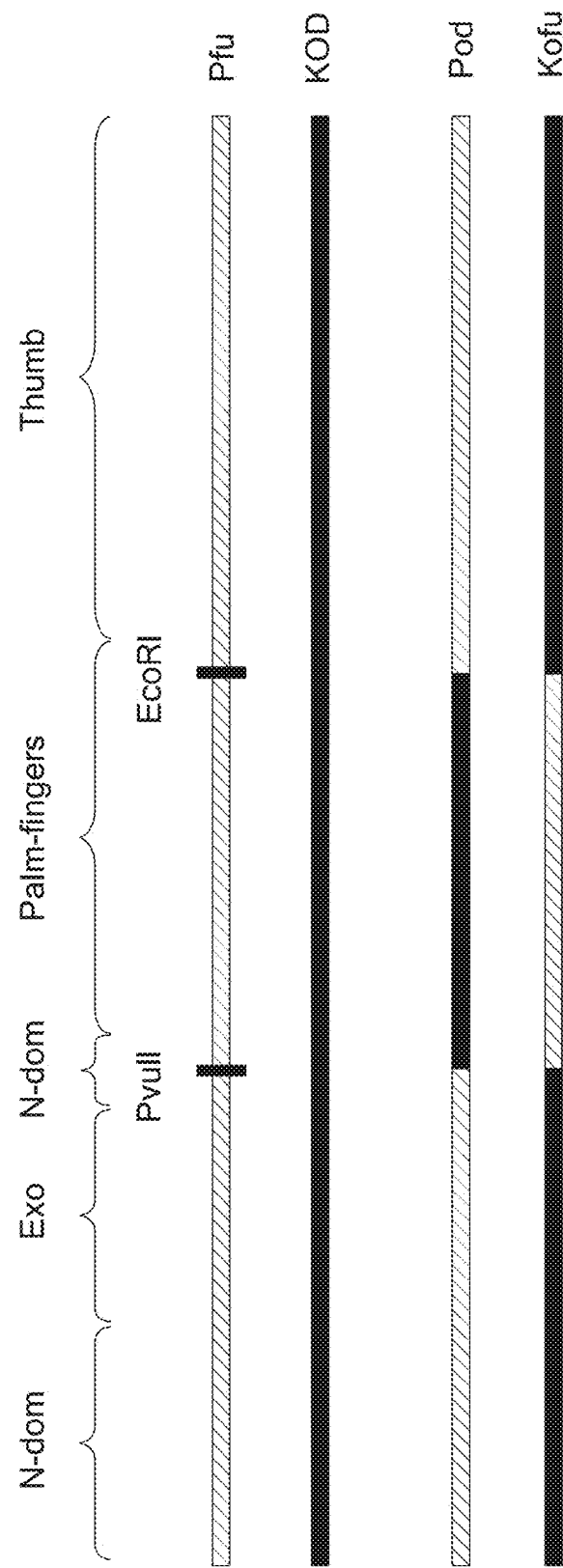
FIG. 2 depicts that an exemplary chimeric polymerase Pod contains the N-terminal domain, the 3'-5' exonuclease domain and the thumb domain of Pfu and the palm and fingers domain of KOD and the reciprocal chimeric polymerase Kofu contains the N-terminal domain, the 3'-5' exonuclease domain and the thumb domain of KOD and the palm and fingers domain of Pfu.

Restriction sites were inserted into the codon-optimized nucleotide sequence of KOD and Pfu polymerases at positions that approximately flank the polymerase domain of the enzymes (see Example 2). For example, PvuII and EcoRI sites flanking the polymerase domain (the palm and fingers domain) were used to replace the polymerase domain of Pfu with that of KOD to generate the chimera deemed Pod (FIG. 2). This chimera contains the N-terminal domain, the 3'-5' exonuclease domain and the thumb domain of Pfu and the palm and fingers domain of KOD. The reciprocal swap, yielding the chimera Kofu, was generated by replacing the polymerase domain (palm and fingers) of KOD with that of Pfu.

Example 2

Codon Optimization and Synthesis of *Pyrococcus Furiosus* and *Thermococcus Kodakarensis* DNA Polymerases Native DNA sequences for *Pyrococcus furiosus* polymerase I (SEQ ID NO:1) and *Thermococcus kodakarensis* polymerase I (SEQ ID NO:2) were retrieved from Genbank. These two DNA sequences were in silico codon optimized by Codon Devices (Cambridge, Mass.) for expression in *E. Coli* resulting in SEQ ID NO:3 for the Pfu polymerase I codon optimized gene DNA sequence and SEQ ID NO:4 for the KOD polymerase I codon optimized gene DNA sequence. The two codon optimized genes were chemically synthesized and cloned into pUC19 by Codon Devices (Cambridge, Mass.) resulting in SEQ ID NO:7 for Pfu polymerase I and SEQ ID NO:8 for KOD polymerase I.

Example 3

Cloning of Codon Optimized KOD and Pfu Polymerase I Sequences into Expression Vector pKBexp KOD (SEQ ID NO:8) and Pfu (SEQ ID NO:7) polymerase codon optimized pUC 19 constructs were cloned into the pKBexp vector as follows:

The pKBexp vector contains two Eco31I sites with non-complementary overhangs enabling directional cloning of inserts using a single restriction enzyme. KOD and Pfu polymerase genes were designed with two flanking Eco31I sites that enabled directional and in-frame cloning into pKBexp.

Purified DNA from the pKBexp vector was digested with Eco31I and purified from an agarose gel. KOD and Pfu codon optimized pUC DNA constructs (SEQ ID NO.8 and SEQ ID NO.7) were likewise digested with Eco31I and the roughly 2.3 kilobase insert fragments were cut out from an agarose gel and purified. 30 ng of KOD or Pfu polymerase genes were ligated with 15 ng of digested pKBexp using T4 DNA ligase. The ligation reactions were purified and used to transform competent *E. coli* DH10B. DNA minipreps were made of ampicillin resistant clones. The presence of inserts was confirmed by digestion of the minipreps with XbaI and HindIII, two enzymes that flank the insert. The cloning of the KOD polymerase gene sequence in pKBexp deemed pKB11 and the Pfu polymerase gene in pKBexp deemed pKB14 were confirmed by DNA sequencing.

Example 4

Domain Swapping of DNA Sequences from KOD and Pfu Polymerase I Genes

The codon-optimized sequences of KOD (SEQ ID NO:5) and Pfu (SEQ ID NO:3) polymerase I genes were designed with restriction sites that approximately flank the finger and palm domains of KOD and Pfu polymerases. The KOD codon optimized sequence contains a PvuII restriction site and an EcoRI restriction site. The Pfu codon optimized sequence contains a PvuII restriction site and an EcoRI restriction site.

Purified DNA from pKB11 and pKB14 were each digested the restriction enzymes EcoRI and PvuII. The large fragment (4.7 kb) and small fragment (0.7 kb) from each digest were separately extracted and purified from an agarose gel. The small fragments from each restriction digest contained the finger and palm domains of KOD and Pfu respectively. The digested and purified large fragments (containing the expression vector and remaining polymerase fragments) were dephosphorylated using Shrimp Alkaline Phosphate. The construct deemed POD was created by ligation of 30 ng of the 4.7 kb Pfu large fragment (aa residues 1 to 335 and 567 to 778 of Pfu DNA polymerase with 10 ng of the 0.7 kb KOD small fragment (corresponding to amino acid residues 336 to 565 of KOD DNA polymerase SEQ ID NO:11). POD thus includes N-terminal, exonuclease and thumb domains from Pfu DNA polymerase and palm and finger domains from KOD. The construct deemed Kofu was made by ligation of 30 ng of the 4.7 kb KOD large fragment (corresponding to amino acid residues 1 to 335 and 566 to 777 of KOD DNA polymerase SEQ ID NO:11) with 10 ng of the 0.7 kb Pfu small fragment (corresponding to amino acid residues 336 to 566 of Pfu DNA polymerase SEQ ID NO:11). Kofu thus includes N-terminal, exonuclease and thumb domains from KOD DNA polymerase and palm and finger domains from Pfu. The ligation reactions were used to transform *E. coli* DH10B. The construction of Pod (SEQ ID NO:13) and Kofu (SEQ ID NO:14) was confirmed by DNA sequencing. The domain structures of POD and Kofu are illustrated in FIG. 1. Expression and purification of chimeric polymerases are done using methods known in the art, for example, as reviewed in "Detailed description of the invention."

Example 5

Figure 3:
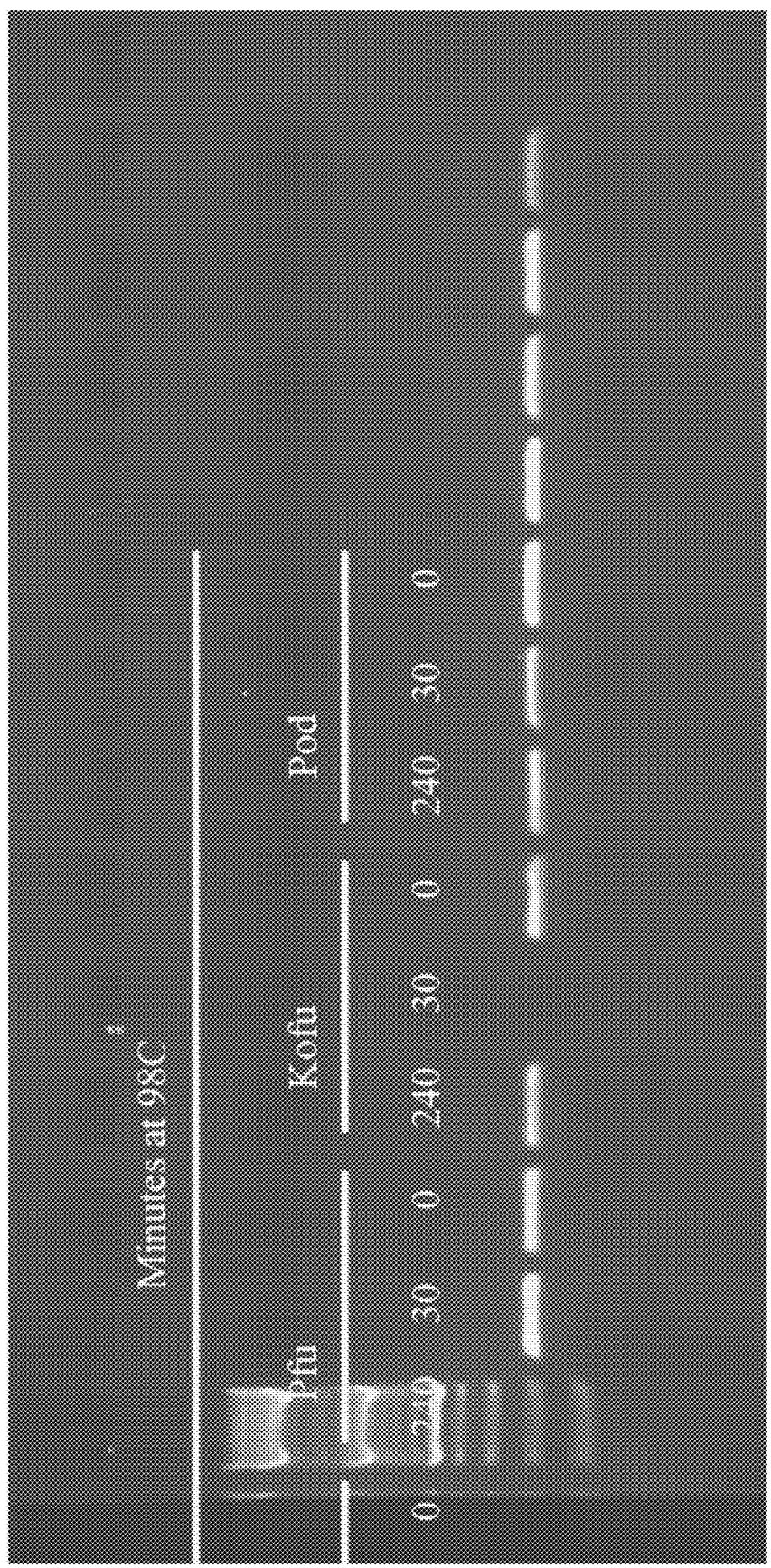
FIG. 3 depicts exemplary results showing the thermostability of KOD, Pfu, Kofu and Pod.

Thermostability of KOD, Pfu, Kofu and Pod 10 ng of each enzyme was incubated at 98° C. for 240, 120, 60, 30, 15, 8, 4, 2, 1 or 0 min in a 10 µl volume containing the following: 20 mM Tris-HCl pH 8.0, 2 mM $MgCl_2$, 6 mM $(NH4)_2SO_4$, 25 or 50 mM KCl (25 mM for Pfu and Pod, 50 mM for KOD and Kofu). 10 µl of primer/template mix was added to each tube after the heat incubation. The primer template mix contained the following: 20 mM Tris-HCl pH 8.0, 2 mM $MgCl_2$, 6 mM $(NH4)_2SO_4$, 0.6 mM dNTP, 0.6 04 each of primers HPRT1-F1 (5'-tttggaaacatctggagtcct -3' (SEQ ID NO:40)) and HPRT1-R1 (5'-gcccaaagggaactgatagtc -3' (SEQ ID NO:41)), 2 ng human genomic DNA per µl, and 25 or 50 mM KCl (25 mM for Pfu and Pod, 50 mM for KOD and Kofu). The amplifications were performed with the following cycling protocol: 3 minutes at 95° C., 35×(20 seconds at 98° C., 20 seconds at 60° C., 20 seconds at 72° C.), 20 seconds at 72° C. The PCR products were analysed on an agarose gel (see FIG. 3). As illustrated in FIG. 3, no amplification was observed for Pfu after pre-incubation of the enzyme for 4 hours at 98° C. In contrast, KOD, Kofu and Pod were able to amplify a PCR product for all time points tested.

Example 6 Fidelity Assays

The fidelity of enzymes was determined by a method similar to that described by Cline et al. and references therein (*Nucl. Acids Res.*, 1996, 24(18): 3546-3551). LacI was PCR amplified from *E. coli* and cloned into pUC19 to degenerate plasmid pKB-LacIQZalpha (SEQ ID NO:17). pKB-LacIQZalpha served both as template for PCR amplification of LacI in the fidelity assays and as vector for cloning the amplified LacI into for blue/white colony screening.

2×50 µl PCR reactions (for each enzyme) were set-up, using 70 ng of pKB-LacIQZalfa plasmid template (equivalent to 25 ng of lad target) and 2.5U of each enzyme to amplify the 1.386 Kb lacIOZalpha fragment. The PCR conditions were as follows: amplification with Pfu and Pod were done in Pfu buffer (Fermentas); KOD and Kofu in Novagen KOD buffer 1. Final concentrations of 2 mM MgCl2, 0.4 µM each of primers M13-40 (GTTTTCCCAGTCACGAC (SEQ ID NO:42)) and PKBLac-1R (GGTATCTTTATAGTCCTGTCG (SEQ ID NO:43)) and 0.2 mM each dNTP. Cycling parameters for Pfu and Pod were: 94° C. 4 minutes, 30×(94° C. 15 seconds, 55° C. 15 seconds, 72° C. 3 minutes), 72° C. 6 minutes. Cycling parameters for KOD and Kofu were: 94° C. 2 minutes, 30×(98° C. 15 seconds, 55° C. 2 seconds, 72° C. 20 seconds), 72° C. 30 seconds.

PCR product yields were quantitated by means of gel electrophoresis and the number of template doublings were calculated. PCR products were digested with XbaI, NcoI and DpnI, gel-purified (without exposure to UV light) and ligated into XbaI-NcoI-digested pKB-LacIQZalpha. *E. coli* was transformed with the ligation mixtures and the cells were plated onto LB-Amp-X-gal plates. The number of blue colonies, white colonies and total number of colonies were recorded. The error rate f was calculated as $f=-\ln(F)/(d \times (bp))$, where F=fraction of white colonies ((total colonies minus blue colonies)/total colonies), d=number of template doublings and b=349 (only 349 bp of the lad amplicon are scored). Exemplary results are summarized in Table 4. As shown in Table 4, Pfu and Kofu have similar fidelity and that their fidelity is higher than that of KOD and Pod.

TABLE 4

Fidelity of KOD, Pfu, Kofu and Pod

| | White colonies | Doublings d | Blue colonies | Total colonies | Fidelity $f(\times 10^{-6})$ |
|---|---|---|---|---|---|
| KOD | 21130 | 7.77 | 246 | 21376 | 4.27 |
| Pfu | 19270 | 7.76 | 77 | 19347 | 1.47 |
| Kofu | 12817 | 5.8 | 39 | 12856 | 1.50 |
| Pod | 22039 | 7.19 | 221 | 22260 | 3.98 |

Example 7

Processivity Assays

Processivity can be determined and calculated using assays described in (Wang et al. *Nucl. Acids Res*, 2004, 32(3): 1197-1207; and Von Hippel et al. *NY Acad Sci* 1994; 726:118-131). Briefly, 0.8 pmoles of a 5'FAM-labelled primer (-40M13LFF, 5'FAM-GTTTTCCCAGTCACGACGTTG-TAAAACGACGGCC-3' (SEQ ID NO:44)) is added to 1.6 pmoles of ssM13mp18 DNA in the presence of 20 mM Tris-HCl pH 8.0, 25 mM KCl, 2.5 mM MgCl2, 0.3 mM dNTP in a 16 microL volume. The primer is annealed to the template by heating to 95° C. for 2 minutes followed by slow cooling to 72° C. in a thermocycler at a rate of 0.1° C/second, incubation for 10 minutes at 72° C. and further cooling at 0.1° C./second to 4° C. The polymerases are diluted in 20 mM Tris-HCl pH 8.0, 25 mM KCl. The primed template and the diluted polymerases are heated to 72° C. and the reaction is started by adding 4 µl diluted polymerase to 16 µl of primed template. The polymerases are diluted to give polymerase: template ratios of 1:10-1:10000. The reactions are terminated after various timepoints by adding EDTA to a final concentration of 10 mM.

The extension reactions are analyzed on an ABI 3130XL Genetic Analyzer. The median product length is determined for each reaction. The median product length is defined as the length of the product at which the total fluorescence intensity of all products up to that length equals 50% of the sum of fluorescence intensities of all detectable products. The traces for those samples where the median product length does not change with a change in polymerase concentration or incubation time are used to calculate the processivity according to Von Hippel et al. (Von Hippel et al. *NY Acad Sci* 1994; 726:118-131). Each peak (I) with a fluorescence level significantly above background level is integrated to give the fluorescence intensity of that peak (ni). The total fluorescence intensity (nT) is the sum of the fluorescence of all peaks. The integration data are plotted as $\log(n_i/n_T)$ vs $n-1$, where n is the number of nucleotides incorporated. The data is fitted to the following equation: $\log(n_i/n_T)=(n-1)\log P_i + \log(1-P_i)$. Pi, the microscopic processivity factor, is defined as the probability of not terminating extension at position i. The average primer extension length is determined from $1/(1-P_i)$.

Example 8

Salt Resistance of KOD, Pfu, Kofu and Pod

Previous studies (Pavlov et al. (2002) *Proc Natl Acad Sci.* 99(21), 13510-13515; Wang et al. (2004) *Nucl Acids Res.*

32(3), 1197-1207) have shown that there is a direct correlation between increased tolerance of polymerases to salt and the processivity of polymerases. For all polymerases tested (from family A or family B), it was found that polymerases with increased salt tolerance also have increased processivity. We therefore compared the salt tolerance of our chimeras with that of the parental polymerases as a proxy for processivity.

Figure 4:
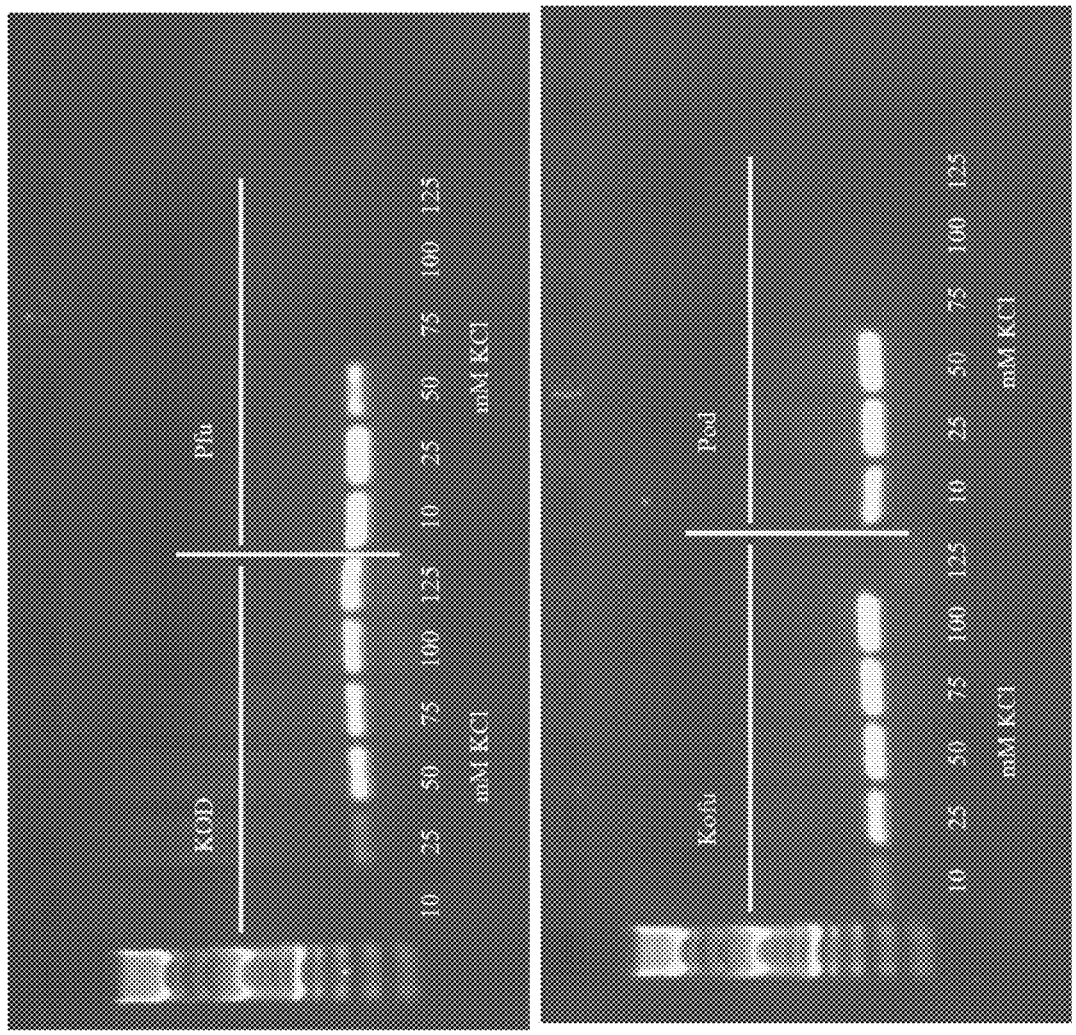
FIG. 4 depicts exemplary results showing the salt resistance of KOD, Pfu, Kofu and Pod.

The protein concentration of the purified KOD, Pfu, Kofu and Pod where determined using a Bioanalyzer 2100 (Agilent, Santa Clara, Calif., USA) with the Protein 230 Kit from the same supplier. The polymerases were tested in real-time PCR with increasing amounts of KCl added. The reactions were performed in a 20 µl volume containing 20 mM Tris-HCl pH 8.0, 6 mM $(NH_4)_2SO_4$, 2 mM $MgCl_2$, 3% DMSO, 10 ng polymerase, 20 ng human genomic DNA, 0.3 mM each dNTP, 0.25×SYBR Green (Invitrogen, Carlsbad, Calif., USA). A diluted stock 20×SYBR Green in DMSO was made), 0.3 04 forward primer HPRT1-F1 (5'-tttggaaacatctggagtcct-3' (SEQ ID NO:40)) and 0.3 µM reverse primer HPRT1-R1(5'-gcccaaagggaactgatagtc-3' (SEQ ID NO:41)). KCl was added to final concentrations of 10, 25, 50, 75, 100 or 125 mM. PCR amplification was performed in a Corbett 6000 HRM real-time thermocycler (Corbett Life Science, Sidney, Australia) with the following cycling protocol: 3 minutes at 95° C., 40 cycles of (10 seconds at 95° C., 20 seconds at 60° C., 20 seconds at 72° C., data acquisition), followed by a melting curve analysis step of: ramp from 72° C. to 95° C. in 1° C. steps, wait for 5 seconds before data acquisition at the end of each step. 8 µl of each sample was analysed on a 1.5% agarose gel. 5 µl of Fermentas GeneRuler™ Mix, cat no. SM0333 (Fermentas, Vilnius, Lithuania) was loaded onto the gel as a DNA marker. Exemplary results are shown in FIG. 4.

Example 9

TMAC Tolerance of KOD, Pfu, Kofu and Pod

Tetra-methyl ammonium-containing salts enhance PCR reactions as shown by Kovarova et al. (Kovarova, M. and Draber, P.; *Nucl. Acids Res.* (2000) 28(13) e70-). One such salt is tetra-methyl ammonium chloride (TMAC). We therefore compared the TMAC tolerance of our chimeras with that of the parental polymerases.

Figure 5:
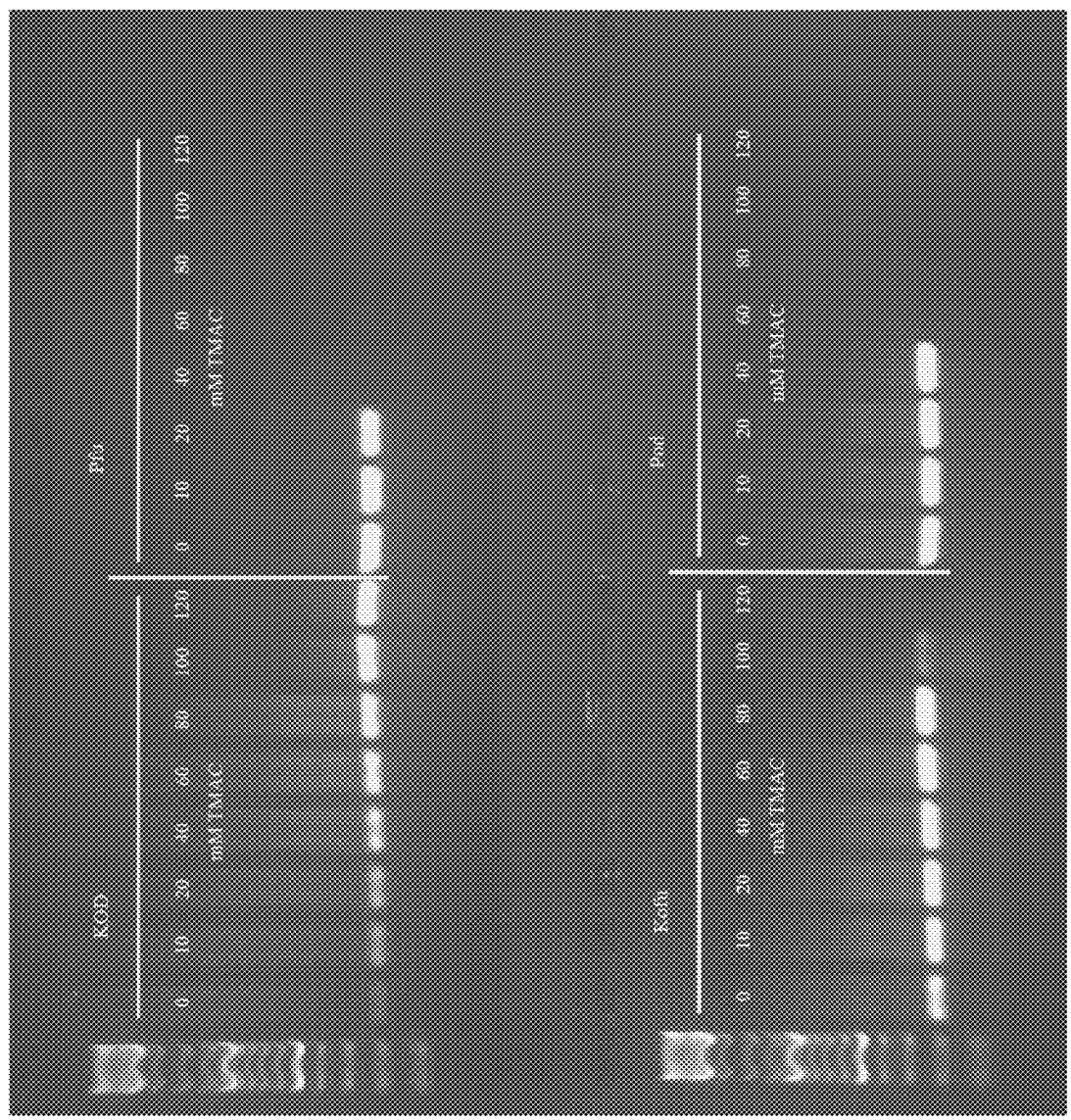
FIG. 5 depicts exemplary results showing the TMAC tolerance of KOD, Pfu, Kofu and Pod.

The polymerases were tested in real-time PCR with increasing amounts of TMAC added. The reactions were performed in a 20 µl volume containing 20 mM Tris-HCl pH 8.0, 6 mM $(NH_4)_2SO_4$, 2 mM $MgCl_2$, 25 mM KCl, 10 ng polymerase, 20 ng human genomic DNA, 0.3 mM each dNTP, 0.25×SYBR Green (Invitrogen, Carlsbad, Calif., USA. A diluted stock 20×SYBR Green in DMSO was made), 0.3 µM forward primer HPRT1-F1 (5'-tttggaaacatctggagtcct-3' (SEQ ID NO:40)) and 0.3 µM reverse primer HPRT1-R1 (5'-gcccaaagggaactgatagtc-3' (SEQ ID NO:41)). TMAC was added to final concentrations of 0, 10, 20, 40, 60, 80, 100 or 120 mM. PCR amplification was performed in a Corbett 6000 HRM real-time thermocycler (Corbett Life Science, Sidney, Australia) with the following cycling protocol: 3 minutes at 95° C., 40 cycles of (10 seconds at 95° C., 20 seconds at 50° C., 20 seconds at 72° C., data acquisition), followed by a melting curve analysis step of: ramp from 72° C. to 95° C. in 1° C. steps, wait for 5 seconds before data acquisition at the end of each step. 8 µl of each sample was analysed on a 1.5% agarose gel. 5 µl of Fermentas GeneRuler™ Mix, cat no. SM0333 (Fermentas, Vilnius, Lithuania) was loaded onto the gel as a DNA marker. Exemplary results are shown in FIG. 5.

Example 10

Additional Chimeras of KOD and Pfu Polymerases

This example is designed to show that the positions where the swapping between domains take place may vary.

Additional chimeras are made by swapping the palm and finger domains of KOD and Pfu polymerases where the exact position of the swap varies slightly compared to positions for Kofu and Pod. Kofu-II (SEQ ID NO:26) is made by replacing amino acid residues 305 to 615 of KOD (SEQ ID NO: 12) with amino acids 305 to 616 of Pfu (SEQ ID NO:10). Pod-II (SEQ ID NO:27) is made by replacing amino acids 305 to 616 of Pfu (SEQ ID NO:10) with amino acids 305 to 615 of KOD (SEQ ID NO:12).

Kofu-III (SEQ ID NO:28) is made by replacing amino acid residues 396 to 564 of KOD (SEQ ID NO: 12) with amino acids 397 to 565 of Pfu (SEQ ID NO:10). Pod-III (SEQ ID NO:29) is made by replacing amino acids 397 to 565 of Pfu (SEQ ID NO:10) with amino acids 396 to 564 of KOD (SEQ ID NO:12).

The amino acid sequence of chimeras Kofu-II, Pod-II, Kofu-III and Pod-III are reverse translated and codon-optimized for expression in *E. coli*. Additional nucleotide sequences containing Eco31I restriction sites are added to the 5' and 3' ends of the construct to facilitate cloning into an expression vector. More specifically, the 5' and 3' sequences can be designed so that the overhangs, after digestion of the DNA with Eco31I, are complementary to the overhangs in a particular expression vector (e.g., pKB). Codon optimization and gene synthesis is performed by GeneArt Gmbh. Expression and purification of chimeric polymerases are done using methods known in the art, for example, as reviewed in "Detailed description of the invention". The thermostability, fidelity, processivity, salt resistance and TMAC resistance of the chimeric polymerases are determined as described in Examples 5 through 9.

Example 11

Chimeras of *T. Litoralis* and 9 Degrees N-7 Polymerases

Chimeras 9Nli and Li9N are designed based on the alignment in FIG. 1. They are made by swapping the palm and finger domains between the DNA polymerases of *T. litoralis* and *Thermococcus* sp. 9 degrees N-7. The overall sequence identity between these two polymerases are 77% on the amino acid level.

Chimera 9Nli can be made by replacing the palm and finger region of the 9N polymerase with the palm and finger region of the *T. litoralis* polymerase. In this particular example, 9Nli is made by replacing amino acids 347 to 580 of 9N polymerase (SEQ ID NO:18) with amino acids 349 to 583 of *T. litoralis* polymerase (SEQ ID NO:19). The sequence of the coding region of 9Nli is provided as SEQ ID NO:20.

Chimera LiN9 can be made by replacing the palm and finger domain of the DNA polymerase of *T. litoralis* with the finger domain of the DNA polymerase of 9 degrees North. In this particular example, LiN9 is made by replacing amino acids 349 to 583 of *T. litoralis* polymerase (SEQ ID NO:19) with amino acids 347 to 580 of 9 degrees N-7 polymerase (SEQ ID NO:18). The sequence of the coding region of LiN9 is provided as SEQ ID NO:21.

Example 12

Chimeras of *T. Gorgonarius* and *T. zilligii* Type B DNA Polymerases

Chimerase GoZi and ZiGo are designed based on the alignment in FIG. 1. They are made by swapping the palm and finger domains between the DNA polymerases of *T. gorgonarius* and *T. zilligii*. The overall sequence identity between these two polymerases are 94% on the amino acid level.

Chimera GoZi can be made by replacing the palm and finger region of the *T. gorgonarius* polymerase with the palm and finger region of the *T. zilligii* polymerase. In this particular example, GoZi is made by replacing amino acids 391 to 559 of *T. gorgonarius* polymerase (SEQ ID NO:22) with amino acids 391 to 559 of *T. zilligii* polymerase (SEQ ID NO:23). The sequence of the resulting chimera GoZi is provided as SEQ ID NO:24.

Chimera ZiGo can be made by replacing the palm and finger domain of the DNA polymerase of *T. zilligii* with the finger domain of the DNA polymerase of *T. gorgonarius*. In this particular example, ZiGo is made by replacing amino acids 391 to 559 of *T. zilligii* polymerase (SEQ ID NO:23) with amino acids 391 to 559 of *T. gorgonarius* polymerase (SEQ ID NO:22). The sequence of the coding region of ZiGo is provided as SEQ ID NO:25.

TABLE 5

Sequences

Native DNA sequences of Pfu and KOD

```
Sequence 1 (SEQ ID NO: 1)
>Native Pfu nucleotide sequence from genomic sequence (Acc. No. AE010147)
   1 ATGATTTTAG ATGTGGATTA CATAACTGAA GAAGGAAAAC CTGTTATTAG GCTATTCAAA
  61 AAAGAGAACG GAAAATTTAA GATAGAGCAT GATAGAACTT TTAGACCATA CATTTACGCT
 121 CTTCTCAGGG ATGATTCAAA GATTGAAGAA GTTAAGAAAA TAACGGGGGA AAGGCATGGA
 181 AAGATTGTGA GAATTGTTGA TGTAGAGAAG GTTGAGAAAA AGTTTCTCGG CAAGCCTATT
 241 ACCGTGTGGA AACTTTATTT GGAACATCCC CAAGATGTTC CCACTATTAG AGAAAAAGTT
 301 AGAGAACATC CAGCAGTTGT GGACATCTTC GAATACGATA TTCCATTTGC AAAGAGATAC
 361 CTCATCGACA AAGGCCTAAT ACCAATGGAG GGGGAAGAAG AGCTAAAGAT TCTTGCCTTC
 421 GATATAGAAA CCCTCTATCA CGAAGGAGAA GAGTTTGGAA AAGGCCCAAT TATAATGATT
 481 AGTTATGCAG ATGAAAATGA AGCAAAGGTG ATTACTTGGA AAAACATAGA TCTTCCATAC
 541 GTTGAGGTTG TATCAAGCGA GAGAGAGATG ATAAAGAGAT TTCTCAGGAT TATCAGGGAG
 601 AAGGATCCTG ACATTATAGT TACTTATAAT GGAGACTCAT TCGACTTCCC ATATTTAGCG
 661 AAAAGGGCAG AAAAACTTGG GATTAAATTA ACCATTGGAA GAGATGGAAG CGAGCCCAAG
 721 ATGCAGAGAA TAGGCGATAT GACGGCTGTA GAAGTCAAGG GAAGAATACA TTTCGACTTG
 781 TATCATGTAA TAACAAGGAC AATAAATCTC CCAACATACA CACTAGAGGC TGTATATGAA
 841 GCAATTTTTG GAAAGCCAAA GGAGAAGGTA TACGCCGACG AGATAGCAAA AGCCTGGGAA
 901 AGTGGAGAGA ACCTTGAGAG AGTTGCCAAA TACTCGATGG AAGATGCAAA GGCAACTTAT
 961 GAACTCGGGA AGAATTCCT TCCAATGGAA ATTCAGCTTT CAAGATTAGT TGGACAACCT
1021 TTATGGGATG TTTCAAGGTC AAGCACAGGG AACCTTGTAG AGTGGTTCTT ACTTAGGAAA
1081 GCCTACGAAA GAAACGAAGT AGCTCCAAAC AAGCCAAGTG AAGAGGAGTA TCAAAGAAGG
1141 CTCAGGGAGA GCTACACAGG TGGATTCGTT AAAGAGCCAG AAAAGGGGTT GTGGGAAAAC
1201 ATAGTATACC TAGATTTTAG AGCCCTATAT CCCTCGATTA TAATTACCCA CAATGTTTCT
1261 CCCGATACTC TAAATCTTGA GGGATGCAAG AACTATGATA TCGCTCCTCA AGTAGGCCAC
1321 AAGTTCTGCA AGGACATCCC TGGTTTTATA CCAAGTCTCT TGGGACATTT GTTAGAGGAA
1381 AGACAAAAGA TTAAGACAAA AATGAAGGAA ACTCAAGATC CTATAGAAAA AATACTCCTT
1441 GACTATAGAC AAAAAGCGAT AAAACTCTTA GCAAATTCTT TCTACGGATA TTATGGCTAT
1501 GCAAAAGCAA GATGGTACTG TAAGGAGTGT GCTGAGAGCG TTACTGCCTG GGGAAGAAAG
1561 TACATCGAGT TAGTATGGAA GGAGCTCGAA GAAAAGTTTG GATTTAAAGT CCTCTACATT
1621 GACACTGATG GTCTCTATGC AACTATCCCA GGAGGAGAAA GTGAGGAAAT AAAGAAAAAG
1681 GCTCTAGAAT TTGTAAAATA CATAAATTCA AAGCTCCCTG GACTGCTAGA GCTTGAATAT
1741 GAAGGGTTTT ATAAGAGGGG ATTCTTCGTT ACGAAGAAGA GGTATGCAGT AATAGATGAA
1801 GAAGGAAAAG TCATTACTCG TGGTTTAGAG ATAGTTAGGA GAGATTGGAG TGAAATTGCA
1861 AAAGAAACTC AAGCTAGAGT TTTGGAGACA ATACTAAAAC ACGGAGATGT TGAAGAAGCT
1921 GTGAGAATAG TAAAAGAAGT AATACAAAAG CTTGCCAATT ATGAAATTCC ACCAGAGAAG
1981 CTCGCAATAT ATGAGCAGAT AACAAGACCA TTACATGAGT ATAAGGCGAT AGGTCCTCAC
2041 GTAGCTGTTG CAAAGAAACT AGCTGCTAAA GGAGTTAAAA TAAAGCCAGG AATGGTAATT
2101 GGATACATAG TACTTAGAGG CGATGGTCCA ATTAGCAATA GGGCAATTCT AGCTGAGGAA
2161 TACGATCCCA AAAAGCACAA GTATGACGCA GAATATTACA TTGAGAACCA GGTTCTTCCA
2221 GCGGTACTTA GGATATTGGA GGGATTTGGA TACAGAAAGG AAGACCTCAG ATACCAAAAG
2281 ACAAGACAAG TCGGCCTAAC TTCCTGGCTT AACATTAAAA AATCCTAG Sequence 2 (SEQ ID NO: 2)
>Native KOD nucleotide sequence (from genomic sequence, Acc. no. AP006878)
   1 ATGATCCTCG ACACTGACTA CATAACCGAG GATGGAAAGC CTGTCATAAG AATTTTCAAG
  61 AAGGAAAACG GCGAGTTTAA GATTGAGTAC GACCGGACTT TTGAACCCTA CTTCTACGCC
 121 CTCCTGAAGG ACGATTCTGC CATTGAGGAA GTCAAGAAGA TAACCGCCGA GAGGCACGGG
 181 ACGGTTGTAA CGGTTAAGCG GGTTGAAAAG GTTCAGAAGA AGTTCCTCGG GAGACCAGTT
 241 GAGGTCTGGA AACTCTACTT TACTCATCCG CAGGACGTCC CAGCGATAAG GGACAAGATA
 301 CGAGAGCATC CAGCAGTTAT TGACATCTAC GAGTACGACA TACCCTTCGC CAAGCGCTAC
 361 CTCATAGACA AGGGATTAGT GCCAATGGAA GGCGACGAGG AGCTGAAAAT GCTCGCCTTC
 421 GACATTGAAA CTCTCTACCA TGAGGGCGAA GAGTTCGCCG AGGGGCCAAT CCTTATGATA
 481 AGCTACGCCG ACGAGGAAGG GGCCAGGGTG ATAACTTGGA AGAACGTGGA TCTCCCCTAC
 541 GTTGACGTCG TCTCGACGGA GAGGGAGATG ATAAAGCGCT TCCTCCGTGT TGTGAAGGAG
 601 AAAGACCCGG ACGTTCTCAT AACCTACAAC GGCGACAACT TCGACTTCGC CTATCTGAAA
 661 AAGCGCTGTG AAAAGCTCGG AATAAACTTC GCCCTCGGAA GGGATGGAAG CGAGCCGAAG
 721 ATTCAGAGGA TGGGCGACAG GTTTGCCGTC GAAGTGAAGG GACGGATACA CTTCGATCTC
```

TABLE 5-continued

Sequences

```
 781 TATCCTGTGA TAAGACGGAC GATAAACCTG CCCACATACA CGCTTGAGGC CGTTTATGAA
 841 GCCGTCTTCG GTCAGCCGAA GGAGAAGGTT TACGCTGAGG AAATAACCAC AGCCTGGGAA
 901 ACCGGCGAGA ACCTTGAGAG AGTCGCCCGC TACTCGATGG AAGATGCGAA GGTCACATAC
 961 GAGCTTGGGA AGGAGTTCCT TCCGATGGAG GCCCAGCTTT CTCGCTTAAT CGGCCAGTCC
1021 CTCTGGGACG TCTCCCGCTC CAGCACTGGC AACCTCGTTG AGTGGTTCCT CCTCAGGAAG
1081 GCCTATGAGA GGAATGAGCT GGCCCCGAAC AAGCCCGATG AAAAGGAGCT GGCCAGAGAA
1141 CGGCAGAGCT ATGAAGGAGG CTATGTAAAA GAGCCCGAGA GAGGGTTGTG GGAGAACATA
1201 GTGTACCTAG ATTTTAGATC CCTGTACCCC TCAATCATCA TCACCCACAA CGTCTCGCCG
1261 GATACGCTCA ACAGAGAAGG ATGCAAGGAA TATGACGTTG CCCCACAGGT CGGCCACCGC
1321 TTCTGCAAGG ACTTCCCAGG ATTTATCCCG AGCCTGCTTG GAGACCTCCT AGAGGAGAGG
1381 CAGAAGATAA AGAAGAAGAT GAAGGCCACG ATTGACCCGA TCGAGAGGAA GCTCCTCGAT
1441 TACAGGCAGA GGGCCATCAA GATCCTGGCA AACAGCTACT ACGGTTACTA CGGCTATGCA
1501 AGGGCGCGCT GGTACTGCAA GGAGTGTGCA GAGAGCGTAA CGGCCTGGGG AAGGGAGTAC
1561 ATAACGATGA CCATCAAGGA GATAGAGGAA AAGTACGGCT TTAAGGTAAT CTACAGCGAC
1621 ACCGACGGAT TTTTTGCCAC AATACCTGGA GCCGATGCTG AAACCGTCAA AAAGAAGGCT
1681 ATGGAGTTCC TCAAGTATAT CAACGCCAAA CTTCCGGGCG CGCTTGAGCT CGAGTACGAG
1741 GGCTTCTACA ACGCGGCTT CTTCGTCACG AAGAAGAAGT ATGCGGTGAT AGACGAGGAA
1801 GGCAAGATAA CAACGCGCGG ACTTGAGATT GTGAGGCGTG ACTGGAGCGA GATAGCGAAA
1861 GAGACGCAGG CGAGGGTTCT TGAAGCTTTG CTAAAGGACG GTGACGTCGA GAAGGCCGTG
1921 AGGATAGTCA AGAAGTTAC CGAAAAGCTG AGCAAGTACG AGGTTCCGCC GGAGAAGCTG
1981 GTGATCCACG AGCAGATAAC GAGGGATTTA AAGGACTACA AGGCAACCGG TCCCCACGTT
2041 GCCGTTGCCA AGAGGTTGGC CGCGAGAGGA GTCAAATAC GCCCTGGAAC GGTGATAAGC
2101 TACATCGTGC TCAAGGGCTC TGGGAGGATA GGCGACAGGG CGATACCGTT CGACGAGTTC
2161 GACCCGACGA AGCACAAGTA CGACGCCGAG TACTACATTG AGAACCAGGT TCTCCCAGCC
2221 GTTGAGAGAA TTCTGAGAGC CTTCGGTTAC CGCAAGGAAG ACCTGCGCTA CCAGAAGACG
2281 AGACAGGTTG GTTTGAGTGC TTGGCTGAAG CCGAAGGGAA CTTGA
```

Codon optimized sequences of Pfu and KOD

Sequence 3 (SEQ ID NO: 3)
>Pfu codon optimized nucleotide sequence
```
   1 ATGATTCTGG ATGTGGACTA TATCACCGAA GAGGGCAAAC CGGTTATACG TTTATTTAAG
  61 AAAGAGAATG GTAAATTCAA GATCGAGCAT GACCGCACGT TCCGTCCATA CATTTACGCG
 121 TTGCTTCGGG ATGATAGCAA AATTGAGGAA GTCAAAAGA TCACCGGGGA ACGTCATGGA
 181 AAAATAGTAA GAATTGTGGA CGTTGAAAAA GTCGAAAAGA AATTTCTGGG CAAACCGATC
 241 ACTGTATGGA AGCTCTATCT GGAACATCCT CAGGATGTGC CCACAATTCG AGAAAAAGTT
 301 CGTGAGCACC CAGCCGTCGT GGATATATTT GAATATGACA TCCCTTTTGC AAAACGCTAC
 361 TTAATTGATA AAGGCCTGAT CCCGATGGAG GGGGAAGAAG AACTTAAAAT TCTGGCTTTT
 421 GACATAGAAA CGCTCTATCA TGAGGGAGAA GAATTTGGCA AAGGTCCCAT CATTATGATT
 481 TCTTACGCGG ATGAGAACGA AGCCAAGGTA ATCACTTGGA AAATATTGA CCTGACGCAT
 541 GTTGAAGTGG TCAGTTCAGA GCGGGAAATG ATTAAACGTT TTTTACGCAT CATTAGAGAG
 601 AAAGATCCAG ATATAATCGT TACATATAAC GGCGACTCCT TCGATTTTCC TTACCTGGCA
 661 AAACGAGCTG AAAAATTGGG TATTAAACTT ACCATCGGGC GTGACGGATC GGAACCGAAA
 721 ATGCAACGCA TTGGCGATAT GACGGCGGTA GAGGTGAAAG GTCGGATACA CTTTGATCTG
 781 TATCATGTCA TCACCCGTAC TATTAATCTC CCCACATACA CGTTAGAAGC CGTTTATGAG
 841 GCAATATTCG GCAAGCCGAA AGAAAAAGTG TACGCTGACG AAATCGCGAA GGCATGGGAG
 901 AGCGGCGAAA ACCTGGAGCG CGTAGCAAAA TATTCTATGG AAGATGCTAA AGCGACCTAC
 961 GAATTGGGGA AAGAATTTCT TCCAATGGAA ATTCAGCTGA GTCGTTTAGT CGGACAACCT
1021 CTGTGGGACG TTTCACGCTC CTCGACTGGC AATCTCGTGG AGTGGTTCCT GTTGAGAAAA
1081 GCCTATGAAC GAAACGAAGT AGCACCGAAT AAACCAAGCG AGGAAGAATA TCAGCGTCGC
1141 CTTCGCGAGT CTTACACAGG TGGGTTTGTT AAGGAACCGG AGAAAGGTCT TTGGGAAAAC
1201 ATCGTGTATT TAGATTTCCG TGCGCTGTAC CCCAGTATTA TAATCACCCA CAATGTCTCA
1261 CCTGACACGC TCAACTTGGA AGGTTGCAAA AATTATGATA TTGCTCCGCA AGTTGGACAT
1321 AAGTTTTGTA AAGATATTCC GGGCTTCATC CCGTCCCTGC TTGGTCACTT ACTGGAAGAG
1381 CGCCAAAAAA TTAAGACCAA AATGAAAGAG ACTCAGGATC CCATTGAAAA GATCCTGCTC
1441 GATTACCGGC AAAAAGCCAT TAAATTGCTT GCAAACTCGT TTTATGGGTA CTATGGCTAT
1501 GCGAAGGCTC GTTGGTACTG CAAAGAATGT GCCGAGAGCC TGACAGCATG GGGTCGCAAA
1561 TATATAGAAT TAGTATGGAA GGAGCTGGAA GAAAAATTCG GATTCAAAGT CCTGTACATC
1621 GATACGGATG GCCTCTATGC GACCATTCCT GGTGGGGAGT CTGAAGAAAT CAAGAAAAAA
1681 GCCTTGGAAT TCGTTAAGTA CATTAATAGT AAATTACCGG GACTGCTTGA ACTGGAGTAT
1741 GAAGGCTTCT ACAAAAGAGG TTTTTTCGTT ACTAAGAAAC GATATGCCGT AATAGATGAA
1801 GAGGGGAAAG TCATCACACG TGGCCTCGAG ATTGTTCGCC GGGACTGGTC AGAGATAGCA
1861 AAGGAAACGC AGGCGCGCGT GCTCGAAACC ATCTTGAAAC ATGGTGATGT AGAGGAAGCC
1921 GTCCGCATTG TTAAAGAGGT GATCCAGAAG TTAGCAAACT ATGAAATTCC ACCGGAAAAA
1981 CTGGCGATAT ACGAGCAAAT CACTCGTCCC CTTCATGAAT ATAAGCTAT TGGACCTCAT
2041 GTAGCCGTCG CGAAGAAACT GGCTGCAAAA GGCGTTAAGA TAAAACCAGG TATGGTGATC
2101 GGGTACATTG TACTCCGCGG CGACGGTCCG ATTTCCAATA GAGCCATCTT GGCGGAGGAA
2161 TATGATCCTA AAAAGCATAA ATACGACGCT GAATATTACA TTGAGAACCA GGTCTTGCCG
2221 GCAGTTCTGC GGATACTTGA AGGATTTGGC TATCGTAAAG AAGATCTGCG CTATCAAAAG
2281 ACGCGACAGG TGGGTCTGAC TAGCTGGTTG AATATCAAAA AATCGTAA
```

Sequence 4 (SEQ ID NO: 4)
>Pfu codon optimized nucleotide sequence, extra 9 nt in 5' area.
```
   1 ATGGCTAGCG CCATTCTGGA TGTGGACTAT ATCACCGAAG AGGGCAAACC GGTTATACGT
  61 TTATTTAAGA AAGAGAATGG TAAATTCAAG ATCGAGCATG ACCGCACGTT CCGTCCATAC
 121 ATTTACGCGT TGCTTCGGGA TGATAGCAAA ATTGAGGAAG TCAAAAGAT CACCGGGGAA
 181 CGTCATGGAA AAATAGTAAG AATTGTGGAC GTTGAAAAAG TCGAAAAGAA ATTTCTGGGC
 241 AAACCGATCA CTGTATGGAA GCTCTATCTG GAACATCCTC AGGATGTGCC CACAATTCGA
```

TABLE 5-continued

Sequences

```
 301 GAAAAAGTTC GTGAGCACCC AGCCGTCGTG GATATATTTG AATATGACAT CCCTTTTGCA
 361 AAACGTCTACT TAATTGATAA AGGCCTGATC CCGATGGAGG GGGAAGAAGA ACTTAAAATT
 421 CTGGCTTTTG ACATAGAAAC GCTCTATCAT GAGGGAGAAG AATTTGGCAA AGGTCCCATC
 481 ATTATGATTT CTTACGCGGA TGAGAACGAA GCCAAGGTAA TCACTTGGAA AAATATTGAC
 541 CTGCCGTACG TTGAAGTGGT CAGTTCAGAG CGGGAAATGA TTAAACGTTT TTTACGCATC
 601 ATTAGAGAGA AAGATCCAGA TATAATCGTT ACATATAACG GCGACTCCTT CGATTTTCCT
 661 TACCTGGCAA AACGAGCTGA AAAATTGGGT ATTAAACTTA CCATCGGGCG TGACGGATCG
 721 GAACCGAAAA TGCAACGCAT TGGCGATATG ACGCGGTAG AGGTGAAAGG TCGGATACAC
 781 TTTGATCTGT ATCATGTCAT CACCCGTACT ATTAATCTCC CCACATACAC GTTAGAAGCC
 841 GTTTATGAGG CAATATTCGG CAAGCCGAAA GAAAAGTGT ACGCTGACGA AATCGCGAAG
 901 GCATGGGAGA GCGGCGAAAA CCTGGAGCGC GTAGCAAAAT ATTCTATGGA AGATGCTAAA
 961 GCGACCTACG AATTGGGAA AGAATTTCTT CCAATGGAAA TTCAGCTGAG TCGTTTAGTC
1021 GGACAACCTC TGTGGGACGT TCACGCTCC TCGACTGGCA ATCTCGTGGA GTGGTTCCTG
1081 TTGAGAAAAG CCTATGAACG AAACGAAGTA GCACCGAATA AACCAAGCGA GGAAGAATAT
1141 CAGCGTCGCC TTCGCGAGTC TTACACAGGT GGGTTTGTTA AGGAACCGGA GAAAGGTCTT
1201 TGGGAAAACA TCGTGTATTT AGATTTCCGT GCGCTGTACC CCAGTATTAT AATCACCCAC
1261 AATGTCTCAC CTGACACGCT CAACTTGGAA GGTTGCAAAA ATTATGATAT TGCTCCGCAA
1321 GTTGACATA AGTTTTGTAA AGATATTCCG GGCTTCATCC CGTCCCTGCT TGGTCACTTA
1381 CTGGAAGAGC GCCAAAAAAT TAAGACCAAA CATGAAAGA CTCAGGATCC CATTGAAAAG
1441 ATCCTGCTCG ATTACCGGCA AAAAGCCATT AAATTGCTTG CAAACTCGTT TTATGGGTAC
1501 TATGGCTATG CGAAGGCTCG TTGGTACTGC AAAGAATGTG CCGAGAGCGT GACAGCATGG
1561 GGTCGCAAAT ATATAGAATT AGTATGGAAG GAGCTGGAAG AAAAATTCGG ATTCAAAGTC
1621 CTGTACATCG ATACGGATGG CCTCTATGCG ACCATTCCTG GTGGGGAGTC TGAAGAAATC
1681 AAGAAAAAAG CCTTGGAATT CGTTAAGTAC ATTAATAGTA AATTACCGGG ACTGCTTGAA
1741 CTGGAGTATG AAGGCTTCTA CAAAAGAGGT TTTTTCGTTA CTAAGAAACG ATATGCCGTA
1801 ATAGATGAAG AGGGGAAAGT CATCACACGT GGCCTCGAGA TTGTTCGCCG GGACTGGTCA
1861 GAGATAGCAA AGGAAACGCA GGCGCGCGTG CTCGAAACCA TCTTGAAACA TGGTGATGTA
1921 GAGGAAGCCG TCCGCATTGT TAAAGAGGTG ATCCAGAAGT TAGCAAACTA TGAAATTCCA
1981 CCGGAAAAAC TGGCGATATA CGAGCAAATC ACTCGTCCCC TTCACGAATA TAAGCTATT
2041 GGACCTCATG TAGCCGTCGC GAAGAAACTG GCTGCAAAAG GCGTTAAGAT AAAACCAGGT
2101 ATGGTGATCG GGTACATTGT ACTCCGCGGC GACGGTCCGA TTTCCAATAG AGCCATCTTG
2161 GCGGAGGAAT ATGATCCTAA AAAGCATAAA TACGACGCTG AATATTACAT TGAGAACCAG
2221 GTCTTGCCGG CAGTTCTGCG GATACTTGAA GGATTTGGCT ATCGTAAAGA AGATCTGCGC
2281 TATCAAAAGA CGCGACAGGT GGGTCTGACT AGCTGGTTGA ATATCAAAAA ATCGTAA
```

Sequence 5 (SEQ ID NO: 5)
>KOD codon optimized nucleotide sequence

```
   1 ATGATTCTGG ATACCGACTA TATCACGGAA GATGGCAAAC CGGTGATACG TATTTTTAAG
  61 AAAGAGAATG GTGAGTTCAA AATCGAGTAC GACCGCACTT TTGAGCCATA TTTCTACGCG
 121 TTACTGAAGG ACGATAGCGC CATTGAAGAA GTTAAAAAA TCACCGCAGA GCGGCATGGG
 181 ACAGTGGTAA CCGTGAAGAG AGTTGAAAAA GTCCAGAAAA ATTTTTGGG ACGACCTGTA
 241 GAAGTGTGGA AACTTTATTT CACTCACCCC CAAGATGTTC CGGCTATACG TGATAAAATT
 301 CGCGAACATC CAGCGGTCAT TGATATTTAC GAATATGATA TACCTTTTGC CAAGCGTTAC
 361 CTCATCGACA AAGGCCTGGT GCCGATGGAA GGTGATGAAG AATTAAAAAT GTTGGCATTC
 421 GACATTGAAA CACTTTATCA CGAGGGGGAA GAGTTTGCTG AGGGTCCCAT CCTGATGATT
 481 TCTTATGCGG ATGAAGAGGG TGCCCGCGTA ATAACCTGGA AGAACGTTGA TCTCCCGTAC
 541 GTGGACGTCG TTAGTACGGA ACGGGAAATG ATCAAACGTT TCCTGCGCGT AGTGAAAGAG
 601 AAAGATCCAG ACGTCTTAAT TACCTATAAT GGTGATAACT TTGATTTTGC ATACCTGAAA
 661 AAAAGATGCG AAAAGTTGGG CATAAATTTC TCTCTTGGTC GAGACGGGTC AGAGCCTAAA
 721 ATCCAGCGTA TGGGAGATCG CTTTGCGGTT GAAGTGAAAG GCCGGATTCA TTTCGACCTG
 781 TATCCGGTAA TTCGTCGCAC TATCAACCTC CCCACATACA CGTTAGAAGC CGTCTATGAG
 841 GCAGTTTTTG GTCAACCGAA GGAAAAAGTT TACGCTGAGG AAATTACCAC TGCGTGGGAA
 901 ACAGGCGAGA ATCTGGAACG TGTAGCCCGC TATTCTATGG AGGATGCAAA AGTTACCTAT
 961 GAATTGGGTA AGGAATTTCT TCCAATGGAG GCGCAGCTGT CGAGATTAAT AGGGCAGAGC
1021 CTGTGGGACG TGTCTCGAAG TTCAACGGGA AACCTGGTCG AATGGTTTCT GTTGCGGAAA
1081 GCATACGAGC GTAATGAACT TGCCCCTAAC AAACCGGATG AAAAGGAGCT GGCACGCCGT
1141 CGCCAATCCT ATGAAGGCGG TTACGTTAAA GAACCAGAGC GGGGGTTATG GAAAATATC
1201 GTGTATCTGG ATTTCCGTTC GCTCTACCCG AGCATTATCA TTACCCACAA CGTATCTCCC
1261 GACACTTTGA ATCGCGAGGG CTGTAAAGAA TATGATGTCG CGCCGCAGGT TGGTCATAGA
1321 TTTTGCAAGG ACTTCCCGGG ATTTATACCA AGTCTGCTTG GCGATTTACT GGAAGAGCGA
1381 CAAAAAATCA AAAGAAAAT GAAAGCTACA ATCGATCCGA TAGAACGTAA GCTGCTCGAC
1441 TACCGCCAGC GGGCCATCAA AATTTTGGCA AACTCTATT ATGGTTACTA TGGGTACGCG
1501 CGTGCTCGCT GGTATTGTAA AGAGTGCGCC GAATCCGTGA CGGCATGGGG CCGTGAATAC
1561 ATCACCATGA CTATTAAGGA GATAGAAGAG AAATATGGTT TCAAAGTAAT CTACTCGGAT
1621 ACAGACGGAT TCTTTGCGAC GATTCCCGGT GCCGATGCGA AAACCGTCAA GAAAAAAGCG
1681 ATGGAATTCC TTAAGTATAT AAATGCTAAA TTACCTGGTG CCCTGGAGCT GGAATACGAA
1741 GGGTTTTACA AACGCGGATT CTTTGTTACT AAGAAAAAAT ATGCGGTGAT CGACGAGGAA
1801 GGCAAGATTA CGACCAGAGG CCTCGAGATT GTACGGCGTG ATTGGAGCGA ATCGCTAAA
1861 GAAACACAGG CACGTGTCTT GGAGGCATTA CTGAAAGATG GGACGTTGA AAAGGCGGTG
1921 CGAATTGTAA AAGAAGTCAC CGAAAAACTT TCTAAGTACG AAGTTCCGCC AGAGAAACTG
1981 GTGATACACG AACAAATCAC TCGTGATCTG AAAGACTATA AGGCTACAGG CCCGCATGTA
2041 GCAGTCGCCA AACGCCTCGC GGCTCGGGGT GTTAAAATTC GTCCCGGAAC GGTGATCAGT
2101 TACATTGTAT TGAAGGGCTC AGGTCGCATA GGGGATAGAG CAATCCCTTT CGACGAGTTT
2161 GATCCAACCA AACACAAATA TGATGCCGAA TACTATATTG AAACCAGGT CTTGCCGGCG
2221 GTTGAGCGTA TACTCGCGCG TTTCGGCTAT CGAAGGGAAG ATCTTCGTTA CCAAAAAACT
2281 AGACAGGTGG GTCTGTCCGC ATGGCTCAAA CCTAAGGGAA CGTAA
```

TABLE 5-continued

Sequences

Sequence 6 (SEQ ID NO: 6)
>KOD codon optimized nucleotide sequence, extra 9 nt in 5' area.
```
   1 ATGGCTAGCG CCATTCTGGA TACCGACTAT ATCACGGAAG ATGCAAACC GGTGATACGT
  61 ATTTTTAAGA AGAGAATGG TGAGTTCAAA ATCGAGTACG ACCGCACTTT TGAGCCATAT
 121 TTCTACGCGT TACTGAAGGA CGATAGCGCC ATTGAAGAAG TTAAAAAAT CACCGCAGAG
 181 CGGCATGGGA CAGTGGTAAC CGTGAAGAGA GTTGAAAAAG TCCAGAAAAA ATTTTTGGGA
 241 CGACCTGTAG AAGTGTGGAA ACTTTATTTC ACTCACCCCC AAGATGTTCC GGCTATACGT
 301 GATAAAATTC GCGAACATCC AGCGGTCATT GATATTTACG AATATGATAT ACCTTTTGCC
 361 AAGCGTTACC TCATCGACAA AGGCCTGGTG CCGATGGAAG GTGATGAAGA ATTAAAAATG
 421 TTGGCATTCG ACATTGAAAC ACTTTATCAC GAGGGGGAAG AGTTTGCTGA GGGTCCCATC
 481 CTGATGATTT CTTATGCGGA TGAAGAGGGT GCCCGCGTAA TAACCTGGAA GAACGTTGAT
 541 CTCCCGTACG TGGACGTCGT TAGTACGGAA CGGGAAATGA TCAAACGTTT CCTGCGCGTA
 601 GTGAAAGAGA AAGATCCAGA CGTCTTAATT ACCTATAATG GTGATAACTT TGATTTTGCA
 661 TACCTGAAAA AAGATGCGA AAAGTTGGGC ATAAATTTCG CTCTTGGTCG AGACGGGTCA
 721 GAGCCTAAAA TCCAGCGTAT GGGAGATCGC TTTGCGGTTG AAGTGAAAGG CCGGATTCAT
 781 TTCGACCTGT ATCCGGTAAT TCGTCGCACT ATCAACCTCC CCACATACAC GTTAGAAGCC
 841 GTCTATGAGG CAGTTTTTGG TCAACCGAAG GAAAAGTTT ACGCTGAGGA AATTACCACT
 901 GCGTGGGAAA CAGGCGAGAA TCTGGAACGT GTAGCCCGCT ATTCTATGGA GGATGCAAAA
 961 GTTACCTATG AATTGGGTAA GGAATTTCTT CCAATGGAGG CGCAGCTGTC GAGATTAATA
1021 GGGCAGAGCC TGTGGGACGT GTCTCGAAGT TCAACGGGAA ACCTCGTCGA ATGGTTTCTG
1081 TTGCGGAAAG CATACGAGCG TAATGAACTT GCCCCTAACA AACCGGATGA AAAGGAGCTG
1141 GCACGCCGTC GCCAATCCTA TGAAGGCGGT TACGTTAAAG AACCAGAGCG GGGGTTATGG
1201 GAAAATATCG TGTATCTGGA TTTCCGTTCG CTCTACCCGA GCATTATCAT TACCCACAAC
1261 GTATCTCCCG ACACTTTGAA TCGCGAGGGC TGTAAAGAAT ATGATGTCGC GCCGCAGGTT
1321 GGTCATAGAT TTTGCAAGGA CTTCCCGGGA TTTATACCAA GTCTGCTTGG CGATTTACTG
1381 GAAGAGCGAC AAAAAATCAA AAAGAAAATG AAAGCTACAA TCGATCCGAT AGAACGTAAG
1441 CTGCTCGACT ACCGCCAGCG GGCCATCAAA ATTTTGGCAA ACTCATATTA TGGTTACTAT
1501 GGGTACGCGC GTGCTCGCTG GTATTGTAAA GAGTGCGCCG AATCCGTGAC GGCATGGGGC
1561 CGTGAATACA TCACCATGAC TATTAAGGAG ATAGAAGAGA AATATGGTTT CAAAGTAATC
1621 TACTCGGATA CAGACGGGAT TCTTTGCGAC GATTCCGGTC CCGATGCAGA AACCGTCAAG
1681 AAAAAAGCGA TGGAATTCCT TAAGTATATA AATGCTAAAT TACCTGGTGC CCTGGAGCTG
1741 GAATACGAAG GGTTTTACAA ACGCGGATTC TTTGTTACTA AGAAAAAATA TGCGGTGATC
1801 GACGAGGAAG GCAAGATTAC GACCAGAGGC CTCGAGATTG TACGGCGTGA TTGGAGCGAA
1861 ATCGCTAAAG AAACACAGGC ACGTGTCTTG GAGGCATTAC TGAAAGATGG GGACGTTGAA
1921 AAGGCGGTGC GAATTGTAAA GAAAGTCACC GAAAAACTTT CTAAGTACGA AGTTCCGCA
1981 GAGAAACTGG TGATACACGA ACAAATCACT CGTGATCTGA AAGACTATAA GGCTACAGGC
2041 CCGCATGTAG CAGTCGCCAA ACGCCTCGCG GCTCGGGGTG TTAAAATTCG TCCCGGAACG
2101 GTGATCAGTT ACATTGTATT GAAGGGCTCA GGTCGCATAG GGGATAGAGC AATCCCTTTC
2161 GACGAGTTTG ATCCAACCAA ACACAAATAT GATGCCGAAT ACTATATTGA AAACCAGGTC
2221 TTGCCGGCGG TTGAGCGTAT ACTGCGCGCT TTCGGCTATC GAAAGGAAGA TCTTCGTTAC
2281 CAAAAAACTA GACAGGTGGG TCTGTCCGCA TGGCTCAAAC CTAAGGGAAC GTAA
```

Sequence 7 (SEQ ID NO: 7)
>pKB13-Pfu codon optimized nucleotide sequence in pUC19 vector
```
   1 TCGCGCGTTT CGGTGATGAC GGTGAAAACC TCTGACACAT GCAGCTCCCG GAGACGGTCA
  61 CAGCTTGTCT GTAAGCGGAT GCCGGGAGCA GACAAGCCCG TCAGGGCGCG TCAGCGGGTG
 121 TTGGCGGGTG TCGGGCTGG CTTAACTATG CGGCATCAGA GCAGATTGTA GGAGAGTGC
 181 ACCATATGCG GTGTGAAATA CCGCACAGAT GCGTAAGGAG AAAATACCGC ATCAGGCGCC
 241 ATTCGCCATT CAGGCTGCGC AACTGTTGGG AAGGGCGATC GGTGCGGGCC TCTTCGCTAT
 301 TACGCCAGCT GGCGAAAGGG GGATGTGCTG CAAGGCGATT AAGTTGGGTA ACGCCAGGGT
 361 TTTCCCAGTC ACGACGTTGT AAAACGACGG CCAGTGAATT CGGTCTCAGC GCCATTCTGG
 421 ATACCGACTA TATCACGGAA GATGGCAAAC CGGTGATACG TATTTTTAAG AAGAGAATGG
 481 GTGAGTTCAA AATCGAGTAC GACCGCACTT TGAGCCATA TTTCTACGCG TTACTGAAGG
 541 ACGATAGCGC CATTGAAGAA GTTAAAAAA TCACCGCAGA GCGGCATGGG ACAGTGGTAA
 601 CCGTGAAGAG AGTTGAAAAA GTCCAGAAAA AATTTTTGGG ACGACCTGTA GAAGTGTGGA
 661 AACTTTATTT CACTCACCCC AAGATGTTCC GGCTATACG TGATAAAATT CGCGAACATC
 721 CAGCGGTCAT TGATATTTAC GAATATGATA TACCTTTTGC CAAGCGTTAC CTCATCGACA
 781 AAGGCCTGGT GCCGATGGAA GGTGATGAAG AATTAAAAAT GTTGGCATTC GACATTGAAA
 841 CACTTTATCA CGAGGGGGAA GAGTTTGCTG AGGGTCCCAT CCTGATGATT TCTTATGCGG
 901 ATGAAGAGGG TGCCCGCGTA ATAACCTGGA AGAACGTTGA TCTCCCGTAC GTGGACGTTG
 961 TTAGTACGGA ACGGGAAATG ATCAAACGTT TCCTGCGCGT AGTGAAAGAG AAAGATCCAG
1021 ACGTCTTAAT TACCTATAAT GGTGATAACT TTGATTTTGC ATACCTGAAA AAAGATGCG
1081 AAAAGTTGGG CATAAATTTC GCTCTTGGTC GAGACGGGTC AGAGCCTAAA ATCCAGCGTA
1141 TGGGAGATCG CTTTGCGGTT GAAGTGAAAG GCCGGATTCA TTTCGACCTG TATCCGGTAA
1201 TTCGTCGCAC TATCAACCTC CCCACATACA CGTTAGAAGC CGTCTATGAG CAGTTTTTG
1261 GTCAACCGAA GGAAAAGTT TACGCTGAGG AAATTACCAC TGCGTGGGAA ACAGGCGAGA
1321 ATCTGGAACG TGTAGCCCGC TATTCTATGG AGGATGCAAA AGTTACCTAT GAATTGGGTA
1381 AGGAATTTCT TCCAATGGAG GCGCAGCTGT CGAGATTAAT AGGGCAGAGC CTGTGGGACG
1441 TGTCTCGAAG TTCAACGGGA AACCTCGTCG AATGGTTTCT GTTGCGGAAA GCATACGAGC
1501 GTAATGAACT TGCCCCTAAC AAACCGGATG AAAAGGAGCT GGCACGCCGT CGCCAATCCT
1561 ATGAAGGCGG TTACGTTAAA GAACCAGAGC GGGGGTTATG GAAAATATC GTGTATCTGG
1621 ATTTCCGTTC GCTCTACCCG AGCATTATCA TTACCCACAA CGTATCTCCC GACACTTTGA
1681 ATCGCGAGGG CTGTAAAGAA TATGATGTCG CGCCGCAGGT TGGTCATAGA TTTTGCAAGG
1741 ACTTCCCGGG ATTTATACCA AGTCTGCTTG GCGATTTACT GGAAGAGCGA CAAAAAATCA
1801 AAAGAAAAT GAAAGCTACA ATCGATCCGA TAGAACGTAA GCTGCTCGAC TACCGCCAGC
1861 GGGCCATCAA AATTTTGGCA AACTCATATT ATGGTTACTA TGGGTACGCG CGTGCTCGCT
1921 GGTATTGTAA AGAGTGCGCC GAATCCGTGA CGGCATGGGG CCGTGAATAC ATCACCATGA
```

TABLE 5-continued

Sequences

```
1981 CTATTAAGGA GATAGAAGAG AAATATGGTT TCAAAGTAAT CTACTCGGAT ACAGACGGAT
2041 TCTTTGCGAC GATTCCCGGT GCCGATGCAG AAACCGTCAA GAAAAAGCG ATGGAATTCC
2101 TTAAGTATAT AAATGCTAAA TTACCTGGTG CCCTGGAGCT GGAATACGAA GGGTTTTACA
2161 AACGCGGATT CTTTGTTACT AAGAAAAAAT ATGCGGTGAT CGACGAGGAA GGCAAGATTA
2221 CGACCAGAGG CCTCGAGATT GTACGGCGTG ATTGGAGCGA AATCGCTAAA GAAACACAGG
2281 CACGTGTCTT GGAGGCATTA CTGAAAGATG GGGACGTTGA AAAGGCGGTG CGAATTGTAA
2341 AAGAAGTCAC CGAAAAACTT TCTAAGTACG AAGTTCCGCC AGAGAAACTG GTGATACACG
2401 AACAAATCAC TCGTGATCTG AAAGACTATA AGGCTACAGG CCCGCATGTA GCAGTCGCCA
2461 AACGCCTCGC GGCTCGGGGT GTTAAAATTC GTCCCGGAAC GGTGATCAGT TACATTGTAT
2521 TGAAGGGCTC AGGTCGCATA GGGGATAGAG CAATCCCTTT CGACGAGTTT GATCCAACCA
2581 AACACAAATA TGATGCCGAA TACTATATTG AAAACCAGGT CTTGCCGGCG GTTGAGCGTA
2641 TACTGCGCGC TTTCGGCTAT CGAAAGGAAG ATCTCGTTA CCAAAAACT AGACAGGTGG
2701 GTCTGTCCGC ATGGCTCAAA CCTAAGGGAA CGTAATGATA TGAGACCGGA TCCTCTAGAG
2761 TCGACCTGCA GGCATGCAAG CTTGGCGTAA TCATGGTCAT AGCTGTTTCC TGTGTGAAAT
2821 TGTTATCCGC TCACAATTCC ACACAACATA CGAGCCGGAA GCATAAAGTG TAAAGCCTGG
2881 GGTGCCTAAT GAGTGAGCTA ACTCACATTA ATTGCGTTGC GCTCACTGCC CGCTTTCCAG
2941 TCGGGAAACC TGTCGTGCCA GCTGCATTAA TGAATCGGCC AACGCGCGGG GAGAGGCGGT
3001 TTGCGTATTG GGCGCTCTTC CGCTTCCTCG CTCACTGACT CGCTGCGCTC GGTCGTTCGG
3061 CTGCGGCGAG CGGTATCAGC TCACTCAAAG GCGGTAATAC GGTTATCCAC AGAATCAGGG
3121 GATAACGCAG GAAAGAACAT GTGAGCAAAA GGCCAGCAAA AGGCCAGGAA CCGTAAAAAG
3181 GCCGCGTTGC TGGCGTTTTT CCATAGGCTC CGCCCCCCTG ACGAGCATCA CAAAAATCGA
3241 CGCTCAAGTC AGAGGTGGCG AAACCCGACA GGACTATAAA GATACCAGGC GTTTCCCCCT
3301 GGAAGCTCCC TCGTGCGCTC TCCTGTTCCG ACCCTGCCGC TTACCGGATA CCTGTCCGCC
3361 TTTCTCCCTT CGGGAAGCGT GGCGCTTTCT CATAGCTCAC GCTGTAGGTA TCTCAGTTCG
3421 GTGTAGGTCG TTCGCTCCAA GCTGGGCTGT GTGCACGAAC CCCCCGTTCA GCCCGACCGC
3481 TGCGCCTTAT CCGGTAACTA TCGTCTTGAG TCCAACCCGG TAAGACACGA CTTATCGCCA
3541 CTGGCAGCAG CCACTGGTAA CAGGATTAGC AGAGCGAGGT ATGTAGGCGG TGCTACAGAG
3601 TTCTTGAAGT GGTGGCCTAA CTACGGCTAC ACTAGAAGAA CAGTATTTGG TATCTGCGCT
3661 CTGCTGAAGC CAGTTACCTT CGGAAAAAGA GTTGGTAGCT CTTGATCCGG CAAACAAACC
3721 ACCGCTGGTA GCGGTGGTTT TTTTGTTTGC AAGCAGCAGA TTACGCGCAG AAAAAAAGGA
3781 TCTCAAGAAG ATCCTTTGAT CTTTTCTACG GGTCTGACG CTCAGTGGAA CGAAAACTCA
3841 CGTTAAGGGA TTTTGGTCAT GAGATTATCA AAAAGGATCT TCACCTAGAT CCTTTTAAAT
3901 TAAAAATGAA GTTTTAAATC AATCTAAAGT ATATATGAGT AAACTTGGTC TGACAGTTAC
3961 CAATGCTTAA TCAGTGAGGC ACCTATCTCA GCGATCTGTC TATTTCGTTC ATCCATAGTT
4021 GCCTGACTCC CCGTCGTGTA GATAACTACG ATACGGGAGG GCTTACCATC TGGCCCCAGT
4081 GCTGCAATGA TACCGCGAGA CCCACGCTCA CCGGCTCCAG ATTTATCAGC AATAAACCAG
4141 CCAGCCGGAA GGGCCGAGCG CAGAAGTGGT CCTGCAACTT TATCCGCCTC CATCCAGTCT
4201 ATTAATTGTT GCCGGGAAGC TAGAGTAAGT AGTTCGCCAG TTAATAGTTT GCGCAACGTT
4261 GTTGCCATTG CTACAGGCAT CGTGGTGTCA CGCTCGTCGT TTGGTATGGC TTCATTCAGC
4321 TCCGGTTCCC AACGATCAAG GCGAGTTACA TGATCCCCCA TGTTGTGCAA AAAAGCGGTT
4381 AGCTCCTTCG GTCCTCCGAT CGTTGTCAGA AGTAAGTTGG CCGCAGTGTT ATCACTCATG
4441 GTTATGGCAG CACTGCATAA TTCTCTTACT GTCATGCCAT CCGTAAGATG CTTTTCTGTG
4501 ACTGGTGAGT ACTCAACCAA GTCATTCTGA GAATAGTGTA TGCGGCGACC GAGTTGCTCT
4561 TGCCCGGCGT CAATACGGGA TAATACCGCG CCACATAGCA GAACTTTAAA AGTGCTCATC
4621 ATTGGAAAAC GTTCTTCGGG GCGAAAACTC TCAAGGATCT TACCGCTGTT GAGATCCAGT
4681 TCGATGTAAC CCACTCGTGC ACCCAACTGA TCTTCAGCAT CTTTTACTTT CACCAGCGTT
4741 TCTGGGTGAG CAAAAACAGG AAGGCAAAAT GCCGCAAAAA AGGGAATAAG GGCGACACGG
4801 AAATGTTGAA TACTCATACT CTTCCTTTTT CAATATTATT GAAGCATTTA TCAGGGTTAT
4861 TGTCTCATGA GCGGATACAT ATTTGAATGT ATTTAGAAAA ATAAACAAAT AGGGGTTCCG
4921 CGCACATTTC CCCGAAAAGT GCCACCTGAC GTCTAAGAAA CCATTATTAT CATGACATTA
4981 ACCTATAAAA ATAGGCGTAT CACGAGGCCC TTTCGTC

Sequence 8 (SEQ ID NO: 8)
>pKB8-KOD codon optimized nucleotide sequence in pUC19 vector
   1 TCGCGCGTTT CGGTGATGAC GGTGAAAACC TCTGACACAT GCAGCTCCCG GAGACGGTCA
  61 CAGCTTGTCT GTAAGCGGAT GCCGGGAGCA GACAAGCCCG TCAGGGCGCG TCAGCGGGTG
 121 TTGGCGGGTG TCGGGGCTGG CTTAACTATG CGGCATCAGA GCAGATTGTA CTGAGAGTGC
 181 ACCATATGCG GTGTGAAATA CCGCACAGAT GCGTAAGGAG AAAATACCGC ATCAGGCGCC
 241 ATTCGCCATT CAGGCTGCGC AACTGTTGGG AAGGGCGATC GGTGCGGGCC TCTTCGCTAT
 301 TACGCCAGCT GGCGAAAGGG GGATGTGCTG CAAGGCGATT AAGTTGGGTA ACGCCAGGGT
 361 TTTCCCAGTC ACGACGTTGT AAAACGACGG CCAGTGAATT CGGTCTCAGC GCCATTCTGG
 421 ATACCGACTA TATCACGGAA GATGGCAAAC CGGTGATACG TATTTTTAAG AAAGAGAATG
 481 GTGAGTTCAA AATCGAGTAC GACCGCACTT TTGAGCCATA TTTCTACGCG TTACTGAAGG
 541 ACGATAGCGC CATTGAAGAA GTTAAAAAAA TCACCGCAGA GCGGCATGGG ACAGTGGTAA
 601 CCGTGAAGCG AGTTGAAAAA GTCCAGAAAA AATTTTTGGC ACGACCTGGA GAAGTGTGGA
 661 AACTTTATTT CACTCACCCC CAAGATGTTC CGGCTATACG TGATAAAATT CGCGAACATC
 721 CAGCGGTCAT TGATATTTAC GAATATGATA TACCTTTTGC CAAGCGTTAC CTCATCGACA
 781 AAGGCCTGGT GCCGATGGAA GGTGATGAAG AATTAAAAAT GTTGGCATTC GACATTGAAA
 841 CACTTTATCA CGAGGGGGAA GAGTTTGCTG GGTCCCCAT CCTGATGATT TCTTATGCGG
 901 ATGAAGAGGG TGCCCGCGTA ATAACCTGGA AGAACGTTGA TCTCCCGTAC GTGGACGTCG
 961 TTAGTACGGA ACGGGAAATG ATCAAACGTT CCTGCGCGT AGTGAAAGAG AAAGATCCAG
1021 ACGTCTTAAT TACCTATAAT GGTGATAACT TTGATTTTGC ATACCTGAAA AAAAGATGCG
1081 AAAAGTTGGG CATAAATTTC GCTCTTGGTC GAGACGGTTC AGAGCCTAAA ATCCAGCGTA
1141 TGGGAGATCG CTTTGCGGTT GAAGTGAAAG GCCGGATTCA TTTCGACCTG TATCCGGTAA
1201 TTCGTCGCAC TATCAACCTC CCCACATACA CGTTAGAAGC CGTCTATGAG GCAGTTTTTG
1261 GTCAACCGAA GGAAAAAGTT TACGCTGAGG AAATTACCAC TGCGTGGGAA ACAGGCGAGA
1321 ATCTGGAACG TGTAGCCCGC TATTCTATGG AGGATGCAAA AGTTACCTAT GAATTGGGTA
1381 AGGAATTTCT TCCAATGGAG GCGCAGCTGT CGAGATTAAT AGGGCAGAGC TGTGGGACG
```

TABLE 5-continued

Sequences

```
1441 TGTCTCGAAG TTCAACGGGA AACCTCGTCG AATGGTTTCT GTTGCGGAAA GCATACGAGC
1501 GTAATGAACT TGCCCCTAAC AAACCGGATG AAAAGGAGCT GGCACGCCGT CGCCAATCCT
1561 ATGAAGGCGG TTACGTTAAA GAACCAGAGC GGGGGTTATG GGAAAATATC GTGTATCTGG
1621 ATTTCCGTTC GCTCTACCCG AGCATTATCA TTACCCACAA CGTATCTCCC GACACTTTGA
1681 ATCGCGAGGG CTGTAAAGAA TATGATGTCG CGCCGCAGGT TGGTCATAGA TTTTGCAAGG
1741 ACTTCCCGGG ATTTATACCA AGTCTGCTTG GCGATTTACT GGAGAGCGA CAAAAAATCA
1801 AAAAGAAAAT GAAAGCTACA ATCGATCCGA TAGAACGTAA GCTGCTCGAC TACCGCCAGC
1861 GGGCCATCAA AATTTTGGCA AACTCATATT ATGGTTACTA TGGGTACGCG CGTGCTCGCT
1921 GGTATTGTAA AGAGTGCGCC GAATCCGTGA CGGCATGGGG CCGTGAATAC ATCACCATGA
1981 CTATTAAGGA GATAGAAGAG AAATATGGTT TCAAAGTAAT CTACTCGGAT ACAGACGGAT
2041 TCTTTGCGAC GATTCCCGGT GCCGATGCAG AAACCGTCAA GAAAAAAGCG ATGGAATTCC
2101 TTAAGTATAT AAATGCTAAA TTACCTGGTG CCCTGGAGCT GGAATACGAA GGGTTTTACA
2161 AACGCGGATT CTTTGTTACT AAGAAAAAAT ATGCGGTGAT CGACGAGGAA GGCAAGATTA
2221 CGACCAGAGG CCTCGAGATT GTACGGCGTG ATTGGAGCGA AATCGCTAAA GAAACACAGG
2281 CACGTGTCTT GGAGGCATTA CTGAAAGATG GGGACGTTGA AAAGGCGGTG CGAATTGTAA
2341 AAGAAGTCAC CGAAAAACTT TCTAAGTACG AAGTTCCGCC AGAGAAACTG GTGATACACG
2401 AACAAATCAC TCGTGATCTG AAAGACTATA AGGCTACAGG CCCGCATGTA GCAGTCGCCA
2461 AACGCCTCGC GGCTCGGGGT GTTAAAATTC GTCCCGGAAC GGTGATCAGT TACATTGTAT
2521 TGAAGGGCTC AGGTCGCATA GGGGATAGAG CAATCCCTTT CGACGAGTTT GATCCAACCA
2581 AACACAAATA TGATGCCGAA TACTATATTG AAAACCAGGT CTTGCCGGCG TTGAGCGTA
2641 TACTGCGCGC TTTCGGCTAT CGAAGGAAG ATCTTCGTTA CCAAAAAACT AGACAGGTGG
2701 GTCTGTCCGA ATGGCTCAAA CCTAAGGGAA CGTAATGATA TGAGACCGGA TCCTCTAGAG
2761 TCGACCTGCA GGCATGCAAG CTTGGCGTAA TCATGGTCAT AGCTGTTTCC TGTGTGAAAT
2821 TGTTATCCGC TCACAATTCC ACACAACATA CGAGCCGGAA GCATAAAGTG TAAAGCCTGG
2881 GGTGCCTAAT GAGTGAGCTA ACTCACATTA ATTGCGTTGC GCTCACTGCC CGCTTTCCAG
2941 TCGGGAAACC TGTCGTGCCA GCTGCATTAA TGAATCGGCC AACGCGCGGG GAGAGGCGGT
3001 TTGCGTATTG GGCGCTCTTC CGCTTCCTCG CTCACTGACT CGCTGCGCTC GGTCGTTCGG
3061 CTGCGGCGAG CGGTATCAGC TCACTCAAAG GCGGTAATAC GGTTATCCAC AGAATCAGGG
3121 GATAACGCAG GAAAGAACAT GTGAGCAAAA GGCCAGCAAA AGGCCAGGAA CCGTAAAAAG
3181 GCCGCGTTGC TGGCGTTTTT CCATAGGCTC CGCCCCCTG ACGAGCATCA CAAAAATCGA
3241 CGCTCAAGTC AGAGGTGGCG AAACCCGACA GGACTATAAA GATACCAGGC GTTTCCCCCT
3301 GGAAGCTCCC TCGTGCGCTC TCCTGTTCCG ACCCTGCCGC TTACCGGATA CCTGTCCGCC
3361 TTTCTCCCTT CGGGAAGCGT GGCGCTTTCT CATAGCTCAC GCTGTAGGTA TCTCAGTTCG
3421 GTGTAGGTCG TTCGCTCCAA GCTGGGCTGT GTGCACGAAC CCCCCGTTCA GCCCGACCGC
3481 TGCGCCTTAT CCGGTAACTA TCGTCTTGAG TCCAACCCGG TAAGACACGA CTTATCGCCA
3541 CTGGCAGCAG CCACTGGTAA CAGGATTAGC AGAGCGAGGT ATGTAGGCGG TGCTACAGAG
3601 TTCTTGAAGT GGTGGCCTAA CTACGGCTAC ACTAGAAGAA CAGTATTTGG TATCTGCGCT
3661 CTGCTGAAGC CAGTTACCTT CGGAAAAAGA GTTGGTAGCT CTTGATCCGG CAAACAAACC
3721 ACCGCTGGTA GCGGTGGTTT TTTTGTTTGC AAGCAGCAGA TTACGCGCAG AAAAAAAGGA
3781 TCTCAAGAAG ATCCTTTGAT CTTTTCTACG GGGTCTGACG CTCAGTGGAA CGAAAACTCA
3841 CGTTAAGGGA TTTTGGTCAT GAGATTATCA AAAAGGATCT TCACCTAGAT CCTTTTAAAT
3901 TAAAAATGAA GTTTTAAATC AATCTAAAGT ATATATGAGT AAACTTGGTC TGACAGTTAC
3961 CAATGCTTAA TCAGTGAGGC ACCTATCTCA GCGATCTGTC TATTTCGTTC ATCCATAGTT
4021 GCCTGACTCC CCGTCGTGTA GATAACTACG ATACGGGAGG GCTTACCATC TGGCCCCAGT
4081 GCTGCAATGA TACCGCGAGA CCCACGCTCA CCGGCTCCAG ATTTATCAGC AATAAACCAG
4141 CCAGCCGGAA GGGCCGAGCG CAGAAGTGGT CCTGCAACTT TATCCGCCTC CATCCAGTCT
4201 ATTAATTGTT GCCGGGAAGC TAGAGTAAGT AGTTCGCCAG TTAATAGTTT GCGCAACGTT
4261 GTTGCCATTG CTACAGGCAT CGTGGTGTCA CGCTCGTCGT TTGGTATGGC TTCATTCAGC
4321 TCCGGTTCCC AACGATCAAG GCGAGTTACA TGATCCCCCA TGTTGTGCAA AAAAGCGGTT
4381 AGCTCCTTCG GTCCTCCGAT CGTTGTCAGA AGTAAGTTGG CCGCAGTGTT ATCACTCATG
4441 GTTATGGCAG CACTGCATAA TTCTCTTACT GTCATGCCAT CCGTAAGATG CTTTTCTGTG
4501 ACTGGTGAGT ACTCAACCAA GTCATTCTGA GAATAGTGTA TGCGGCGACC GAGTTGCTCT
4561 TGCCCGGCGT CAATACGGGA TAATACCGCG CCACATAGCA GAACTTTAAA AGTGCTCATC
4621 ATTGGAAAAC GTTCTTCGGG GCGAAAACTC TCAAGGATCT TACCGCTGTT GAGATCCAGT
4681 TCGATGTAAC CCACTCGTGC ACCCAACTGA TCTTCAGCAT CTTTTACTTT CACCAGCGTT
4741 TCTGGGTGAG CAAAAACAGG AAGGCAAAAT GCCGCAAAAA AGGGAATAAG GGCGACACGG
4801 AAATGTTGAA TACTCATACT CTTCCTTTTT CAATATTATT GAAGCATTTA TCAGGGTTAT
4861 TGTCTCATGA GCGGATACAT ATTTGAATGT ATTTAGAAAA ATAAACAAAT AGGGGTTCCG
4921 CGCACATTTC CCCGAAAAGT GCCACCTGAC GTCTAAGAAA CCATTATTAT CATGACATTA
4981 ACCTATAAAA ATAGGCGTAT CACGAGGCCC TTTCGTC
```

Amino acid sequences of Pfu and KOD

Sequence 9 (SEQ ID NO: 9)
>Pfu amino acid sequence
```
  1 MILDVDYITE EGKPVIRLFK KENGKFKIEH DRTFRPYIYA LLRDDSKIEE VKKITGERHG
 61 KIVRIVDVEK VEKKFLGKPI TVWKLYLEHP QDVPTIREKV REHPAVVDIF EYDIPFAKRY
121 LIDKGLIPME GEEELKILAF DIETLYHEGE EFGKGPIIMI SYADENEAKV ITWKNIDLPY
181 VEVVSSEREM IKRFLRIIRE KDPDIIVTYN GDSFDFPYLA KRAEKLGIKL TIGRDGSEPK
241 MQRIGDMTAV EVKGRIHFDL YHVITRTINL PTYTLEAVYE AIFGKPKEKV YADEIAKAWE
301 SGENLERVAK YSMEDAKATY ELGKEFLPME IQLSRLVGQP LWDVSRSSTG NLVEWFLLRK
361 AYERNEVAPN KPSEEEYQRR LRESYTGGFV KEPEKGLWEN IVYLDFRALY PSIIITHNVS
421 PDTLNLEGCK NYDIAPQVGH KFCKDIPGFI PSLLGHLLEE RQKIKTKMKE TQDPIEKILL
481 DYRQKAIKLL ANSFYGYYGY AKARWYCKEC AESVTAWGRK YIELVWKELE EKFGFKVLYI
541 DTDGLYATIP GGESEEIKKK ALEFVKYINS KLPGLLELEY EGFYKRGFFV TKKRYAVIDE
601 EGKVITRGLE IVRRDWSEIA KETQARVLET ILKHGDVEEA VRIVKEVIQK LANYEIPPEK
661 LAIYEQITRP LHEYKAIGPH VAVAKKLAAK GVKIKPGMVI GYIVLRGDGP ISNRAILAEE
721 YDPKKHKYDA EYYIENQVLP AVLRILEGFG YRKEDLRYQK TRQVGLTSWL NIKKS*
```

TABLE 5-continued

Sequences

Sequence 10 (SEQ ID NO: 10)
>Pfu amino acid sequence, extra 3 aa in 5' area.
```
   1 MASAILDVDY ITEEGKPVIR LFKKENGKFK IEHDRTFRPY IYALLRDDSK IEEVKKITGE
  61 RHGKIVRIVD VEKVEKKFLG KPITVWKLYL EHPQDVPTIR EKVREHPAVV DIFEYDIPFA
 121 KRYLIDKGLI PMEGEEELKI LAFDIETLYH EGEEFGKGPI IMISYADENE AKVITWKNID
 181 LPYVEVVSSE REMIKRFLRI IREKDPDIIV TYNGDSFDFP YLAKRAEKLG IKLTIGRDGS
 241 EPKMQRIGDM TAVEVKGRIH FDLYHVITRT INLPTYTLEA VYEAIFGKPK EKVYADEIAK
 301 AWESGENLER VAKYSMEDAK ATYELGKEFL PMEIQLSRLV GQPLWDVSRS STGNLVEWFL
 361 LRKAYERNEV APNKPSEEEY QRRLRESYTG GFVKEPEKGL WENIVYLDFR ALYPSIIITH
 421 NVSPDTLNLE GCKNYDIAPQ VGHKFCKDIP GFIPSLLGHL LEERQKIKTK MKETQDPIEK
 481 ILLDYRQKAI KLLANSFYGY YGYAKARWYC KECAESVTAW GRKYIELVWK ELEEKFGFKV
 541 LYIDTDGLYA TIPGGESEEI KKKALEFVKY INSKLPGLLE LEYEGFYKRG FFVTKKRYAV
 601 IDEEGKVITR GLEIVRRDWS EIAKETQARV LETILKHGDV EEAVRIVKEV IQKLANYEIP
 661 PEKLAIYEQI TRPLHEYKAI GPHVAVAKKL AAKGVKIKPG MVIGYIVLRG DGPISNRAIL
 721 AEEYDPKKHK YDAEYYIENQ VLPAVLRILE GFGYRKEDLR YQKTRQVGLT SWLNIKKS*
```

Sequence 11 (SEQ ID NO: 11)
>KOD amino acid sequence
```
   1 MILDTDYITE DGKPVIRIFK KENGEFKIEY DRTFEPYFYA LLKDDSAIEE VKKITAERHG
  61 TVVTVKRVEK VQKKFLGRPV EVWKLYFTHP QDVPAIRDKI REHPAVIDIY EYDIPFAKRY
 121 LIDKGLVPME GDEELKMLAF DIETLYHEGE EFAEGPILMI SYADEEGARV ITWKNVDLPY
 181 VDVVSTEREM IKRFLRVVKE KDPDVLITYN GDNFDFAYLK KRCEKLGINF ALGRDGSEPK
 241 IQRMGDRFAV EVKGRIHFDL YPVIRRTINL PTYTLEAVYE AVFGQPKEKV YAEEITTAWE
 301 TGENLERVAR YSMEDAKVTY ELGKEFLPME AQLSRLIGQS LWDVSRSSTG NLVEWFLLRK
 361 AYERNELAPN KPDEKELARR RQSYEGGYVK EPERGLWENI VYLDFRSLYP SIIITHNVSP
 421 DTLNREGCKE YDVAPQVGHR FCKDFPGFIP SLLGDLLEER QKIKKKMKAT IDPIERKLLD
 481 YRQRAIKILA NSYYGYYGYA RARWYCKECA ESVTAWGREY ITMTIKEIEE KYGFKVIYSD
 541 TDGFFATIPG ADAETVKKKA MEFLKYINAK LPGALELEYE GFYKRGFFVT KKKYAVIDEE
 601 GKITTRGLEI VRRDWSEIAK ETQARVLEAL LKDGDVEKAV RIVKEVTEKL SKYEVPPEKL
 661 VIHEQITRDL KDYKATGPHV AVAKRLAARG VKIRPGTVIS YIVLKGSGRI GDRAIPFDEF
 721 DPTKHKYDAE YYIENQVLPA VERILRAFGY RKEDLRYQKT RQVGLSAWLK PKGT
```

Sequence 12 (SEQ ID NO: 12)
>KOD amino acid sequence, extra 3 aa in 5' area.
```
   1 MASAILDTDY ITEDGKPVIR IFKKENGEFK IEYDRTFEPY FYALLKDDSA IEEVKKITAE
  61 RHGTVVTVKR VEKVQKKFLG RPVEVWKLYF THPQDVPAIR DKIREHPAVI DIYEYDIPFA
 121 KRYLIDKGLV PMEGDEELKM LAFDIETLYH EGEEFAEGPI LMISYADEEG ARVITWKNVD
 181 LPYVDVVSTE REMIKRFLRV VKEKDPDVLI TYNGDNFDFA YLKKRCEKLG INFALGRDGS
 241 EPKIQRMGDR FAVEVKGRIH FDLYPVIRRT INLPTYTLEA VYEAVFGQPK EKVYAEEITT
 301 AWETGENLER VARYSMEDAK VTYELGKEFL PMEAQLSRLI GQSLWDVSRS STGNLVEWFL
 361 LRKAYERNEL APNKPDEKEL ARRRQSYEGG YVKEPERGLW ENIVYLDFRS LYPSIIITHN
 421 VSPDTLNREG CKEYDVAPQV GHRFCKDFPG FIPSLLGDLL EERQKIKKKM KATIDPIERK
 481 LLDYRQRAIK ILANSYYGYY GYARARWYCK ECAESVTAWG REYITMTIKE IEEKYGFKVI
 541 YSDTDGFFAT IPGADAETVK KKAMEFLKYI NAKLPGALEL EYEGFYKRGF FVTKKKYAVI
 601 DEEGKITTRG LEIVRRDWSE IAKETQARVL EALLKDGDVE KAVRIVKEVT EKLSKYEVPP
 661 EKLVIHEQIT RDLKDYKATG PHVAVAKRLA ARGVKIRPGT VISYIVLKGS GRIGDRAIPF
 721 DEFDPTKHKY DAEYYIENQV LPAVERILRA FGYRKEDLRY QKTRQVGLSA WLKPKGT*
```

DNA sequences of chimeras Pod and Kofu

Sequence 13 (SEQ ID NO: 13)
>Pod codon optimized nucleotide sequence
```
   1 ATGGCTAGCG CCATTCTGGA TGTGGACTAT ATCACCGAAG AGGGCAAACC GGTTATACGT
  61 TTATTTAAGA AAGAGAATGG TAAATTCAAG ATCGAGCATG ACCGCACGTT CCGTCCATAC
 121 ATTTACGCGT TGCTTCGGGA TGATAGCAAA ATTGAGGAGG TCAAAAAGAT CACCGGGGAA
 181 CGTCATGGAA AAATAGTAAG AATTGTGGAC GTTGAAAAAG TCGAAAAGGA ATTTCTGGGC
 241 AAACCGATCA CTGTATGGAA GCTCTATCTG GAACATCCTC AGGATGTGCC CACAATTCGA
 301 GAAAAAGTTC GTGAGCACCC AGCCGTCGTG GATATATTTG AATATGACAT CCCTTTTGCA
 361 AAACGCTACT TAATTGATAA AGGCCTGATC CCGATGGAGG GGGAAGAAGA ACTTAAAATT
 421 CTGGCTTTTG ACATAGAAAC GCTCTATCAT GAGGGAGAAG AATTTGGCAA AGGTCCCATC
 481 ATTATGATTT CTTACGCGGA TGAGAACGAA GCCAAGGTAA TCACTTGGAA AAATATTGAC
 541 CTGCCGTACG TTGAAGTGGT CAGTTCAGAG CGGGAAATGA TTAAACGTTT TTTACGCATC
 601 ATTAGAGAGA AGATCCAGA TATAATCGTT ACATATAACG GCGACTCCTT CGATTTTCCT
 661 TACCTGGCAA AACGAGCTGA AAAATTGGGT ATTAAACTTA CCATCGGGCG TGACGATCG
 721 GAACCGAAAA TGCAACGCAT TGGCGATATG ACGGCGGTAG AGGTGAAAGG TCGGATACAC
 781 TTTGATCTGT ATCATGTCAT CACCCGTACT ATTAATCTCC CCACATACAC GTTAGAAGCC
 841 GTTTATGAGG CAATATTCGG CAAGCCGAAA GAAAAGTGT ACGCTGACGA AATCGCGAAG
 901 GCATGGGAGA GCGGCGAAAA CCTGAGCGC GTAGCAAAT ATTCTATGA AGATGCTAAA
 961 GCGACCTACG AATTGGGGAA AGAATTTCTT CCAATGGAAA TTCAGCTGTC GAGATTAATA
1021 GGGCAGAGCC TGTGGGACGT GTCTCGAAGT TCAACGGGAA ACCTCGTCGA ATGGTTTCTG
1081 TTGCGGAAAG CATACGAGCG TAATGAACTT GCCCCTAACA AACCGGATGA AAAGGAGCTG
1141 GCACGCCGTC GCCAATCCTA TGAAGGCGGT TACGTTAAGG AACCAGAGCG AGGGTTATGG
1201 GAAAATATCG TGTATCTGGA TTTCCGTTCG CTCTACCCGA GCATTATCAT TACCCACAAC
1261 GTATCTCCCG ACACTTTGAA TCGCGAGGGC TGTAAAGAAT ATGATGTCGC GCCGCAGGTT
1321 GGTCATAGAT TTTGCAAGGA CTTCCCGGGA TTTATACCAA GTCTGCTTGG CGATTTACTG
1381 GAAGAGCGAC AAAAAATCAA AAAGAAAATG AAAGCTACAA TCGATCCGAT AGAACGTAAG
1441 CTGCTCGACT ACCGCCAGCG GGCCATCAAA ATTTTGGCAA ACTCATATTA TGGTTACTAT
```

TABLE 5-continued

Sequences

```
1501 GGGTACGCGC GTGCTCGCTG GTATTGTAAA GAGTGCGCCG AATCCGTGAC GGCATGGGGC
1561 CGTGAATACA TCACCATGAC TATTAAGGAG ATAGAAGAGA AATATGGTTT CAAAGTAATC
1621 TACTCGGATA CAGACGGATT CTTTGCGACG ATTCCCGGTG CCGATGCAGA AACCGTCAAG
1681 AAAAAAGCGA TGGAATTCGT TAAGTACATT AATAGTAAAT ACCGGGACT GCTTGAACTG
1741 GAGTATGAAG CTTCTACAA AAGAGGTTTT TTCGTTACTA AGAAACGATA TGCCGTAATA
1801 GATGAAGAGG GGAAAGTCAT CACACGTGGC CTCGAGATTG TTCGCCGGGA CTGGTCAGAG
1861 ATAGCAAAGG AAACGCAGGC GCGCGTGCTC GAAACCATCT TGAAACATGG TGATGTAGAG
1921 GAAGCCGTCC GCATTGTTAA AGAGGTGATC CAGAAGTTAG CAAACTATGA AATTCCACCG
1981 GAAAAACTGG CGATATACGA GCAAATCACT CGTCCCCTTC ACGAATATAA AGCTATTGGA
2041 CCTCATGTAG CCGTCGCGAA GAAACTGGCT GCAAAAGGCG TTAAGATAAA ACCAGGTATG
2101 GTGATCGGGT ACATTGTACT CCGCGGCGAC GGTCCGATCT CCAATAGAGC CATCTTGGCG
2161 GAGGAATATG ATCCTAAAAA GCATAAATAC GACGCTGAAT ATTACATTGA GAACCAGGTC
2221 TTGCCGGCAG TTCTGCGGAT ACTTGAAGGA TTTGGCTATC GTAAAGAAGA TCTGCGCTAT
2281 CAAAAGACGC GACAGGTGGG TCTGACTAGC TGGTTGAATA TCAAAAATC GTAA
```

Sequence 14 (SEQ ID NO: 14)
>Kofu codon optimized nucleotide sequence
```
   1 ATGGCTAGCG CCATTCTGGA TACCGACTAT ATCACGGAAG ATGGCAAACC GGTGATACGT
  61 ATTTTTAAGA AGAGAATGG TGAGTTCAAA ATCGAGTACG ACCGCACTTT TGAGCCATAT
 121 TTCTACGCGT TACTGAAGGA CGATAGCGCC ATTGAAGAAG TTAAAAAAAT CACCGCAGAG
 181 CGGCATGGGA CAGTGGTAAC CGTGAAGAGA GTTGAAAAAG TCCAGAAAAA ATTTTTGGGA
 241 CGACCTGTAG AAGTGTGGAA ACTTTATTTC ACTCACCCCC AAGATGTTCC GGCTATACGT
 301 GATAAAATTC GCGAACATCC AGCGGTCATT GATATTTACG AATATGATAT ACCTTTTGCC
 361 AAGCGTTACC TCATCGACAA AGGCCTGGTG CCGATGGAAG GTGATGAAGA ATTAAAAATG
 421 TTGGCATTCG ACATTGAAAC ACTTTATCAC GAGGGGGAAG AGTTTGCTGA GGGTCCCATC
 481 CTGATGATTT CTTATGCGGA TGAAGAGGGT GCCCGCGTAA TAACCTGGAA GAACGTTGAT
 541 CTCCCGTACG TGGACGTCGT TAGTACGGAA CGGGAAATGA TCAAACGTTT CCTGCGCGTA
 601 GTGAAAGAGA AGATCCAGA CGTCTTAATT ACCTATAATG GTGATAACTT TGATTTTGCA
 661 TACCTGAAAA AAAGATGCGA AAAGTTGGGC ATAAATTTCG CTCTTGGTCG AGACGGGTCA
 721 GAGCCTAAAA TCCAGCGTAT GGGAGATCGC TTTGCGGTTG AAGTGAAAGG CCGGATTCAT
 781 TTCGACCTGT ATCGGTAAT TCGTCGCACT ATCAACCTCC CCACATACAC GTTAGAAGCC
 841 GTCTATGAGG CAGTTTTTGG TCAACCGAAG GAAAAAGTTT ACGCTGAGGA AATTACCACT
 901 GCGTGGGAAA CAGGCGAGAA TCTGAACGT GTAGCCCGCT ATTCTATGGA GGATGCAAAA
 961 GTTACCTATG AATTGGGTAA GGAATTTCTT CCAATGGAGG CGCAGCTGAG TCGTTTAGTC
1021 GGACAACCTC TGTGGGACGT TTCACGCTCC TCGACTGGCA ATCTCGTGGA GTGGTTCCTG
1081 TTGAGAAAAG CCTATGAACG AAACGAAGTA GCACCGAATA AACCAAGCGA GGAAGAATAT
1141 CAGCGTCGCC TTCGCAGTC TTACACAGGT GGGTTTGTTA AGGAACCGGA GAAAGGTCTG
1201 TGGGAAAACA TCGTGTATTT AGATTTCCGT GCGCTGTACC CCAGTATTAT AATCACCCAC
1261 AATGTCTCAC CTGACACGCT CAACTTGGAA GGTTGCAAAA ATTATGATAT GCTCCGCAA
1321 GTTGGACATA AGTTTTGTAA AGATATTCCG GCCTTCATCC CGTCCCTGCT TGGTCACTTA
1381 CTGGAAGAGC GCCAAAAAAT TAAGACCAAA ATGAAAGAGA CTCAGGATCC CATTGAAAAG
1441 ATCCTGCTCG ATTACCGGCA AAAAGCCATT AAATTGCTTG CAAACTGTTT TTATGGGTAC
1501 TATGGCTATG CGAAGGCTCG TTGGTACTGC AAAGAATGTG CCGAGAGCGT GACAGCATGG
1561 GGTCGCAAAT ATATAGAATT AGTATGGAAG GAGCTGGAAG AAAAATTCGG ATTCAAAGTC
1621 CTGTACATCG ATACGGATGG CCTCTATGCG ACCATTCCTG GTGGGGAGTC TGAAGAAATC
1681 AAGAAAAAAG CCTTGGAATT CCTTAAGTAT ATAAATGCTA AATTACCTGG TGCCCTGGAG
1741 CTGGAATACG AAGGGTTTTA CAAACGCGGA TTCTTTGGTA CTAAGAAAAA ATATGCGGTG
1801 ATCGACGAGG AAGGCAAGAT TACGACCAGA GGCCTCGAGA TTGTACGGCG TGATTGGAGC
1861 GAAATCGCTA AGAAACACA GGCACGTGTC TTGGAGGCAT TACTGAAAGA TGGGGACGTT
1921 GAAAAGGCGG TGCGAATTGT AAAAGAAGTC ACCGAAAAAC TTTCTAAGTA CGAAGTTCCG
1981 CCAGAGAAAC TGGTGATACA CGAACAAATC ACTCGTGATC TGAAAGACTA TAAGGCTACA
2041 GGCCCGCATG TAGCAGTCGC CAAACGCCTC GCGGCTCGGG TGTTAAAAAT TCGTCCCGGA
2101 ACGGTGATCA GTTACATTGT ATTGAAGGGC TCAGGTCGCA TAGGGGATAG AGCAATCCTT
2161 TTCGACGAGT TTGATCCAAC CAAACACAAA TATGATGCCG AATACTATAT TGAAACCAG
2221 GTCTTGCCGG CGGTTGAGCG TATACTGCGC GCTTTCGGCT ATCGAAAGGA AGATCTTCGT
2281 TACCAAAAAA CTAGACAGGT GGGTCTGTCC GCATGGCTCA AACCTAAGGG AACGTAA
```

Amino acid sequences of chimeras Pod and Kofu

Sequence 15 (SEQ ID NO: 15)
>Pod amino acid sequence
```
   1 MASAILDVDY ITEEGKPVIR LFKKENGKFK IEHDRTFRPY IYALLRDDSK IEEVKKITGE
  61 RHGKIVRIVD VEKVEKKFLG KPITVWKLYL EHPQDVPTIR EKVREHPAVV DIFEYDIPFA
 121 KRYLIDKGLI PMEGEEELKI LAFDIETLYH EGEEFGKGPI IMISYADENE AKVITWKNID
 181 LPYVEVVSSE REMIKRFLRI IREKDPDIIV TYNGDSFDFP YLAKRAEKLG IKLTIGRDGS
 241 EPKMQRIGDM TAVEVKGRIH FDLYHVITRT INLPTYTLEA VYEAIFGKPK EKVYADEIAK
 301 AWESGENLER VAKYSMEDAK ATYELGKEFL PMEIQLSRLI GQSLWDVSRS STGNLVEWFL
 361 LRKAYERNEL APNKPDEKEL ARRRQSYEGG YVKEPERGLW ENIVYLDPFRS LYPSIIITHN
 421 VSPDTLNREG CKEYDVAPQV GHRFCKDFPG FIPSLLGDLL EERQKIKKKM KATIDPIERK
 481 LLDYRQRAIK ILANSYGYY GYARARWYCK ECAESVTAWG REYITMTIKE IEEKYGFKVI
 541 YSDTDGFFAT IPGADAETVK KKAMEFVKYI NSKLPGLLEL EYEGFYKRGF FVTKKRYAVI
 601 DEEGKVITRG LEIVRRDWSE IAKETQARVL ETILKHGDVE EAVRIVKEVI QKLANYEIPP
 661 EKLAIYEQIT RPLHEYKAIG PHVAVAKKLA AKGVKIKPGM VIGYIVLRGD GPISNRAILA
 721 EEYDPKKHKY DAEYYIENQV LPAVLRILEG FGYRKEDLRY QKTRQVGLTS WLNIKKS*
```

TABLE 5-continued

Sequences

```
Sequence 16 (SEQ ID NO: 16)
>Kofu amino acid sequence
    1 MASAILDTDY ITEDGKPVIR IFKKENGEFK IEYDRTFEPY FYALLKDDSA IEEVKKITAE
   61 RHGTVVTVKR VEKVQKKFLG RPVEVWKLYF THPQDVPAIR DKIREHPAVI DIYEYDIPFA
  121 KRYLIDKGLV PMEGDEELKM LAFDIETLYH EGEEFAEGPI LMISYADEEG ARVITWKNVD
  181 LPYVDVVSTE REMIKRFLRV VKEKDPDVLI TYNGDNFDFA YLKKRCEKLG INFALGRDGS
  241 EPKIQRMGDR FAVEVKGRIH FDLYPVIRRT INLPTYTLEA VYEAVFGQPK EKVYAEEITT
  301 AWETGENLER VARYSMEDAK VTYELGKEFL PMEAQLSRLV GQPLWDVSRS STGNLVEWFL
  361 LRKAYERNEV APNKPSEEEY QRRLRESYTG GFVKEPEKGL WENIVYLDFR ALYPSIIITH
  421 NVSPDTLNLE GCKNYDIAPQ VGHKFCKDIP GFIPSLLGHL LEERQKIKTK MKETQDPIEK
  481 ILLDYRQKAI KLLANSFYGY YGYAKARWYC KECAESVTAW GRKYIELVWK ELEEKFGFKV
  541 LYIDTDGLYA TIPGGESEEI KKKALEFLKY INAKLPGALE LEYEGFYKRG FFVTKKKYAV
  601 IDEEGKITTR GLEIVRRDWS EIAKETQARV LEALLKDGDV EKAVRIVKEV TEKLSKYEVP
  661 PEKLVIHEQI TRDLKDYKAT GPHVAVAKRL AARGVKIRPG TVISYIVLKG SGRIGDRAIP
  721 FDEFDPTKHK YDAEYYIENQ VLPAVERILR AFGYRKEDLR YQKTRQVGLS AWLKPKGT*

Sequence 17 (SEQ ID NO: 17)
>pLACIQZa
    1 TCGCGCGTTTCGGTGATGACGGTGAAAACCTCTGACACATGCAGCTCCCGGAGACGGTCA
   61 CAGCTTGTCTGTAAGCGGATGCCGGGAGCAGACAAGCCCGTCAGGGCGCGTCAGCGGGTG
  121 TTGGCGGGTGTCGGGGCTGGCTTAACTATGCGGCATCAGAGCAGATTGTACTGAGAGTGC
  181 ACCATATGCGGTGTGAAATACCGCACAGATGCGTAAGGAGAAAATACCGCATCAGGCGCC
  241 ATTCGCCATTCAGGCTGCGCAACTGTTGGGAAGGGCGATCGGTGCGGGCCTCTTCGCTAT
                                                                GT
  301 TACGCCAGCTGGCGAAAGGGGGATGTGCTGCAAGGCGATTAAGTTGGGTAACGCCAGGGT
       TTTCCCAGTCACGAC >>> Primer M13-40 (SEQ ID NO: 42)
  361 TTTCCCAGTCACGACGTTGTAAAACGACGGCCAGTGAATTCGAGCTCGGTACCCGGGGAT
           XbaI
  421 CCTCTAGAGCCGTAATCATGGTCATAGCTGTTTCCTGTGTGAAATTGTTATCCGCTCACA
  481 ATTCCACACAACATACGAGCCGGAAGCATAAAGTGTAAAGCCTGGGGTGCCTAATGAGTG
  541 AGCTAACTCACATTAATTGCGTTGCGCTCACTGCCCGCTTTCCAGTCGGGAAACCTGTCG
  601 TGCCAGCTGCATTAATGAATCGGCCAACGCGCGGGGAGAGGCGGTTTGCGTATTGGGCGC
  661 CAGGGTGGTTTTTCTTTTCACCAGTGAGACGGGCAACAGCTGATTGCCCTTCACCGCCTG
  721 GCCCTGAGAGAGTTGCAGCAAGCGGTCCACGCTGGTTTGCCCCAGCAGGCGAAAATCCTG
  781 TTTGATGGTGGTTGACGGCGGGATATAACATGAGCTGTCTTGTCGGTATCGTCGTATCCCAC
  841 TACCGAGATATCCGCACCAACGCGCAGCCCGGACTCGGTAATGGCGCGCATTGCGCCCAG
  901 CGCCATCTGATCGTTGGCAACCAGCATCGCAGTGGGAACGATGCCCTCATTCAGCATTTG
  961 CATGGTTTGTTGAAAACCGGACATGGCACTCCAGTCGCCTTCCCGTTCCGCTATCGGCTG
 1021 AATTTGATTGCGAGTGAGATATTTATGCCAGCCAGCCAGACGCAGACGCGCCGAGACAGA
 1081 ACTTAATGGGCCCGCTAACAGCGCGATTTGCTGGTGACCCAATGCGACCAGATGCTCCAC
 1141 GCCCAGTCGCGTACCGTCTTCATGGGAGAAAATAATACTGTTGATGGGTGTCTGGTCAGA
 1201 GACATCAAGAAATAACGCCGGAACATTAGTGCAGGCAGCTTCCACAGCAATGGCATCCTG
 1261 GTCATCCAGCGGATAGTTAATGATCAGCCCACTGACGCGTTGCGCGAGAAGATTGTGCAC
 1321 CGCCGCTTTACAGGCTTCGACGCCGCTTCGTTCTACCATCGACACCACCACGCTGGCACC
 1381 CAGTTGATCGGCGCGAGATTTAATCGCCGCGACAATTTGCGACGGCGCGTGCAGGGCCAG
 1441 ACTGGAGGTGGCAACGCCAATCAGCAACGACTGTTTGCCCGCCAGTTGTTGTGCCACGCG
 1501 GTTGGGAATGTAATTCAGCTCCGCCATCGCCGCTTCCACTTTTTCCCGCGTTTTCGCAGA
 1561 AACGTGGCTGGCCTGGTTCACCACGCGGGAAACGGTCTGATAAGAGACACCGGCATACTC
 1621 TGCGACATCGTATAACGTTACTGGTTTCACATTCACCACCCTGAATTGACTCTCTTCCGG
 1681 GCGCTATCATGCCATACCGCGAAAGGTTTTGCGCCATTCGATGGTGTCAACGTAAATGCA
                                                             NcoI
 1741 TGCCGCTTCGCCTTCCGGCCACCAGAATAGCCTGCGCCATGGGCTTCCTCGCTCACTGAC
 1801 TCGCTGCGCTCGGTCGTTCGGCTGCGGCGAGCGGTATCAGCTCACTCAAAGGCGGTAATA
 1861 CGGTTATCCACAGAATCAGGGGATAACGCAGGAAAGAACATGTGAGCAAAAGGCCAGCAA
 1921 AAGGCCAGGAACCGTAAAAAGGCCGCGTTGCTGGCGTTTTTCCATAGGCTCCGCCCCCCT
 1981 GACGAGCATCACAAAAATCGACGCTCAAGTCAGAGGTGGCGAAACCCGACAGGACTATAA
                          PRIMER PKBLACIR <<< GCTGTCCTGATATT
       TCTATGG (SEQ ID NO: 43)
 2041 AGATACCAGGCGTTTCCCCCTGGAAGCTCCCTCGTGCGCTCTCCTGTTCCGACCCTGCCG
 2101 CTTACCGGATACCTGTCCGCCTTTCTCCCTTCGGGAAGCGTGGCGCTTTCTCATAGCTCA
 2161 CGCTGTAGGTATCTCAGTTCGGTGTAGGTCGTTCGCTCCAAGCTGGGCTGTGTGCACGAA
 2221 CCCCCCGTTCAGCCCGACCGCTGCGCCTTATCCGGTAACTATCGTCTTGAGTCCAACCCG
 2281 GTAAGACACGACTTATCGCCACTGGCAGCAGCCACTGGTAACAGGATTAGCAGAGCGAGG
 2341 TATGTAGGCGGTGCTACAGAGTTCTTGAAGTGGTGGCCTAACTACGGCTACACTAGAAGA
 2401 ACAGTATTTGGTATCTGCGCTCTGCTGAAGCCAGTTACCTTCGGAAAAAGAGTTGGTAGC
 2461 TCTTGATCCGGCAAACAAACCACCGCTGGTAGCGGTGGTTTTTTTGTTTGCAAGCAGCAG
 2521 ATTACGCGCAGAAAAAAAGGATCTCAAGAAGATCCTTTGATCTTTTCTACGGGGTCTGAC
 2581 GCTCAGTGGAACGAAAACTCACGTTAAGGGATTTTGGTCATGAGATTATCAAAAAGGATC
 2641 TTCACCTAGATCCTTTTAAATTAAAAATGAAGTTTTAAATCAATCTAAAGTATATATGAG
 2701 TAAACTTGGTCTGACAGTTACCAATGCTTAATCAGTGAGGCACCTATCTCAGCGATCTGT
 2761 CTATTTCGTTCATCCATAGTTGCCTGACTCCCCGTCGTGTAGATAACTACGATACGGGAG
 2821 GGCTTACCATCTGGCCCCAGTGCTGCAATGATACCGCGAGACCCACGCTCACCGGCTCCA
 2881 GATTTATCAGCAATAAACCAGCCAGCCGGAAGGGCCGAGCGCAGAAGTGGTCCTGCAACT
 2941 TTATCCGCCTCCATCCAGTCTATTAATTGTTGCCGGGAAGCTAGAGTAAGTAGTTCGCCA
 3001 GTTAATAGTTTGCGCAACGTTGTTGCCATTGCTACAGGCATCGTGGTGTCACGCTCGTCG
 3061 TTTGGTATGGCTTCATTCAGCTCCGGTTCCCAACGATCAAGGCGAGTTACATGATCCCCC
 3121 ATGTTGTGCAAAAAAGCGGTTAGCTCCTTCGGTCCTCCGATCGTTGTCAGAAGTAAGTTG
```

TABLE 5-continued

Sequences

```
3181 GCCGCAGTGTTATCACTCATGGTTATGGCAGCACTGCATAATTCTCTTACTGTCATGCCA
3241 TCCGTAAGATGCTTTTCTGTGACTGGTGAGTACTCAACCAAGTCATTCTGAGAATAGTGT
3301 ATGCGGCGACCGAGTTGCTCTTGCCCGGCGTCAATACGGGATAATACCGCGCCACATAGC
3361 AGAACTTTAAAAGTGCTCATCATTGGAAAACGTTCTTCGGGGCGAAAACTCTCAAGGATC
3421 TTACCGCTGTTGAGATCCAGTTCGATGTAACCCACTCGTGCACCCAACTGATCTTCAGCA
3481 TCTTTTACTTTCACCAGCGTTTCTGGGTGAGCAAAAACAGGAAGGCAAAATGCCGCAAAA
3541 AAGGGAATAAGGGCGACACGGAAATGTTGAATACTCATACTCTTCCTTTTTCAATATTAT
3601 TGAAGCATTTATCAGGGTTATTGTCTCATGAGCGGATACATATTTGAATGTATTTAGAAA
3661 AATAAACAAATAGGGGTTCCGCGCACATTTCCCCGAAAAGTGCCACCTGACGTCTAAGAA
3721 ACCATTATTATCATGACATTAACCTATAAAAATAGGCGTATCACGAGGCCCTTTCGTC
```

Amino acid sequences of DNA polymerases from *T. litoralis*, *Thermococcus* sp. 9 degrees N-7 and chimeras thereof.

Sequence 18 (SEQ ID NO: 18)
*Thermococcus* sp. 9 degrees N-7 DNA polymerase amino acid sequence (acc no. U47108)

```
  1 MILDTDYITE NGKPVIRVFK KENGEFKIEY DRTFEPYFYA LLKDDSAIED VKKVTAKRHG
 61 TVVKVKRAEK VQKKFLGRPI EVWKLYFNHP QDVPAIRDRI RAHPAVVDIY EYDIPFAKRY
121 LIDKGLIPME GDEELTMLAF DIETLYHEGE EFGTGPILMI SYADGSEARV ITWKKIDLPY
181 VDVVSTEKEM IKRFLRVVRE KDPDVLITYN GDNFDFAYLK KRCEELGIKF TLGRDGSEPK
241 IQRMGDRFAV EVKGRIHFDL YPVIRRTINL PTYTLEAVYE AVFGKPKEKV YAEEIAQAWE
301 SGEGLERVAR YSMEDAKVTY ELGREFFPME AQLSRLIGQS LWDVSRSSTG NLVEWFLLRV
361 AYKRNELAPN KPDERELARR RGGYAGGYVK EPERGLWDNI VYLDFRSLYP SIIITHNVSP
421 DTLNREGCKE YDVAPEVGHK FCKDFPGFIP SLLGDLLEER QKIKRKMKAT VDPLEKKLLD
481 YRQRAIKILA NSFYGYYGYA KARWYCKECA ESVTAWGREY IEMVIRELEE KFGFKVLYAD
541 TDGLHATIPG ADAETVKKKA KEFLKYINPK LPGLLELEYE GFYVRGFFVT KKKYAVIDEE
601 GKITTRGLEI VRRDWSEIAK ETQARVLEAI LKHGDVEEAV RIVKEVTEKL SKYEVPPEKL
661 VIHEQITRDL RDYKATGPHV AVAKRLAARG VKIRPGTVIS YIVLKGSGRI GDRAIPADEF
721 DPTKHRYDAE YYIENQVLPA VERILKAFGY RKEDLRYQKT KQVGLGAWLK VKGKK
```

Sequence 19 (SEQ ID NO: 19)
*T. litoralis* DNA polymerase amino acid sequence (acc no. M74198.1)

```
  1 MILDTDYITK DGKPIIRIFK KENGEFKIEL DPHFQPYIYA LLKDDSAIEE IKAIKGERHG
 61 KTVRVLDAVK VRKKFLGREV EVWKLIFEHP QDVPAMRGKI REHPAVVDIY EYDIPFAKRY
121 LIDKGLIPME GDEELKLLAF DIETFYHEGD EFGKGEIIMI SYADEEEARV ITWKNIDLPY
181 VDVVSNEREM IKRFVQVVKE KDPDVIITYN GDNFDLPYLI KRAEKLGVRL VLGRDKEHPE
241 PKIQRMGDSF AVEIKGRIHF DLFPVVRRTI NLPTYTLEAV YEAVLGKTKS KLGAEEIAAI
301 WETEESMKKL AQYSMEDARA TYELGKEFFP MEAELAKLIG QSVWDVSRSS TGNLVEWYLL
361 RVAYARNELA PNKPDEEEYK RRLRTTYLGG YVKEPEKGLW ENIIYLDFRS LYPSIIVTHN
421 VSPDTLEKEG CKNYDVAPIV GYRFCKDFPG FIPSILGDLI AMRQDIKKKM KSTIDPIEKK
481 MLDYRQRAIK LLANSYYGYM GYPKARWYSK ECAESVTAWG RHYIEMTIRE IEEKFGFKVL
541 YADTDGFYAT IPGEKPELIK KKAKEFLNYI NSKLPGLLEL DEGFYLRGF FVTKKRYAVI
601 DEEGRITTRG LEVVRRDWSE IAKETQAKVL EAILKEGSVE KAVEVVRDVV EKIAKYRVPL
661 EKLVIHEQIT RDLKDYKAIG PHVAIAKRLA ARGIKVKPGT IISYIVLKGS GKISDRVILL
721 TEYDPRKHKY DPDYYIENQV LPAVLRILEA FGYRKEDLRY QSSKQTGLDA WLKR
```

Sequence 20 (SEQ ID NO: 20)
Amino acid sequence of chimeric DNA polymerase 9Nli

```
  1 MILDTDYITE NGKPVIRVFK KENGEFKIEY DRTFEPYFYA LLKDDSAIED VKKVTAKRHG
 61 TVVKVKRAEK VQKKFLGRPI EVWKLYFNHP QDVPAIRDRI RAHPAVVDIY EYDIPFAKRY
121 LIDKGLIPME GDEELTMLAF DIETLYHEGE EFGTGPILMI SYADGSEARV ITWKKIDLPY
181 VDVVSTEKEM IKRFLRVVRE KDPDVLITYN GDNFDFAYLK KRCEELGIKF TLGRDGSEPK
241 IQRMGDRFAV EVKGRIHFDL YPVIRRTINL PTYTLEAVYE AVFGKPKEKV YAEEIAQAWE
301 SGEGLERVAR YSMEDAKVTY ELGREFFPME AQLSRLIGQS LWDVSRSSTG NLVEWYLLRV
361 AYARNELAPN KPDEEEYKRR LRTTYLGGYV KEPEKGLWEN IIYLDFRSLY PSIIVTHNVS
421 PDTLEKEGCK NYDVAPIVGY RFCKDFPGFI PSILGDLIAM RQDIKKKMKS TIDPIEKKML
481 DYRQRAIKLL ANSYYGYMGY PKARWYSKEC AESVTAWGRH YIEMTIREIE EKFGFKVLYA
541 DTDGFYATIP GEKPELIKKK AKEFLNYINS KLPGLLELEY EGFYVRGFFV TKKKYAVIDE
601 EGKITTRGLE IVRRDWSEIA KETQARVLEA ILKHGDVEEA VRIVKEVTEK LSKYEVPPEK
661 LVIHEQITRD LRDYKATGPH VAVAKRLAAR GVKIRPGTVI SYIVLKGSGR IGDRAIPADE
721 FDPTKHRYDA EYYIENQVLP AVERILKAFG YRKEDLRYQK TKQVGLGAWL KVKGKK
```

Sequence 21 (SEQ ID NO: 21)
Amino acid sequence of chimeric DNA polymerase Li9N

```
  1 MILDTDYITK DGKPIIRIFK KENGEFKIEL DPHFQPYIYA LLKDDSAIEE IKAIKGERHG
 61 KTVRVLDAVK VRKKFLGREV EVWKLIFEHP QDVPAMRGKI REHPAVVDIY EYDIPFAKRY
121 LIDKGLIPME GDEELKLLAF DIETFYHEGD EFGKGEIIMI SYADEEEARV ITWKNIDLPY
181 VDVVSNEREM IKRFVQVVKE KDPDVIITYN GDNFDLPYLI KRAEKLGVRL VLGRDKEHPE
241 PKIQRMGDSF AVEIKGRIHF DLFPVVRRTI NLPTYTLEAV YEAVLGKTKS KLGAEEIAAI
301 WETEESMKKL AQYSMEDARA TYELGKEFFP MEAELAKLIG QSVWDVSRSS TGNLVEWFLL
361 RKAYKRNELA PNKPDERELA RRRGGYAGGY VKEPERGLWD NIVYLDFRSL YPSIIITHNV
421 SPDTLNREGC KEYDVAPEVG HKFCKDFPGF IPSLLGDLLE ERQKIKRKMK ATVDPLEKKL
481 LDYRQRAIKI LANSFYGYYG YAKARWYCKE CAESVTAWGR EYIEMVIREL EEKFGFKVLY
541 ADTDGLHATI PGADAETVKK KAKEFLKYIN PKLPGLLELE YEGFYLRGFF VTKKRYAVID
```

TABLE 5-continued

Sequences

```
601 EEGRITTRGL EVVRRDWSEI AKETQAKVLE AILKEGSVEK AVEVVRDVVE KIAKYRVPLE
661 KLVIHEQITR DLKDYKAIGP HVAIAKRLAA RGIKVKPGTI ISYIVLKGSG KISDRVILLT
721 EYDPRKHKYD PDYYIENQVL PAVLRILEAF GYRKEDLRYQ SSKQTGLDAW LKR
```

Amino acid sequences of DNA polymerases from *T. gorgonarius*, *T. zilligii* and chimeras thereof.

Sequence 22 (SEQ ID NO: 22)
*T. gorgonarius* DNA polymerase amino acid sequence (acc no. 4699806)
```
  1 MILDTDYITE DGKPVIRIFK KENGEFKIDY DRNFEPYIYA LLKDDSAIED VKKITAERHG
 61 TTVRVVRAEK VKKKFLGRPI EVWKLYFTHP QDVPAIRDKI KEHPAVVDIY EYDIPFAKRY
121 LIDKGLIPME GDEELKMLAF DIETLYHEGE EFAEGPILMI SYADEEGARV ITWKNIDLPY
181 VDVVSTEKEM IKRFLKVVKE KDPDVLITYN GDNFDFAYLK KRSEKLGVKF ILGREGSEPK
241 IQRMGDRFAV EVKGRIHFDL YPVIRRTINL PTYTLEAVYE AIFGQPKEKV YAEEIAQAWE
301 TGEGLERVAR YSMEDAKVTY ELGKEFFPME AQLSRLVGQS LWDVSRSSTG NLVEWFLLRK
361 AYERNELAPN KPDERELARR RESYAGGYVK EPERGLWENI VYLDFRSLYP SIIITHNVSP
421 DTLNREGCEE YDVAPQVGHK FCKDFPGFIP SLLGDLLEER QKVKKKMKAT IDPIEKKLLD
481 YRQRAIKILA NSFYGYYGYA KARWYCKECA ESVTAWGRQY IETTIREIEE KFGFKVLYAD
541 TDGFFATIPG ADAETVKKKA KEFLDYINAK LPGLLELEYE GFYKRGFFVT KKKYAVIDEE
601 DKITTRGLEI VRRDWSEIAK ETQARVLEAI LKHGDVEEAV RIVKEVTEKL SKYEVPPEKL
661 VIYEQITRDL KDYKATGPHV AVAKRLAARG IKIRPGTVIS YIVLKGSGRI GDRAIPFDEF
721 DPAKHKYDAE YYIENQVLPA VERILRAFGY RKEDLRYQKT RQVGLGAWLK PKT
```

Sequence 23 (SEQ ID NO: 23)
*T. zilligii* DNA polymerase amino acid sequence
```
  1 MILDADYITE DGKPVIRVFK KEKGEFKIDY DRDFEPYIYA LLKDDSAIED IKKITAERHG
 61 TTVRVTRAER VKKKFLGRPV EVWKLYFTHP QDVPAIRDKI REHPAVVDIY EYDIPFAKRY
121 LIDRGLIPME GDEELRMLAF DIETLYHEGE EFGEGPILMI SYADEEGARV ITWKNIDLPY
181 VESVSTEKEM IKRFLKVIQE KDPDVLITYN GDNFDFAYLK KRSETLGVKF ILGRDGSEPK
241 IQRMGDRFAV EVKGRIHFDL YPVIRRTINL PTYTLETVYE AIFGQPKEKV YAEEIARAWE
301 SGEGLERVAR YSMEDAKATY ELGKEFFPME AQLSRLVGQS LWDVSRSSTG NLVEWFLLRK
361 AYERNELAPN KPDERELARR AESYAGGYVK EPEKGLWENI VYLDYKSLYP SIIITHNVSP
421 DTLNREGCRE YDVAPQVGHR FCKDFPGFIP SLLGDLLEER QKVKKKMKAT VDPIERKLLD
481 YRQRAIKILA NSYYGYYGYA NARWYCRECA ESVTAWGRQY IETTMREIEE KFGFKVLYAD
541 TDGFFATIPG ADAETVKKKA KEFLNYINPR LPGLLELEYE GFYRRGFFVT KKKYAVIDEE
601 DKITTRGLEI VRRDWSEIAK ETQARVLEAI LKHGDVEEAV RIVKEVTEKL SRYEVPPEKL
661 VIYEQITRDL RDYRATGPHV AVAKRLAARG IKIRPGTVIS YIVLKGPGRV GDRAIPFDEF
721 DPAKHRYDAE YYIENQVLPA VERILRAFGY RKEDLRYQKT KQAGLGAWLK PKT
```

Sequence 24 (SEQ ID NO: 24)
Amino acid sequence of chimeric DNA polymerase GoZi
```
  1 MILDTDYITE DGKPVIRIFK KENGEFKIDY DRNFEPYIYA LLKDDSAIED VKKITAERHG
 61 TTVRVVRAEK VKKKFLGRPI EVWKLYFTHP QDVPAIRDKI KEHPAVVDIY EYDIPFAKRY
121 LIDKGLIPME GDEELKMLAF DIETLYHEGE EFAEGPILMI SYADEEGARV ITWKNIDLPY
181 VDVVSTEKEM IKRFLKVVKE KDPDVLITYN GDNFDFAYLK KRSEKLGVKF ILGREGSEPK
241 IQRMGDRFAV EVKGRIHFDL YPVIRRTINL PTYTLEAVYE AIFGQPKEKV YAEEIAQAWE
301 TGEGLERVAR YSMEDAKVTY ELGKEFFPME AQLSRLVGQS LWDVSRSSTG NLVEWFLLRK
361 AYERNELAPN KPDERELARR RESYAGGYVK EPEKGLWENI VYLDYKSLYP SIIITHNVSP
421 DTLNREGCRE YDVAPQVGHR FCKDFPGFIP SLLGDLLEER QKVKKKMKAT VDPIERKLLD
481 YRQRAIKILA NSYYGYYGYA NARWYCRECA ESVTAWGRQY IETTMREIEE KFGFKVLYAD
541 TDGFFATIPG ADAETVKKKA KEFLDYINAK LPGLLELEYE GFYKRGFFVT KKKYAVIDEE
601 DKITTRGLEI VRRDWSEIAK ETQARVLEAI LKHGDVEEAV RIVKEVTEKL SKYEVPPEKL
661 VIYEQITRDL KDYKATGPHV AVAKRLAARG IKIRPGTVIS YIVLKGSGRI GDRAIPFDEF
721 DPAKHKYDAE YYIENQVLPA VERILRAFGY RKEDLRYQKT RQVGLGAWLK PKT
```

Sequence 25 (SEQ ID NO: 25)
Amino acid sequence of chimeric DNA polymerase ZiGo
```
  1 MILDADYITE DGKPVIRVFK KEKGEFKIDY DRDFEPYIYA LLKDDSAIED IKKITAERHG
 61 TTVRVTRAER VKKKFLGRPV EVWKLYFTHP QDVPAIRDKI REHPAVVDIY EYDIPFAKRY
121 LIDRGLIPME GDEELRMLAF DIETLYHEGE EFGEGPILMI SYADEEGARV ITWKNIDLPY
181 VESVSTEKEM IKRFLKVIQE KDPDVLITYN GDNFDFAYLK KRSETLGVKF ILGRDGSEPK
241 IQRMGDRFAV EVKGRIHFDL YPVIRRTINL PTYTLETVYE AIFGQPKEKV YAEEIARAWE
301 SGEGLERVAR YSMEDAKATY ELGKEFFPME AQLSRLVGQS LWDVSRSSTG NLVEWFLLRK
361 AYERNELAPN KPDERELARR AESYAGGYVK EPERGLWENI VYLDFRSLYP SIIITHNVSP
421 DTLNREGCEE YDVAPQVGHK FCKDFPGFIP SLLGDLLEER QKVKKKMKAT IDPIEKKLLD
481 YRQRAIKILA NSFYGYYGYA KARWYCKECA ESVTAWGRQY IETTIREIEE KFGFKVLYAD
541 TDGFFATIPG ADAETVKKKA KEFLNYINPR LPGLLELEYE GFYRRGFFVT KKKYAVIDEE
601 DKITTRGLEI VRRDWSEIAK ETQARVLEAI LKHGDVEEAV RIVKEVTEKL SRYEVPPEKL
661 VIYEQITRDL RDYRATGPHV AVAKRLAARG IKIRPGTVIS YIVLKGPGRV GDRAIPFDEF
721 DPAKHRYDAE YYIENQVLPA VERILRAFGY RKEDLRYQKT KQAGLGAWLK PKT
```

Amino acid sequences of additional chimeras of KOD and Pfu DNA polymerases.

Sequence 26 (SEQ ID NO: 26)
Amino acid sequence of chimeric DNA polymerase Kofu-II.
```
  1 MASAILDTDY ITEDGKPVIR IFKKENGEFK IEYDRTFEPY FYALLKDDSA IEEVKKITAE
 61 RHGTVVTVKR VEKVQKKFLG RPVEVWKLYF THPQDVPAIR DKIREHPAVI DIYEYDIPFA
121 KRYLIDKGLV PMEGDEELKM LAFDIETLYH EGEEFAEGPI LMISYADEEG ARVITWKNVD
```

TABLE 5-continued

Sequences

```
181 LPYVDVVSTE REMIKRFLRV VKEKDPDVLI TYNGDNFDFA YLKKRCEKLG INFALGRDGS
241 EPKIQRMGDR FAVEVKGRIH FDLYPVIRRT INLPTYTLEA VYEAVFGQPK EKVYAEEITT
301 AWETGENLER VAKYSMEDAK ATYELGKEFL PMEIQLSRLV GQPLWDVSRS STGNLVEWFL
361 LRKAYERNEV APNKPSEEEY QRRLRESYTG GFVKEPEKGL WENIVYLDFR ALYPSIIITH
421 NVSPDTLNLE GCKNYDIAPQ VGHKFCKDIP GFIPSLLGHL LEERQKIKTK MKETQDPIEK
481 ILLDYRQKAI KLLANSFYGY YGYAKARWYC KECAESVTAW GRKYIELVWK ELEEKFGFKV
541 LYIDTDGLYA TIPGGESEEI KKKALEFVKY INSKLPGLLE LEYEGFYKRG FFVTKKRYAV
601 IDEEGKVITR GLEIVRRDWS EIAKETQARV LEALLKDGDV EKAVRIVKEV TEKLSKYEVP
661 PEKLVIHEQI TRDLKDYKAT GPHVAVAKRL AARGVKIRPG TVISYIVLKG SGRIGDRAIP
721 FDEFDPTKHK YDAEYYIENQ VLPAVERILR AFGYRKEDLR YQKTRQVGLS AWLKPKGT

Sequence 27 (SEQ ID NO: 27)
Amino acid sequence of chimeric DNA polymerase Pod-II.
  1 MASAILDVDY ITEEGKPVIR LFKKENGKFK IEHDRTFRPY IYALLRDDSK IEEVKKITGE
 61 RHGKIVRIVD VEKVEKKFLG KPITVWKLYL EHPQDVPTIR EKVREHPAVV DIFEYDIPFA
121 KRYLIDKGLI PMEGEEELKI LAFDIETLYH EGEEFGKGPI IMISYADENE AKVITWKNID
181 LPYVEVVSSE REMIKRFLRI IREKDPDIIV TYNGDSFDFP YLAKRAEKLG IKLTIGRDGS
241 EPKMQRIGDM TAVEVKGRIH FDLYHVITRT INLPTYTLEA VYEAIFGKPK EKVYADEIAK
301 AWESGENLER VARYSMEDAK VTYELGKEFL PMEAQLSRLI GQSLWDVSRS STGNLVEWFL
361 LRKAYERNEL APNKPDEKEL ARRRQSYEGG YVKEPERGLW ENIVYLDFRS LYPSIIITHN
421 VSPDTLNREG CKEYDVAPQV GHRFCKDFPG FIPSLLGDLL EERQKIKKKM KATIDPIERK
481 LLDYRQRAIK ILANSYYGYY GYARARWYCK ECAESVTAWG REYITMTIKE IEEKYGFKVI
541 YSDTDGFFAT IPGADAETVK KKAMEFLKYI NAKLPGALEL EYEGFYKRGF FVTKKKYAVI
601 DEEGKITTRG LEIVRRDWSE IAKETQARVL ETILKHGDVE EAVRIVKEVI QKLANYEIPP
661 EKLAIYEQIT RPLHEYKAIG PHVAVAKKLA AKGVKIKPGM VIGYIVLRGD GPISNRAILA
721 EEYDPKKHKY DAEYYIENQV LPAVLRILEG FGYRKEDLRY QKTRQVGLTS WLNIKKS Sequence 28 (SEQ ID NO: 28)
Amino acid sequence of chimeric DNA polymerase Kofu-III.
  1 MASAILDTDY ITEDGKPVIR IFKKENGEFK IEYDRTFEPY FYALLKDDSA IEEVKKITAE
 61 RHGTVVTVKR VEKVQKKFLG RPVEVWKLYF THPQDVPAIR DKIREHPAVI DIYEYDIPFA
121 KRYLIDKGLV PMEGDEELKM LAFDIETLYH EGEEFAEGPI LMISYADEEG ARVITWKNVD
181 LPYVDVVSTE REMIKRFLRV VKEKDPDVLI TYNGDNFDFA YLKKRCEKLG INFALGRDGS
241 EPKIQRMGDR FAVEVKGRIH FDLYPVIRRT INLPTYTLEA VYEAVFGQPK EKVYAEEITT
301 AWETGENLER VARYSMEDAK VTYELGKEFL PMEAQLSRLI GQSLWDVSRS STGNLVEWFL
361 LRKAYERNEL APNKPDEKEL ARRRQSYEGG YVKEPEKGLW ENIVYLDFRA LYPSIIITHN
421 VSPDTLNLEG CKNYDIAPQV GHKFCKDIPG FIPSLLGHLL EERQKIKTKM KETQDPIEKI
481 LLDYRQKAIK LLANSFYGYY GYAKARWYCK ECAESVTAWG RKYIELVWKE LEEKFGFKVL
541 YIDTDGLYAT IPGGESEEIK KKALEFLKYI NAKLPGALEL EYEGFYKRGF FVTKKKYAVI
601 DEEGKITTRG LEIVRRDWSE IAKETQARVL EALLKDGDVE KAVRIVKEVT EKLSKYEVPP
661 EKLVIHEQIT RDLKDYKATG PHVAVAKRLA ARGVKIRPGT VISYIVLKGS GRIGDRAIPF
721 DEFDPTKHKY DAEYYIENQV LPAVERILRA FGYRKEDLRY QKTRQVGLSA WLKPKGT Sequence 29 (SEQ ID NO: 29)
Amino acid sequence of chimeric DNA polymerase Pod-III.
  1 MASAILDVDY ITEEGKPVIR LFKKENGKFK IEHDRTFRPY IYALLRDDSK IEEVKKITGE
 61 RHGKIVRIVD VEKVEKKFLG KPITVWKLYL EHPQDVPTIR EKVREHPAVV DIFEYDIPFA
121 KRYLIDKGLI PMEGEEELKI LAFDIETLYH EGEEFGKGPI IMISYADENE AKVITWKNID
181 LPYVEVVSSE REMIKRFLRI IREKDPDIIV TYNGDSFDFP YLAKRAEKLG IKLTIGRDGS
241 EPKMQRIGDM TAVEVKGRIH FDLYHVITRT INLPTYTLEA VYEAIFGKPK EKVYADEIAK
301 AWESGENLER VAKYSMEDAK ATYELGKEFL PMEIQLSRLV GQPLWDVSRS STGNLVEWFL
361 LRKAYERNEV APNKPSEEEY QRRLRESYTG GFVKEPERGL WENIVYLDFR SLYPSIIITH
421 NVSPDTLNRE GCKEYDVAPQ VGHRFCKDFP GFIPSLLGDL LEERQKIKKK MKATIDPIER
481 KLLDYRQRAI KILANSYYGY YGYARARWYC KECAESVTAW GREYITMTIK EIEEKYGFKV
541 IYSDTDGFFA TIPGADAETV KKKAMEFVKY INSKLPGLLE LEYEGFYKRG FFVTKKRYAV
601 IDEEGKVITR GLEIVRRDWS EIAKETQARV LETILKHGDV EEAVRIVKEV IQKLANYEIP
661 PEKLAIYEQI TRPLHEYKAI GPHVAVAKKL AAKGVKIKPG MVIGYIVLRG DGPISNRAIL
721 AEEYDPKKHK YDAEYYIENQ VLPAVLRILE GFGYRKEDLR YQKTRQVGLT SWLNIKKS
```

Equivalents

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses variations, combinations, and permutations in which one or more limitations, elements, clauses, descriptive terms, etc., from one or more of the claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention, e.g., any embodiment found within the prior art, can be explicitly excluded from the claims, regardless of whether the specific exclusion is recited in the specification.

It should also be understood that, unless clearly indicated to the contrary, in any methods claimed herein that include more than one act, the order of the acts of the method is not necessarily limited to the order in which the acts of the method are recited, but the invention includes embodiments in which the order is so limited. Furthermore, where the claims recite a composition, the invention encompasses methods of using the composition and methods of making the composition. Where the claims recite a composition, it should be understood that the invention encompasses methods of using the composition and methods of making the composition.

Incorporation of References

All publications and patent documents cited in this application are incorporated by reference in their entirety to the same extent as if the contents of each individual publication or patent document were incorporated herein.

What is claimed is:

1. A DNA polymerase of whose amino acid sequence shows at least 95% overall identity with SEQ ID NO:16, the DNA polymerase characterized in that:
   a) it shows a higher fidelity than a wildtype KOD polymerase; and
   b) it shows higher salt tolerance or thermostability than a wildtype Pfu polymerase.

2. A DNA polymerase of claim 1 whose amino acid sequence comprises:
   a first consensus sequence selected from the group consisting of
   (1)
   XXLXXXXXXXXEGXRXXXXXX-VXXXXXDXXXTXXXXXXXXXXV-VKXXXXXV LIXXXXXNXXXAXXKXX-CXXXXXXNFALXXXXXXXXXXXXIXXMXXRF XXXX XXXXXXXX-PXXRXXXXXXXXXXXXXXXXXVXX-QXXXXXXXXEXXTTXXXT (SEQ ID NO:30), wherein X is any amino acid or a peptide bond;

(2)
   XXEXXXXYXXXXEXXFXXXXKXXX-AXXXXXXXXAXXXXTVXTVKRXXXXQ XXXXXRXVEXXXXFTXXXXXXAXXDX-IXXXXX (SEQ ID NO:31), wherein X is any amino acid or a peptide bond;

(3)
   XXXXXXXXXXXXXXX-ALXXDXXXXKXXXXXXXXTEXXSKXX-VXXXXXVX HXXXXXDXKDXXX-TXXXXXXXXRXXXRXXXXRXXTXXSXXXX KXSXRXGD XXXPFDXFXX-TXXXXXXXXXXXXXXXXXEXXXRAXX (SEQ ID NO:32), wherein X is any amino acid or a peptide bond;

(4)
   NGX$_1$FKIEX$_2$DRTFX$_3$PYX$_4$YALLX$_5$DDSX$_6$IEEVK KITX$_7$ERHGX$_8$X$_9$VX$_{10}$X$_{11}$X$_{12}$X$_{13}$ VEKVX$_{14}$KKFLGX$_{15}$PX$_{16}$X$_{17}$VWKLYX$_{18}$X$_{19}$HP QDVPX$_{20}$IRX$_{21}$KX$_{22}$REHPA (SEQ ID NO:33), wherein X$_1$ is not K; X$_2$ is not H; X$_3$ is not R; X$_4$ is not I; $X_5$ is not R; $X_6$ is not K; $X_7$ is not G; $X_8$ is not K; $X_9$ is not I; $X_{10}$ is not R; $X_{11}$ is not I; $X_{12}$ is not V; $X_{13}$ is not D; $X_{14}$ is not E; $X_{15}$ is not K; $X_{16}$ is not I; $X_{17}$ is not T; $X_{18}$ is not L; $X_{19}$ is not E; $X_{20}$ is not T; $X_{21}$ is not E; and $X_{22}$ is not V;

(5)

PI$X_1$MISYADE$X_2X_3$A$X_4$VITWKN$X_5$DLPYV$X_6$VVS$X_7$EREMIKRFLR$X_8X_9X_{10}$EKDPD$X_{11}X_{12}X_{13}$TYNGD$X_{14}$FDF$X_{15}$YL$X_{16}$KR$X_{17}$EKLGI$X_{18}X_{19}X_{20}X_{21}$GRDGSEPK$X_{22}$QR$X_{23}$GD$X_{24}X_{25}$AVEVKGRIHFDLY$X_{26}$VI$X_{27}$RTINLPTYTLEAVYEA$X_{28}$FG$X_{29}$PKEKVYA$X_{30}$EI$X_{31}X_{32}$AWE$X_{33}$ (SEQ ID NO:34), wherein $X_1$ is not I; $X_2$ is not N; $X_3$ is not E; $X_4$ is not K; $X_5$ is not I; $X_6$ is not E; $X_7$ is not S; $X_8$ is not I; $X_9$ is not I; $X_{10}$ is not R; $X_{11}$ is not I; $X_{12}$ is not I; $X_{13}$ is not V; $X_{14}$ is not S; $X_{15}$ is not P; $X_{16}$ is not A; $X_{17}$ is not A; $X_{18}$ is not K; $X_{19}$ is not L; $X_{20}$ is not T; $X_{21}$ is not I; $X_{22}$ is not M; $X_{23}$ is not I; $X_{24}$ is not M; $X_{25}$ is not T; $X_{26}$ is not H; $X_{27}$ is not T; $X_{28}$ is not I; $X_{29}$ is not K; $X_{30}$ is not D; $X_{31}$ is not A; $X_{32}$ is not K; and $X_{33}$ is not S; and (6)

RDWSEIAKETQARVLE$X_1X_2$LK$X_3$GDVE$X_4$AVRIVKEV$X_5X_6$KL$X_7X_8$YE$X_9$PPEKL$X_{10}$I$X_{11}$EQITR$X_{12}$L$X_{13}X_{14}$YKA$X_{15}$GPHVAVAK$X_{16}$LAA$X_{17}$GVKI$X_{18}$PG$X_{19}$VI$X_{20}$YIVL$X_{21}$G$X_{22}$G$X_{23}$I$X_{24}X_{25}$RAI$X_{26}X_{27}X_{28}$E$X_{29}$DP$X_{30}$KHKYDAEYYIENQVLPAV$X_{31}$RIL$X_{32}X_{33}$FG (SEQ ID NO:35), wherein $X_1$ is not T; $X_2$ is not I; $X_3$ is not H; $X_4$ is not E; $X_5$ is not I; $X_6$ is not Q; $X_7$ is not A; $X_8$ is not N; $X_9$ is not I; $X_{10}$ is not A; $X_{11}$ is not Y; $X_{12}$ is not P; $X_{13}$ is not H; $X_{14}$ is not E; $X_{15}$ is not I; $X_{16}$ is not K; $X_{17}$ is not K; $X_{18}$ is not K; $X_{19}$ is not M; $X_{20}$ is not G; $X_{21}$ is not R; $X_{22}$ is not D; $X_{23}$ is not P; $X_{24}$ is not S; $X_{25}$ is not N; $X_{26}$ is not L; $X_{27}$ is not A; $X_{28}$ is not E; $X_{29}$ is not Y; $X_{30}$ is not K; $X_{31}$ is not L; $X_{32}$ is not E; and $X_{33}$ is not G;

and a second consensus sequence selected from the group consisting of (1)

XKXXXXXXXXXXXXX-
AXXXXXXXXXXXXXXXXXXLXXXXNXX-
IXXXXXXKXX XXIXXXXXXXXXX-
HXXXXXXXXXTXXXEXQXXXXKIXXXXXX
KXXXLXXXXF
XXXXXXXKXXXXXXXXXXXXXXXXXXKXX-
ELVWXXLXXXFXXXXLXIXXXXL
YXXXXXGESXEIXXXXLX (SEQ ID NO:36), wherein X is any amino acid or a peptide bond;

(2)

E$X_1$GLWENIVYLDFR$X_2$LYPSIIITHNVSPDTLN$X_3$EGCK$X_4$YD$X_5$APQVGH$X_6$FCKD$X_7$PGFIPSLLG$X_8$LLEERQKIK$X_0$KMK$X_{10}$T$X_{11}$DPIE$X_{12}X_{13}$LLD

YRQ$X_{14}$AIK$X_{15}$LANS$X_{16}$YGYYGYA$X_{17}$ARWYCKECAESVTAWGR$X_{18}$YI$X_{19}X_{20}X_{21}X_{22}$KE$X_{23}$EEK$X_{24}$GFKV$X_{25}$Y$X_{26}$DTDG$X_{27}X_{28}$ATIPG$X_{29}X_{30}X_{31}$E$X_{32}X_{33}$KKKA$X_{34}$E (SEQ ID NO:37), wherein $X_1$ is not R; $X_2$ is not S; $X_3$ is not R; $X_4$ is not E; $X_5$ is not V; $X_6$ is not R; $X_7$ is not F; $X_8$ is not D; $X_9$ is not K; $X_{10}$ is not A; $X_{11}$ is not I; $X_{12}$ is not R; $X_{13}$ is not K; $X_{14}$ is not R; $X_{15}$ is not I; $X_{16}$ is not Y; $X_{17}$ is not R; $X_{18}$ is not E; $X_{19}$ is not T; $X_{20}$ is not M; $X_{21}$ is not T; $X_{22}$ is not I; $X_{23}$ is not I; $X_{24}$ is not Y; $X_{25}$ is not I; $X_{26}$ is not S; $X_{27}$ is not F; $X_{28}$ is not F; $X_{29}$ is not A; $X_{30}$ is not D; $X_{31}$ is not A; $X_{32}$ is not T; $X_{33}$ is not V; $X_{34}$ is not M.

3. The DNA polymerase of claim 1, wherein the amino acid sequence is identical to SEQ ID NO:16.

4. The DNA polymerase of claim 1, whose amino acid sequence comprises:

XXXXTXXXXXDXXXXXXIXXXXXX-
EXXXXYXXXXEXXFXXXXFXXXAXXXXXXXX
AXXXXTVXTVKRXXXXQXXXXXRX-
VEXXXXXFTXXXXXXAXXDXIXXXXXXIXXYX
XXXXXXXXXXXXXXX-
VXXXXDXXXXMXXXXXXXXXXXXXXX-
AEXXXLXXXXXXX EGXRXXXXXX-
VXXXXXDXXXTXXXXXXXXXXVVKXXXXVLI
XXXXXNXXXAXXK XXCXXXXXN-
FALXXXXXXXXXXIXXMXXR-
FXXXXXXXXXXXXPXXRXXXXXXXX
XXXXXXXXVXXQXXXXXXXEXXTTXXX-
TXXXXXXXXRXXXXXXXVXXXXXXXXX XXX-
AXXXXXVXX-
PXXXXXXXXXXXXXXXXXXXXXXXXXXVXX
XXXSXEXYQXXX XEXX-
TXXFXXXXXKXXXXXXXXXXXX-
AXXXXXXXXXXXXXXXXXLXXXXNXXIXX
XXXXKXXXXIXXXXXXXXX-
HXXXXXXXXXTXXXEX-
QXXXXKIXXXXXXKXXXLXX
XXFXXXXXXXKXXXXXXXXXXXXXXXXXXKX
XELVWXXLXXXFXXXXLXIXXXXLY
XXXXXGESXEIXXXXLXXLXXXXAXXXX-
AXXXXXXXXXXXXXXXXXXKXXXXXXX
XXITXXXXXXXXXXXXXXXXXXXXXXX-
ALXXDXXXXKXXXXXXXXXTEXXSKXXV
XXXXXVXHXXXXXDXKDXXX-
TXXXXXXXXRXXXRXXXXRXXTXX-
SXXXXKXSXRX GDXXXPFDXFXX-
TXXXXXXXXXXXXXXXXXEXXXRAXXXXX
XXXXXXXXXXXXX SAXXKPXGT (SEQ ID NO:38)

wherein X is any amino acid or a peptide bond.

5. A kit comprising a DNA polymerase of claim 1.

* * * * *

UNITED STATES PATENT AND TRADEMARK OFFICE
CERTIFICATE OF CORRECTION

PATENT NO. : 9,023,633 B2
APPLICATION NO. : 13/127420
DATED : May 5, 2015
INVENTOR(S) : Faurholm et al.

It is certified that error appears in the above-identified patent and that said Letters Patent is hereby corrected as shown below:

In the Claims

Column 225, line 48, after "polymerase", delete "of". Claim 1 should read: "A DNA polymerase whose amino acid sequence...".

Column 225, line 55, claim 2 should read: "2. The DNA polymerase...".

Column 225, beginning at line 59, please replace the entire depicted sequence with the following text, replacing the existing text:
(1)
XXLXXXXXXXEGXRXXXXXXVXXXXXDXXXTXXXXXXXXXXVVKXXXXXVLIXXXXXN
XXXAXXKXXCXXXXXNFALXXXXXXXXXXXIXXMXXRFXXXXXXXXXXXXXPXXRXX
XXXXXXXXXXXXXVXXQXXXXXXXEXXTTXXXT (SEQ ID NO:30), wherein X is any amino acid or a peptide bond;
(2)
XXEXXXXYXXXXEXXFXXXXKXXXAXXXXXXXXAXXXXTVXTVKRXXXXQXXXXXRXV
EXXXXXXFTXXXXXXAXXDXIXXXXX (SEQ ID NO:31), wherein X is any amino acid or a peptide bond;
(3)
XXXXXXXXXXXXXXXALXXDXXXXKXXXXXXXXXTEXXSKXXVXXXXXVXHXXXXXD
XKDXXXTXXXXXXXXRXXXRXXXXRXXTXXSXXXXKXSRXGDXXXPFDXFXXTXXXXX
XXXXXXXXXXXXEXXXRAXX (SEQ ID NO:32), wherein X is any amino acid or a peptide bond;
(4)
NGX$_1$FKIEX$_2$DRTFX$_3$PYX$_4$YALLX$_5$DDSX$_6$IEEVKKITX$_7$ERHGX$_8$X$_9$VX$_{10}$X$_{11}$X$_{12}$X$_{13}$VEKVX$_{14}$KKF
LGX$_{15}$PX$_{16}$X$_{17}$VWKLYX$_{18}$X$_{19}$HPQDVPX$_{20}$IRX$_{21}$KX$_{22}$REHPA (SEQ ID NO:33), wherein X$_1$ is not K; X$_2$ is not H; X$_3$ is not R; X$_4$ is not I; X$_5$ is not R; X$_6$ is not K; X$_7$ is not G; X$_8$ is not K; X$_9$ is not I; X$_{10}$ is not R; X$_{11}$ is not I; X$_{12}$ is not V; X$_{13}$ is not D; X$_{14}$ is not E; X$_{15}$ is not K; X$_{16}$ is not I; X$_{17}$ is not T; X$_{18}$ is not L; X$_{19}$ is not E; X$_{20}$ is not T; X$_{21}$ is not E; and X$_{22}$ is not V;

Signed and Sealed this
Twenty-fifth Day of August, 2015

Michelle K. Lee
*Director of the United States Patent and Trademark Office*

CERTIFICATE OF CORRECTION (continued)
U.S. Pat. No. 9,023,633 B2

Please insert the following to replace existing text:

Column 225, continued from page 1 of this Certificate:

--(5)
PIX$_1$MISYADEX$_2$X$_3$AX$_4$VITWKNX$_5$DLPYVX$_6$VVSX$_7$EREMIKRFLRX$_8$X$_9$X$_{10}$EKDPDX$_{11}$X$_{12}$X$_{13}$TYNGDX$_{14}$FDFX$_{15}$YLX$_{16}$KRX$_{17}$EKLGIX$_{18}$X$_{19}$X$_{20}$X$_{21}$GRDGSEPKX$_{22}$QRX$_{23}$GDX$_{24}$X$_{25}$AVEVKGRIHFDLYX$_{26}$VIX$_{27}$RTINLPTYTLEAVYEAX$_{28}$FGX$_{29}$PKEKVYAX$_{30}$EIX$_{31}$X$_{32}$AWEX$_{33}$ (SEQ ID NO:34), wherein X1 is not I; X2 is not N; X3 is not E; X4 is not K; X5 is not I; X6 is not E; X7 is not S; X8 is not I; X9 is not I; X10 is not R; X11 is not I; X12 is not I; X13 is not V; X14 is not S; X15 is not P; X16 is not A; X17 is not A; X18 is not K; X19 is not L; X20 is not T; X21 is not I; X22 is not M; X23 is not I; X24 is not M; X25 is not T; X26 is not H; X27 is not T; X28 is not I; X29 is not K; X30 is not D; X31 is not A; X32 is not K; and X33 is not S; and
(6)
RDWSEIAKETQARVLEX$_1$X$_2$LKX$_3$GDVEX$_4$AVRIVKEVX$_5$X$_6$KLX$_7$X$_8$YEX$_9$PPEKLX$_{10}$IX$_{11}$EQITRX$_{12}$LX$_{13}$X$_{14}$YKAX$_{15}$GPHVAVAKX$_{16}$LAAX$_{17}$GVKIX$_{18}$PGX$_{19}$VIX$_{20}$YIVLX$_{21}$GX$_{22}$GX$_{23}$IX$_{24}$X$_{25}$RAIX$_{26}$X$_{27}$X$_{28}$EX$_{29}$DPX$_{30}$KHKYDAEYYIENQVLPAVX$_{31}$RILX$_{32}$X$_{33}$FG (SEQ ID NO:35), wherein X$_1$ is not T; X$_2$ is not I; X$_3$ is not H; X$_4$ is not E; X$_5$ is not I; X$_6$ is not Q; X$_7$ is not A; X$_8$ is not N; X$_9$ is not I; X$_{10}$ is not A; X$_{11}$ is not Y; X$_{12}$ is not P; X$_{13}$ is not H; X$_{14}$ is not E; X$_{15}$ is not I; X$_{16}$ is not K; X$_{17}$ is not K; X$_{18}$ is not K; X$_{19}$ is not M; X$_{20}$ is not G; X$_{21}$ is not R; X$_{22}$ is not D; X$_{23}$ is not P; X$_{24}$ is not S; X$_{25}$ is not N; X$_{26}$ is not L; X$_{27}$ is not A; X$_{28}$ is not E; X$_{29}$ is not Y, X$_{30}$ is not K; X$_{31}$ is not L, X$_{32}$ is not E; and X$_{33}$ is not G;

and a second consensus sequence selected from the group consisting of (1)
XKXXXXXXXXXXXXAXXXXXXXXXXXXXXXXLXXXXNXXIXXXXXXKXXXXIXXXXXXXXXHXXXXXXXXXXTXXXEXQXXXXKIXXXXXXXKXXXLXXXXFXXXXXXXXKXXXXXXXXXXXXXXXXKXXELVWXXLXXXFXXXXLXIXXXXLYXXXXXGESXEIXXXXLX (SEQ ID NO:36), wherein X is any amino acid or a peptide bond; and
(2)
EX$_1$GLWENIVYLDFRX$_2$LYPSIIITHNVSPDTLNX$_3$EGCKX$_4$YDX$_5$APQVGHX$_6$FCKDX$_7$PGFIPSLLGX$_8$LLEERQKIKX$_9$KMKX$_{10}$TX$_{11}$DPIEX$_{12}$X$_{13}$LLDYRQX$_{14}$AIKX$_{15}$LANSX$_{16}$YGYYGYAX$_{17}$ARWYCKECAESVTAWGRX$_{18}$YIX$_{19}$X$_{20}$X$_{21}$X$_{22}$KEX$_{23}$EEKX$_{24}$GFKVX$_{25}$YX$_{26}$DTDGX$_{27}$X$_{28}$ATIPGX$_{29}$X$_{30}$X$_{31}$EX$_{32}$X$_{33}$KKKAX$_{34}$E (SEQ ID NO:37), wherein X$_1$ is not R; X$_2$ is not S; X$_3$ is not R; X$_4$ is not E; X$_5$ is not V; X$_6$ is not R; X$_7$ is not F; X$_8$ is not D; X$_9$ is not K; X$_{10}$ is not A; X$_{11}$ is not I; X$_{12}$ is not R; X$_{13}$ is not K; X$_{14}$ is not R; X$_{15}$ is not I; X$_{16}$ is not Y; X$_{17}$ is not R; X$_{18}$ is not E; X$_{19}$ is not T; X$_{20}$ is not M; X$_{21}$ is not T; X$_{22}$ is not I; X$_{23}$ is not I; X$_{24}$ is not Y; X$_{25}$ is not I; X$_{26}$ is not S; X$_{27}$ is not F; X$_{28}$ is not F; X$_{29}$ is not A; X$_{30}$ is not D; X$_{31}$ is not A; X$_{32}$ is not T; X$_{33}$ is not V; X$_{34}$ is not M.--.

Column 228, line 19, the 19th letter should be "K" instead of "F"; --X-- should be inserted between the 28th letter ("X") and the 29th letter ("V") of line 53; and, --X-- should be inserted after the last "X" of line 43.

CERTIFICATE OF CORRECTION (continued)
U.S. Pat. No. 9,023,633 B2

Please insert the following to replace existing text:

Column 228, beginning at line 18:

--XXXXTXXXXXDXXXXXIXXXXXEXXXYXXXEXXFXXXXKXXXAXXXXXXXAX
XXXTVXTVKRXXXXQXXXXXRXVEXXXXFTXXXXXXAXXDXIXXXXXXIXXYXXXXX
XXXXXXXXXXVXXXDXXXXMXXXXXXXXXXXXXAEXXXLXXXXXXXEGXRXXXX
XXVXXXXDXXXTXXXXXXXXXVVKXXXXXVLIXXXXXNXXXAXXKXXCXXXXXNFA
LXXXXXXXXXXXIXXMXXRFXXXXXXXXXXXXPXXRXXXXXXXXXXXXXXXVXXQXX
XXXXXEXXTTXXXTXXXXXXXXRXXXXXXVXXXXXXXXXXXXAXXXXVXXPXXXXX
XXXXXXXXXXXXXXXXXXXVXXXXXSXEXYQXXXXEXXTXXFXXXXXKXXXXXXXX
XXXXAXXXXXXXXXXXXXXXLXXXXNXXIXXXXXKXXXXIXXXXXXXXHXXXXX
XXXXTXXXEXQXXXXKIXXXXXXKXXXLXXXFXXXXXXXKXXXXXXXXXXXXXXXX
KXXELVWXXLXXXFXXXXLXIXXXXLYXXXXXGESXEIXXXXLXXLXXXXAXXXXAXXX
XXXXXXXXXXXXXXKXXXXXXXXXITXXXXXXXXXXXXXXXXXXXXXALXXDX
XXXKXXXXXXXXTEXXSKXXVXXXXXVXHXXXXXDXKDXXXTXXXXXXXXRXXXRXX
XXRXXTXXSXXXXKXSXRXGDXXXPFDXFXXTXXXXXXXXXXXXXXXXEXXXRAXX
XXXXXXXXXXXXXXXXSAXXKPXGT (SEQ ID NO:38) wherein X is any amino acid or a peptide bond.--.